(12) United States Patent
Breault et al.

(10) Patent No.: US 8,124,602 B2
(45) Date of Patent: Feb. 28, 2012

(54) COMPOUNDS FOR THE TREATMENT OF MULTI-DRUG RESISTANT BACTERIAL INFECTIONS

(75) Inventors: Gloria Breault, Waltham, MA (US); Charles Joseph Eyermann, Waltham, MA (US); Bolin Geng, Waltham, MA (US); Marshall Morningstar, Waltham, MA (US); Folkert Reck, Waltham, MA (US)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 12/964,366

(22) Filed: Dec. 9, 2010

(65) Prior Publication Data

US 2011/0092495 A1   Apr. 21, 2011

Related U.S. Application Data

(63) Continuation of application No. 11/917,394, filed as application No. PCT/GB2006/002207 on Jun. 16, 2006, now Pat. No. 7,875,715.

(60) Provisional application No. 60/691,340, filed on Jun. 16, 2005.

(51) Int. Cl.
*A61K 31/438* (2006.01)
*A61K 31/498* (2006.01)
*C07D 401/06* (2006.01)
*C07D 403/06* (2006.01)

(52) U.S. Cl. ............... 514/224.2; 514/230.5; 514/312; 544/48; 544/105; 546/157

(58) Field of Classification Search .......... 544/48, 544/105; 546/157; 514/224.2, 230.5, 312
See application file for complete search history.

(56) References Cited

U.S. PATENT DOCUMENTS

| 5,861,413 | A | 1/1999 | Habich et al. |
|---|---|---|---|
| 6,603,005 | B2 | 8/2003 | Baque et al. |
| 6,903,217 | B2 | 6/2005 | Bacque et al. |
| 7,223,776 | B2 | 5/2007 | Surivet et al. |
| 7,498,326 | B2 | 3/2009 | Axten et al. |
| 7,875,715 | B2 | 1/2011 | Breault et al. |
| 2002/0111492 | A1 | 8/2002 | Baque et al. |
| 2004/0082610 | A1 | 4/2004 | Bacque et al. |
| 2004/0147518 | A1 | 7/2004 | Bacque et al. |
| 2006/0040949 | A1 | 2/2006 | Surivet et al. |
| 2006/0205719 | A1 | 9/2006 | Hubschwerlen et al. |
| 2009/0198063 | A1 | 8/2009 | Kiyoto et al. |
| 2010/0144717 | A1 | 6/2010 | Comita-Prevoir et al. |
| 2010/0168418 | A1 | 7/2010 | Kiyoto et al. |
| 2010/0324030 | A1 | 12/2010 | Dale et al. |

FOREIGN PATENT DOCUMENTS

| DE | 19601265 A1 | 7/1997 |
|---|---|---|
| WO | 97/37635 A1 | 10/1997 |
| WO | 00/21948 A1 | 4/2000 |
| WO | 00/21952 A1 | 4/2000 |
| WO | 00/43383 A1 | 7/2000 |
| WO | 00/78748 A1 | 12/2000 |
| WO | 01/07432 A2 | 2/2001 |
| WO | 01/07433 A2 | 2/2001 |
| WO | 02/08224 A1 | 1/2002 |
| WO | 02/20238 A1 | 3/2002 |
| WO | 02/24661 A2 | 3/2002 |
| WO | 02/24684 A1 | 3/2002 |
| WO | 02/50040 A1 | 6/2002 |
| WO | 02/50061 A1 | 6/2002 |
| WO | 02/056882 A1 | 7/2002 |
| WO | 02/096907 A1 | 12/2002 |
| WO | 03/064421 A1 | 8/2003 |
| WO | 03/064431 A2 | 8/2003 |
| WO | 2004/002490 A2 | 1/2004 |
| WO | 2004/002992 A1 | 1/2004 |
| WO | 2004/014361 A1 | 2/2004 |
| WO | 2004/058144 A2 | 7/2004 |
| WO | 2004/087145 A2 | 10/2004 |
| WO | 2006/002047 A2 | 1/2006 |
| WO | 2006/003148 A1 | 1/2006 |
| WO | 2006/014580 A1 | 2/2006 |

(Continued)

OTHER PUBLICATIONS

Snyder et al., J. Med. Liban 48(4): 208-214, 2000 (one page abstract).*
Cristau. "Synthesis of Diphenyldialkylphosphonium Salts". Synthesis (1988). vol. 11; 911-912.
Gray. "The Catalytic Hydrogenation of Indolylethylpyridines. 4-(Indolylethyl)-1-aralkylpiperidines as Potent Analgesics". Journal of Medicinal Chemistry (1961). vol. 26; 3368-3373.
International Search Report for PCT/GB2006/002207, (Oct. 4, 2006).

(Continued)

*Primary Examiner* — Kahsay T Habte

(57) ABSTRACT

The present invention relates to compounds of Formula V(A):

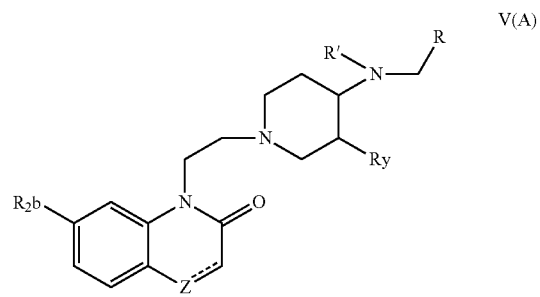

that demonstrate antibacterial activity, processes for their preparation, pharmaceutical compositions containing them as the active ingredient, to their use as medicaments and to their use in the manufacture of medicaments for use in the treatment of bacterial infections in warm-blooded animals such as humans. In particular this invention relates to compounds of Formula V(A) useful for the treatment of bacterial infections in warm-blooded animals such as humans, more particularly to the use of these compounds in the manufacture of medicaments for use in the treatment of bacterial infections in warm-blooded animals such as humans.

4 Claims, No Drawings

FOREIGN PATENT DOCUMENTS

| | | |
|---|---|---|
| WO | 2006/020561 A2 | 2/2006 |
| WO | 2006/021448 A1 | 3/2006 |
| WO | 2006/032466 A2 | 3/2006 |
| WO | 2006/038172 A1 | 4/2006 |
| WO | 2006/046552 A1 | 5/2006 |
| WO | 2006/087543 A1 | 8/2006 |
| WO | 2006/099884 A1 | 9/2006 |
| WO | 2006/125974 A1 | 11/2006 |
| WO | 2007/118130 A2 | 10/2007 |
| WO | 2008/071961 A8 | 6/2008 |

OTHER PUBLICATIONS

Izumi et al. "1H-Imidazo[4,5-c]quinoline Derivatives as Novel Potent TNF-x Suppressors: Synthesis and Structure—Activity Relationship of 1-, 2-and 4-Substituted 1H-imidazo[4,5-c]quinolines or 1H-imidazo[4,5-c]pyridines". Bioorganic & Medicinal Chemistry (2003). vol. 11; 2541-2550.

Zhao et al. "Indoline and Piperazine Containing Derivatives as a Novel Class of Mixed D2/D4 Receptor Antagonists. Part 1: Identification and Structure—Activity Relationships". Bioorganic & Medicinal Chemistry Letters (2002). vol. 12; 3105-3109.

* cited by examiner

COMPOUNDS FOR THE TREATMENT OF MULTI-DRUG RESISTANT BACTERIAL INFECTIONS

CROSS-REFERENCE TO RELATED APPLICATIONS

This application is a continuation application of U.S. application Ser. No. 11/917,394 (filed Dec. 13, 2007), which is a US National Stage under 35 U.S.C §371 of International Application No. PCT/GB2006/002207 (filed Jun. 16, 2006) which claims priority under 35 U.S.C. §119(e) to U.S. Provisional Application No. 60/691,340 (filed Jun. 16, 2005).

BACKGROUND OF THE INVENTION

The international health community continues to express serious concern that the evolution of antibacterial resistance will result in strains against which currently available antibacterial agents will be ineffective. For example, resistant strains of Gram-positive pathogens such as methicillin-resistant *Staphylococcus aureus* (MRSA), methicillin-resistant coagulase-negative staphylococci (MRCNS), penicillin-resistant *Streptococcus pneumoniae* and multiple resistant *Enterococcus faecium* are both difficult to treat and difficult to eradicate. Consequently, in order to overcome the threat of widespread multi-drug resistant organisms, there is an ongoing need to develop new antibiotics, particularly those with either a novel mechanism of action and/or containing new pharmacophoric groups.

SUMMARY OF THE INVENTION

These and other needs are met by the invention disclosed herein which is directed to a compound of formula I:

$$L-U_1-M-U_2-R \qquad I$$

or a pharmaceutically acceptable salt thereof, or N-oxides thereof, wherein:

L is a group of formula L1-L15:

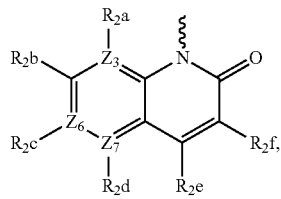

L1

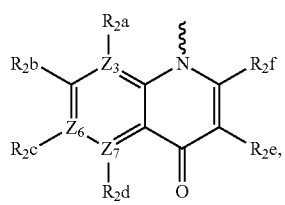

L2

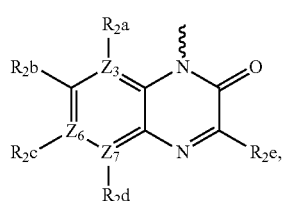

L3

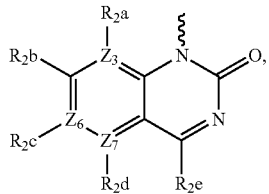

L4

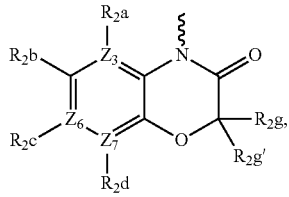

L5

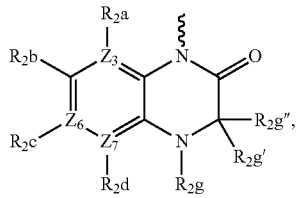

L6

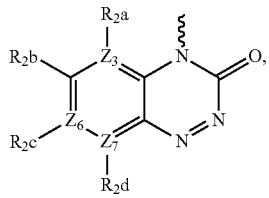

L7

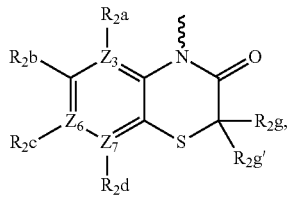

L8

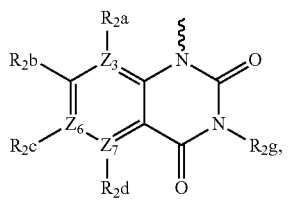

L9

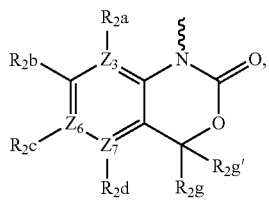

L10

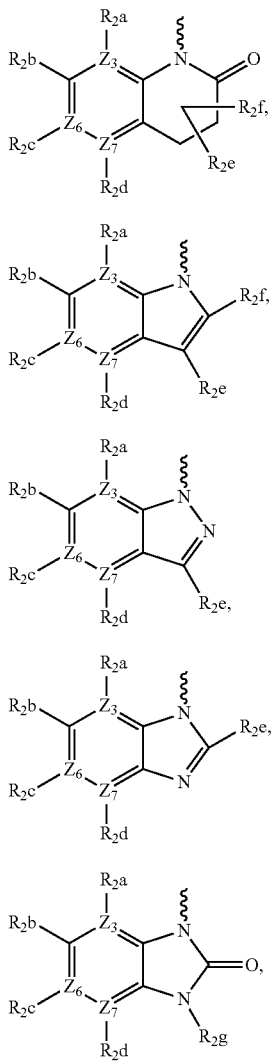

wherein "~~~" indicates the point of attachment;

Z₃, Z₆, and Z₇ are C or N provided that when Z₃, Z₆, or Z₇ is N, then R₂a, R₂c, or R₂d are absent;

R₂a, R₂b, R₂c, R₂d, R₂e, and R₂f, are each independently H, halo, cyano, carboxy, nitro, carbamoyl, —CO—(C₁-C₆)alkyl, CO₂—(C₁-C₆)alkyl, (C₁-C₆)alkyl, hydroxy, halo(C₁-C₆)alkyl, halo(C₁-C₆)alkoxy, (C₁-C₆)alkoxy, NHCO—(C₁-C₆)alkyl, SO₂(C₁-C₆)alkyl, SO₂NH(C₁-C₆)alkyl, or SO₂N((C₁-C₆)alkyl)₂;

R₂g, R₂g', and R₂g'' are each independently H, (C₁-C₆)alkyl, or halo(C₁-C₆)alkyl;

U₁ is CRaRb-CRcRd or CRaRb-CRcRd-CReRf, wherein Ra, Rb, Rc, Rd, Re, and Rf are each independently hydrogen or (C₁-C₆)alkyl;

M is a group of formula M1-M5:

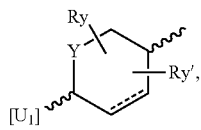

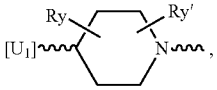

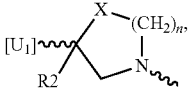

wherein R2 is H or carboxy, and wherein " ~~~ " indicate points of attachment;

Ry and Ry' are each independently H, halo, hydroxy, (C₁-C₆)alkyl, (C₁-C₆)alkoxy, CO₂R'', wherein R'' is H, (C₁-C₆)alkyl, or halo(C₁-C₆)alkyl, or Ry and Ry' together with the carbon to which they are attached form C=O; or Ry and Ry' together form a bridge;

X and Y are each independently CH₂, O, or NR';

" ---- " is a bond or is absent;

n is 1, or 2, or 3;

when M is a group of formula M1 or M4, U₂ is NR'—W, wherein W is CH₂, CO, SO₂,

CH₂CH₂, CH₂CH=CH, or CH₂C≡C, wherein each hydrogen may be optionally replaced by halo or (C₁-C₆)alkyl;

when M is a group of formula M2, M3, or M5, U₂ is W wherein W is as defined herein above;

R' at each occurrence is independently H, (C₁-C₆)alkyl, —(C₁-C₆)alkylcarboxy, —CO—(C₁-C₆)alkyl, —CO₂(C₁-C₆)alkyl, —CO—NH(C₁-C₆)alkyl, —CO—N((C₁-C₆)alkyl)₂, or SO₂(C₁-C₆)alkyl, any of which may be optionally substituted on carbon with halo, hydroxy, (C₁-C₆)alkyl, (C₁-C₆)alkoxy, SO₂(C₁-C₆)alkyl, NH₂, NH(C₁-C₆)alkyl, or N((C₁-C₆)alkyl)₂;

when W is CH₂, CO or SO₂, R is aryl, heteroaryl, heterocyclyl or ortho-fused bicyclic heteroaryl, or when W is

CH₂CH₂, CH₂CH=CH, or CH₂C≡C, R is aryl, heteroaryl, heteroaryloxy, heteroarylthio, heteroarylsulfinyl, heteroarylsulfonyl, heteroarylamino; wherein any R may be optionally substituted on carbon; and wherein any ring nitrogen in R may be optionally substituted by (C₁-C₆)alkyl; and any of L, U₁, M, U₂, or R may be optionally substituted on carbon by one, two or three substituents selected from halo, nitro, cyano, hydroxy, oxo, trifluoromethoxy, trifluoromethyl, amino, carboxy, carbamoyl, mercapto, sulphamoyl, methyl, ethyl, ethenyl, ethynyl, methoxy, ethoxy, methoxycarbonyl, ethoxycarbonyl, heteroaryl, heterocyclyl, acetyl, acetoxy, methylamino, ethylamino, dimethylamino, diethylamino, N-methyl-N-ethylamino, or acetylamino;
with the proviso that when L is a group of formula L8 or L15, W is not CO.

What is also provided is a compound of formula I which is a compound of formula II:

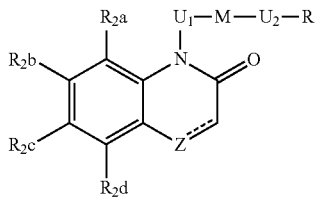

or a pharmaceutically acceptable salt thereof, wherein
$R_2a$, $R_2b$, $R_2c$, and $R_2d$ are each independently H, fluoro, chloro, cyano, $(C_1-C_6)$alkyl, halo$(C_1-C_6)$alkyl, halo$(C_1-C_6)$alkoxy, $(C_1-C_6)$alkoxy;

" ---- " is a bond or is absent;

Z is CH or N when " ---- " is a bond, or Z is O or NH when " ---- " is absent;

$U_1$ is CRaRb-CRcRd or CRaRb-CRcRd-CReRf, wherein Ra, Rb, Rc, Rd, Re and Rf are each independently hydrogen or $(C_1-C_6)$alkyl;

M is a group of formula M1a or M2-M5:

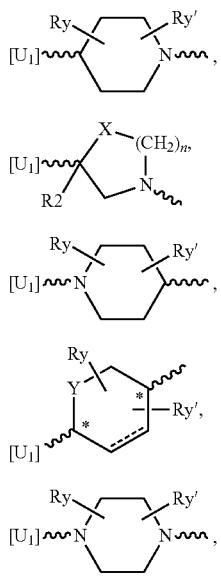

in the trans configuration relative to "*", wherein R2 is H or carboxy;

Ry and Ry' are each independently H, hydroxy, fluoro, chloro, methoxy, carboxy, $CO_2(C_1-C_6)$alkyl, or $(C_1-C_6)$alkyl, or together with the carbon to which they are attached form C=O; or Ry and Ry' together form a bridge;

X is $CH_2$, NH, N[CO—$(C_1-C_6)$alkyl], N[$SO_2(C_1-C_6)$alkyl], N$(C_1-C_6)$alkyl, or O;

Y is $CH_2$, NH, N[CO—$(C_1-C_6)$alkyl], N[$SO_2(C_1-C_6)$alkyl], N$(C_1-C_6)$alkyl, or O;

" ---- " is a bond or is absent;

n is 1, 2, or 3;

when M is a group of formula M1a or M4, $U_2$ is NR'—W, wherein R' is H, $(C_1-C_6)$alkyl, —$(C_1-C_6)$alkylcarboxy, —CO—$(C_1-C_6)$alkyl, —$CO_2(C_1-C_6)$alkyl, —CO—NH$(C_1-C_6)$alkyl, —CO—N$((C_1-C_6)$alkyl$)_2$, any of which may be optionally substituted on carbon with halo, hydroxy, $(C_1-C_6)$alkyl, $(C_1-C_6)$alkoxy, $SO_2(C_1-C_6)$alkyl, $NH_2$, NH$(C_1-C_6)$alkyl, or N$((C_1-C_6)$alkyl$)_2$;

W is $CH_2$, CO, $SO_2$, $CH_2CH_2$, $CH_2CH=CH$, or $CH_2C\equiv C$, wherein each hydrogen may be optionally replaced by halo or $(C_1-C_6)$alkyl;

when M is a group of formula M2, M3, or M5, $U_2$ is W; and when W is $CH_2$, CO or $SO_2$, R is aryl, heteroaryl, heterocyclyl or ortho-fused bicyclic heteroaryl, or when W is $CH_2CH_2$, $CH_2CH=CH$, or $CH_2C\equiv C$, R is aryl, heteroaryl, heteroaryl$(C_1-C_6)$alkyloxy, heteroaryl$(C_1-C_6)$alkylthio, heteroaryl$(C_1-C_6)$alkylsulfinyl, heteroaryl$(C_1-C_6)$alkylsulfonyl, heteroaryl$(C_1-C_6)$alkylamino; wherein any R may be optionally substituted on carbon; and wherein any ring nitrogen in R may be optionally substituted by $(C_1-C_6)$alkyl.

What is also provided is a compound of formula I which is a compound of formula III:

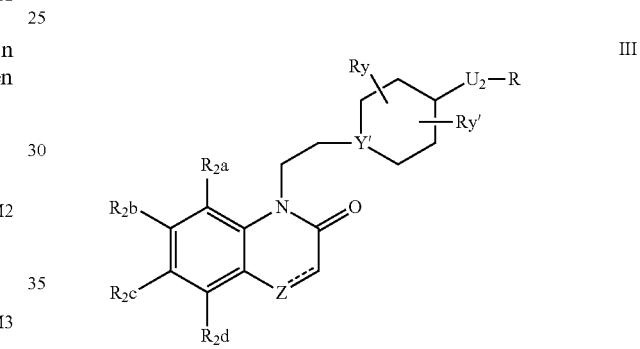

or a pharmaceutically acceptable salt thereof, wherein
$R_2a$, $R_2b$, $R_2c$, and $R_2d$ are each independently H, fluoro, chloro, cyano, $(C_1-C_6)$alkyl, halo$(C_1-C_6)$alkyl, halo$(C_1-C_6)$alkoxy, $(C_1-C_6)$alkoxy;

Z is CH or N when " ---- " is a bond, or, when " ---- " is absent, Z is O or NH;

Y' is N or $CR_2$, wherein $R_2$ is H, hydroxy, or carboxy;

$U_2$ is NR'—W, wherein W is $CH_2$, CO, $SO_2$, $CH_2CH_2$, $CH_2CH=CH$, or $CH_2C\equiv C$, wherein each hydrogen may be optionally replaced by halo or $(C_1-C_6)$alkyl; and R is

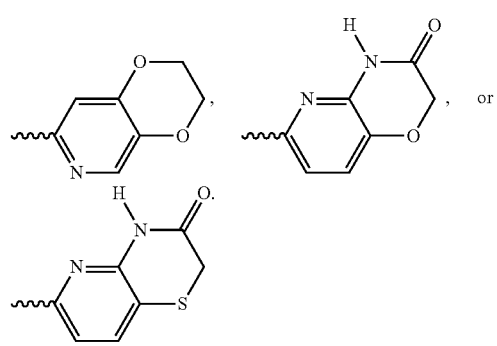

What is also provided is a compound of formula I which is a compound of formula IV:

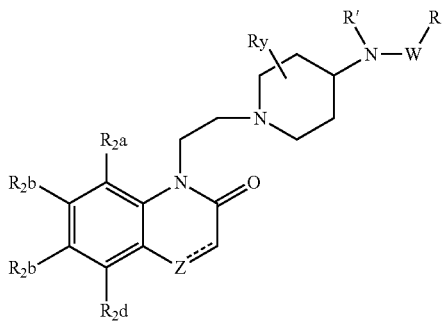

or a pharmaceutically acceptable salt thereof, wherein
$R_2a$, $R_2b$, $R_2c$, and $R_2d$ are each independently H, fluoro, chloro, cyano, nitro, $(C_1-C_6)$alkanoyl, $(C_1-C_6)$alkoxycarbonyl, $(C_1-C_6)$alkyl, halo$(C_1-C_6)$alkyl, halo$(C_1-C_6)$alkoxy, $(C_1-C_6)$alkoxy, NHCO—$(C_1-C_6)$alkyl, $SO_2(C_1-C_6)$alkyl, $SO_2NH(C_1-C_6)$alkyl, or $SO_2N((C_1-C_6)alkyl)_2$;
Z is CH or N when " .... " is a bond, or, when " .... " is absent, Z is O or NH;
R' is H or $(C_1-C_6)$alkyl;
W is CO, $SO_2$, or $CH_2$, wherein each hydrogen may be optionally replaced by halo or $(C_1-C_6)$alkyl; and
R is

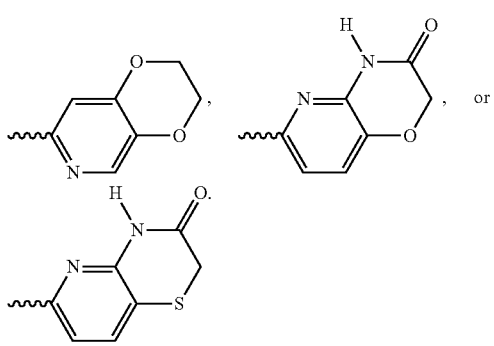

What is also provided is a compound of formula I which is a compound of formula V:

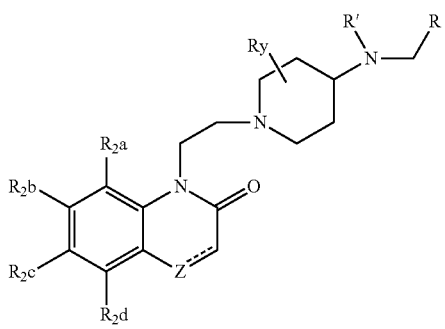

or a pharmaceutically acceptable salt thereof, wherein
$R_2a$, $R_2b$, $R_2c$, and $R_2d$ are each independently H, fluoro, chloro, cyano, nitro, $(C_1-C_6)$alkanoyl, $(C_1-C_6)$alkoxycarbonyl, $(C_1-C_6)$alkyl, halo$(C_1-C_6)$alkyl, halo$(C_1-C_6)$alkoxy, $(C_1-C_6)$alkoxy, NHCO—$(C_1-C_6)$alkyl, $SO_2(C_1-C_6)$alkyl, $SO_2NH(C_1-C_6)$alkyl, or $SO_2N((C_1-C_6)alkyl)_2$;
Z is CH or N when " .... " is a bond, or, when " .... " is absent, Z is O or NH; and
R is

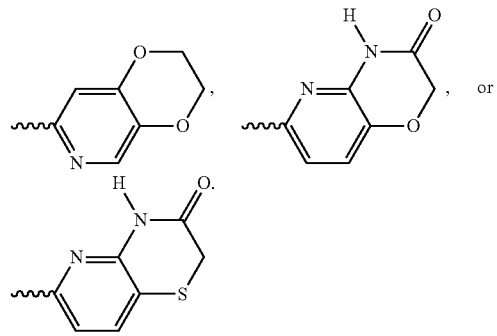

What is also provided by the invention is a compound which is:
1-(2-{4-[(2,3-Dihydro[1,4]dioxino[2,3-c]pyridin-7-ylmethyl)amino]piperidin-1-yl}ethyl)-7-methoxyquinolin-2 (1H)-one;
1-(2-{4-[(2,3-Dihydro[1,4]dioxino[2,3-c]pyridin-7-ylmethyl)amino]piperidin-1-yl}ethyl)-7-methoxyquinolin-4 (1H)-one;
Methyl 1-(2-{4-[(2,3-dihydro[1,4]dioxino[2,3-c]pyridin-7-ylmethyl)amino]piperidin-1-yl}ethyl)-6-methoxy-1H-indole-2-carboxylate;
6-[({1-[2-(7-Methoxy-2-oxoquinolin-1(2H)-yl)ethyl]piperidin-4-yl}amino)methyl]-2H-pyrido[3,2-b][1,4]oxazin-3(4H)-one;
1-(2-{4-[(2,3-Dihydro[1,4]dioxino[2,3-c]pyridin-7-ylmethyl)amino]piperidin-1-yl}ethyl)-2-oxo-1,2-dihydroquinoline-7-carbonitrile;
2-Oxo-1-[2-(4-{[(3-oxo-3,4-dihydro-2H-pyrido[3,2-b][1,4]oxazin-6-yl)methyl]amino}piperidin-1-yl)ethyl]-1,2-dihydroquinoline-7-carbonitrile;
6-[({1-[2-(7,8-Difluoro-2-oxoquinolin-1(2H)-yl)ethyl]piperidin-4-yl}amino)methyl]-2H-pyrido[3,2-b][1,4]oxazin-3(4H)-one;
6-[({1-[2-(5,7-Difluoro-2-oxoquinolin-1(2H)-yl)ethyl]piperidin-4-yl}amino)methyl]-2H-pyrido[3,2-b][1,4]oxazin-3(4H)-one;
6-[({1-[2-(7-Fluoro-2-oxoquinolin-1(2H)-yl)ethyl]piperidin-4-yl}amino)methyl]-2H-pyrido[3,2-b][1,4]oxazin-3(4H)-one;
1-(2-{4-[(2,3-Dihydro[1,4]dioxino[2,3-c]pyridin-7-ylmethyl)amino]piperidin-1-yl}ethyl)-7-fluoroquinolin-2(1H)-one;
6-[({1-[2-(7-Methoxy-2-oxo-3,4-dihydroquinolin-1(2H)-yl)ethyl]piperidin-4-yl}amino)methyl]-2H-pyrido[3,2-b][1,4]oxazin-3(4H)-one;
(3S,4R)-1-[2-(5,7-Difluoro-2-oxoquinolin-1(2H)-yl)ethyl]-4-[(2,3-dihydro[1,4]dioxino[2,3-c]pyridin-7-ylmethyl)amino]piperidine-3-carboxylic acid;
(3S,4R)-1-[2-(5,7-Difluoro-2-oxoquinolin-1(2H)-yl)ethyl]-4-{[(2E)-3-(2,5-difluorophenyl)prop-2-en-1-yl]amino}piperidine-3-carboxylic acid;
Methyl(3S,4R)-1-[2-(5,7-difluoro-2-oxoquinolin-1(2H)-yl)ethyl]-4-[(2,3-dihydro[1,4]dioxino[2,3-c]pyridin-7-ylmethyl)amino]piperidine-3-carboxylate;

Methyl(3S,4R)-1-[2-(5,7-difluoro-2-oxoquinolin-1(2H)-yl)ethyl]-4-{[(2E)-3-(2,5-difluorophenyl)prop-2-en-1-yl]amino}piperidine-3-carboxylate;

(3R,4R)-1-[2-(5,7-Difluoro-2-oxoquinolin-1(2H)-yl)ethyl]-4-[(2,3-dihydro[1,4]dioxino[2,3-c]pyridin-7-ylmethyl)amino]piperidine-3-carboxylic acid;

(3R,4R)-1-[2-(5,7-Difluoro-2-oxoquinolin-1(2H)-yl)ethyl]-4-{[(2E)-3-(2,5-difluorophenyl)prop-2-en-1-yl]amino}piperidine-3-carboxylic acid;

Methyl(3R,4R)-1-[2-(5,7-difluoro-2-oxoquinolin-1(2H)-yl)ethyl]-4-[(2,3-dihydro[1,4]dioxino[2,3-c]pyridin-7-ylmethyl)amino]piperidine-3-carboxylate;

Methyl(3R,4R)-1-[2-(5,7-difluoro-2-oxoquinolin-1(2H)-yl)ethyl]-4-{[(2E)-3-(2,5-difluorophenyl)prop-2-en-1-yl]amino}piperidine-3-carboxylate;

Cis(±)6-[({1-[2-(5,7-Difluoro-2-oxoquinolin-1(2H)-yl)ethyl]-3-hydroxypiperidin-4-yl}amino)methyl]-2H-pyrido[3,2-b][1,4]oxazin-3(4H)-one;

4-(2-{4-[(2,3-Dihydro[1,4]dioxino[2,3-c]pyridin-7-ylmethyl)amino]piperidin-1-yl}ethyl)-6-methoxy-2H-1,4-benzoxazin-3(4H)-one;

6-[({1-[2-(6-Methoxy-3-oxo-2,3-dihydro-4H-1,4-benzoxazin-4-yl)ethyl]piperidin-4-yl}amino)methyl]-2H-pyrido[3,2-b][1,4]oxazin-3(4H)-one;

6-[({1-[2-(6-Methoxy-3-oxo-2,3-dihydro-4H-1,4-benzothiazin-4-yl)ethyl]piperidin-4-yl}amino)methyl]-2H-pyrido[3,2-b][1,4]oxazin-3(4H)-one;

4-(2-{4-[(2,3-Dihydro[1,4]dioxino[2,3-c]pyridin-7-ylmethyl)amino]piperidin-1-yl}ethyl)-6-methoxy-2H-1,4-benzothiazin-3(4H)-one;

6-[({1-[2-(6-Fluoro-3-oxo-2,3-dihydro-4H-1,4-benzoxazin-4-yl)ethyl]piperidin-4-yl}amino)methyl]-2H-pyrido[3,2-b][1,4]oxazin-3(4H)-one;

4-(2-{4-[(2,3-Dihydro[1,4]dioxino[2,3-c]pyridin-7-ylmethyl)amino]piperidin-1-yl}ethyl)-6-fluoro-2H-1,4-benzoxazin-3(4H)-one;

6-[({1-[2-(6-Chloro-3-oxo-2,3-dihydro-4H-1,4-benzoxazin-4-yl)ethyl]piperidin-4-yl}amino)methyl]-2H-pyrido[3,2-b][1,4]oxazin-3(4H)-one;

6-[({1-[2-(6-Methoxy-3-oxo-2,3-dihydro-4H-1,4-benzoxazin-4-yl)ethyl]piperidin-4-yl}amino)methyl]-2H-pyrido[3,2-b][1,4]thiazin-3(4H)-one;

3-Oxo-4-[2-(4-{[(3-oxo-3,4-dihydro-2H-pyrido[3,2-b][1,4]oxazin-6-yl)methyl]amino}piperidin-1-yl)ethyl]-3,4-dihydro-2H-1,4-benzoxazine-6-carbonitrile;

6-{[(1-{2-[3-Oxo-6-(trifluoromethoxy)-2,3-dihydro-4H-1,4-benzoxazin-4-yl]ethyl}piperidin-4-yl)amino]methyl}-2H-pyrido[3,2-b][1,4]oxazin-3(4H)-one;

6-[({1-[2-(6-Fluoro-3-oxo-2,3-dihydro-4H-1,4-benzoxazin-4-yl)ethyl]piperidin-4-yl}amino)methyl]-2H-pyrido[3,2-b][1,4]thiazin-3(4H)-one;

4-(2-{4-[(2,3-Dihydro[1,4]dioxino[2,3-c]pyridin-7-ylmethyl)amino]piperidin-1-yl}ethyl)-3-oxo-3,4-dihydro-2H-1,4-benzoxazine-6-carbonitrile;

6-[({1-[2-(6-Bromo-3-oxo-2,3-dihydro-4H-1,4-benzoxazin-4-yl)ethyl]piperidin-4-yl}amino)methyl]-2H-pyrido[3,2-b][1,4]oxazin-3(4H)-one;

6-[({1-[2-(6-Hydroxy-3-oxo-2,3-dihydro-4H-1,4-benzoxazin-4-yl)ethyl]piperidin-4-yl}amino)methyl]-2H-pyrido[3,2-b][1,4]oxazin-3(4H)-one;

4-{2-[4-({[2-(2,5-Difluorophenyl)cyclopropyl]methyl}amino)piperidin-1-yl]ethyl}-3-oxo-3,4-dihydro-2H-1,4-benzoxazine-6-carbonitrile;

6-[({1-[2-(6,8-Difluoro-3-oxo-2,3-dihydro-4H-1,4-benzoxazin-4-yl)ethyl]piperidin-4-yl}amino)methyl]-2H-pyrido[3,2-b][1,4]oxazin-3(4H)-one;

4-[2-(4-{[(2E)-3-(2,5-Difluorophenyl)prop-2-en-1-yl]amino}piperidin-1-yl)ethyl]-3-oxo-3,4-dihydro-2H-1,4-benzoxazine-6-carbonitrile;

6-[({trans-4-[2-(6-Methoxy-3-oxo-2,3-dihydro-4H-1,4-benzoxazin-4-yl)ethyl]cyclohexyl}amino)methyl]-2H-pyrido[3,2-b][1,4]oxazin-3(4H)-one;

3-Oxo-4-[2-(trans-4-{[(3-oxo-3,4-dihydro-2H-pyrido[3,2-b][1,4]oxazin-6-yl)methyl]amino}cyclohexyl)ethyl]-3,4-dihydro-2H-1,4-benzoxazine-6-carbonitrile;

6-Bromo-4-[2-(4-{[(3-oxo-3,4-dihydro-2H-pyrido[3,2-b][1,4]oxazin-6-yl)methyl]amino}piperidin-1-yl)ethyl]-2H-pyrido[3,2-b][1,4]oxazin-3(4H)-one;

6-[({1-[2-(6-Nitro-3-oxo-2,3-dihydro-4H-1,4-benzoxazin-4-yl)ethyl]piperidin-4-yl}amino)methyl]-2H-pyrido[3,2-b][1,4]oxazin-3(4H)-one;

3-Oxo-4-[2-(4-{[(3-oxo-3,4-dihydro-2H-pyrido[3,2-b][1,4]oxazin-6-yl)methyl]amino}piperidin-1-yl)ethyl]-3,4-dihydro-2H-pyrido[3,2-b][1,4]oxazine-6-carbonitrile;

3-Oxo-4-[2-(4-{[(3-oxo-3,4-dihydro-2H-pyrido[3,2-b][1,4]oxazin-6-yl)methyl]amino}piperidin-1-yl)ethyl]-3,4-dihydro-2H-pyrido[3,2-b][1,4]oxazine-6-carboxamide;

Methyl 3-oxo-4-[2-(4-{[(3-oxo-3,4-dihydro-2H-pyrido[3,2-b][1,4]oxazin-6-yl)methyl]amino}piperidin-1-yl)ethyl]-3,4-dihydro-2H-1,4-benzoxazine-6-carboxylate;

6-[({1-[2-(6-Acetyl-3-oxo-2,3-dihydro-4H-1,4-benzoxazin-4-yl)ethyl]piperidin-4-yl}amino)methyl]-2H-pyrido[3,2-b][1,4]oxazin-3(4H)-one;

6-Acetyl-4-(2-{4-[(2,3-dihydro[1,4]dioxino[2,3-c]pyridin-7-ylmethyl)amino]piperidin-1-yl}ethyl)-2H-1,4-benzoxazin-3(4H)-one;

4-(2-{4-[(2,3-Dihydro[1,4]dioxino[2,3-c]pyridin-7-ylmethyl)amino]piperidin-1-yl}ethyl)-6-methyl-2H-1,4-benzoxazin-3(4H)-one;

3-Oxo-4-[2-(6-{[(3-oxo-3,4-dihydro-2H-pyrido[3,2-b][1,4]oxazin-6-yl)methyl]amino}-3-azabicyclo[3.1.0]hex-3-yl)ethyl]-3,4-dihydro-2H-1,4-benzoxazine-6-carbonitrile;

4-(2-{4-[(2,3-Dihydro[1,4]dioxino[2,3-c]pyridin-7-ylmethyl)amino]piperidin-1-yl}ethyl)-2H-1,4-benzoxazin-3(4H)-one;

6-{[(1-{2-[6-(1-Hydroxyethyl)-3-oxo-2,3-dihydro-4H-1,4-benzoxazin-4-yl]ethyl}piperidin-4-yl)amino]methyl}-2H-pyrido[3,2-b][1,4]oxazin-3(4H)-one;

Ethyl N-{1-[2-(6-cyano-3-oxo-2,3-dihydro-4H-1,4-benzoxazin-4-yl)ethyl]piperidin-4-yl}-N-[(2E)-3-(2,5-difluorophenyl)prop-2-en-1-yl]glycinate;

6-{[(1-{2-[6-(Methylsulfonyl)-3-oxo-2,3-dihydro-4H-1,4-benzoxazin-4-yl]ethyl}piperidin-4-yl)amino]methyl}-2H-pyrido[3,2-b][1,4]oxazin-3(4H)-one;

6-{[(1-{2-[6-(Ethylsulfonyl)-3-oxo-2,3-dihydro-4H-1,4-benzoxazin-4-yl]ethyl}piperidin-4-yl)amino]methyl}-2H-pyrido[3,2-b][1,4]oxazin-3(4H)-one;

6-[({1-[2-(7-Methoxy-2-oxo-2H-3,1-benzoxazin-1(4H)-yl)ethyl]piperidin-4-yl}amino)methyl]-2H-pyrido[3,2-b][1,4]oxazin-3(4H)-one;

7-Methoxy-3-methyl-1-[2-(4-{[(3-oxo-3,4-dihydro-2H-pyrido[3,2-b][1,4]oxazin-6-yl)methyl]amino}piperidin-1-yl)ethyl]quinazoline-2,4(1H,3H)-dione;

4-(2-{4-[(2,3-Dihydro[1,4]dioxino[2,3-c]pyridin-7-ylmethyl)amino]-2-oxopiperidin-1-yl}ethyl)-6-methoxy-2H-1,4-benzoxazin-3(4H)-one;

6-[({1-[2-(6-Methoxy-3-oxo-2,3-dihydro-4H-1,4-benzoxazin-4-yl)ethyl]-2-oxopiperidin-4-yl}amino)methyl]-2H-pyrido[3,2-b][1,4]oxazin-3(4H)-one;

3-Oxo-4-[2-(2-oxo-4-{[(3-oxo-3,4-dihydro-2H-pyrido[3,2-b][1,4]oxazin-6-yl)methyl]amino}piperidin-1-yl)ethyl]-3,4-dihydro-2H-1,4-benzoxazine-6-carbonitrile;

6-({4-[3-(7-Methoxy-2-oxo-2H-3,1-benzoxazin-1(4H)-yl) propyl]piperazin-1-yl}methyl)-2H-pyrido[3,2-b][1,4]oxazin-3(4H)-one;

4-{3-[4-(2,3-Dihydro[1,4]dioxino[2,3-c]pyridin-7-ylmethyl)piperazin-1-yl]propyl}-6-methoxy-2H-1,4-benzoxazin-3(4H)-one;

4-[2-({1-[(2E)-3-(2,5-Difluorophenyl)prop-2-en-1-yl]piperidin-4-yl}amino)ethyl]-6-methoxy-2H-1,4-benzoxazin-3(4H)-one;

4-(3-{4-[(2E)-3-(2,5-Difluorophenyl)prop-2-en-1-yl]piperazin-1-yl}propyl)-6-methoxy-2H-1,4-benzoxazin-3(4H)-one;

6-[({1-[2-(6-Methoxy-2-oxo-1,7-naphthyridin-1(2H)-yl) ethyl]piperidin-4-yl}amino)methyl]-2H-pyrido[3,2-b][1,4]oxazin-3(4H)-one;

Methyl 1-[(2E)-3-(2,5-difluorophenyl)prop-2-en-1-yl]-4-[3-(6-cyano-3-oxo-2,3-dihydro-4H-1,4-benzoxazin-4-yl) propyl]piperidine-3-carboxylate;

4-[3-(6-Cyano-3-oxo-2,3-dihydro-4H-1,4-benzoxazin-4-yl) propyl]-1-[(2E)-3-(2,5-difluorophenyl)prop-2-en-1-yl]piperidine-3-carboxylic acid;

7-Fluoro-3-methyl-1-[2-(4-{[(3-oxo-3,4-dihydro-2H-pyrido [3,2-b][1,4]oxazin-6-yl)methyl]amino}piperidin-1-yl) ethyl]quinazoline-2,4(1H,3H)-dione;

7-Chloro-1-(2-{4-[(2,3-dihydro[1,4]dioxino[2,3-c]pyridin-7-ylmethyl)amino]piperidin-1-yl}ethyl)-1,8-naphthyridin-2(1H)-one;

1-(2-{4-[(2,3-Dihydro[1,4]dioxino[2,3-c]pyridin-7-ylmethyl)amino]piperidin-1-yl}ethyl)-7-methoxy-1,8-naphthyridin-2(1H)-one;

1-(2-{4-[(2,3-Dihydro[1,4]dioxino[2,3-c]pyridin-7-ylmethyl)amino]piperidin-1-yl}ethyl)-7-fluoroquinoxalin-2 (1H)-one;

6-[({1-[2-(7-Fluoro-2-oxoquinoxalin-1(2H)-yl)ethyl]piperidin-4-yl}amino)methyl]-2H-pyrido[3,2-b][1,4]oxazin-3 (4H)-one;

1-(2-{4-[(2,3-Dihydro[1,4]dioxino[2,3-c]pyridin-7-ylmethyl)amino]piperidin-1-yl}ethyl)-6-fluoroquinoxalin-2 (1H)-one;

1-(2-{4-[(2,3-Dihydro[1,4]dioxino[2,3-c]pyridin-7-ylmethyl)amino]piperidin-1-yl}ethyl)-7-methoxyquinoxalin-2(1H)-one;

6-[({1-[2-(7-Methoxy-2-oxoquinoxalin-1(2H)-yl)ethyl]piperidin-4-yl}amino)methyl]-2H-pyrido[3,2-b][1,4]oxazin-3(4H)-one;

6-[({1-[2-(7-Methoxy-2-oxoquinoxalin-1(2H)-yl)ethyl]piperidin-4-yl}amino)methyl]-2H-pyrido[3,2-b][1,4]thiazin-3(4H)-one;

1-(2-{4-[(2,3-Dihydro[1,4]dioxino[2,3-c]pyridin-7-ylmethyl)amino]piperidin-1-yl}ethyl)-6,7-difluoroquinoxalin-2(1H)-one;

6-[({1-[2-(6,7-Difluoro-2-oxoquinoxalin-1(2H)-yl)ethyl]piperidin-4-yl}amino)methyl]-2H-pyrido[3,2-b][1,4]oxazin-3(4H)-one;

1-(2-{4-[(2,3-Dihydro[1,4]dioxino[2,3-c]pyridin-7-ylmethyl)amino]piperidin-1-yl}ethyl)-7,8-difluoroquinoxalin-2(1H)-one;

6-[({1-[2-(7,8-Difluoro-2-oxoquinoxalin-1(2H)-yl)piperidin-4-yl}amino)methyl]-2H-pyrido[3,2-b][1,4]oxazin-3(4H)-one;

6-[({1-[2-(6,7-Dimethoxy-2-oxo quinoxalin-1(2H)-yl)ethyl] piperidin-4-yl}amino)methyl]-2H-pyrido[3,2-b][1,4]oxazin-3(4H)-one;

6-[({1-[2-(7-Methoxy-3-methyl-2-oxoquinoxalin-1(2H)-yl) ethyl]piperidin-4-yl}amino)methyl]-2H-pyrido[3,2-b][1, 4]oxazin-3(4H)-one;

1-(2-{4-[(2,3-Dihydro[1,4]dioxino[2,3-c]pyridin-7-ylmethyl)amino]piperidin-1-yl}ethyl)quinolin-2(1H)-one;

1-(2-{4-[(2,3-Dihydro[1,4]dioxino[2,3-c]pyridin-7-ylmethyl)amino]piperidin-1-yl}ethyl)quinolin-4(1H)-one;

Cis(±)6-[({1-[2-(5,7-difluoro-2-oxo quinolin-1(2H)-yl) ethyl]-3-methoxypiperidin-4-yl}amino)methyl]-2H-pyrido[3,2-b][1,4]oxazin-3(4H)-one;

7-Fluoro-2-oxo-1-[2-(4-{[(3-oxo-3,4-dihydro-2H-pyrido[3, 2-b][1,4]oxazin-6-yl)methyl]amino}piperidin-1-yl) ethyl]-1,2-dihydroquinoline-5-carbonitrile;

5-Fluoro-2-oxo-1-[2-(4-{[(3-oxo-3,4-dihydro-2H-pyrido[3, 2-b][1,4]oxazin-6-yl)methyl]amino}piperidin-1-yl) ethyl]-1,2-dihydroquinoline-7-carbonitrile;

7-Fluoro-1-[2-(4-{[(2-oxo-1,2-dihydro quinolin-3-yl)methyl]amino}piperidin-1-yl)ethyl]quinoxalin-2(1H)-one;

1-[2-(4-{[(2,2-Dimethyl-3,4-dihydro-2H-chromen-6-yl)methyl]amino}piperidin-1-yl)ethyl]-5,7-difluoro quinolin-2 (1H)-one;

1-[2-(4-{[(1,3-Dimethyl-2-oxo-2,3-dihydro-1H-benzimidazol-5-yl)methyl]amino}piperidin-1-yl)ethyl]-57-difluoroquinolin-2(1H)-one;

5,7-Difluoro-1-(2-{4-[(5,6,7,8-tetrahydronaphthalen-2-ylmethyl)amino]piperidin-1-yl}ethyl)quinolin-2(1H)-one;

5,7-Difluoro-1-[2-(4-{[(6-fluoro-4H-1,3-benzodioxin-8-yl) methyl]amino}piperidin-1-yl)ethyl]quinolin-2(1H)-one;

5,7-Difluoro-1-(2-{4-[(1H-indol-6-ylmethyl)amino]piperidin-1-yl}ethyl)quinolin-2(1H)-one;

1-(2-{4-[(2,3-Dihydro-1H-inden-5-ylmethyl)amino]piperidin-1-yl}ethyl)-5,7-difluoroquinolin-2(1H)-one;

5,7-Difluoro-1-[2-(4-{[(1-methyl-1H-1,2,3-benzotriazol-5-yl)methyl]amino}piperidin-1-yl)ethyl]quinolin-2(1H)-one;

5,7-Difluoro-1-(2-{4-[(1H-indol-5-ylmethyl)amino]piperidin-1-yl}ethyl)quinolin-2(1H)-one;

5,7-Difluoro-1-[2-(4-{[(4-methyl-3,4-dihydro-2H-1,4-benzoxazin-7-yl)methyl]amino}piperidin-1-yl)ethyl]quinolin-2(1H)-one;

1-(2-{4-[(2,1,3-Benzoxadiazol-5-ylmethyl)amino]piperidin-1-yl}ethyl)-7-fluoroquinoxalin-2(1H)-one;

N-{1-[2-(7-Fluoro-2-oxoquinoxalin-1(2H)-yl)ethyl]piperidin-4-yl}-2,3-dihydro-1,4-benzodioxine-6-sulfonamide;

N-{1-[2-(7-Fluoro-2-oxoquinoxalin-1(2H)-yl)ethyl]piperidin-4-yl}-3-oxo-3,4-dihydro-2H-1,4-benzoxazine-6-sulfonamide;

5-Fluoro-N-{1-[2-(7-fluoro-2-oxoquinoxalin-1(2H)-yl) ethyl]piperidin-4-yl}-1H-indole-2-carboxamide;

N-{1-[2-(5,7-Difluoro-2-oxoquinolin-1(2H)-yl)ethyl]piperidin-4-yl}-6-morpholin-4-ylnicotinamide;

N-{1-[2-(5,7-Difluoro-2-oxoquinolin-1(2H)-yl)ethyl]piperidin-4-yl}-2,3-dihydro-1,4-benzodioxine-2-carboxamide;

N-{1-[2-(5,7-Difluoro-2-oxoquinolin-1(2H)-yl)ethyl]piperidin-4-yl}-1-methyl-1H-1,2,3-benzotriazole-5-carboxamide;

N-{1-[2-(5,7-Difluoro-2-oxoquinolin-1(2H)-yl)ethyl]piperidin-4-yl}-3-(2-methyl-1,3-thiazol-4-yl)benzamide;

N-{1-[2-(5,7-Difluoro-2-oxoquinolin-1(2H)-yl)ethyl]piperidin-4-yl}-4-(5-methyl-1,2,4-oxadiazol-3-yl)benzamide;

3-Oxo-4-[2-((2R,5S)-5-{[(3-oxo-3,4-dihydro-2H-pyrido[3, 2-b][1,4]oxazin-6-yl)methyl]amino}piperidin-2-yl) ethyl]-3,4-dihydro-2H-1,4-benzoxazine-6-carbonitrile;

3-Oxo-4-[2-((2S,5R)-5-{[(3-oxo-3,4-dihydro-2H-pyrido[3, 2-b][1,4]oxazin-6-yl)methyl]amino}piperidin-2-yl) ethyl]-3,4-dihydro-2H-1,4-benzoxazine-6-carbonitrile 6-[({1-[2-(5,7-Difluoro-2-oxoquinoxalin-1(2H)-yl)ethyl]piperidin-4-yl}amino)methyl]-2H-pyrido[3,2-b][1,4]oxazin-3(4H)-one;

6-[({1-[2-(6,8-Difluoro-2-oxoquinoxalin-1(2H)-yl)ethyl]piperidin-4-yl}amino)methyl]-2H-pyrido[3,2-b][1,4]oxazin-3(4H)-one;

2-oxo-1-[2-(4-{[(3-oxo-3,4-dihydro-2H-pyrido[3,2-b][1,4]oxazin-6-yl)methyl]amino}piperidin-1-yl)ethyl]-1,2-dihydroquinoxaline-6-carbonitrile;

3-Oxo-4-[2-(4-{[(3-oxo-3,4-dihydro-2H-pyrido[3,2-b][1,4]oxazin-6-yl)methyl]amino}piperidin-1-yl)ethyl]-3,4-dihydroquinoxaline-6-carbonitrile;

6-[({1-[2-(6-Methoxy-3-oxopyrido[2,3-b]pyrazin-4(3H)-yl)ethyl]piperidin-4-yl}amino)methyl]-2H-pyrido[3,2-b][1,4]oxazin-3(4H)-one;

4-(2-{4-[(2,3-Dihydro[1,4]dioxino[2,3-c]pyridin-7-ylmethyl)amino]piperidin-1-yl}ethyl)-6-methoxypyrido[2,3-b]pyrazin-3(4H)-one;

6-[({1-[2-(6-Chloro-1-oxido-3-oxo-1,2,4-benzotriazin-4(3H)-yl)ethyl]piperidin-4-yl}amino)methyl]-2H-pyrido[3,2-b][1,4]oxazin-3(4H)-one;

6-Chloro-4-(2-{4-[(2,3-dihydro[1,4]dioxino[2,3-c]pyridin-7-ylmethyl)amino]piperidin-1-yl}ethyl)-1,2,4-benzotriazin-3(4H)-one 1-oxide;

6-[({1-[2-(6-Chloro-3-oxo-1,2,4-benzotriazin-4(3H)-yl)ethyl]piperidin-4-yl}amino)methyl]-2H-pyrido[3,2-b][1,4]oxazin-3(4H)-one;

4-(2-{(2S,5R)-5-[(2,3-Dihydro[1,4]dioxino[2,3-c]pyridin-7-ylmethyl)amino]piperidin-2-yl}ethyl)-3-oxo-3,4-dihydro-2H-1,4-benzoxazine-6-carbonitrile;

6-[({1-[2-(7-Bromo-2-oxo-2,3-dihydro-1H-pyrido[2,3-b][1,4]oxazin-1-yl)ethyl]piperidin-4-yl}amino)methyl]-2H-pyrido[3,2-b][1,4]oxazin-3(4H)-one;

2-Oxo-1-[2-(4-{[(3-oxo-3,4-dihydro-2H-pyrido[3,2-b][1,4]oxazin-6-yl)methyl]amino}piperidin-1-yl)ethyl]-2,3-dihydro-1H-pyrido[2,3-b][1,4]oxazine-7-carbonitrile;

2-Oxo-1-[2-(4-{[(3-oxo-3,4-dihydro-2H-pyrido[3,2-b][1,4]oxazin-6-yl)methyl]amino}piperidin-1-yl)ethyl]-2,3-dihydro-1H-pyrido[2,3-b][1,4]oxazine-7-carboxamide;

1-(2-{4-[(2,3-Dihydro[1,4]dioxino[2,3-c]pyridin-7-ylmethyl)amino]-2-methylpiperidin-1-yl}ethyl)-5,7-difluoroquinolin-2(1H)-one;

1-(2-{4-[(2,3-Dihydro[1,4]dioxino[2,3-c]pyridin-7-ylmethyl)amino]piperidin-1-yl}ethyl)-2-oxo-1,2-dihydroquinoline-7-carbonitrile;

Cis±4(1-[(2E)-3-(2,5-difluorophenyl)prop-2-en-1-yl]-4-[3-(6-methoxy-3-oxo-2,3-dihydro-4H-1,4-benzoxazin-4-yl)propyl]piperidine-3-carboxylic acid;

Methyl(Cis±4)-1-[(2E)-3-(2,5-difluorophenyl)prop-2-en-1-yl]-4-[3-(6-methoxy-3-oxo-2,3-dihydro-4H-1,4-benzoxazin-4-yl)propyl]piperidine-3-carboxylate;

Cis±1-(2-{4-[(2,3-dihydro[1,4]dioxino[2,3-c]pyridin-7-ylmethyl)amino]-3-hydroxypiperidin-1-yl}ethyl)-2-oxo-1,2-dihydroquinoline-7-carbonitrile;

Cis±1-[2-(3-hydroxy-4-{[(3-oxo-3,4-dihydro-2H-pyrido[3,2-b][1,4]oxazin-6-yl)methyl]amino}piperidin-1-yl)ethyl]-2-oxo-1,2-dihydroquinoline-7-carbonitrile;

5,7-Difluoro-1-(2-{4-[(5,6,7,8-tetrahydro-1,8-naphthyridin-2-ylmethyl)amino]piperidin-1-yl}ethyl)quinolin-2(1H)-one;

Cis±1-(2-{4-[(2,3-dihydro[1,4]dioxino[2,3-c]pyridin-7-ylmethyl)amino]-3-methoxypiperidin-1-yl}ethyl)-2-oxo-1,2-dihydroquinoline-7-carbonitrile;

Cis±1-[2-(3-methoxy-4-{[(3-oxo-3,4-dihydro-2H-pyrido[3,2-b][1,4]oxazin-6-yl)methyl]amino}piperidin-1-yl)ethyl]-2-oxo-1,2-dihydroquinoline-7-carbonitrile;

Cis±1-(2-{4-[(2,3-dihydro[1,4]dioxino[2,3-c]pyridin-7-ylmethyl)amino]-3-fluoropiperidin-1-yl}ethyl)-2-oxo-1,2-dihydroquinoline-7-carbonitrile;

Cis±1-[2-(3-fluoro-4-{[(3-oxo-3,4-dihydro-2H-pyrido[3,2-b][1,4]oxazin-6-yl)methyl]amino}piperidin-1-yl)ethyl]-2-oxo-1,2-dihydroquinoline-7-carbonitrile;

Cis±1-(2-{4-[(2,3-dihydro[1,4]dioxino[2,3-c]pyridin-7-ylmethyl)amino]-3-hydroxypiperidin-1-yl}ethyl)-7-fluoroquinoxalin-2(1H)-one;

Cis±6-[({1-[2-(7-fluoro-2-oxoquinoxalin-1(2H)-yl)ethyl]-3-hydroxypiperidin-4-yl}amino)methyl]-2H-pyrido[3,2-b][1,4]oxazin-3(4H)-one;

Cis±1-(2-{4-[(2,3-dihydro[1,4]dioxino[2,3-c]pyridin-7-ylmethyl)amino]-3-methoxypiperidin-1-yl}ethyl)-7-fluoroquinoxalin-2(1H)-one;

Cis±6-[({1-[2-(7-fluoro-2-oxoquinoxalin-1(2H)-yl)ethyl]-3-methoxypiperidin-4-yl}amino)methyl]-2H-pyrido[3,2-b][1,4]oxazin-3(4H)-one;

Cis±1-(2-{4-[(2,3-dihydro[1,4]dioxino[2,3-c]pyridin-7-ylmethyl)amino]-3-fluoropiperidin-1-yl}ethyl)-7-fluoroquinoxalin-2(1H)-one;

Cis±6-[({1-[2-(7-fluoro-2-oxoquinoxalin-1(2H)-yl)ethyl]-3-fluoropiperidin-4-yl}amino)methyl]-2H-pyrido[3,2-b][1,4]oxazin-3(4H)-one;

Cis±1-(2-{4-[(2,3-dihydro[1,4]dioxino[2,3-c]pyridin-7-ylmethyl)amino]-3-hydroxypiperidin-1-yl}ethyl)-7-methoxyquinoxalin-2(1H)-one;

Cis±6-[({1-[2-(7-methoxy-2-oxoquinoxalin-1(2H)-yl)ethyl]-3-hydroxypiperidin-4-yl}amino)methyl]-2H-pyrido[3,2-b][1,4]oxazin-3(4H)-one;

Cis±1-(2-{4-[(2,3-dihydro[1,4]dioxino[2,3-c]pyridin-7-ylmethyl)amino]-3-methoxypiperidin-1-yl}ethyl)-7-methoxyquinoxalin-2(1H)-one;

Cis±6-[({1-[2-(7-methoxy-2-oxoquinoxalin-1(2H)-yl)ethyl]-3-methoxypiperidin-4-yl}amino)methyl]-2H-pyrido[3,2-b][1,4]oxazin-3(4H)-one;

Cis±1-(2-{4-[(2,3-dihydro[1,4]dioxino[2,3-c]pyridin-7-ylmethyl)amino]-3-fluoropiperidin-1-yl}ethyl)-7-methoxyquinoxalin-2(1H)-one;

Cis±6-[({1-[2-(7-methoxy-2-oxoquinoxalin-1(2H)-yl)ethyl]-3-fluoropiperidin-4-yl}amino)methyl]-2H-pyrido[3,2-b][1,4]oxazin-3(4H)-one;

Cis±4-[2-(3-hydroxy-4-{[(3-oxo-3,4-dihydro-2H-pyrido[3,2-b][1,4]oxazin-6-yl)methyl]amino}piperidin-1-yl)ethyl]-3-oxo-3,4-dihydro-2H-1,4-benzoxazine-6-carbonitrile;

Cis±4-[2-(3-methoxy-4-{[(3-oxo-3,4-dihydro-2H-pyrido[3,2-b][1,4]oxazin-6-yl)methyl]amino}piperidin-1-yl)ethyl]-3-oxo-3,4-dihydro-2H-1,4-benzoxazine-6-carbonitrile;

Cis±4-[2-(3-fluoro-4-{[(3-oxo-3,4-dihydro-2H-pyrido[3,2-b][1,4]oxazin-6-yl)methyl]amino}piperidin-1-yl)ethyl]-3-oxo-3,4-dihydro-2H-1,4-benzoxazine-6-carbonitrile;

1-(2-{4-[(2,3-Dihydro[1,4]dioxino[2,3-c]pyridin-7-ylmethyl)amino]piperidin-1-yl}ethyl)-7-methoxy-3,4-dihydroquinoxalin-2(1H)-one;

5,7-Difluoro-1-[2-(4-{[(1-oxo-1,3-dihydro-2-benzofuran-5-yl)methyl]amino}piperidin-1-yl)ethyl]quinolin-2(1H)-one;

6-[({1-[2-(7-Methoxy-2-oxoquinoxalin-1(2H)-yl)propyl]piperidin-4-yl}amino)methyl]-2H-pyrido[3,2-b][1,4]oxazin-3(4H)-one; or 5,7-Difluoro-1-(2-{4-[(5,6,7,8-tetrahydro-1,8-naphthyridin-2-ylmethyl)amino]piperidin-1-yl}ethyl)quinolin-2(1H)-one.

The invention also provides a pharmaceutical composition comprising a compound of formulas I-V admixed with a pharmaceutically acceptable adjuvant, carrier, or excipient.

The invention also provides a method of treating a bacterial infection comprising administering a therapeutically effective amount of a compound of formulas I-V to a mammal in need thereof.

The invention also provides a method of treating a bacterial infection in a warm-blooded animal, such as a human being, in need of such treatment, which comprises administering to said animal an effective amount of a compound of formulas I-V or a pharmaceutically-acceptable salt thereof.

The invention also provides a method for inhibiting bacterial DNA gyrase in a warm-blooded animal, such as a human being, in need of such treatment which comprises administering to said animal an effective amount of a compound of formulas I-V or a pharmaceutically acceptable salt.

The invention also provides a compound of formulas I-V and pharmaceutically acceptable salts thereof for use as a medicament.

The invention also provides the use of a compound of formulas I-V or a pharmaceutically acceptable salt thereof in the manufacture of a medicament for use in the production of an anti-bacterial effect in a warm-blooded animal such as a human being.

The invention also provides the use of a compound of formulas I-V or a pharmaceutically acceptable salt thereof in the manufacture of a medicament for use in the treatment of a bacterial infection in a warm-blooded animal such as a human being.

The invention also provides a process for making a compound of formulas I-V, comprising one of the following:

(a) N-alkylation of L with X—$U_1$M, wherein X is a leaving group in the presence of a base to form L$U_1$M, wherein $U_1$ is $CH_2CH_2$, followed by attachment of $U_2$ and R via functional group manipulation, alkylation, or reductive amination;

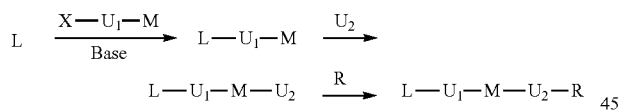

(b) N-alkylation of L with HO—$U_1$M, under Mitsunobu conditions to form L$U_1$M, followed by attachment of $U_2$ and R via functional group manipulation, alkylation, or reductive amination;

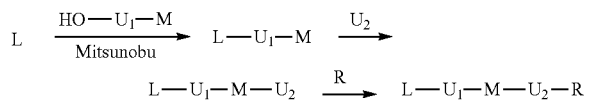

(c) N-alkylation of L with bromo- or chloroacetic acid or a derivative thereof to form L-$CH_2CO_2H$ followed by
   i) activation of the acid moiety in L-$CH_2CO_2H$;
   ii) amide coupling to form L$U_1$M, wherein $U_1$ is $CH_2CO$,
   iii) attachment of $U_2$ and R via functional group manipulation, alkylation, or reductive amination; and
   iv) optional reduction of the carbonyl moiety in $U_1$ to form a compound wherein $U_1$ is $CH_2CH_2$.

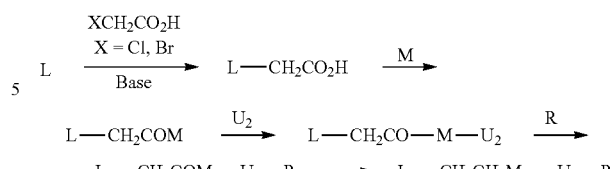

(d) N-alkylation of L with X—$(CH_2)_n$CH=$CH_2$ wherein X is a leaving group and n is 1 or 2 to form L-$(CH_2)_n$CH=$CH_2$, followed by:
   i) oxidative cleavage using an oxidant such as ozone or sodium periodate (with reductive workup) to form L-$(CH_2)_n CH_2OH$;
   ii) conversion of the alcohol moiety in L-$(CH_2)_n CH_2OH$ to a leaving group;
   iii) reaction of L—$(CH_2)_n CH_2$—Y with M, in the presence of a base to form L$U_1$M; and
   iv) attachment of $U_2$ and R via functional group manipulation, alkylation, or reductive amination;

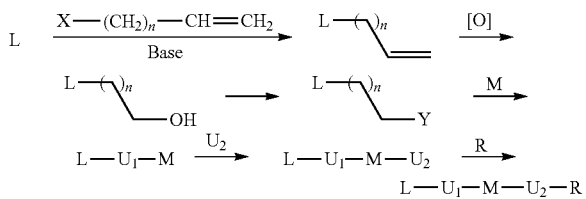

X,Y=leaving group n=1 or 2

(e) N-alkylation of L with X—$(CH_2)_n$CH=$CH_2$ wherein X is a leaving group and n is 0 or 1 to form L-$(CH_2)_n$CH=$CH_2$, provided that when n is 0, a metal catalyst is optionally used, followed by:
   i) hydroboration followed by an oxidative workup to form to form L-$(CH_2)_n CH_2CH_2OH$;
   ii) conversion of the alcohol moiety in L-$(CH_2)_n CH_2CH_2OH$ to a leaving group;
   iii) reaction of L-$(CH_2)_n CH_2CH_2$-"LG" with M, in the presence of a base to form L$U_1$M; and
   iv) followed by attachment of $U_2$ and R via functional group manipulation, alkylation, or reductive amination;

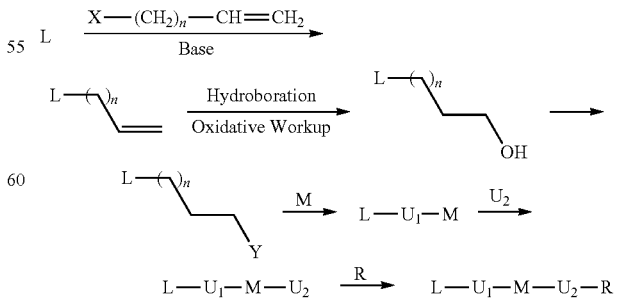

X,Y=leaving group n=1 or 2

(f) Oxidation of the alcohol intermediate

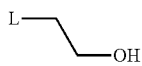

in d) and e) supra to the aldehyde

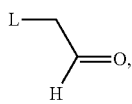

followed by
i) reductive amination with $MU_2$; to form $LU_1MU_2$, wherein U1 is $CH_2CH_2$;
ii) reductive amination with R; or

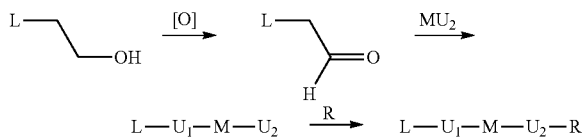

(g) N-alkylation of L with X—$(CH_2)_n CH_2CH_2OH$, wherein X is a leaving group and n is 0 or 1 to form the intermediate L-$(CH_2)_n CH_2CH_2OH$ as depicted in (e), supra, followed by
i) conversion of the alcohol moiety in L-$(CH_2)_n$ $CH_2CH_2OH$ to a leaving group;
ii) reaction of L-$(CH_2)_n CH_2CH_2$-"LG" with M, in the presence of a base to form $LU_1M$; and
iii) followed by attachment of $U_2$ and R via functional group manipulation, alkylation, or reductive amination.

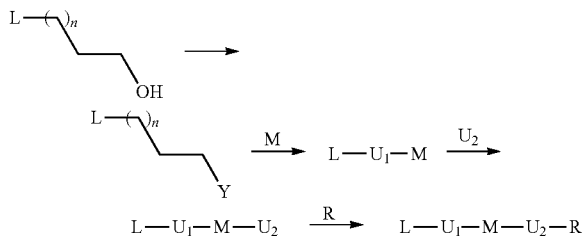

X,Y=leaving group n=1 or 2

DETAILED DESCRIPTION OF THE INVENTION

Unless otherwise stated, the following terms used in the specification and claims have the following meanings

DEFINITIONS

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, pentyl, and the like, that may be optionally substituted.

"Alkenyl" means a linear monovalent hydrocarbon radical of two to six carbon atoms or a branched monovalent hydrocarbon radical of three to six carbon atoms, containing at least one double bond, e.g., ethenyl (—CH=$CH_2$), propenyl, and the like that may be optionally substituted.

"Alkylene" means a linear saturated divalent hydrocarbon radical of one to six carbon atoms or a branched saturated divalent hydrocarbon radical of three to six carbon atoms, e.g., methylene (—$CH_2$—), ethylene (—$CH_2CH_2$—), propylene, 2-methylpropylene, pentylene, and the like that may be optionally substituted.

"Acyl" means a radical —C(O)R where R is hydrogen, alkyl, alkenyl, cycloalkyl, heteroalkyl, haloalkyl, aryl, aralkyl, heteroaralkyl or heteroaryl, e.g., acetyl, benzoyl, thienyl, and the like that may be optionally substituted.

"Acyloxy" means a radical —OC(O)R where R is hydrogen, alkyl, alkenyl, cycloalkyl, heteroalkyl, haloalkyl or optionally substituted phenyl, e.g., acetoxy, benzoyloxy, and the like that may be optionally substituted.

"Halo" means fluoro, chloro, bromo or iodo.

"Haloalkyl" means alkyl substituted with one or more same or different halo atoms, e.g., —$CH_2Cl$, —$CF_3$, —$CH_2CF_3$, —$CH_2CCl_3$, and the like.

"Cycloalkyl" means a saturated monovalent cyclic hydrocarbon radical of three to six ring carbons, e.g., cyclopropyl, cyclohexyl, and the like that may be optionally substituted.

"Amine" or "amino" refers to radicals of the general formula —NRR', wherein R and R' are independently selected from hydrogen or a hydrocarbyl radical, or wherein R and R' combined form a heterocycle. Examples of amino groups include: —$NH_2$, methyl amino, diethyl amino, anilino, benzyl amino, piperidinyl, piperazinyl and indolinyl.

"Monosubstituted amino" means a radical —NHR where R is alkyl, heteroalkyl, haloalkyl, cycloalkyl, cycloalkylalkyl or optionally substituted phenyl, e.g., methylamino, (1-methylethyl)amino, phenylamino, and the like.

"Disubstituted amino" means a radical —NRR' where R and R' are independently alkyl, alkenyl, heteroalkyl, haloalkyl, cycloalkyl, cycloalkylalkyl or optionally substituted phenyl. Representative examples include, but are not limited to, dimethylamino, methylethylamino, di(1-methylethyl)amino, methylbenzylamino, and the like.

"Aryl" means a monovalent monocyclic or bicyclic aromatic hydrocarbon radical of 6 to 10 ring atoms, and optionally substituted independently with one or more substituents, preferably one, two or three substituents selected from alkyl, haloalkyl, heteroalkyl, cycloalkyl, cycloalkylalkyl, halo, cyano, nitro, acyloxy, alkoxy, optionally substituted phenyl, heteroaryl, heteroaralkyl, amino, monosubstituted amino, disubstituted amino, acylamino, hydroxyamino, amidino, guanidino, cyanoguanidinyl, hydrazino, hydrazido, —OR [where R is hydrogen, alkyl, haloalkyl, alkenyl, cycloalkyl, cycloalkylalkyl, optionally substituted phenyl, heteroaryl or heteroaralkyl], —$S(O)_n R$ [where n is an integer from 0 to 2 and R is hydrogen, alkyl, haloalkyl, alkenyl, cycloalkyl, cycloalkylalkyl, optionally substituted phenyl, heteroaryl, heteroaralkyl, amino, mono or disubstituted amino], —$NRSO_2R'$ (where R is hydrogen or alkyl and R' is alkyl, amino, monosubstituted or disubstituted amino) —C(O)R (where R is hydrogen, alkyl, alkenyl, cycloalkyl, heteroalkyl, haloalkyl or optionally substituted phenyl), —COOR (where R is hydrogen, alkyl, optionally substituted phenyl, heteroaryl or heteroaralkyl), —(alkylene)-COOR (where R is hydrogen, alkyl, optionally substituted phenyl, heteroaryl or heteroaralkyl), methylenedioxy, 1,2-ethylenedioxy, —CONR'R" or -(alkylene)CONR'R" (where R' and R" are independently selected from hydrogen, alkyl, cycloalkyl, haloalkyl, cycloalkylalkyl, optionally substituted phenyl, heteroaryl and heteroaralkyl). More specifically the term aryl includes, but is not limited to, phenyl, 1-naphthyl, 2-naphthyl, and derivatives thereof.

The term "ortho-fused" as used in the phrase "ortho-fused bicyclic subunit" means a bicyclic saturated, partially aromatic or fully aromatic, fully unsaturated or partially saturated, carbocyclic or heterocyclic ring system wherein the two rings have only two atoms and one bond in common. Both rings may be aromatic; for example, such as in naphthalene, pteridine, cinnoline, quinazoline, quinoxaline, naphthyridine, phthalazine, quinoline, isoquinoline, quinolizine, purine, indazole, indole, isoindole, indolizine, or pyrrolizine and the like.

"Heteroaryl" means a monovalent monocyclic or bicyclic aromatic radical of 5 to 10 ring atoms containing one, two, or three ring heteroatoms selected from N, O, or S, the remaining ring atoms being C. For the avoidance of doubt, "heteroaryl" includes "ortho-fused bicyclic heteroaryl". The aromatic radical is optionally substituted independently with one or more substituents, preferably one or two substituents selected from oxo, alkyl, haloalkyl, heteroalkyl, cycloalkyl, cycloalkylalkyl, halo, cyano, nitro, acyloxy, optionally substituted phenyl, amino, monosubstituted amino, disubstituted amino, acylamino, hydroxyamino, amidino, guanidino, cyanoguanidinyl, hydrazino, hydrazido, —OR [where R is hydrogen, alkyl, haloalkyl, alkenyl, cycloalkyl, cycloalkylalkyl or optionally substituted phenyl], S(O)$_n$R [where n is an integer from 0 to 2 and R is hydrogen, alkyl, haloalkyl, alkenyl, cycloalkyl, cycloalkylalkyl, optionally substituted phenyl, amino, mono or disubstituted amino], —C(O)R (where R is hydrogen, alkyl, alkenyl, cycloalkyl, heteroalkyl, haloalkyl or optionally substituted phenyl), —COOR (where R is hydrogen, alkyl, or optionally substituted phenyl), -(alkylene)-COOR (where R is hydrogen, alkyl or optionally substituted phenyl), methylenedioxy, 1,2-ethylenedioxy, —CONR'R" or -(alkylene)-CONR'R" (where R' and R" are independently selected from hydrogen, alkyl, cycloalkyl, haloalkyl, cycloalkylalkyl or optionally substituted phenyl). The term heteroaryl includes, but is not limited to pyridyl, pyrrolyl, thiophene, pyrazolyl, thiazolyl, imidazolyl, pyrimidinyl, thiadiazolyl, indolyl, carbazolyl, azaindolyl, benzofuranyl, benzotriazolyl, benzisoxazolyl, purinyl, quinolinyl, benzopyranyl, and derivatives thereof.

"Heterocycle" or "Heterocyclyl" means a saturated, partially unsaturated or fully unsaturated cyclic radical of 3 to 8 ring atoms in which one or two ring atoms are heteroatoms selected from N, O, or S(O)$_n$ (where n is an integer from 0 to 2). The heterocyclo ring may be optionally substituted independently with one, two or three substituents selected from alkyl, haloalkyl, cycloalkyl, cycloalkylalkyl, aryl, aralkyl, heteroaryl, heteroaralkyl, halo, cyano, acyl, acylamino, amino, monosubstituted amino, disubstituted amino, —COOR (where R is hydrogen or alkyl), —XR (where X is O or S(O)$_n$ where n is an integer from 0 to 2 and R is hydrogen, alkyl, haloalkyl, cycloalkyl, aralkyl, aryl, heteroaryl or heteroaralkyl) or —CONR'R" (where R' and R" are independently selected from hydrogen or alkyl). Representative examples include, but are not limited to tetrahydropyranyl, piperidino, 1-(4-chlorophenyl)piperidino, and the like.

In one aspect of the invention "Ry and Ry' together form a bridge". A bridge is a bond, a carbon atom or two carbon atoms connecting two different ring atoms of M which are meta or para to each other. Particularly the bridge is a bond. Particularly the bridge is one carbon atom. Alternatively the bridge is two carbon atoms. Examples of M where"Ry and Ry' together form a bridge" are:

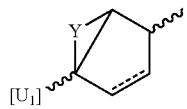

(M1, bridge is a bond, atoms of M are meta to each other),

(M2, bridge is one carbon atom, atoms of M are meta to each other),

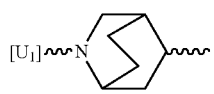

(M4, bridge is two carbon atoms, atoms of M are para to each other), and

(M5, bridge is a bond, atoms of M are meta to each other).

"Aralkyl" means a radical —R$_a$—R$_b$ where R$_a$ is bound to R$_b$ and R$_a$ is an alkylene group and R$_b$ is an aryl group as defined above e.g., benzyl, phenylethyl, 3-(3-chlorophenyl)-2-methylpentyl, and the like.

"Heteroaralkyl" means a radical —R$_a$—R$_b$ where R$_a$ is bound to R$_b$ and R$_a$ is an alkylene group and R$_b$ is a heteroaryl group as defined above e.g., pyridin-3-ylmethyl, 3-(benzofuran-2-yl)propyl, and the like.

"Alkoxy", "aryloxy" or "heteroaryloxy" means a radical —OR where R is an alkyl, aryl or heteroaryl, respectively as defined above e.g., methoxy, phenoxy, pyridin-2-yloxy and the like.

"Alkylthio" and "heteroarylthio" respectively mean an alkyl group or heteroaryl group attached via a thioether linkage.

"Alkylsulfinyl" and "heteroarylsulfinyl" respectively mean an alkyl group or heteroaryl group attached via a sulfinyl linkage.

"Alkylcarbonyloxy" refers to an alkyl group attached to a CO$_2$ group, as in alkyl-CO$_2$—, alkenyl-CO$_2$—, aryl-CO$_2$—, respectively, where alkyl is as defined herein. For example, alkylcarbonyloxy includes but is not limited to, acetoxy, ethylcarbonyloxy, n- or iso-propylcarbonyloxy, n-, iso-, sec- or tert-butylcarbonyloxy, n-pentylcarbonyloxy, n-hexylcarbonyloxy.

"Optionally substituted" means that the group at issue is optionally substituted independently with one, two or three substituents selected from halo, nitro, cyano, hydroxy, trifluoromethoxy, trifluoromethyl, amino, carboxy, carbamoyl, mercapto, sulphamoyl, methyl, ethyl, ethenyl, ethynyl, methoxy, ethoxy, acetyl, acetoxy, methylamino, ethylamino, dimethylamino, diethylamino, N-methyl-N-ethylamino, acetylamino, or as otherwise provided.

"Amino-protecting group" refers to those organic groups intended to protect nitrogen atoms against undesirable reactions during synthetic procedures e.g., benzyl, benzyloxycarbonyl (CBZ), t-butoxycarbonyl (BOC), trifluoroacetyl, and the like.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. For example, if the Y and Y' substituents in a compound of formula I are attached to the same carbon are different, then the carbon to which they are attached is an asymmetric center and the compound of formula I can exist as an (R)- or (S)-stereoisomer relative to that carbon. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001).

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the specification and claims includes both one and more than one such excipient.

A "pharmaceutically acceptable counterion" means an ion having a charge opposite to that of the substance with which it is associated and that is pharmaceutically acceptable. Representative examples include, but are not limited to, chloride, bromide, iodide, methanesulfonate, p-tolylsulfonate, trifluoroacetate, acetate, and the like.

A "pharmaceutically acceptable salt" of a compound means a salt that is pharmaceutically acceptable and that possesses the desired pharmacological activity of the parent compound. Such salts include:
1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-napthalenesulfonic acid, 4-toluenesulfonic acid, camphorsulfonic acid, 4-methylbicyclo[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynapthoic acid, salicylic acid, stearic acid, muconic acid, and the like; or
2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.
3) "Leaving group" has the meaning conventionally associated with it in synthetic organic chemistry i.e., an atom or group capable of being displaced by a nucleophile and includes halogen (such as chloro, bromo, iodo), alkanesulfonyloxy (such as mesyloxy or trifluorosulfonyloxy) or arenesulfonyloxy (such as tosyloxy), ester, or amino, and the like.

"Pro-drugs" means any compound which releases an active parent drug according to formula I in vivo when such prodrug is administered to a mammalian subject. Prodrugs of a compound of formula I are prepared by modifying functional groups present in the compound of formula I in such a way that the modifications may be cleaved in vivo to release the parent compound. Prodrugs include compounds of formula I wherein a hydroxy, thio or amino group in compound I is bonded to any group that may be cleaved in vivo to regenerate the free hydroxy, amino, or thio group, respectively. Examples of prodrugs include, but are not limited to esters (e.g., acetate, formate, and benzoate derivatives), carbamates (e.g., N,N-dimethylaminocarbonyl) of hydroxy functional groups in compounds of formula I, and the like.

"Treating" or "treatment" of a disease includes:
1) preventing the disease, i.e. causing the clinical symptoms of the disease not to develop in a mammal that may be exposed to or predisposed to the disease but does not yet experience or display symptoms of the disease;
2) inhibiting the disease, i.e., arresting or reducing the development of the disease or its clinical symptoms; or
3) relieving the disease, i.e., causing regression of the disease or its clinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

Invention Compounds

Referring again to a compound of the invention, the following specific values are disclosed.

In a compound of formula I, a specific value for L is

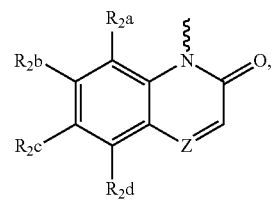

wherein " ~~~ " indicates the point of attachment and Z is CH or N. Other specific values for L include the following structures, wherein " ~~~ " has the same meaning.

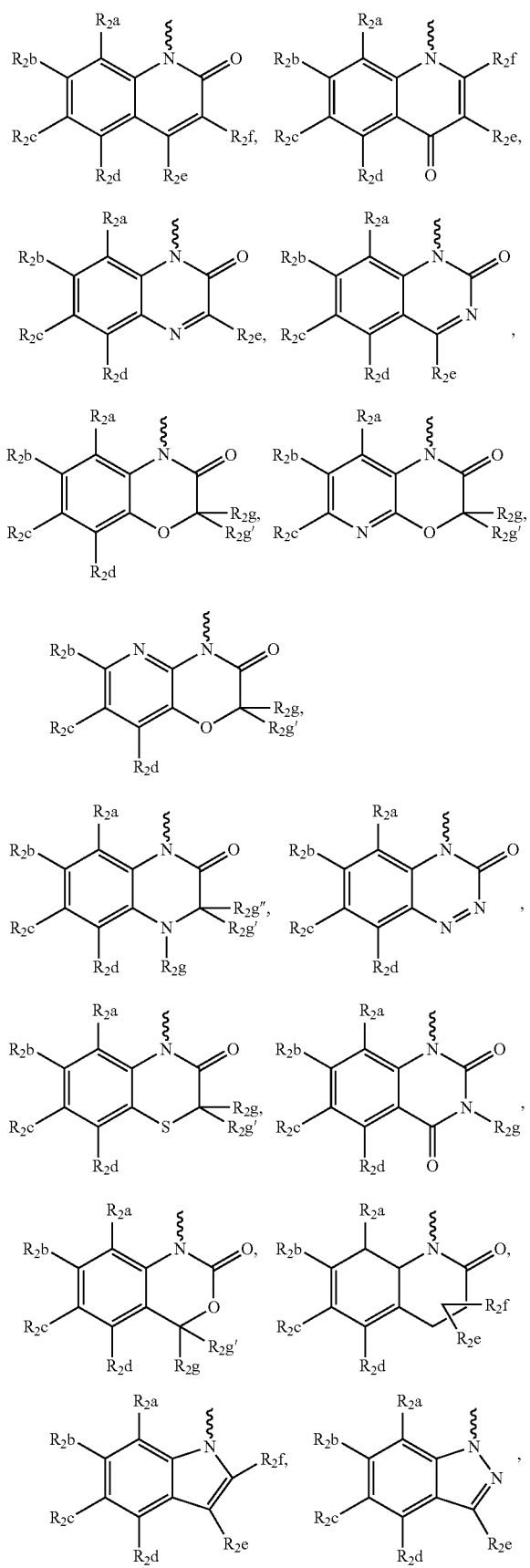
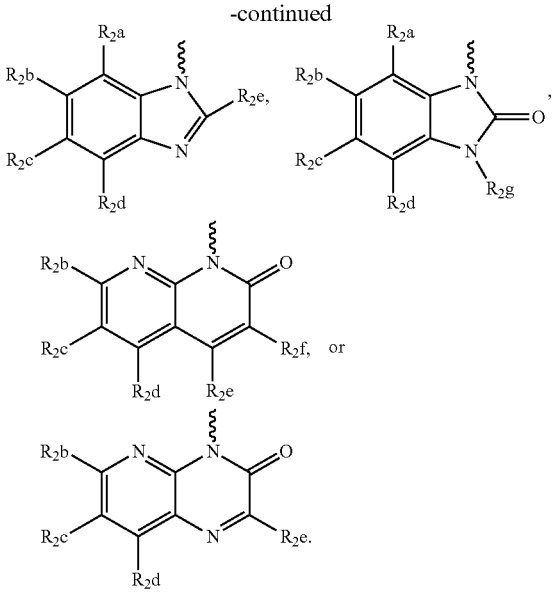

A specific value for R$_2$b is H. Other specific values for R$_2$b include halo, (C$_1$-C$_6$)alkanoyl, cyano, carboxy, (C$_1$-C$_6$)alkoxycarbonyl, (C$_1$-C$_6$)alkyl, hydroxy, halo(C$_1$-C$_6$)alkyl, halo(C$_1$-C$_6$)alkoxy, (C$_1$-C$_6$)alkoxy, NHCO—(C$_1$-C$_6$)alkyl, SO$_2$(C$_1$-C$_6$)alkyl, SO$_2$NH(C$_1$-C$_6$)alkyl, or SO$_2$N((C$_1$-C$_6$) alkyl)$_2$.

To that end, specific values for R$_2$b include H, methoxy, cyano, fluoro, chloro, trifluoromethoxy, bromo, hydroxy, CONH$_2$, CO$_2$Me, MeCO, methyl, 1-hydroxyethyl, 2-hydroxyethyl, SO$_2$Me, and SO$_2$Et.

A specific value for R$_2$a, is H. Other specific values for R$_2$a include halo, (C$_1$-C$_6$)alkanoyl, cyano, carboxy, (C$_1$-C$_6$)alkoxycarbonyl, (C$_1$-C$_6$)alkyl, hydroxy, halo(C$_1$-C$_6$)alkyl, halo(C$_1$-C$_6$)alkoxy, (C$_1$-C$_6$)alkoxy, NHCO—(C$_1$-C$_6$)alkyl, SO$_2$(C$_1$-C$_6$)alkyl, SO$_2$NH(C$_1$-C$_6$)alkyl, or SO$_2$N((C$_1$-C$_6$) alkyl)$_2$.

To that end, specific values for R$_2$a include H, methoxy, cyano, fluoro, chloro, trifluoromethoxy, bromo, hydroxy, CONH$_2$, CO$_2$Me, MeCO, methyl, 1-hydroxyethyl, 2-hydroxyethyl, SO$_2$Me, and SO$_2$Et.

A specific value for R$_2$c is H. Other specific values for R$_2$c include halo, (C$_1$-C$_6$)alkanoyl, cyano, carboxy, (C$_1$-C$_6$)alkoxycarbonyl, (C$_1$-C$_6$)alkyl, hydroxy, halo(C$_1$-C$_6$)alkyl, halo(C$_1$-C$_6$)alkoxy, (C$_1$-C$_6$)alkoxy, NHCO—(C$_1$-C$_6$)alkyl, SO$_2$(C$_1$-C$_6$)alkyl, SO$_2$NH(C$_1$-C$_6$)alkyl, or SO$_2$N((C$_1$-C$_6$) alkyl)$_2$.

To that end, specific values for R$_2$c include H, methoxy, cyano, fluoro, chloro, trifluoromethoxy, bromo, hydroxy, CONH$_2$, CO$_2$Me, MeCO, methyl, 1-hydroxyethyl, 2-hydroxyethyl, SO$_2$Me, and SO$_2$Et.

A specific value for R$_2$d is H. Other specific values for R$_2$d include halo, (C$_1$-C$_6$)alkanoyl, cyano, carboxy, (C$_1$-C$_6$)alkoxycarbonyl, (C$_1$-C$_6$)alkyl, hydroxy, halo(C$_1$-C$_6$)alkyl, halo(C$_1$-C$_6$)alkoxy, (C$_1$-C$_6$)alkoxy, NHCO—(C$_1$-C$_6$)alkyl, SO$_2$(C$_1$-C$_6$)alkyl, SO$_2$NH(C$_1$-C$_6$)alkyl, or SO$_2$N((C$_1$-C$_6$) alkyl)$_2$.

To that end, specific values for R$_2$d include H, methoxy, cyano, fluoro, chloro, trifluoromethoxy, bromo, hydroxy, CONH$_2$, CO$_2$Me, MeCO, methyl, 1-hydroxyethyl, 2-hydroxyethyl, SO$_2$Me, and SO$_2$Et.

A specific value for R$_2$e is H. Other specific values for R$_2$e include halo, (C$_1$-C$_6$)alkanoyl, cyano, carboxy, (C$_1$-C$_6$)alkoxycarbonyl, (C$_1$-C$_6$)alkyl, hydroxy, halo(C$_1$-C$_6$)alkyl, halo(C$_1$-C$_6$)alkoxy, (C$_1$-C$_6$)alkoxy, NHCO—(C$_1$-C$_6$)alkyl, SO$_2$(C$_1$-C$_6$)alkyl, SO$_2$NH(C$_1$-C$_6$)alkyl, or SO$_2$N((C$_1$-C$_6$)alkyl)$_2$.

To that end, specific values for R$_2$e include H, methoxy, cyano, fluoro, chloro, trifluoromethoxy, bromo, hydroxy, CONH$_2$, CO$_2$Me, MeCO, methyl, 1-hydroxyethyl, 2-hydroxyethyl, SO$_2$Me, and SO$_2$Et.

A specific value for R$_2$f is H. Other specific values for R$_2$f include halo, (C$_1$-C$_6$)alkanoyl, cyano, carboxy, (C$_1$-C$_6$)alkoxycarbonyl, (C$_1$-C$_6$)alkyl, hydroxy, halo(C$_1$-C$_6$)alkyl, halo(C$_1$-C$_6$)alkoxy, (C$_1$-C$_6$)alkoxy, NHCO—(C$_1$-C$_6$)alkyl, SO$_2$(C$_1$-C$_6$)alkyl, SO$_2$NH(C$_1$-C$_6$)alkyl, or SO$_2$N((C$_1$-C$_6$)alkyl)$_2$.

To that end, specific values for R$_2$f include H, methoxy, cyano, fluoro, chloro, trifluoromethoxy, bromo, hydroxy, CONH$_2$, CO$_2$Me, MeCO, methyl, 1-hydroxyethyl, 2-hydroxyethyl, SO$_2$Me, and SO$_2$Et.

A specific value for R$_2$g and R$_2$g' is H. Other specific values for R$_2$g and R$_2$g' include (C$_1$-C$_6$)alkyl, and halo(C$_1$-C$_6$)alkyl.

A specific value for U$_1$ is CH$_2$CH$_2$. Other specific values for U$_1$ include CH$_2$CH$_2$CH$_2$ and CH$_2$CH(Me). A further specific value for U$_1$ is CH(Me)CH$_2$.

A specific value for M is wherein Y is O, NH or CH$_2$ and " ---- " is absent or is a bond. Other specific values for M include a group of formula M5 which is a group of formula M4 which is or a group of formula M2 which is wherein " ~~~ " indicates the point of attachment and [U$_1$] and R2 is H or carboxy, n is 1, 2, or 3, and Ry is H, F, hydroxy, (C$_1$-C$_6$)alkyl, (C$_1$-C$_6$)alkoxy, or carboxy.

A specific value for M is a group of formula M4 which is

Other specific values for M include groups of formula M4 which are wherein " ~~~ " indicates the point of attachment.

When M is a group of formula M1 or M4, a specific value for [M]-U$_2$ is [M]-NHCH$_2$. When M is a group of formula M1 or M4, other specific values for [M]-U$_2$ include [M]-NHCH$_2$CH=CH, [M]-NHSO$_2$, when M is a group of formula M2, M3, or M5, a specific value for [M]-U$_2$ is [M]-CH$_2$CH=CH— or [M]-CH$_2$CH$_2$—.

A specific value for R is 2,1,3-benzothiadiazol-5-yl;
3-oxo-3,4-dihydro-2H-1,4-benzothiazin-6-yl;
2,3-dihydro-benzo[1,4]dioxin-6-yl;
1,2,3-benzothiadiazol-5-yl;
3-oxo-3,4-dihydro-2H-1,4-benzoxazin-6-yl;
7-fluoro-3-oxo-3,4-dihydro-2H-1,4-benzoxazin-6-yl;
2-oxo-2,3-dihydro-1H-pyrido[2,3-b][1,4]thiazin-7-yl;
2,3-dihydro-[1,4]dioxino[2,3-c]pyridin-7-yl;
3-oxo-3,4-dihydro-2H-pyrido[3,2-b][1,4]oxazin-6-yl;
[1,2,3]thiadiazolo[5,4-b]pyridin-6-yl;
3-oxo-3,4-dihydro-2H-pyrido[3,2-b][14]thiazin-6-yl;
7-chloro-3-oxo-3,4-dihydro-2H-pyrido[3,2-b][1,4]thiazin-6-yl;
7-fluoro-3-oxo-3,4-dihydro-2H-pyrido[3,2-b][1,4]thiazin-6-yl;
2-thienylthio; or
2,5-difluorophenyl.

More specifically R is

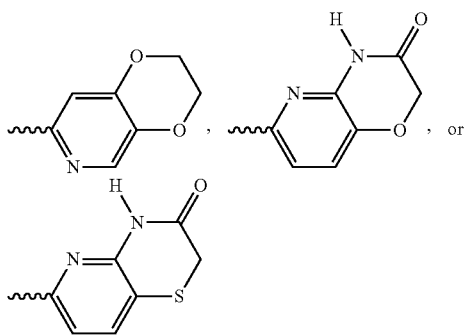

wherein " ~~~ " indicates the point of attachment.

A specific group of compounds of the invention are compounds wherein L is

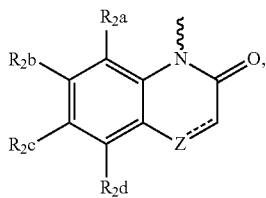

wherein " ~~~ " indicates the point of attachment;

" ---- " is a bond or is absent;

Z is CH or N when " ---- " is a bond, or, when " ---- " is absent, Z is O or NH;

$R_2a$, $R_2b$, $R_2c$, and $R_2d$ are each independently H, halo, cyano, $(C_1-C_6)$alkanoyl, carboxy, $(C_1-C_6)$alkoxycarbonyl, $(C_1-C_6)$alkyl, halo$(C_1-C_6)$alkyl, halo$(C_1-C_6)$alkoxy, $(C_1-C_6)$alkoxy, NHCO—$(C_1-C_6)$alkyl, $SO_2(C_1-C_6)$alkyl, $SO_2NH(C_1-C_6)$alkyl, or $SO_2N((C_1-C_6)$alkyl$)_2$.

A specific group of compounds of the invention are compounds wherein $U_1$-M-$U_2$

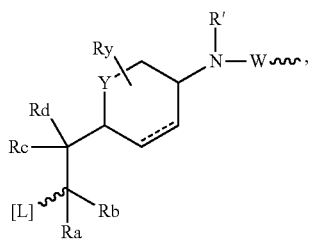

is Y is O, NH, $N(C_1-C_6)$alkyl, N[CO—$(C_1-C_6)$alkyl], $N[SO_2 (C_1-C_6)$alkyl] or $CH_2$ and " ---- " is absent or is a bond. Other specific groups of compounds of the invention are compounds wherein $U_1$-M-$U_2$ is

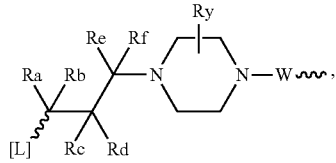

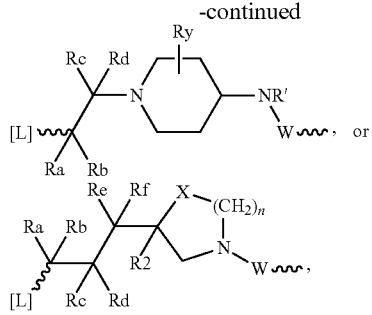

wherein

"[L] ~~~ " indicates the point of attachment to L and " ~~~ " indicates the point of attachment to R, and wherein R2 is H or carboxy and n is 1, 2, or 3;

Ra, Rb, Rc, Rd, Re, and Rf are each independently H or $(C_1-C_6)$alkyl;

Ry is H, F, hydroxy, $(C_1-C_6)$alkyl, $(C_1-C_6)$alkoxy, or carboxy;

R' is H, $(C_1-C_6)$alkyl, or —$(C_1-C_6)$alkylcarboxy; and

W is $CH_2$, CO, $SO_2$, $CH_2CH_2$, $CH_2CH=CH$, or $CH_2C≡C$, wherein each hydrogen may be optionally replaced by halo or $(C_1-C_6)$alkyl;

X is $CH_2$, NH, $N(C_1-C_6)$alkyl, $N[CO—(C_1-C_6)$alkyl], $N[SO_2(C_1-C_6)$alkyl] or O.

A specific group of compounds of the invention are compounds of formula I which are compounds of formula II:

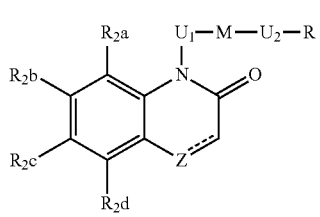

or a pharmaceutically acceptable salt thereof, wherein $R_2a$, $R_2b$, $R_2c$, and $R_2d$ are each independently H, fluoro, chloro, cyano, $(C_1-C_6)$alkyl, halo$(C_1-C_6)$alkyl, halo$(C_1-C_6)$alkoxy, $(C_1-C_6)$alkoxy;

" ---- " is a bond or is absent;

Z is CH or N when " ---- " is a bond, or Z is O or NH when " ---- " is absent;

$U_1$ is CRaRb-CRcRd or CRaRb-CRcRd-CReRf, wherein Ra, Rb, Rc, Rd, Re and Rf are each independently hydrogen or $(C_1-C_6)$alkyl;

M is a group of formula M1a or M2-M5:

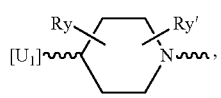

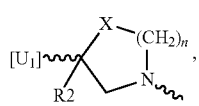

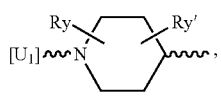
M4

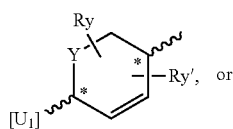
M1a

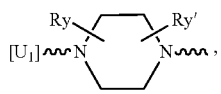
M5 in the trans configuration relative to "*", wherein R2 is H or carboxy;

Ry and Ry' are each independently H, halo, $(C_1-C_6)$alkyl, or together with the carbon to which they are attached form C=O; or Ry and Ry' together form a bridge;

X is $CH_2$, or provided n is 2 or 3, X is NH, $N(C_1-C_6)$alkyl, or O;

Y is $CH_2$, NH, $N(C_1-C_6)$alkyl, or O;

" ---- " is a bond or is absent;

n is 1, 2, or 3;

when M is a group of formula M1a or M4, $U_2$ is NR'—W, wherein R' is H, $(C_1-C_6)$alkyl,

and W is $CH_2$, CO, $SO_2$,

$CH_2CH_2$, $CH_2CH=CH$, or $CH_2C\equiv C$, wherein each hydrogen may be optionally replaced by halo or $(C_1-C_6)$alkyl, provided that when M is a group of formula M2, M3, or M5, $U_2$ is W; and when W is $CH_2$, CO or $SO_2$, R is aryl, heteroaryl, heterocyclyl or ortho-fused bicyclic heteroaryl, or when W is

$CH_2CH_2$, $CH_2CH=CH$, or $CH_2C\equiv C$, R is aryl, heteroaryl, heteroaryl$(C_1-C_6)$alkyloxy, heteroaryl$(C_1-C_6)$alkylthio, heteroaryl$(C_1-C_6)$alkylsulfinyl, heteroaryl$(C_1-C_6)$alkylsulfonyl, heteroaryl$(C_1-C_6)$alkylamino wherein any R may be optionally substituted on carbon; and wherein any ring nitrogen in R may be optionally substituted by $(C_1-C_6)$alkyl.

A specific group of compounds of the invention are compounds of formula I which are compounds of formula III:

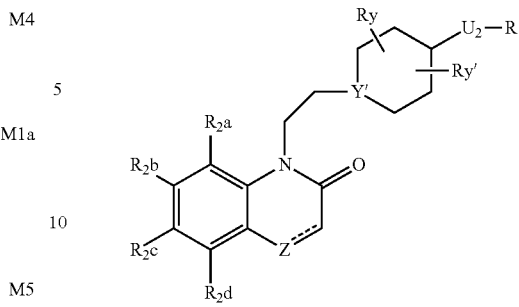
III or a pharmaceutically acceptable salt thereof, wherein $R_2a$, $R_2b$, $R_2c$, and $R_2d$ are each independently H, fluoro, chloro, cyano, $(C_1-C_6)$alkyl, halo$(C_1-C_6)$alkyl, halo$(C_1-C_6)$alkoxy, $(C_1-C_6)$alkoxy;

Z is CH or N when " ---- " is a bond, or, when " ---- " is absent, Z is O or NH;

Y' is N or $CR_2$, wherein R2 is H or carboxy;

Ry is H, fluoro, hydroxy, methoxy, carbomethoxy, or carboxy;

$U_2$ is NR'—W, wherein R' is H, $(C_1-C_6)$alkyl,

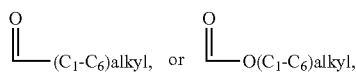

or, and W is $CH_2$, CO, $SO_2$, $CH_2CH_2$, $CH_2CH=CH$, or $CH_2C\equiv C$, wherein each hydrogen may be optionally replaced by halo or $(C_1-C_6)$alkyl; and R is 2,1,3-benzothiadiazol-5-yl;
3-oxo-3,4-dihydro-2H-1,4-benzothiazin-6-yl;
2,3-dihydro-benzo[1,4]dioxin-6-yl;
1,2,3-benzothiadiazol-5-yl;
3-oxo-3,4-dihydro-2H-1,4-benzoxazin-6-yl;
7-fluoro-3-oxo-3,4-dihydro-2H-1,4-benzoxazin-6-yl;
2-oxo-2,3-dihydro-1H-pyrido[2,3-b][1,4]thiazin-7-yl;
2,3-dihydro-[1,4]dioxino[2,3-c]pyridin-7-yl;
3-oxo-3,4-dihydro-2H-pyrido[3,2-b][1,4]oxazin-6-yl;
[1,2,3]thiadiazolo[5,4-b]pyridin-6-yl;
3-oxo-3,4-dihydro-2H-pyrido[3,2-b][1,4]thiazin-6-yl;
7-chloro-3-oxo-3,4-dihydro-2H-pyrido[3,2-b][1,4]thiazin-6-yl;
7-fluoro-3-oxo-3,4-dihydro-2H-pyrido[3,2-b][1,4]thiazin-6-yl;
2-thienylthio; or
2,5-difluorophenyl.

A specific group of compounds of the invention are compounds of formula I which are compounds of formula IV:

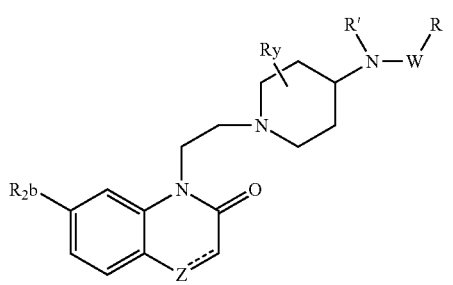
IV or a pharmaceutically acceptable salt thereof, wherein $R_2b$ is H, halo, cyano, nitro, $(C_1-C_6)$alkanoyl, carboxy, $(C_1-C_6)$alkoxycarbonyl, $(C_1-C_6)$alkyl, hydroxy, halo$(C_1-C_6)$ alkyl, halo($C_1$-$C_6$)alkoxy, ($C_1$-$C_6$)alkoxy, NHCO—($C_1$-$C_6$)alkyl, $SO_2$($C_1$-$C_6$)alkyl, $SO_2$NH($C_1$-$C_6$)alkyl, or $SO_2$N(($C_1$-$C_6$)alkyl)$_2$;

Z is CH or N when "----" is a bond, or, when "----" is absent, Z is O or NH;

Ry is H, fluoro, hydroxy, methoxy, carbomethoxy, or carboxy;

R' is H or ($C_1$-$C_6$)alkyl;

W is CO, $SO_2$, or $CH_2$, wherein each hydrogen may be optionally replaced by halo or ($C_1$-$C_6$)alkyl; and R is

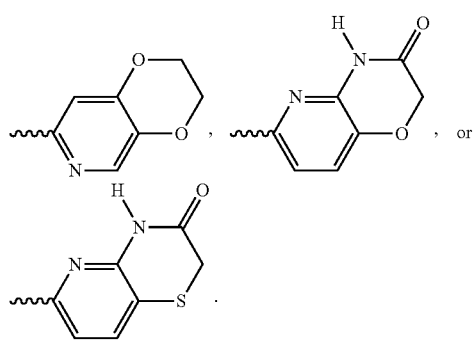

A specific group of compounds of the invention are compounds of formula V:

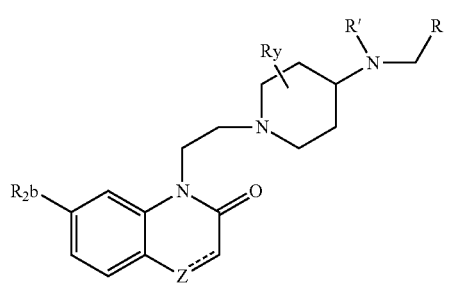

or a pharmaceutically acceptable salt thereof, wherein $R_2$b is H, halo, cyano, nitro, ($C_1$-$C_6$)alkanoyl, carboxy, ($C_1$-$C_6$)alkoxycarbonyl, ($C_1$-$C_6$)alkyl, hydroxy, halo($C_1$-$C_6$)alkyl, halo($C_1$-$C_6$)alkoxy, ($C_1$-$C_6$)alkoxy, NHCO—($C_1$-$C_6$)alkyl, $SO_2$($C_1$-$C_6$)alkyl, $SO_2$NH($C_1$-$C_6$)alkyl, or $SO_2$N(($C_1$-$C_6$)alkyl)$_2$;

Z is CH or N when "----" is a bond, or, when "----" is absent, Z is O or NH;

Ry is H, fluoro, hydroxy, methoxy, carbomethoxy, or carboxy;

R' is H or ($C_1$-$C_6$)alkyl; and

R is

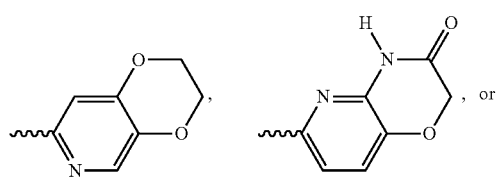

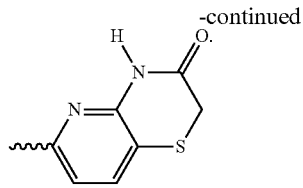

A specific group of compounds of the invention are compounds wherein L is a group of formula L1.

A specific group of compounds of the invention are compounds wherein L is a group of formula L2.

A specific group of compounds of the invention are compounds wherein L is a group of formula L3.

A specific group of compounds of the invention are compounds wherein L is a group of formula L4.

A specific group of compounds of the invention are compounds wherein L is a group of formula L5.

A specific group of compounds of the invention are compounds wherein L is a group of formula L6.

A specific group of compounds of the invention are compounds wherein L is a group of formula L7.

A specific group of compounds of the invention are compounds wherein L is a group of formula L8.

A specific group of compounds of the invention are compounds wherein L is a group of formula L9.

A specific group of compounds of the invention are compounds wherein L is a group of formula L10.

A specific group of compounds of the invention are compounds wherein L is a group of formula L11.

A specific group of compounds of the invention are compounds wherein L is a group of formula L12.

A specific group of compounds of the invention are compounds wherein L is a group of formula L13.

A specific group of compounds of the invention are compounds wherein L is a group of formula L14.

A specific group of compounds of the invention are compounds wherein L is a group of formula L15.

A specific group of compounds of the invention are compounds wherein M is a group of formula M1.

A specific group of compounds of the invention are compounds wherein M is a group of formula M1a.

A specific group of compounds of the invention are compounds wherein M is a group of formula M2.

A specific group of compounds of the invention are compounds wherein M is a group of formula M3.

A specific group of compounds of the invention are compounds wherein M is a group of formula M4.

A specific group of compounds of the invention are compounds wherein M is a group of formula M5.

A specific group of compounds of the invention are compounds wherein when M is a group of formula M1 or M2, W is $CH_2$, CO or $SO_2$.

Preparation of Invention Compounds

In a further aspect, the present invention provides a process for preparing a compound of the invention or a pharmaceutically-acceptable salt or an in-vivo hydrolysable ester thereof. It will be appreciated that during certain of the following processes, certain substituents may require protection to prevent their undesired reaction. The skilled chemist will appreciate when such protection is required, and how such protecting groups may be put in place and later removed.

Examples of protecting groups are disclosed in, for example, 'Protective Groups in Organic Synthesis' by Theodora Green (John Wiley & Sons, 1999). Protecting groups may be removed by any convenient method described in the literature or known to the skilled chemist as appropriate for the removal of the protecting group in question, such methods being chosen so as to effect removal of the protecting group with minimum disturbance of groups elsewhere in the molecule.

Thus, if reactants include, for example, groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group.

Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris (trifluoroacetate). A suitable alternative protecting group for a primary amino group is, for example, a phthaloyl group that may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon. Resins may also be used as a protecting group.

The protecting groups may be removed at any convenient stage in the synthesis using conventional techniques well known in the chemical art.

A compound of the invention, or a pharmaceutically-acceptable salt or an in vivo hydrolysable ester thereof, may be prepared by any process known to be applicable to the preparation of chemically-related compounds. Such processes, when used to prepare a compound of the invention, or a pharmaceutically-acceptable salt or an in vivo hydrolysable ester thereof, are provided as a further feature of the invention and are illustrated by the following representative examples. Necessary starting materials may be obtained by standard procedures of organic chemistry (see, for example, Advanced Organic Chemistry (Wiley-Interscience, 2001), Jerry March or Houben-Weyl, Methoden der Organischen Chemie). The preparation of such starting materials is described within the accompanying non-limiting Examples. Alternatively, necessary starting materials are obtainable by analogous procedures to those illustrated that are within the ordinary skill of an organic chemist. Information on the preparation of necessary starting materials or related compounds (which may be adapted to form necessary starting materials) may also be found in the certain patent application Publications, the contents of the relevant process sections of which are incorporated herein by reference; for example WO2004/058144; US2004/0224946; WO2004/002992.

The skilled organic chemist will be able to use and adapt the information contained and referenced within the above references, and accompanying Examples therein and also the Examples herein, to obtain necessary starting materials, and products.

Thus, the present invention also provides that the compounds of the invention and pharmaceutically-acceptable salts and in vivo hydrolysable esters thereof, can be prepared by a process (a) to (h); and thereafter if necessary:

i) removing any protecting groups;
ii) forming a pro-drug (for example an in-vivo hydrolysable ester); and/or
iii) forming a pharmaceutically-acceptable salt;
wherein said processes (a) to (h) are as follows (wherein the variables are as defined above unless otherwise stated):

Thus, the present invention also provides that the compounds of the invention and pharmaceutically-acceptable salts and in vivo hydrolysable esters thereof, can be prepared by a process (a) to (h); and thereafter if necessary:

i) removing any protecting groups;
ii) forming a pro-drug (for example an in-vivo hydrolysable ester); and/or
iii) forming a pharmaceutically-acceptable salt;
wherein said processes (a) to (g) are as follows (wherein the variables are as defined above unless otherwise stated):

a) By modifying a substituent in, or introducing a substituent into another compound of the invention by using standard chemistry (see for example, Comprehensive Organic Functional Group Transformations (Pergamon), Katritzky, Meth-Cohn & Rees). For example:

a hydroxy group may be converted into a fluoro group, an acyloxy group (for instance an acetoxy group), an amino group, a heterocyclyl group linked through nitrogen (optionally substituted on a carbon other than a carbon atom adjacent to the linking nitrogen ring atom—for instance an optionally substituted amino group). The skilled artisan understands that such reactions of the hydroxy group take place directly (for instance by acylation or Mitsunobu reaction) or through the intermediacy of one or more derivatives (for instance a mesylate or an azide);

an acyloxy group may be converted into a hydroxy group or into the groups that may be obtained from a hydroxy group (either directly or through the intermediacy of a hydroxy group); an alkyl halide group may be converted to a hydroxy group, an amino group, a thioalkyl group or a heterocyclyl group linked through nitrogen; a keto group may be reduced to a hydroxy group or an saturated alkyl group.

b) as depicted in Scheme 1, by alkylation of a suitable bicyclic ring system containing a NH group in the ring with a suitable alkylating reagent containing a leaving group (such as an O-mesylate, chloro, bromo or iodo) in the presence of a base. Alkylation may be followed by functional group manipulations and/or further alkylations or reductive aminations.

Scheme 1

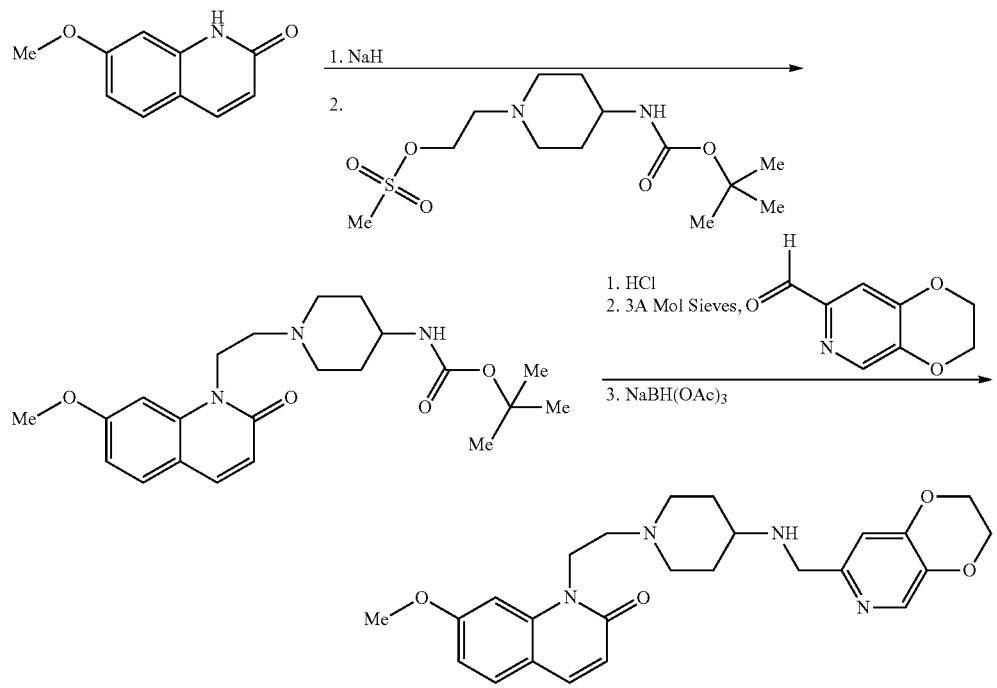

c) As depicted in Scheme 2, by reaction of a suitable bicyclic ring system containing a NH group in the ring with a suitable alcohol under Mitsunobu conditions, followed by deprotection and reductive amination with an aldehyde. This sequence may be followed by functional group manipulations and/or further alkylations or reductive aminations.

d) As depicted in Scheme 3, by alkylation of a suitable bicyclic ring system containing a NH group in the ring with bromo- or chloroacetic acid or with a derivative thereof, followed by activation of the acid and amide coupling. The amide coupling reaction may be followed by functional group manipulations and/or further alkylations or reductive aminations and optional reduction of the amide moiety.

Scheme 2

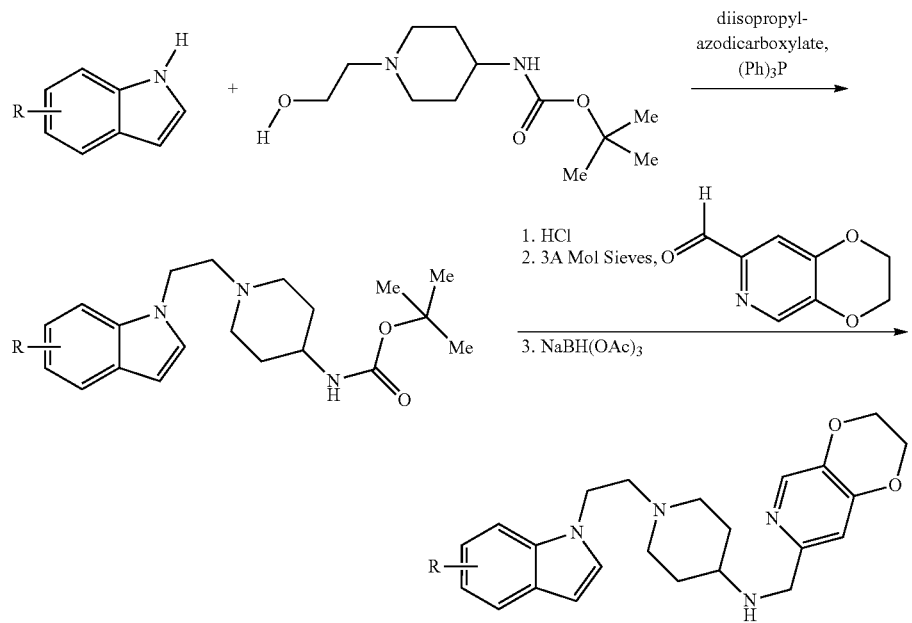

Scheme 3

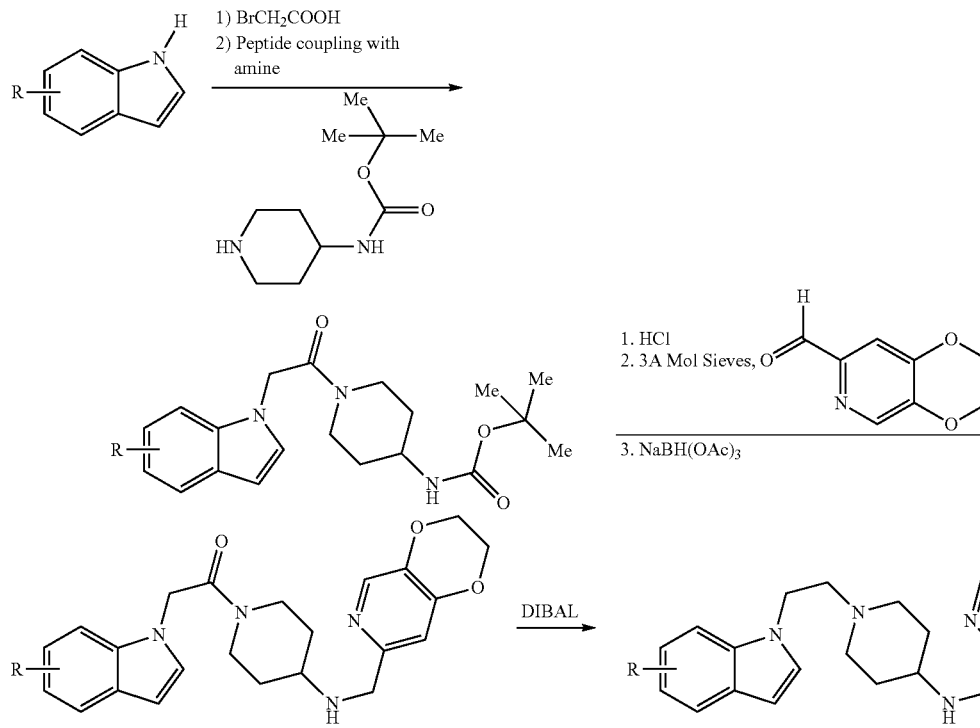

e) As depicted in Scheme 4, by alkylation of a suitable bicyclic ring system containing a NH group in the ring with allylbromide, followed by oxidative cleavage of the double bond with a suitable oxidizing agent, such as ozone or periodate and subsequent manipulation of the resulting alcohol, e.g., by conversion to a mesylate, followed by alkylation. The alkylation reaction may be followed by functional group manipulations and/or further alkylations or reductive aminations.

Scheme 4

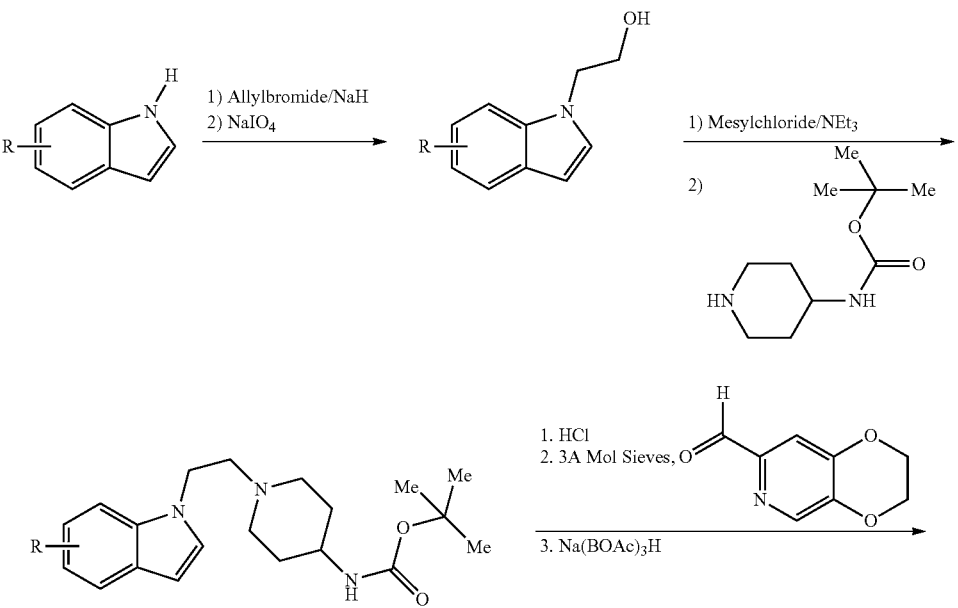

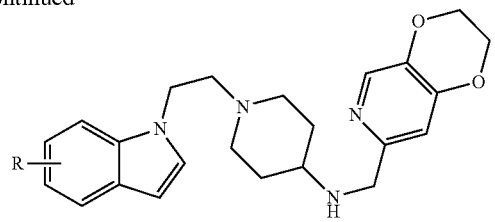

f) As depicted in Scheme 5, by alkylation of a suitable bicyclic ring system containing a NH group in the ring with allylbromide, followed hydroboration and subsequent manipulation of the resulting alcohol, e.g. by conversion to a mesylate, followed by alkylation. The alkylation reaction may be followed by functional group manipulations and/or further alkylations or reductive aminations.

Scheme 5

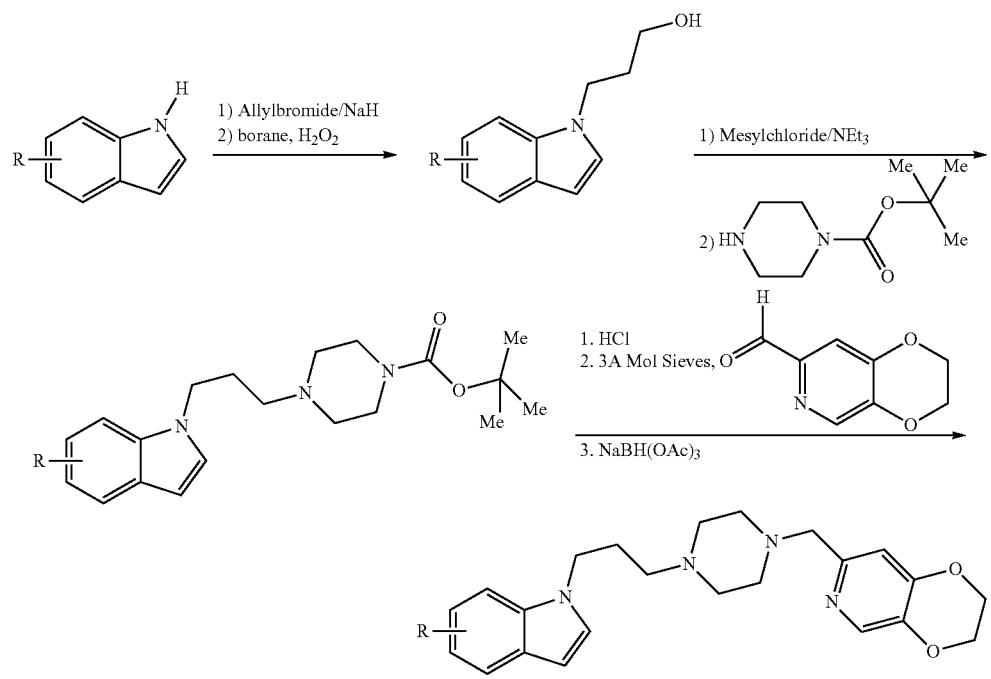

g) Alternatively, as depicted in Scheme 6, the alcohol intermediate in Scheme 5 may be oxidized to the aldehyde, followed by reductive amination to arrive at the same intermediate.

Scheme 6

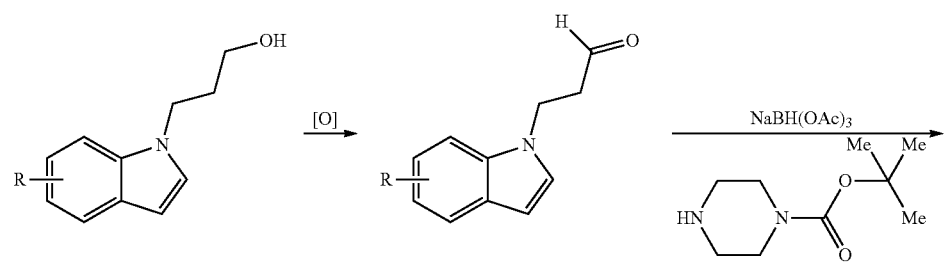

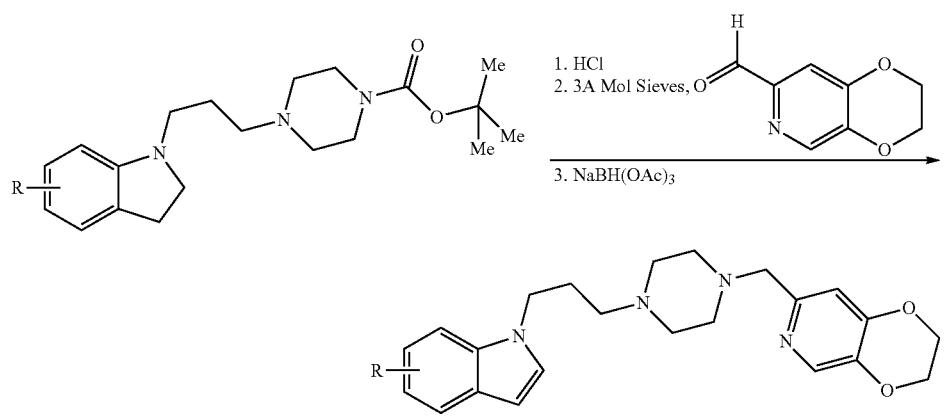

h) using essentially the procedure described under c), by reaction of a suitable bicyclic ring system containing a NH group in the ring with an alcohol (II)

X = O or NR under Mitsunobu conditions; or by alkylation of a suitable bicyclic ring system containing a NH group with a derivative of (II), where the alcohol moiety is converted to a leaving group, such as O-mesylate, followed by deprotection and reductive amination with an aldehyde. This sequence may be followed by functional group manipulations and/or further alkylations or reductive aminations, also using essentially the procedure described under c).

For example, as depicted in Scheme 7, an O-mesylate alkylating reagent may be prepared from the alcohol, by reaction with mesyl chloride, in the presence of a base, such as a trialkyl amine or an immobilized version thereof on a resin. It is understood, that such an alkylating reagent is potentially unstable and needs to be prepared fresh under careful, controlled conditions.

Scheme 7

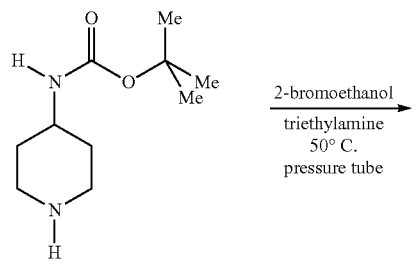

2-bromoethanol
triethylamine
50° C.
pressure tube

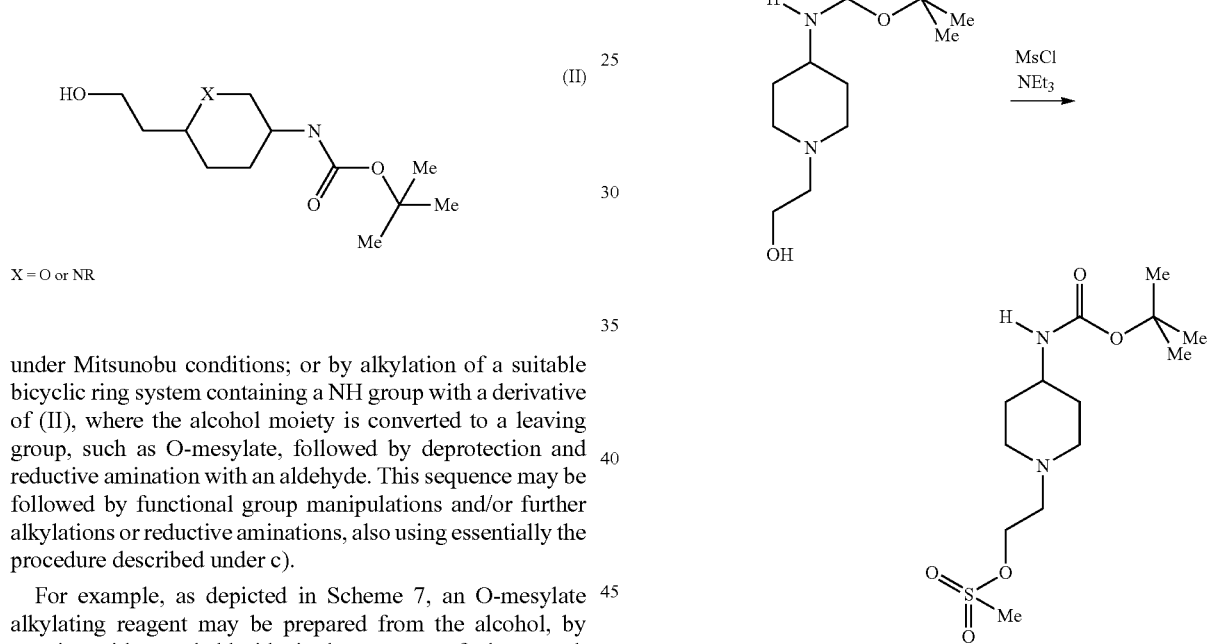

With respect to (a)-(g) and Schemes 1-5 above, the removal of any protecting groups, formation of pharmaceutically-acceptable salts and/or formation of in-vivo hydrolysable esters or amides are within the skill of an ordinary organic chemist using standard techniques. Furthermore, details regarding these transformations; for example, the preparation of in-vivo hydrolysable ester prodrugs has been described in the section above on such esters.

When an optically active form of a compound of the invention is required, it may be obtained by carrying out one of the above procedures using an optically active starting material (formed, for example, by asymmetric induction of a suitable reaction step), or by resolution of a racemic form of the compound or intermediate using a standard procedure, or by chromatographic separation of diastereoisomers (when produced). Enzymatic techniques may also be useful for the preparation of optically active compounds and/or intermediates.

Similarly, when a pure regioisomer of a compound of the invention is required, it may be obtained by carrying out one of the above procedures using a pure regioisomer as a starting material, or by resolution of a mixture of the regioisomers or intermediates using a standard procedure.

Biological Activity

According to a further feature of the invention there is provided a compound of the invention, or a pharmaceutically-acceptable salt, or in-vivo hydrolysable ester thereof for use in a method of treatment of the human or animal body by therapy.

According to a further feature of the present invention there is provided a method for producing an antibacterial effect in a warm blooded animal, such as man, in need of such treatment, which comprises administering to said animal an effective amount of a compound of the present invention, or a pharmaceutically-acceptable salt, or in-vivo hydrolysable ester thereof.

The ability of the invention compounds disclosed herein to achieve an antibacterial effect is demonstrated by the following tests.

Enzyme Potency Testing Methods

Supercoiling Assay Description:

Compounds were tested for inhibition of Escherichia coli DNA supercoiling activity as follows. Assays were performed in polypropylene multiwell plates in 50 μl reactions containing 35 mM Tris-HCl (pH 7.5), 24 mM KCl, 4 mM $MgCl_2$, 2 mM dithiothreitol, 1.8 mM spermidine, 5% (v/v) glycerol, 200 nM bovine serum albumin, 1.25% (v/v) DMSO, 3 mM ATP, 10 ng/ml relaxed pBR322 plasmid, 0.6 nM DNA gyrase, and test compound. Reactions were quenched after 1 hour by the addition of 10 μl of 30% (w/v) Ficoll-400, 10 mM EDTA, and 5% sodium dodecyl sulfate. Twenty-five μl of each sample was loaded onto a 0.8% (w/v) agarose gel and electrophoresed. The gel and gel buffer contained 1×TBE buffer (89 mM Tris base, 89 mM boric acid, and 2 mM EDTA at pH 8.3). After electrophoresis for 3 hours at 70V, the gel was stained with ethidium bromide and visualized by excitation with ultraviolet light. The fluorescence intensity of the most supercoiled plasmid band was used to measure gyrase activity. Compound potency was based $IC_{50}$ measurements determined from reactions performed with eight 2-fold serial dilutions of each compound and a control without compound.

Compounds of the Examples generally have an $IC_{50}$ of <20 μg/ml.

ATPase Assay Description:

Compounds were tested for inhibition of GyrB ATPase activity using an ammonium molybdate/malachite green-based phosphate detection assay (Lanzetta, P. A., L. J. Alvarez, P. S. Reinach, and O. A. Candia, 1979, 100: 95-97). Assays were performed in multiwell plates in 100 μl reactions containing: 50 mM TRIS buffer pH 7.5, 75 mM ammonium acetate, 5.5 mM magnesium chloride, 0.5 mM ethylenediaminetetraacetic acid, 5% glycerol, 1 mM 1,4-dithio-DL-threitol, 200 nM bovine serum albumin, 16 μg/ml sheared salmon sperm DNA, 4 nM E. coli GyrA, 4 nM E. coli GyrB, 250 μM ATP, and compound in dimethylsulfoxide. Reactions were quenched with 150 μL of ammonium molybdate/malachite green detection reagent containing 1.2 mM malachite green hydrochloride, 8.5 mM ammonium molybdate tetrahydrate, and 1 M hydrochloric acid. Plates were read in an absorbance plate reader at 625 nm and percent inhibition values were calculated using dimethylsulfoxide (2%)-containing reactions as 0% inhibition and novobiocin-containing (2 μM) reactions as 100% inhibition controls. Compound potency was based on $IC_{50}$ measurements determined from reactions performed in the presence of 10 different compound concentrations.

Compounds of the invention generally have an $IC_{50}$ of <20 μg/ml.

Bacterial Susceptibility Testing Methods

Compounds were tested for antimicrobial activity by susceptibility testing in liquid media in a 96 well format. Compounds were dissolved in dimethylsulfoxide and tested in 10 doubling dilutions in the susceptibility assays. The organisms used in the assay were grown overnight on suitable agar media and then suspended in a liquid medium appropriate for the growth of the organism. The suspension was a 0.5 McFarland and a further 1 in 10 dilution was made into the same liquid medium to prepare the final organism suspension in 100 μL. Plates were incubated under appropriate conditions at 37° C. for 24 hours prior to reading. The Minimum Inhibitory Concentration (MIC) was determined as the lowest drug concentration able to reduce growth by 80% or more.

Compounds were evaluated against a panel of Gram-positive species, including Staphylococcus aureus, Streptococcus pneumoniae, Streptococcus pyogenes, and Enterococcus faecium. In addition, compounds were evaluated against a panel of Gram-negative species including Haemophilus influenzae, Escherichia coli and Moraxella catarrhalis. Compounds of the present invention have MIC's less than or equal to 8 μg/ml versus one or more of the organisms named above.

Data for several compounds of the invention are depicted below:

| Example | gyrase ATPase [microgram/ml] | gyrase supercoiling [microgram/ml] | E. coli MIC [microgram/ml] | S. pneumo [microgram/ml] |
|---------|------------------------------|-----------------------------------|----------------------------|--------------------------|
| 5       | 0.07                         | 0.051                             | 0.5                        | 0.12                     |
| 66      | 0.3                          | ND                                | 4                          | 8                        |
| 37      | 0.008                        | ND                                | 0.25                       | 0.06                     |
| 26      | ND                           | 0.42                              | 1                          | 0.25                     |
| 49      | ND                           | 3                                 | 8                          | 4                        |

Pharmaceutical Formulations

In another embodiment the present invention provides a pharmaceutical composition which comprises a compound of formula (I) admixed with a pharmaceutically-acceptable carrier, diluent, or excipient.

The invention compositions may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration as eye-drops, for administration by inhalation (for example as a finely divided powder or a liquid aerosol), for administration by insufflation (for example as a finely divided powder) or for parenteral administration (for example as a sterile aqueous or oily solution for intravenous, subcutaneous, sub-lingual, intramuscular or intramuscular dosing or as a suppository for rectal dosing).

In addition to the compounds of the present invention, the pharmaceutical composition of this invention may also contain (i.e. through co-formulation) or be co-administered (simultaneously, sequentially or separately) with one or more known drugs selected from other clinically useful antibacterial agents (for example, β-lactams, macrolides, quinolones or aminoglycosides) and/or other anti-infective agents (for example, an antifungal triazole or amphotericin). These may include carbapenems, for example meropenem or imipenem, to broaden the therapeutic effectiveness. Compounds of this invention may also be co-formulated or co-administered with bactericidal/permeability-increasing protein (BPI) products or efflux pump inhibitors to improve activity against gram negative bacteria and bacteria resistant to antimicrobial agents.

The compositions of the invention may be obtained by conventional procedures using conventional pharmaceutical diluents, carriers, or excipients, well known in the art. Thus, compositions intended for oral use may contain, for example, one or more coloring, sweetening, flavoring and/or preservative agents. A pharmaceutical composition to be dosed intravenously may contain advantageously (for example to enhance stability) a suitable bactericide, antioxidant or reducing agent, or a suitable sequestering agent.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), coloring agents, flavoring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions of the invention may also be in the form of oil in water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol. Solubility enhancing agents, for example cyclodextrins may be used.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. A suitable pharmaceutical composition of this invention is one suitable for oral administration in unit dosage form. For example, a formulation intended for oral administration to humans will generally contain, for example, a therapeutically effective amount of active agent compounded with an appropriate and convenient amount of excipients which may vary from about 1 to about 98 percent by weight of the total composition. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

In another aspect a pharmaceutical composition of the invention is one suitable for intravenous, subcutaneous or intramuscular injection. Each patient may receive, for example, a daily intravenous, subcutaneous or intramuscular dose of a compound of this invention, the composition being administered 1 to 4 times per day. The intravenous, subcutaneous and intramuscular dose may be given by means of a bolus injection. Alternatively, the intravenous dose may be given by continuous infusion over a period of time. Alternatively, each patient may receive a daily oral dose which may be approximately equivalent to the daily parenteral dose, the composition being administered 1 to 4 times per day.

EXAMPLES

The invention will now be illustrated by the following non-limiting examples.

Example 1

1-(2-{4-[(2,3-Dihydro[1,4]dioxino[2,3-c]pyridin-7-ylmethyl)amino]piperidin-1-yl}ethyl)-7-methoxyquinolin-2(1H)-one A solution of 1-[2-(4-aminopiperidin-1-yl)ethyl]-7-methoxyquinolin-2(1H)-one (Intermediate 1, crude, 60 mg, 0.20 mmol) and 2,3-dihydro[1,4]dioxino[2,3-c]pyridine-7-carbaldehyde (WO 2004/058144) (33 mg, 0.20 mmol) in dry chloroform/methanol (5 mL, 1:1) was heated over 3 Å molecular sieves at 70° C. for 3 hours. The reaction mixture was cooled to 0° C., and sodium triacetoxy borohydride (127 mg, 0.6 mmol) was added. The resulting reaction mixture was stirred at room temperature for 30 minutes and then was filtered through a 0.45 μm membrane and concentrated to dryness under reduced pressure. The residue was taken up in dichloromethane (50 mL) and saturated aqueous sodium hydrogen carbonate solution (5 mL). The pH of the aqueous phase was adjusted to a pH of 10 with 1M aqueous sodium hydroxide solution. The aqueous phase was back extracted twice with dichloromethane (2×20 mL) and the combined organic phases were dried over sodium sulfate and concentrated under reduced pressure. Chromatography on silica gel with dichloromethane/methanol (8:1 to 4:1) gave the free base of the title compound as a colorless oil. The free base was taken up in dichloromethane (2 mL), ethanol (7 mL) was added, followed by addition of 1M HCl in ether (0.3 mL). The colorless precipitate was collected by filtration and gave 50 mg (48%) of the bis-hydrochloride salt of the product, mp 243° C.

MS (ES): 451.14 (MH$^+$) for $C_{25}H_{30}N_4O_4$ $^1$H-NMR (DMSO-d$_6$) δ (ppm): 2.00-3.80 (m, 11H); 3.96 (s, 3H); 4.20-4.45 (m, 6H); 4.68 (m, 2H); 6.45 (d, 1H); 6.93 (d, 1H); 7.18 (s, 1H); 7.30 (s, 1H); 7.68 (d, 1H); 7.88 (d, 1H); 8.25 (s, 1H); 9.74 (brs, 2H); 11.18 (brs, 1H).

Intermediate 1

1-[2-(4-Aminopiperidin-1-yl)ethyl]-7-methoxyquinolin-2(1H)-one

A solution of tert-butyl{1-[2-(7-methoxy-2-oxoquinolin-1(2H)-yl)ethyl]piperidin-4-yl}carbamate (Intermediate 2, 150 mg, 0.37 mmol) in dioxane (4 mL) was treated at room temperature under vigorous stirring with a solution of HCl in dioxane (4M, 2 mL). After 18 hours, the reaction mixture was concentrated under reduced pressure. The residue was taken up in dichloromethane (60 mL) and saturated aqueous sodium hydrogen carbonate solution (10 mL). The aqueous phase was extracted three times with dichloromethane (3×50 mL) and the combined organic phases were dried over sodium sulfate and concentrated under reduced pressure to give 113 mg (100% yield) of the crude product as an oil.

MS (ES): 302.24 (MH$^+$) for $C_{17}H_{23}N_3O_2$ $^1$H-NMR (DMSO-d$_6$) δ: 1.21 (m, 2H); 1.65 (m, 2H); 2.04 (t, 2H); 2.40-2.52 (m, 2H); 2.89 (m, 2H); 3.69 (m, 1H); 3.88 (s, 3H); 4.31 (t, 2H); 6.40 (m, 1H); 6.88 (m, 1H); 6.94 (m, 1H); 7.63 (m, 1H); 7.80 (m, 1H). (The NH$_2$ protons were not observed)

Intermediate 2 tert-Butyl{1-[2-(7-methoxy-2-oxoquinolin-1(2H)-yl)ethyl]piperidin-4-yl}carbamate A solution of 7-methoxyquinolin-2(1H)-one (Intermediate 3, 340 mg, 2.2 mmol) in dry dimethylformamide (DMF) (10 mL) was treated at 0° C. with a cooling bath under stirring with sodium hydride (88 mg, 60% in oil, 2.2 mmol). The cooling bath was removed and the mixture was stirred for 30 minutes at room temperature. A solution of 2-{4-[(tert-butoxycarbonyl)amino]piperidin-1-yl}ethyl methanesulfonate in N,N-dimethylformamide (DMF) (Intermediate 6, 0.58 mmol/mL, 3.5 mL, 2.03 mmol) was then added and the resulting mixture was stirred over night at room temperature. Thin Layer Chromatography (TLC): Rf=0.1 (hexanes/acetone, 1:1) (the O-alkylated product was observed as a minor product and has a rf value of 0.3). The DMF was removed under reduced pressure, and the residue was taken up in ethyl acetate (100 mL) and saturated aqueous sodium hydrogen carbonate solution (30 mL). The aqueous phase was back extracted once with ethyl acetate (50 mL). The combined organic phases were dried over sodium sulfate and concentrated under reduced pressure. Chromatography on silica gel with hexanes/acetone (1:1) gave 153 mg (20% yield) of the product as a colorless hard foam.

MS (ES): 402.25 (MH$^+$) for $C_{22}H_{31}N_3O_4$ $^1$H-NMR (DMSO-d$_6$) δ: 1.30-1.42 (m, 2H); 1.36 (s, 9H); 1.66 (m, 2H); 2.04 (m, 2H); 2.45-2.53 (m, 2H); 2.92 (m, 2H); 3.15 (m, 1H); 3.88 (s, 3H); 4.31 (t, 2H); 6.39 (m, 1H); 6.76 (m, 1H); 6.88 (m, 1H); 6.93 (m, 1H); 7.62 (d, 1H); 7.80 (d, 1H). (The structure was confirmed by an HMBC-NMR experiment)

Intermediate 3

7-Methoxyquinolin-2(1H)-one

A solution of methyl(2E)-3-(2-amino-4-methoxyphenyl)acrylate (Intermediate 4, 500 mg, 2.4 mmol) in acetonitrile (600 mL) was deoxygenated under vacuum, purged with nitrogen and irradiated at 365 nm with a long wave UV lamp (B-100AP, Blak Ray) for 28 hours. The solvent was removed under reduced pressure and the product was precipitated from dichloromethane (20 mL) by the addition of hexanes (100 mL) to give 357 mg (76% yield) of the crude product as a colorless solid, 90% pure by $^1$H-NMR (together with 10% dimer), mp 190° C.

MS (ES): 176.21 (MH$^+$) for $C_{10}H_9NO_2$ $^1$H-NMR (DMSO-d$_6$) δ: 3.79 (s, 3H); 6.28 (d, 1H); 6.75-6.81 (m, 2H); 7.55 (d, 1H); 7.79 (d, 1H); 11.59 (s, 1H).

Intermediate 4

Methyl(2E)-3-(2-amino-4-methoxyphenyl)acrylate

To a solution of methyl(2E)-3-(4-methoxy-2-nitrophenyl)acrylate (Intermediate 5, 4.9 g, 20.66 mmol) in acetic acid (150 mL) at room temperature under nitrogen was added zinc powder (7.7 g, 118 mmol) in portions. After 4 hours, another 5 g of zinc was added and the resulting reaction mixture was heated at 50° C. for two hours. The reaction mixture was then cooled to room temperature, filtered, and the filtrate was concentrated to dryness under reduced pressure. The residue was chromatographed on silica gel with hexanes/ethyl acetate (3:1) to give 1.0 g (23% yield) of product as a yellow solid, mp 149° C.

MS (ES): 208.17 (MH$^+$ for $C_{11}H_{13}NO_3$ $^1$H-NMR (DMSO-d$_6$) δ: 3.67 (s, 3H); 3.68 (s, 3H); 5.68 (brs, 2H); 6.14 (dd, 1H); 6.21 (d, 1H); 6.23 (s, 1H); 7.40 (d, 1H); 7.82 (d, 1H).

Intermediate 5

(2E)-3-(4-Methoxy-2-nitrophenyl)acrylate

A solution of 4-iodo-3-nitroanisole (10 g, 36 mmol), methylacrylate (3.87 mL, 43 mmol), tris(4-methylphenyl)phosphine (1.1 g, 3.6 mmol) and triethylamine (6.05 mL, 43 mmol) was degassed and flushed with nitrogen. Palladium(II) acetate (1.2 g, 1.8 mmol) was added and the mixture was heated at 70° C. overnight. It was filtered through a 0.45 μm membrane and the solvent was removed under reduced pressure. The residue was taken up in ethyl acetate (300 mL), it was washed with potassium phosphate buffer (1M, pH 7, 2×300 mL) and dried over sodium sulfate. Chromatography on silica gel with dichloromethane, followed by precipitation from dichloromethane (50 mL) with hexanes (500 mL) gave 4.96 g (58% yield) of product as a yellow solid.

MS (ES): 260.20 (MNa$^+$) for $C_{11}H_{11}NO_5$ $^1$H-NMR (DMSO-d$_6$) δ: 3.73 (s, 3H); 3.88 (s, 3H); 6.59 (d, 1H); 7.33 (dd, 1H); 7.57 (d, 1H); 7.78 (d, 1H); 7.94 (d, 1H).

Intermediate 6

2-{4-[tert-Butoxycarbonyl)amino]piperidin-1-yl}ethyl methanesulfonate

A mixture of tert-butyl[1-(2-hydroxyethyl)piperidin-4-yl]carbamate (Intermediate 7, 1.7 g, 7 mmol) in dry dichloromethane (20 mL) and triethyl amine (1.4 mL, 9.8 mmol) was treated at 0° C. with methanesulfonyl chloride (0.65 mL, 8.4 mmol). After 45 minutes the reaction was complete by TLC (chloroform/methanol 6:1, rf 0.54). Potassium phosphate buffer (pH 7, 1M, 50 mL) was added, dichloromethane was removed under reduced pressure and it was extracted with ice-cold ethyl acetate (2×100 mL) and dried over sodium sulfate. The solvent was removed under reduced pressure and the crude preparation of the mesylate was used without delay for the next step.

MS (ES): 323.18 (MH$^+$) for $C_{13}H_{26}N_2O_5S$

Intermediate 7 tert-Butyl[1-(2-hydroxyethyl)piperidin-4-yl]carbamate

A mixture of tert-butyl piperidin-4-ylcarbamate (5 g, 25 mmol), 2-bromoethanol (1.77 mL, 25 mmol) and triethylamine (3.86 mL, 27.5 mmol) in acetonitrile (20 mL) was heated in a sealed tube at 50° C. for 16 hours. The solvent was removed under reduced pressure, and the residue was taken up in ethyl acetate (300 mL) and washed with saturated aqueous sodium hydrogen carbonate solution (100 mL). The aqueous phase was back-extracted once with ethyl acetate (100 mL) and the combined organic phases were dried over sodium sulfate and concentrated under reduced pressure. Chromatography on silica gel with dichloromethane/methanol (4:1) gave 4.04 g (66% yield) of product as a colorless solid, mp 66° C.

MS (ES): 245.28 (MH$^+$) for $C_{12}H_{24}N_2O_3$ $^1$H-NMR (DMSO-d$_6$) δ: 1.33 (m, 2H); 1.36 (s, 9H); 1.62 (m, 2H); 1.92 (t, 2H); 2.32 (t, 2H); 2.77 (m, 2H); 3.17 (m, 1H); 3.43 (m, 2H); 4.34 (t, 1H); 6.73 (d, 1H).

Example 2

1-(2-{4-[(2,3-Dihydro[1,4]dioxino[2,3-c]pyridin-7-ylmethyl)amino]piperidin-1-yl}ethyl)-7-methoxyquinolin-4(1H)-one A solution of 1-[2-(4-aminopiperidin-1-yl)ethyl]-7-methoxyquinolin-4(1H)-one (Intermediate 8, 60 mg, 0.20 mmol) and 2,3-dihydro[1,4]dioxino[2,3-c]pyridine-7-carbaldehyde (WO 2004/058144) (33 mg, 0.20 mmol) in dry chloroform/methanol (5 mL, 1:1) was heated over 3 Å molecular sieves at 70° C. for 3 hours. The reaction mixture was cooled to 0° C., and sodium triacetoxyborohydride (127 mg, 0.6 mmol) was added and the resulting mixture was stirred at room temperature for 30 minutes. The mixture was then filtered through a 0.45 μm membrane, acidified with conc. HCl to pH 1 and concentrated to dryness under reduced pressure. The residue was taken up in dichloromethane (50 mL) and saturated aqueous sodium hydrogen carbonate solution (5 mL). The pH of the aqueous phase was adjusted to pH10 with 1M aqueous sodium hydroxide solution. The aqueous phase was back extracted twice with dichloromethane (2×20 mL) and the combined organic phases were dried over sodium sulfate. Chromatography on silica gel with dichloromethane/methanol (4:1), containing 0.125% ammonium hydroxide, gave the free base of the title compound as a colorless oil. The free base was taken up in dichloromethane (2 mL), ethanol (7 mL) was added, followed by addition of 1M HCl in ether (0.45 mL). The colorless precipitate was collected by filtration and gave 84 mg (81% yield) of the bis-hydrochloride salt of the product, mp 260° C.

MS (ES): 451.21 (MH$^+$) for $C_{25}H_{30}N_4O_4$ $^1$H-NMR (DMSO-d$_6$) δ: 2.00-3.80 (m, 11H); 4.07 (s, 3H); 4.30-4.46 (m, 6H); 5.06 (m, 2H); 6.83 (d, 1H); 7.28 (d, 1H); 7.45-7.58 (m, 2H); 8.22 (d, 1H); 8.37 (s, 1H); 8.61 (d, 1H); 9.94 (brs, 2H); 11.90 (brs, 1H).

Intermediate 8

1-[2-(4-Aminopiperidin-1-yl)ethyl]-7-methoxyquinolin-4(1H)-one

A mixture of tert-butyl{1-[2-(7-methoxy-4-oxoquinolin-1(4H)-yl)ethyl]piperidin-4-yl}carbamate (Intermediate 9, 370 mg, 0.92 mmol) in dioxane (10 mL) was treated at room temperature under vigorous stirring with a solution of HCl in dioxane (4M, 4 mL). After 18 hours, the reaction mixture was diluted with isopropanol (10 mL) and with water (4 mL) and more HCl in dioxane (4M, 5 mL) was added. After 1 hour, the reaction mixture was concentrated under reduced pressure to give the hydrochloride of the product as a colorless solid. The hydrochloride salt was taken up in aqueous sodium hydroxide solution (1M, 10 mL) and extracted with dichloromethane (60 mL). The aqueous phase was extracted three times with dichloromethane (3×60 mL) and the combined organic phases were dried over sodium sulfate to give 278 mg (100% yield) of the crude product as an oil.

MS (ES): 302.24 (MH$^+$) for $C_{17}H_{23}N_3O_2$ $^1$H-NMR (DMSO-d$_6$) (data for the hydrochloride salt) δ: 1.80-2.30 (m, 4H); 3.14 (m, 2H); 3.36 (m, 1H); 3.48 (m, 2H); 3.68 (m, 2H); 4.06 (s, 3H); 5.03 (m, 2H); 6.74 (d, 1H); 7.24 (d, 1H); 7.45 (s, 1H); 8.21 (d, 1H); 8.46 (brs, 2H); 8.55 (d, 1H); 8.60 (brs, 1H); 11.95 (brs, 1H).

Intermediate 9 tert-Butyl{1-[2-(7-methoxy-4-oxo quinolin-1(4H)-yl)ethyl]piperidin-4-yl}carbamate A solution of 7-methoxyquinolin-4-ol (Intermediate 10, 500 mg, 2.85 mmol) in dry DMF (10 mL) was treated at 0° C. with a cooling bath under stirring with sodium hydride (114 mg, 60% in oil, 2.85 mmol). The cooling bath was removed and the mixture was stirred for 30 minutes at room temperature. A solution of 2-{4-[(tert-butoxycarbonyl)amino]piperidin-1-yl}ethyl methanesulfonate in DMF (Intermediate 6, 0.58 mmol/mL, 5 mL, 2.9 mmol) was added and the resulting solution was stirred over night at room temperature. DMF was removed under reduced pressure, the residue was taken up in ethyl acetate (100 mL) and saturated aqueous sodium hydrogen carbonate solution (30 mL) and the aqueous phase was back extracted three times with ethyl acetate (3×70 mL). The combined organic phases were dried over sodium sulfate. Some starting 7-methoxyquinolin-4-ol was precipitated from dichloromethane (30 mL) with hexanes (20 mL) and removed by filtration. The filtrate was concentrated to dryness under reduced pressure. Chromatography of the residue on silica gel with acetonitrile/water (15:1 to 10:1) gave 373 mg (33% yield) of the product as a colorless solid, mp 207° C.

MS (ES): 402.36 (MH$^+$) for C$_{22}$H$_{31}$N$_3$O$_4$
$^1$H-NMR (DMSO-d$_6$) δ: 1.25-1.37 (m, 2H); 1.35 (s, 9H); 1.63 (m, 2H); 2.02 (m, 2H); 2.60 (t, 2H); 2.82 (m, 2H); 3.16 (m, 1H); 3.89 (s, 3H); 4.28 (t, 2H); 5.92 (d, 1H); 6.75 (d, 1H); 6.96 (dd, 1H); 7.00 (d, 1H); 7.82 (d, 1H); 8.06 (d, 1H).

Intermediate 10

7-Methoxyquinolin-4-ol

5-{[(3-Methoxyphenyl)amino]methylene}-2,2-dimethyl-1,3-dioxane-4,6-dione (Intermediate 11, 43.5 g, 157 mmol) was added in small portions to phenylether (200 mL) at 225-260° C. under stirring. The reaction mixture was stirred for an additional 5 minutes, until the evolution of gas had stopped. The reaction mixture was cooled to room temperature and the precipitate was collected by filtration and washed with hexanes. Purification by recrystallization from methanol gave 12.4 g (45% yield) of product as a green solid, mp 210° C.

MS (ES): 176.21 (MH$^+$) for C$_{10}$H$_9$NO$_2$
$^1$H-NMR (DMSO-d$_6$) δ: 3.83 (s, 3H); 5.93 (d, 1H); 6.85-6.95 (m, 2H); 7.80 (m, 1H); 7.97 (d, 1H); 11.55 (brs, 1H).

Intermediate 11

5-{[(3-Methoxyphenyl)amino]methylene}-2,2-dimethyl-1,3-dioxane-4,6-dione

A mixture of m-anisidine (22 g, 178 mmol), 2,2-dimethyl-1,3-dioxane-4,6-dione (30.75 g, 214 mmol) and triethylorthoformate (30 mL, 178 mmol) in ethanol (200 mL) was heated at 85° C. for two hours. The mixture was allowed to cool to room temperature and the precipitate was collected by filtration and washed with ethanol to give 43.7 g (89% yield) of product as a pale yellow solid, mp 108° C.

MS (ES): 276.12 (M-H$^-$) for C$_{14}$H$_{15}$NO$_5$
$^1$H-NMR (DMSO-d$_6$) δ: 1.66 (s, 6H); 3.78 (s, 3H); 6.81 (d, 1H); 7.09 (d, 1H); 7.19 (m, 1H); 7.32 (dd, 1H); 8.59 (d, 1H); 11.19 (d, 1H).

Example 3

Methyl 1-(2-{4-[(2,3-dihydro[1,4]dioxino[2,3-c]pyridin-7-ylmethyl)amino]piperidin-1-yl}ethyl)-6-methoxy-1H-indole-2-carboxylate A solution of methyl 1-[2-(4-aminopiperidin-1-yl)ethyl]-6-methoxy-1H-indole-2-carboxylate (Intermediate 12, 200 mg, 0.60 mmol) and 2,3-dihydro[1,4]dioxino[2,3-c]pyridine-7-carbaldehyde (WO 2004/058144) (100 mg, 0.60 mmol) in dry chloroform/methanol (10 mL, 1:1) was heated over 3 Å molecular sieves at 70° C. for 3 hours. The reaction mixture was cooled to 0° C., sodium triacetoxy borohydride (384 mg, 1.8 mmol) was added and the resulting mixture was stirred at room temperature for 30 minutes. The reaction mixture was filtered through a 0.45 μm membrane and concentrated to dryness under reduced pressure. The residue was taken up in dichloromethane (150 mL) and saturated aqueous sodium hydrogen carbonate solution (30 mL), the aqueous phase back extracted once with dichloromethane (70 mL) and the combined organic phases were dried over sodium sulfate. Chromatography on silica gel with dichloromethane/methanol (5:1), containing 0.125% ammonium hydroxide, gave the free base of the title compound, 239 mg (82% yield), as a colorless solid, mp 130° C.

MS (ES): 481.15 (MH$^+$) for C$_{26}$H$_{32}$N$_4$O$_5$
$^1$H-NMR (DMSO-d$_6$) δ: 1.10-1.25 (m, 2H); 1.70 (m, 2H); 1.96 (t, 2H); 2.12 (m, 2H); 2.30 (m, 2H); 2.79 (m, 2H); 3.62 (s, 2H); 3.80 (s, 3H); 3.82 (s, 3H); 4.22-4.35 (m, 4H); 4.58 (t, 2H); 6.75 (m, 1H); 6.91 (s, 1H); 7.01 (s, 1H); 7.17 (s, 1H); 7.52 (d, 1H); 7.98 (s, 1H).

Intermediate 12

Methyl 1-[2-(4-aminopiperidin-1-yl)ethyl]-6-methoxy-1H-indole-2-carboxylate

A solution of methyl 1-(2-{4-[(tert-butoxycarbonyl)amino]piperidin-1-yl}ethyl)-6-methoxy-1H-indole-2-carboxylate (Intermediate 13, 520 mg, 1.2 mmol) in dioxane (4 mL) was treated at room temperature under vigorous stirring with a solution of HCl in dioxane (4M, 2 mL). After 3 days, the reaction mixture was concentrated under reduced pressure. The residue was taken up in dichloromethane (60 mL) and saturated aqueous sodium hydrogen carbonate solution (10 mL), the aqueous phase was extracted three times with dichloromethane (3×50 mL) and the combined organic phases were dried over sodium sulfate to give 407 mg (100% yield) of the crude product as colorless solid, mp 101° C.

MS (ES): 332.23 (MH$^+$) for C$_{18}$H$_{25}$N$_3$O$_3$
$^1$H-NMR (DMSO-d$_6$) δ: 1.15 (m, 2H); 1.61 (m, 2H); 1.99 (t, 2H); 2.51 (m, 2H); 2.79 (m, 2H); 3.49 (m, 1H); 3.81 (s, 3H); 3.83 (s, 3H); 4.59 (t, 2H); 6.76 (m, 1H); 7.02 (brs, 1H); 7.18 (s, 1H); 7.53 (d, 1H). (The NH$_2$ protons were not observed)

Intermediate 13

Methyl 1-(2-{4-[(tert-butoxycarbonyl)amino]piperidin-1-yl}ethyl)-6-methoxy-1H-indole-2-carboxylate A solution of methyl 6-methoxy-2-indole-carboxylate (574 mg, 2.8 mmol) in dry DMF (10 mL) was treated at 0° C. with a cooling bath under stirring with sodium hydride (123 mg, 60% in oil, 3.08 mmol). The cooling bath was removed and the mixture was stirred for 30 minutes at room temperature. A solution of 2-{4-[(tert-butoxycarbonyl)amino]piperidin-1-yl}ethyl methanesulfonate in DMF (Intermediate 6, 0.58 mmol/mL, 3.4 mL, 2.0 mmol) was added and the resulting mixture was stirred over night at room temperature. The DMF was removed under reduced pressure, the residue was taken up in ethyl acetate (100 mL) and saturated aqueous sodium hydrogencarbonate solution (30 mL) and the aqueous phase was back extracted once with ethyl acetate (70 mL). The combined organic phases were dried over sodium sulfate. Chromatography on silica gel with hexanes/ethyl acetate (1:1 to pure ethyl acetate) gave 523 mg (43% yield) of the product as a colorless solid, mp 158° C.

MS (ES): 432.25 (MH$^+$) for $C_{23}H_{33}N_3O_5$ $^1$H-NMR (DMSO-d$_6$) δ: 1.23-1.37 (m, 2H); 1.35 (s, 9H); 1.63 (m, 2H); 1.99 (t, 2H); 2.51 (m, 2H); 2.81 (m, 2H); 3.15 (m, 1H); 3.81 (s, 3H); 3.83 (s, 3H); 4.58 (t, 2H); 6.72-6.78 (m, 2H); 7.01 (brs, 1H); 7.17 (s, 1H); 7.53 (d, 1H).

Example 4

6-[({1-[2-(7-Methoxy-2-oxoquinolin-1(2H)-yl)ethyl] piperidin-4-yl}amino)methyl]-2H-pyrido[3,2-b][1,4] oxazin-3(4H)-one 1-[2-(4-Aminopiperidin-1-yl)ethyl]-7-methoxyquinolin-2 (1H)-one (Intermediate 1, crude, 60 mg, 0.20 mmol), 3-oxo-3,4-dihydro-2H-pyrido[3,2-b][1,4]oxazine-6-carbaldehyde (WO 2004/058144) (43 mg, 0.24 mmol) in dry dichloroethane/methanol (10 mL, 1:1) were heated over 3 Å molecular sieves at reflux for 4 hours. The reaction mixture was cooled to 0° C., and sodium cyanoborohydride (19 mg, 0.30 mmol) was added and it was stirred at room temperature for 2 hours. The mixture was filtered through a fritted funnel and concentrated to dryness under reduced pressure. The residue was taken up in ethyl acetate and washed with saturated sodium bicarbonate followed by saturated sodium chloride. The saturated sodium bicarbonate was extracted with chloroform, and the chloroform was washed with saturated sodium chloride. The ethyl acetate and chloroform extracts were combined, dried over sodium sulfate and concentrated to dryness under reduced pressure. Silica gel chromatography with dichloromethane/methanol/ammonia ammonia (8:2:0.01) gave title compound as a colorless oil, 27 mg (30%).

MS (ES): 464.34 (MH$^+$) for $C_{25}H_{29}N_5O_4$ $^1$H-NMR (CDCl$_3$-d) δ: 1.93 (m, 4H); 2.94 (m, 3H); 3.38 (m, 2H); 3.48 (s, 2H); 4.02 (m, 6H); 4.64 (s, 2H); 4.66 (m, 1H); 6.51 (d, J=9.4 Hz, 1H); 6.83 (dd, J=6.5, 2.1 Hz, 1H); 7.22 (d, J=8.1 Hz, 1H); 7.46 (m, 2H); 7.62 (m, 2H).

Example 5

1-(2-{4-[(2,3-Dihydro[1,4]dioxino[2,3-c]pyridin-7-ylmethyl)amino]piperidin-1-yl}ethyl)-2-oxo-1,2-dihydroquinoline-7-carbonitrile 1-[2-(4-Aminopiperidin-1-yl)ethyl]-2-oxo-1,2-dihydroquinoline-7-carbonitrile (Intermediate 14, 70 mg, 0.24 mmol), 2,3-dihydro[1,4]dioxino[2,3-c]pyridine-7-carbaldehyde (WO 2004/058144) (40 mg, 0.24 mmol) and sodium triacetoxy borohydride (150 mg, 0.75 mmol) were reacted as described for Example 1, but the aqueous workup was omitted. Chromatography on silica gel with dichloromethane/methanol (6:1) and crystallization from dichloromethane/ether/hexanes gave the monoacetate salt of the product as a colorless solid, 69 mg (58%), mp 130-135° C.

MS (ES): 446.24 (MH$^+$) for $C_{25}H_{27}N_5O_3$ $^1$H-NMR (DMSO-d$_6$) δ: 1.19 (m, 2H); 1.73 (m, 2H); 1.89 (s, 3H); 2.00 (t, 2H); 2.34 (m, 1H); 2.51 (m, 2H, under solvent peak); 2.88 (m, 2H); 3.65 (s, 2H); 4.24-4.37 (m, 6H); 6.76 (d, 1H); 6.92 (s, 1H); 7.63 (dd, 1H); 7.90 (d, 1H); 7.97-8.00 (m, 2H); 8.07 (brs, 1H).

Intermediate 14

1-[2-(4-Aminopiperidin-1-yl)ethyl]-2-oxo-1,2-dihydroquinoline-7-carbonitrile

A solution of tert-butyl{1-[2-(7-cyano-2-oxoquinolin-1 (2H)-yl)ethyl]piperidin-4-yl}carbamate (Intermediate 15) (6.57 g, 16.57 mmol) in dichloromethane (100 mL) was treated with trifluoroacetic acid (40 mL) at 0° C. for 30 minutes. The solvent was removed under reduced pressure and the residue codistilled once with dichloromethane, then taken up in dichloromethane (200 mL) and washed with saturated sodium hydrogencarbonate solution (50 mL, pH adjusted to 10 with sodium hydroxide). The aqueous phase was back-extracted three times with dichloromethane (3×100 mL) and dried over sodium sulfate. The solvent was removed under reduced pressure to give the product as off-white solid, 5 g, mp 138° C.

MS (ES): 296.91 (MH$^+$) for $C_{17}H_{20}N_4O$ $^1$H-NMR (DMSO-d$_6$) δ: 1.13 (m, 2H); 1.48 (m, 1H); 1.62 (m, 2H); 2.01 (t, 2H); 2.50 (m, 2H, under solvent peak); 2.86 (m, 2H); 4.35 (t, 2H); 6.76 (d, 1H); 7.63 (d, 1H); 7.90 (d, 1H); 7.98 (d, 1H); 8.07 (s, 1H).

Intermediate 15 tert-Butyl{1-[2-(7-cyano-2-oxoquinolin-1(2H)-yl) ethyl]piperidin-4-yl}carbamate

A mixture of tert-butyl{1-[2-(7-bromo-2-oxoquinolin-1 (2H)-yl)ethyl]piperidin-4-yl}carbamate (Intermediate 16) (9.85 g, 21.9 mmol) and potassium cyanide (2.14 g, 32.8 mmol) in dry acetonitrile (60 mL) was degassed and flushed with nitrogen three times. Tributyltinchloride (0.059 mmol, 1.13 mL of a 51.6 mM solution in heptane) was added, followed by 4,5-bis(diphenylphosphino)-9,9-dimethylxanthene (63 mg, 0.11 mmol) and tris(dibenzylideneacetone)dipalladium (0) (100 mg, 0.11 mmol) and it was degassed and flushed with nitrogen like above. The mixture was stirred for 30 minutes at room temperature and then degassed and flushed with nitrogen again. It was heated at 85° C. for 20 hours. The solvent was removed under reduced pressure and the residue taken up in dichloromethane (500 mL) and washed with water (200 mL). The aqueous phase was back-extracted once with dichloromethane (200 mL) and combined organic phases were dried over sodium sulfate. Solvent was removed under reduced pressure and the residue was crystallized from acetonitrile (60 mL) to give the product as a colorless solid, 6.57 g (76%), mp 202° C.

MS (ES): 397.21 (MH$^+$) for $C_{22}H_{28}N_4O_3$ $^1$H-NMR (DMSO-d$_6$) δ: 1.30 (m, 2H); 1.36 (s, 9H); 1.64 (m, 2H); 2.02 (m, 2H); 2.50 (m, 2H, under solvent peak); 2.90 (m, 2H); 3.15 (m, 1H); 4.34 (t, 2H); 6.74-6.78 (m, 2H); 7.63 (m, 1H); 7.89 (d, 1H); 7.99 (d, 1H); 8.05 (s, 1H).

Intermediate 16 tert-Butyl {1-[2-(7-bromo-2-oxoquinolin-1(2H)-yl) ethyl]piperidin-4-yl}carbamate 7-Bromoquinolin-2(1H)-one (Intermediate 17) (7.4 g, 33 mmol) was deprotonated with sodium hydride (1.45 g, 60% in oil, 36 mmol) and alkylated with 2-{4-[tert-butoxycarbonyl)

amino]piperidin-1-yl}ethyl methanesulfonate (Intermediate 6) (40 mmol) as described for Intermediate 2; Chromatography on silica gel with hexanes/acetone (5:2) gave 9.87 g (66%) of the product as a colorless solid, mp 155° C.

MS (ES): 450\452 (MH$^+$) for $C_{21}H_{28}BrN_3O_3$ $^1$H-NMR (DMSO-d$_6$) δ: 1.32 (m, 2H); 1.36 (s, 9H); 1.65 (m, 2H); 2.01 (t, 2H); 2.46 (m, 2H); 2.90 (m, 2H); 3.19 (m, 1H); 4.29 (t, 2H); 6.61 (d, 1H); 6.75 (d, 1H); 7.41 (d, 1H); 7.65 (d, 1H); 7.73 (brs, 1H); 7.89 (d, 1H).

Intermediate 17

7-Bromoquinolin-2(1H)-one (2E)-N-(3-bromophenyl)-3-phenylacrylamide (Intermediate 18) (16 g, 53 mmol) and aluminium trichloride (31.8 g, 238 mmol) were heated in chlorobenzene (100 mL) at 90° C. bath temperature for one hour. The reaction mixture was cooled to room temperature and poured onto ice. It was stirred until the ice was completely melted, the mixture was filtered and washed with water and ethyl acetate to give the crude product as slightly brown solid in a mixture with the minor product 5-bromoquinolin-2(1H)-one (3:2), 8.8 g (70%). This mixture could not be separated. The mixture was heated in phosphoroxychloride (50 mL) at 65° C. for one hour. The reaction mixture was cooled to room temperature and poured onto ice. It was carefully neutralized at 0° C. with sodium carbonate, extracted into ethyl acetate (300 mL), washed with brine, dried over sodium sulfate and concentrated to give the crude mixture of 7-bromo-2-chloroquinoline and 5-bromo-2-chloroquinoline. The mixture was taken up in dichloromethane (100 mL), treated with silica gel (20 g), filtered and the filter cake was washed with dichloromethane. Filtrate and wash were combined and concentrated. The residue was crystallized from toluene/hexanes (70 mL, 1:1) to provide pure 7-bromo-2-chloroquinoline, 3.74 g as a colorless solid mp 113° C.

MS (ES): 242/244/246 (MH$^+$) for $C_9H_5BrClN$ $^1$H-NMR (DMSO-d$_6$) δ: 7.63 (d, J 8.4 Hz, 1H); 7.81 (dd, J 8.4, 1.6 Hz, 1H); 8.03 (d, J 8.4 Hz, 1H); 8.18 (d, J 1.6 Hz, 1H); 8.48 (d, J 8.4 Hz, 1H).

7-Bromo-2-chloroquinoline was heated in 5M HCl (100 mL) and dioxane (10 mL) for 1 hour at reflux. The Reaction mixture was cooled, filtered and washed with water to give the title compound, 2.89 g, as a colorless solid, mp 295° C.

MS (ES): 224.13/226.13 (MH$^+$) for $C_9H_6BrNO$ $^1$H-NMR (DMSO-d$_6$) δ: 6.51 (d, J 9.6 Hz, 1H); 7.32 (dd, J 8.6, 1.6 Hz, 1H); 7.46 (d, J 1.6 Hz, 1H); 7.61 (d, J 8.6 Hz, 1H); 7.88 (d, J 9.6 Hz, 1H); 11.80 (brs, 1H).

Intermediate 18

(2E)-N-(3-Bromophenyl)-3-phenylacrylamide

To a solution of 3-bromoaniline (13.1 mL, 120 mmol) in dichloromethane (100 mL) and 2,6-lutidine (21 mL, 180 mmol) at 0° C. was added a solution of cinnamoylchloride (20 g, 120 mmol) in dichloromethane (50 mL) dropwise. The reaction mixture was allowed to reach room temperature and was stirred for 2 hours. It was quenched with potassium phosphate buffer (100 mL, 1M, pH 7) and stirred for 15 minutes. Dichloromethane was removed under reduced pressure. The residue was extracted with ethyl acetate. The organic phase was washed with phosphate buffer (200 mL), dried over sodium sulfate and concentrated to dryness. The residue was crystallized from toluene/hexanes to give the product as colorless solid (33.4 g, 92%).

MS (ES): 302/304 (MH$^+$) for $C_{15}H_{12}BrNO$ $^1$H-NMR (DMSO-d$_6$) δ: 6.79 (d, 1H); 7.23-7.70 (m, 9H); 8.07 (s, 1H); 10.38 (s, 1H).

Example 6

2-Oxo-1-[2-(4-{[(3-oxo-3,4-dihydro-2H-pyrido[3,2-b][1,4]oxazine-6-yl)methyl]amino}piperidin-1-yl)ethyl]-1,2-dihydroquinoline-7-carbonitrile 1-[2-(4-Aminopiperidin-1-yl)ethyl]-2-oxo-1,2-dihydroquinoline-7-carbonitrile (Intermediate 14, 70 mg, 0.24 mmol), 3-oxo-3,4-dihydro-2H-pyrido[3,2-b][1,4]oxazine-6-carbaldehyde (WO 2004/058144) (42 mg, 0.24 mmol) and sodium triacetoxy borohydride (150 mg, 0.75 mmol) were reacted as described for Example 5. Chromatography on silica gel with dichloromethane/methanol (6:1) and crystallization from ethyl acetate/hexanes gave the product as a colorless solid, 73 mg (67%), mp 212° C.

MS (ES): 459.37 (MH$^+$) for $C_{25}H_{26}N_6O_3$ $^1$H-NMR (DMSO-d$_6$) δ: 1.19 (m, 2H); 1.74 (m, 2H); 2.01 (t, 2H); 2.35 (m, 1H); 2.51 (m, 2H, under solvent peak); 2.88 (m, 2H); 3.65 (s, 2H); 4.35 (t, 2H); 4.59 (s, 2H); 6.76 (d, 1H); 7.00 (d, 1H); 7.28 (d, 1H); 7.63 (dd, 1H); 7.89 (d, 1H); 7.99 (d, 1H); 8.06 (brs, 1H); 11.08 (brs, 1H).

Example 7

6-[({1-[2-(7,8-Difluoro-2-oxoquinolin-1(2H)-yl)ethyl]piperidin-4-yl}amino)methyl]-2H-pyrido[3,2-b][1,4]oxazin-3(4H)-one 1-[2-(4-Aminopiperidin-1-yl)ethyl]-7,8-difluoroquinolin-2(1H)-one (Intermediate 19) (100 mg, 0.325 mmol), 3-oxo-3,4-dihydro-2H-pyrido[3,2-b][1,4]oxazine-6-carbaldehyde (WO 2004/058144) (58 mg, 0.325 mmol) and sodium triacetoxy borohydride (207 mg, 0.98 mmol) were reacted as described for Example 1, but the aqueous workup was omitted, to give 107 mg of the mono acetate salt of the product after chromatography, as a colorless solid, mp 158-170° C.

MS (ES): 470.13 (MH$^+$) for $C_{24}H_{25}F_2N_5O_3$ $^1$H-NMR (DMSO-d$_6$) δ: 1.20 (m, 2H); 1.75 (m, 2H); 1.89 (s, 3H); 2.03 (t, 2H); 2.36 (m, 1H); 2.55 (m, 2H); 2.82 (m, 2H); 3.66 (s, 2H); 4.40 (m, 2H); 4.59 (s, 2H); 6.60 (d, 1H); 7.00 (d, 1H); 7.28 (d, 1H); 7.34 (m, 1H); 7.60 (m, 1H); 7.91 (d, 1H); 11.17 (brs, 1H).

Intermediate 19

1-[2-(4-Aminopiperidin-1-yl)ethyl]-7,8-difluoro-quinolin-2(1H)-one

The title compound was obtained from tert-butyl{1-[2-(7,8-difluoro-2-oxoquinolin-1(2H)-yl)ethyl]piperidin-4-yl}carbamate (Intermediate 20) (412 mg, 1.01 mmol) by the procedure described for Intermediate 1, 316 mg (quantitative yield), as a colorless gum.

MS (ES): 308.29 (MH$^+$) for $C_{16}H_{19}F_2N_3O$ $^1$H-NMR (DMSO-d$_6$) δ: 1.15 (m, 2H); 1.46 (m, 1H); 1.62 (m, 2H); 2.03 (t, 2H); 2.53 (m, 2H, under solvent peak); 2.79 (m, 2H); 4.39 (m, 2H); 6.60 (d, 1H); 7.34 (m, 1H); 7.59 (m, 1H); 7.91 (d, 1H).

Intermediate 20 tert-Butyl{1-[2-(7,8-difluoro-2-oxoquinolin-1(2H)-yl)ethyl]piperidin-4-yl}carbamate 7,8-Difluoroquinolin-2(1H)-one (Intermediate 21) (500 mg, 2.8 mmol) was deprotonated with sodium hydride (121 mg, 60% in oil, 3.04 mmol) and alkylated with 2-{4-[(tert-butoxycarbonyl)amino]piperidin-1-yl}ethyl methanesulfonate (Intermediate 6) (3.3 mmol) as described for Intermediate 2. Chromatography on silica gel with hexanes/acetone 2:1 gave the product as a colorless solid, 414 mg (37%).

MS (ES): 408.30 (MH$^+$) for $C_{21}H_{27}F_2N_3O_3$ $^1$H-NMR (DMSO-d$_6$) δ: 1.32 (m, 2H); 1.36 (s, 9H); 1.65 (m, 2H); 2.04 (t, 2H); 2.53 (m, 2H); 2.83 (m, 2H); 3.16 (m, 1H); 4.38 (m, 2H); 6.61 (d, 1H); 6.75 (d, 1H); 7.34 (m, 1H); 7.60 (m, 1H); 7.91 (m, 1H).

Intermediate 21

7,8-Difluoroquinolin-2(1H)-one

The compound was prepared from (2E)-N-(2,3-difluorophenyl)-3-phenylacrylamide (Intermediate 22) (7.4 g, 28.5 mmol) and aluminium trichloride (19 g, 142 mmol) as described for Intermediate 17. The crude cyclization product was obtained as a single regioisomer, which was used without further purification, 2 g light brown solid (37%).

MS (ES): 182.04 (MH$^+$) for $C_9H_5F_2NO$ $^1$H-NMR (DMSO-d$_6$) δ: 6.51 (d, 1H); 7.22 (m, 1H); 7.52 (m, 1H); 7.91 (m, 1H).

Intermediate 22

(2E)-N-(2,3-Difluorophenyl)-3-phenylacrylamide

The compound was prepared from 2,3-difluoroaniline (5 g, 38.7 mmol) and cinnamoylchloride (6.45 g, 38.7 mmol) in the presence of 2,6-lutidine (6.8 mL, 58 mmol) as described for Intermediate 18 to give a colorless solid, 7.4 g (74%).

MS (ES): 260.08 (MH$^+$) for $C_{15}H_{11}F_2NO$ $^1$H-NMR (DMSO-d$_6$) δ: 7.05 (d, 1H); 7.14-7.22 (m, 2H); 7.40-7.50 (m, 3H); 7.59-7.64 (m, 3H); 7.89 (m, 1H); 10.16 (brs, 1H).

Example 8

6-[({1-[2-(5,7-Difluoro-2-oxoquinolin-1(2H)-yl)ethyl]piperidin-4-yl}amino)methyl]-2H-pyrido[3,2-b][1,4]oxazin-3(4H)-one 1-[2-(4-Aminopiperidin-1-yl)ethyl]-5,7-difluoroquinolin-2(1H)-one (Intermediate 23) (100 mg, 0.325 mmol), 3-oxo-3,4-dihydro-2H-pyrido[3,2-b][1,4]oxazine-6-carbaldehyde (WO 2004/058144) (58 mg, 0.325 mmol) and sodium triacetoxy borohydride (207 mg, 0.98 mmol) were reacted as described for Example 6, to give 114 mg of the mono acetate salt of the product as a colorless solid, mp 170-180° C.

MS (ES): 470.32 (MH$^+$) for $C_{24}H_{25}F_2N_5O_3$ $^1$H-NMR (DMSO-d$_6$) δ: 1.20 (m, 2H); 1.74 (m, 2H); 1.89 (s, 3H); 2.00 (t, 2H); 2.36 (m, 1H); 2.48 (m, 2H); 2.88 (m, 2H); 3.66 (s, 2H); 4.29 (t, 2H); 4.59 (s, 2H); 6.61 (d, 1H); 7.00 (d, 1H); 7.18-7.33 (m, 3H); 7.96 (d, 1H); 11.16 (brs, 1H).

Intermediate 23

1-[2-(4-Aminopiperidin-1-yl)ethyl]-5,7-difluoroquinolin-2(1H)-one

The title compound was obtained from tert-butyl{1-[2-(5,7-difluoro-2-oxoquinolin-1(2H)-yl)ethyl]piperidin-4-yl}carbamate (Intermediate 24) (637 mg, 1.01 mmol) by the procedure described for Intermediate 1, 483 mg (quantitative), as a colorless solid.

MS (ES): 308.27 (MH$^+$) for $C_{16}H_{19}F_2N_3O$ $^1$H-NMR (DMSO-d$_6$) δ: 1.15 (m, 2H); 1.46-1.64 (m, 3H); 2.00 (t, 2H); 2.46 (m, 2H, under solvent peak); 2.85 (m, 2H); 4.28 (t, 2H); 6.61 (d, 1H); 7.21 (m, 1H); 7.30 (d, 1H); 7.95 (d, 1H).

Intermediate 24 tert-Butyl{1-[2-(5,7-difluoro-2-oxoquinolin-1(2H)-yl)ethyl]piperidin-4-yl}carbamate 5,7-Difluoroquinolin-2(1H)-one (Intermediate 25) (500 mg, 2.8 mmol) was deprotonated with sodium hydride (121 mg, 60% in oil, 3.04 mmol) and alkylated with 2-{4-[(tert-butoxycarbonyl)amino]piperidin-1-yl}ethyl methanesulfonate (Intermediate 6) (3.3 mmol) as described for Intermediate 20. Colorless solid, 637 mg (57%).

MS (ES): 408.30 (MH$^+$) for $C_{21}H_{27}F_2N_3O_3$ $^1$H-NMR (DMSO-d$_6$) δ: 1.32 (m, 2H); 1.36 (s, 9H); 1.64 (m, 2H); 2.01 (t, 2H); 2.48 (m, 2H); 2.88 (m, 2H); 3.18 (m, 1H); 4.28 (m, 2H); 6.61 (d, 1H); 6.75 (d, 1H); 7.21 (m, 1H); 7.30 (d, 1H); 7.95 (m, 1H).

Intermediate 25

5,7-Difluoroquinolin-2(1H)-one

The compound was prepared from (2E)-N-(3,5-difluorophenyl)-3-phenylacrylamide (Intermediate 26) (8.1 g, 31.2 mmol) and aluminium trichloride (21 g, 156 mmol) in a similar way as described for Intermediate 21. 3.47 g light brown solid (61%), mp 292-318° C.

MS (ES): 181.98 (MH$^+$) for $C_9H_5F_2NO$ $^1$H-NMR (DMSO-d$_6$) δ: 6.51 (d, 1H); 6.90 (m, 1H); 7.10 (ddd, 1H); 7.93 (d, 1H); 12.05 (brs, 1H).

Intermediate 26

(2E)-N-(3,5-Difluorophenyl)-3-phenylacrylamide

The compound was prepared from 3,5-difluoroaniline (5 g, 38.7 mmol) and cinnamoylchloride (6.45 g, 38.7 mmol) in the presence of 2,6-lutidine (6.8 mL, 58 mmol) as described for Intermediate 18 to give a colorless solid, 8.1 g (81%).

MS (ES): 260.10 (MH$^+$) for $C_{15}H_{11}F_2NO$ $^1$H-NMR (DMSO-d$_6$) δ: 6.76 (d, 1H); 6.92 (m, 1H); 7.35-7.49 (m, 5H); 7.60-7.65 (m, 3H); 10.59 (s, 1H).

Example 9

6-[({1-[2-(7-Fluoro-2-oxoquinolin-1(2H)-yl)ethyl]piperidin-4-yl}amino)methyl]-2H-pyrido[3,2-b][1,4]oxazin-3(4H)-one 1-[2-(4-Aminopiperidin-1-yl)ethyl]-7-fluoroquinolin-2(1H)-one (Intermediate 27) (100 mg, 0.346 mmol), 3-oxo-3,4-dihydro-2H-pyrido[3,2-b][1,4]oxazine-6-carbaldehyde (WO 2004/058144) (62 mg, 0.346 mmol) and sodium triacetoxy borohydride (220 mg, 1.04 mmol) were reacted as described for Example 7 to give 115 mg (74%) of the monoacetate salt of the product as a colorless solid, mp 150-155° C.

MS (ES): 452.22 (MH$^+$) for $C_{24}H_{26}FN_5O_3$ $^1$H-NMR (DMSO-d$_6$) δ: 1.22 (m, 2H); 1.75 (m, 2H); 1.89 (s, 3H); 2.01 (t, 2H); 2.37 (m, 1H); 2.48 (m, 2H); 2.89 (m, 2H); 3.67 (s, 2H); 4.29 (t, 2H); 4.59 (s, 2H); 6.55 (d, 1H); 7.00 (d, 1H); 7.12 (ddd, 1H); 7.28 (d, 1H); 7.38 (dd, 1H); 7.78 (dd, 1H); 7.90 (d, 1H); 11.16 (brs, 1H).

Intermediate 27

1-[2-(4-Aminopiperidin-1-yl)ethyl]-7-fluoroquinolin-2(1H)-one

The title compound was obtained from tert-butyl{1-[2-(7-fluoro-2-oxoquinolin-1(2H)-yl)ethyl]piperidin-4-yl}carbamate (Intermediate 28) (565 mg, 1.45 mmol) by the procedure described for Intermediate 1, 425 mg (quantitative), as a colorless solid.

MS (ES): 290.19 (MH$^+$) for $C_{16}H_{20}FN_3O$ $^1$H-NMR (DMSO-d$_6$) δ: 1.16 (m, 2H); 1.62 (m, 2H); 2.00 (t, 2H); 2.46 (m, 2H, under solvent peak); 2.85 (m, 2H); 3.46 (m, 1H); 4.28 (t, 2H); 6.54 (d, 1H); 7.12 (ddd, 1H); 7.36 (dd, 1H); 7.76 (dd, 1H); 7.89 (d, 1H).

Intermediate 28 tert-Butyl{1-[2-(7-fluoro-2-oxoquinolin-1(2H)-yl)ethyl]piperidin-4-yl}carbamate

7-Fluoroquinolin-2(1H)-one (Intermediate 29) (500 mg, 3.06 mmol) was deprotonated with sodium hydride (135 mg, 60% in oil, 3.37 mmol) and alkylated with 2-{4-[(tert-butoxycarbonyl)amino]piperidin-1-yl}ethyl methanesulfonate (Intermediate 6) (3.7 mmol) as described for Intermediate 20. Colorless solid, 570 mg (48%).

MS (ES): 390.21 (MH$^+$) for $C_{21}H_{28}FN_3O_3$ $^1$H-NMR (DMSO-d$_6$) δ: 1.32 (m, 2H); 1.36 (s, 9H); 1.64 (m, 2H); 2.02 (t, 2H); 2.48 (m, 2H); 2.90 (m, 2H); 3.19 (m, 1H); 4.28 (m, 2H); 6.54 (d, 1H); 6.75 (d, 1H); 7.12 (m, 1H); 7.38 (m, 1H); 7.78 (dd, 1H); 7.90 (d, 1H).

Intermediate 29

7-Fluoroquinolin-2(1H)-one

The compound was prepared from 2E)-N-(3-fluorophenyl)-3-phenylacrylamide (Intermediate 30) (13.8 g, 57.2 mmol) and aluminium trichloride (30.5 g, 229 mmol) in a similar way as described for Intermediate 21 to give a mixture of the title compound together with the corresponding 5-fluoro regioisomer in a ratio of 3:1. This mixture was vigorously stirred in dichloromethane (100 mL) for 3 hours at room temperature and then filtered. The solid obtained was resuspended in diethyl ether (200 mL) and stirred like above and filtered to give 3.63 g (34%) of the crude product containing 12% of the 5-fluoro regioisomer. This was used without further purification for the next step.

MS (ES): 164.02 (MH$^+$) for $C_9H_6FNO$ $^1$H-NMR (CDCl$_3$/MeOD) δ: 6.31 (d, 1H); 6.73 (ddd); 6.79 (dd, 1H); 7.35 (dd, 1H); 7.60 (d, 1H).

Intermediate 30

(2E)-N-(3-Fluorophenyl)-3-phenylacrylamide

The compound was prepared from 3-fluoroaniline (5.8 mL, 60 mmol) and cinnamoylchloride (10 g, 60 mmol) in the presence of 2,6-lutidine (10.5 mL, 90 mmol) as described for Intermediate 18 to give a colorless solid, 13.9 g (96%), mp 110° C.

MS (ES): 242.20 (MH$^+$) for $C_{15}H_{12}FNO$ $^1$H-NMR (DMSO-d$_6$) δ: 6.80 (d, 1H); 6.89 (m, 1H); 7.31-7.48 (m, 5H); 7.58-7.65 (m, 3H); 7.73 (m, 1H); 10.43 (s, 1H).

Example 10

1-(2-{4-[(2,3-Dihydro[1,4]dioxino[2,3-c]pyridin-7-ylmethyl)amino]piperidin-1-yl}ethyl)-7-fluoroquinolin-2(1H)-one 1-[2-(4-Aminopiperidin-1-yl)ethyl]-7-fluoroquinolin-2 (1H)-one (Intermediate 27) (100 mg, 0.346 mmol), 2,3-dihydro[1,4]dioxino[2,3-c]pyridine-7-carbaldehyde (WO 2004/058144) (57 mg, 0.346 mmol) and sodium triacetoxy borohydride (220 mg, 1.04 mmol) were reacted as described for Example 7. The free base obtained after chromatography was dissolved in dichloromethane/ether (10 mL, 1:1) and HCl in ether (1M, 1 mL) was added under vigorous stirring. It was evaporated to dryness under reduced pressure and the residue was taken up as a suspension in dichloromethane/hexanes (10 mL, 1:1). It was filtered and dried to give 118 mg (78%) of the bis HCl salt of the product as a colorless solid, mp>275° C. (decomposed).

MS (ES): 439.23 (MH$^+$) for $C_{24}H_{27}FN_4O_3$ $^1$H-NMR (DMSO-d$_6$) δ: 2.10 (m, 2H); 2.37 (m, 2H); 3.10 (m, 2H); 3.20-3.38 (m, 3H); 3.78 (m, 2H); 4.27 (m, 2H); 4.37 (m, 2H); 4.43 (m, 2H); 4.62 (t, 2H); 6.60 (d, 1H); 7.19 (ddd, 1H); 7.41 (s, 1H); 7.78 (dd, 1H); 7.84 (dd, 1H); 7.98 (d, 1H); 8.31 (s, 1H); 9.91 (brs, 2H); 11.04 (brs, 1H).

Example 11

6-[({1-[2-(7-Methoxy-2-oxo-3,4-dihydroquinolin-1 (2H)-yl)ethyl]piperidin-4-yl}amino)methyl]-2H-pyrido[3,2-b][1,4]oxazin-3(4H)-one 1-[2-(4-Aminopiperidin-1-yl)ethyl]-7-methoxy-3,4-dihydroquinolin-2(1H)-one (Intermediate 31) (110 mg, 0.36 mmol), 3-oxo-3,4-dihydro-2H-pyrido[3,2-b][1,4]oxazine-6-carbaldehyde (WO 2004/058144) (65 mg, 0.325 mmol) and sodium triacetoxy borohydride (220 mg, 1.04 mmol) were reacted as described for Example 1, but the aqueous workup was omitted. Chromatography on a Phenomenex Synergy Polar-RP4 μm column, eluent: 30-60% acetonitrile, 10 mM ammonium acetate pH8, followed by chromatography on silica gel with dichloromethane/methanol (7:1). The bis HCl salt of the product was prepared as described for Example 10 to give 46 mg (24%) as a colorless solid, mp>285° C. (dec).

MS (ES): 466.21 (MH$^+$) for $C_{25}H_{31}N_5O_4$ $^1$H-NMR (DMSO-d$_6$) δ: 2.10 (m, 2H); 2.36 (m, 2H); 2.53 (t, 2H); 2.86 (t, 2H); 3.10 (m, 2H); 3.16 (m, 2H); 3.36 (m, 1H); 3.70 (m, 2H); 3.73 (s, 3H); 4.16 (m, 2H); 4.28 (m, 2H); 4.70 (s, 2H); 6.80 (m, 1H); 6.86 (s, 1H); 7.23-7.28 (m, 2H); 7.45 (d, 1H); 9.70 (brs, 2H); 11.07 (brs, 1H); 11.37 (s, 1H).

Intermediate 31

1-[2-(4-Aminopiperidin-1-yl)ethyl]-7-methoxy-3,4-dihydroquinolin-2(1H)-one

The title compound was obtained from tert-butyl{1-[2-(7-methoxy-2-oxo-3,4-dihydroquinolin-1(2H)-yl)ethyl]piperidin-4-yl}carbamate (Intermediate 32) (550 mg, 1.36 mmol) by the procedure described for Intermediate 1, 338 mg (82%), as a colorless oil.

MS (ES): 304.23 (MH$^+$) for $C_{17}H_{25}N_3O_4$ $^1$H-NMR (DMSO-d$_6$) δ: 1.19 (m, 2H); 1.62 (m, 2H); 1.96 (t, 2H); 2.36 (t, 2H); 2.46 (m, 2H); 2.73-2.80 (m, 5H); 3.71 (s, 3H); 3.91 (m, 2H); 6.77-6.84 (m, 2H); 7.04 (m, 1H).

Intermediate 32 tert-Butyl{1-[2-(7-methoxy-2-oxo-3,4-dihydroquinolin-1(2H)-yl)ethyl]piperidin-4-yl}carbamate 7-Methoxy-3,4-dihydroquinolin-2(1H)-one (Intermediate 33) (300 mg, 1.78 mmol) was deprotonated with sodium hydride (75 mg, 60% in oil, 1.86 mmol) and alkylated with 2-{4-[(tert-butoxycarbonyl)amino]piperidin-1-yl}ethyl methanesulfonate (Intermediate 6) (2.03 mmol) as described for Intermediate 2. Chromatography on silica gel eluting with ethyl acetate and then acetone/dichloromethane (4:1) gave the product as a colorless oil, 559 mg (82%).

MS (ES): 404.21 (MH$^+$) for $C_{22}H_{33}N_3O_4$ $^1$H-NMR (DMSO-d$_6$) δ: 1.32 (m, 2H); 1.36 (s, 9H); 1.64 (m, 2H); 1.93-2.00 (m, 4H); 2.37 (m, 2H); 2.47 (m, 2H); 2.78 (m, 2H); 3.16 (m, 1H); 3.71 (s, 3H); 3.91 (t, 2H); 6.72-6.82 (m, 3H); 7.05 (d, 1H).

Intermediate 33

7-Methoxy-3,4-dihydroquinolin-2(1H)-one

A mixture of 7-hydroxy-3,4-dihydroquinolin-2(1H)-one (3.0 g, 17 mmol) and triethyl amine (3.14 mL, 22 mmol) in dichloromethane/methanol/acetonitrile (10:1:10, 168 mL) was treated with (trimethylsilyl)diazomethane (2M solution in hexanes, 10.25 mL, 20.5 mmol). It was stirred over night at room temperature, the solvent was removed under reduced pressure and chromatography on silica gel with hexanes/acetone (1:1) gave 2.2 g (67%) of the product as a colorless solid.

MS (ES): 178.16 (MH$^+$) for $C_{10}H_{11}NO_2$ $^1$H-NMR (DMSO-d$_6$) δ: 2.38 (t, 2H); 2.81 (t, 2H); 3.68 (s, 3H); 6.68-6.78 (m, 3H); 9.90 (brs, 1H).

Example 12

(3S,4R)-1-[2-(5,7-Difluoro-2-oxoquinolin-1(2H)-yl) ethyl]-4-[(2,3-dihydro[1,4]dioxino[2,3-c]pyridin-7-ylmethyl)amino]piperidine-3-carboxylic acid A solution of methyl(3S,4R)-1-[2-(5,7-difluoro-2-oxoquinolin-1(2H)-yl)ethyl]-4-[(2,3-dihydro[1,4]dioxino[2,3-c]pyridin-7-ylmethyl)amino]piperidine-3-carboxylate (Example 13) (120 mg, 0.233 mmol) in tetrahydrofuran/water (1:1, 10 mL) was treated with sodium hydroxide (15% aqueous, 0.2 mL) at room temperature for 3 hours. It was quenched with glacial acetic acid (1 mL) and concentrated to dryness under reduced pressure. Chromatography on a C18 cartridge (RediSep, ISCO) with 0-25% acetonitrile in water, containing 0.1% acetic acid and treatment with HCl as described for Example 10 gave 113 mg (90%) of the mono hydrochloride salt of the product as a colorless solid, mp 100-180° C.

MS (ES): 501.03 (MH$^+$) for $C_{25}H_{26}F_2N_4O_5$ $^1$H-NMR (DMSO-d$_6$) δ: 2.02 (m, 2H); 2.60 (m, 2H); 3.15-3.51 (m, 8H); 4.18 (m, 2H); 4.33 (m, 2H); 4.37 (m, 2H); 4.50 (m, 1H); 6.62 (d, 1H); 7.12 (s, 1H); 7.24 (m, 1H); 7.41 (m, 1H); 7.98 (d, 1H); 8.15 (s, 1H).

Example 13

(3S,4R)-1-[2-(5,7-Difluoro-2-oxoquinolin-1(2H)-yl) ethyl]-4-{[(2E)-3-(2,5-difluorophenyl)prop-2-en-1-yl]amino}piperidine-3-carboxylic acid Methyl(3S,4R)-1-[2-(5,7-difluoro-2-oxoquinolin-1(2H)-yl)ethyl]-4-{[(2E)-3-(2,5-difluorophenyl)prop-2-en-1-yl]amino}piperidine-3-carboxylate (Example 15) (80 mg, 0.155 mmol) was treated with sodium hydroxide as described for Example 12 to give 51 mg (61%) of the mono hydrochloride salt of the product as a colorless solid, mp 150-180° C.

MS (ES): 504.19 (MH$^+$) for $C_{26}H_{25}F_4N_3O_3$ $^1$H-NMR (DMSO-d$_6$) δ: 2.10 (m, 2H); 2.75-3.75 (m, 8H); 3.86 (m, 2H); 4.33 (m, 1H); 4.54 (m, 1H); 6.50 (m, 1H); 6.64 (d, 1H); 6.91 (d, 1H); 7.19-7.34 (m, 3H); 7.48 (m, 2H); 8.00 (s, 1H); 9.19 (brs, 1H).

Example 14

Methyl(3S,4R)-1-[2-(5,7-difluoro-2-oxoquinolin-1(2H)-yl)ethyl]-4-[(2,3-dihydro[1,4]dioxino[2,3-c]pyridin-7-ylmethyl)amino]piperidine-3-carboxylate Methyl(3S,4R)-4-amino-1-[2-(5,7-difluoro-2-oxoquinolin-1(2H)-yl)ethyl]piperidine-3-carboxylate (Intermediate 34) (120 mg, 0.328 mmol), 2,3-dihydro[1,4]dioxino[2,3-c]pyridine-7-carbaldehyde (WO 2004/058144) (54 mg, 0.328 mmol) and sodium triacetoxy borohydride (209 mg, 0.98 mmol) were reacted as described for Example 6. Chromatography on silica gel with dichloromethane/methanol (20:1) gave 130 mg (77%) of product as a colorless hard foam.

MS (ES): 515.03 (MH$^+$) for $C_{26}H_{28}F_2N_4O_5$ $^1$H-NMR (DMSO-d$_6$) δ: 1.52 (m, 1H); 1.75 (m, 1H); 2.43 (m, 1H); 2.50 (m, 1H); 2.54 (m, 2H); 2.60-2.73 (m, 3H); 2.87 (m, 1H); 3.51 (s, 3H); 3.53 (d, 1H); 3.69 (d, 1H); 4.22-4.34 (m, 6H); 6.61 (d, 1H); 6.86 (s, 1H); 7.21 (m, 1H); 7.30 (m, 1H); 7.95 (d, 1H); 7.97 (s, 1H).

Example 15

Methyl(3S,4R)-1-[2-(5,7-difluoro-2-oxoquinolin-1(2H)-yl)ethyl]-4-{[(2E)-3-(2,5-difluorophenyl)prop-2-en-1-yl]amino}piperidine-3-carboxylate Methyl(3S,4R)-4-amino-1-[2-(5,7-difluoro-2-oxoquinolin-1(2H)-yl)ethyl]piperidine-3-carboxylate (Intermediate 34) (120 mg, 0.328 mmol), (2E)-3-(2,5-difluorophenyl)acrylaldehyde (FR 2872164) (54 mg, 0.328 mmol) and sodium triacetoxy borohydride (209 mg, 0.98 mmol) were reacted as described for Example 6. Chromatography on silica gel with dichloromethane/N,N-dimethylformamide (30:1) gave 83 mg (49%) of product as a colorless hard foam.

MS (ES): 518.10 (MH$^+$) for $C_{27}H_{27}F_4N_3O_3$ $^1$H-NMR (DMSO-d$_6$) δ: 1.56 (m, 1H); 1.75 (m, 1H); 1.90 (m, 1H); 2.41 (m, 1H); 2.51-2.72 (m, 5H); 2.90 (m, 1H); 3.25 (dd, 1H); 3.39 (dd, 1H); 3.51 (s, 3H); 4.29 (m, 2H); 6.42 (m, 1H); 6.57 (d, 1H); 6.61 (d, 1H); 7.09 (m, 1H); 7.17-7.24 (m, 2H); 7.30 (m, 1H); 7.43 (m, 1H); 7.95 (d, 1H).

Intermediate 34

Methyl(3S,4R)-4-amino-1-[2-(5,7-difluoro-2-oxoquinolin-1(2H)-yl)ethyl]piperidine-3-carboxylate A solution of methyl(3S,4R)-4-{[(benzyloxy)carbonyl] amino}-1-[2-(5,7-difluoro-2-oxoquinolin-1(2H)-yl)ethyl] piperidine-3-carboxylate (Intermediate 35) (595 mg, 1.19 mmol) in methanol (10 mL) was hydrogenated over palladium on carbon (10%, wet) at normal pressure and room temperature for 30 minutes. It was filtered through a 0.45 μm membrane, washed with methanol and the wash and filtrate were concentrated under reduced pressure to give 395 mg (91%) of the product as a colorless hard foam.

MS (ES): 365.98 (MH$^+$) for $C_{18}H_{21}F_2N_3O_3$ $^1$H-NMR (DMSO-d$_6$) δ: 1.58 (m, 2H); 2.37-2.69 (m, 7H); 3.14 (m, 1H); 3.53 (s, 3H); 4.28 (m, 2H); 6.60 (d, 1H); 7.21 (m, 1H); 7.30 (m, 1H); 7.95 (d, 1H).

Intermediate 35

Methyl(3S,4R)-4-{[(benzyloxy)carbonyl]amino}-1-[2-(5,7-difluoro-2-oxoquinolin-1(2H)-yl)ethyl]piperidine-3-carboxylate 5,7-Difluoroquinolin-2(1H)-one (Intermediate 25) (350 mg, 1.93 mmol) was deprotonated with sodium hydride (85 mg, 60% in oil, 2.13 mmol) and alkylated with methyl (3S,4R)-4-{[(benzyloxy)carbonyl]amino}-1-(2-chloroethyl)piperidine-3-carboxylate (Intermediate 36) (1.93 mmol) as described for Intermediate 20. Colorless hard foam, 604 mg (63%).

MS (ES): 500.05 (MH$^+$) for $C_{26}H_{27}F_2N_3O_5$ $^1$H-NMR (60° C.) (DMSO-d$_6$) δ: 1.64 (m, 1H); 1.72 (m, 1H); 2.44 (m, 1H); 2.59 (t, 2H); 2.61-2.76 (m, 3H); 2.85 (dd, 1H); 3.49 (s, 3H); 3.93 (m, 1H); 4.28 (m, 2H); 4.99 (d, 1H); 5.03 (d, 1H); 6.60 (d, 1H); 6.90 (m, 1H); 7.13 (m, 1H); 7.24-7.37 (m, 6H); 7.93 (d, 1H).

Intermediate 36

Methyl(3S,4R)-4-{[(benzyloxy)carbonyl]amino}-1-(2-chloroethyl)piperidine-3-carboxylate Methyl(3S,4R)-4-{[(benzyloxy)carbonyl]amino}-1-(2-hydroxyethyl)piperidine-3-carboxylate (Intermediate 37) (650 mg, 1.93 mmol) was reacted with methanesulfonyl chloride (0.18 mL, 2.32 mmol) in the presence of triethylamine (0.38 mL, 2.7 mmol) as described for Intermediate 6. The crude chloride was used without delay for the next step.

MS (ES): 355/357 (MH$^+$) for $C_{17}H_{23}N_2O_4$

Intermediate 37

Methyl(3S,4R)-4-{[(benzyloxy)carbonyl]amino}-1-(2-hydroxyethyl)piperidine-3-carboxylate A mixture of methyl(3S,4R)-4-{[(benzyloxy)carbonyl]amino}piperidine-3-carboxylate (WO 2005/066176) (2.29 g, 7.83 mmol), N,N-diisopropylethylamine (2.05 mL, 11.75 mmol and 2-bromoethanol (0.722 mL, 10.18 mmol) in dry acetonitrile (17 mL) was heated in the microwave at 70° C. for 4.5 hours. The solvent was removed under reduced pressure and the residue taken up in ethyl acetate (200 mL) and washed with saturated aqueous sodium hydrogencarbonate solution (100 mL). The aqueous phase was back extracted once with ethyl acetate (100 mL) and the combined organic phases were dried over sodium sulfate. Chromatography on silica gel with dichloromethane/methanol (12:1) gave 2.0 g (76%), mp 73° C.

MS (ES): 337.16 (MH$^+$) for $C_{17}H_{24}N_2O_5$ $^1$H-NMR (DMSO-d$_6$) δ: 1.66 (m, 2H); 2.34-2.55 (m, 5H); 2.67-2.79 (m, 2H); 3.44 (dt, 2H); 3.51 (s, 3H); 3.95 (m, 1H); 4.31 (t, 1H); 4.97 (d, 1H); 5.02 (d, 1H); 7.21 (d, 1H); 7.25-7.38 (m, 5H).

Example 16

(3R,4R)-1-[2-(5,7-Difluoro-2-oxoquinolin-1(2H)-yl)ethyl]-4-[(2,3-dihydro[1,4]dioxino[2,3-c]pyridin-7-ylmethyl)amino]piperidine-3-carboxylic acid Methyl(3R,4R)-1-[2-(5,7-difluoro-2-oxoquinolin-1(2H)-yl)ethyl]-4-[(2,3-dihydro[1,4]dioxino[2,3-c]pyridin-7-ylmethyl)amino]piperidine-3-carboxylate (Example 18) (201 mg, 0.4 mmol) was saponified and converted into the bis hydrochloride salt as described for Example 12, 194 mg (87%), colorless solid, mp>190° C.

MS (ES): 501.22 (MH$^+$) for $C_{25}H_{26}F_2N_4O_5$ $^1$H-NMR (DMSO-d$_6$) δ: 2.24 (m, 1H); 2.46 (m, 1H); 3.12 (m, 1H); 3.34 (m, 4H); 3.58 (m, 1H); 3.83 (m, 1H); 3.93 (m, 1H); 4.24 (d, 1H); 4.31-4.44 (m, 5H); 4.63 (m, 2H); 6.66 (d, 1H); 7.26-7.31 (m, 2H); 7.69 (d, 1H); 8.02 (d, 1H); 8.25 (s, 1H); 11.51 (bs, 1H).

Example 17

(3R,4R)-1-[2-(5,7-Difluoro-2-oxoquinolin-1(2H)-yl)ethyl]-4-{[(2E)-3-(2,5-difluorophenyl)prop-2-en-1-yl]amino}piperidine-3-carboxylic acid Methyl(3R,4R)-1-[2-(5,7-difluoro-2-oxoquinolin-1(2H)-yl)ethyl]-4-{[(2E)-3-(2,5-difluorophenyl)prop-2-en-1-yl]amino}piperidine-3-carboxylate (Example 19) (106 mg, 0.2 mmol) was treated with sodium hydroxide as described for Example 12 to give 82 mg (69%) of the bis hydrochloride salt of the product as a colorless solid, mp>205° C.

MS (ES): 504.23 (MH$^+$) for $C_{26}H_{25}F_4N_3O_3$ $^1$H-NMR (DMSO-d$_6$) δ: 2.15 (m, 1H); 2.40 (m, 1H); 3.01-3.98 (m, 10H); 4.60 (m, 2H); 6.50 (m, 1H); 6.67 (d, 1H); 6.95 (d, 1H); 7.20-7.35 (m, 3H); 7.47 (m, 1H); 7.62 (m, 1H); 8.02 (d, 1H).

Example 18

Methyl(3R,4R)-1-[2-(5,7-difluoro-2-oxoquinolin-1(2H)-yl)ethyl]-4-[(2,3-dihydro[1,4]dioxino[2,3-c]pyridin-7-ylmethyl)amino]piperidine-3-carboxylate Methyl(3R,4R)-4-amino-1-[2-(5,7-difluoro-2-oxoquinolin-1(2H)-yl)ethyl]piperidine-3-carboxylate (Intermediate 38) (195 mg, 0.53 mmol), 2,3-dihydro[1,4]dioxino[2,3-c]pyridine-7-carbaldehyde (WO 2004/058144) (88 mg, 0.53 mmol) and sodium triacetoxy borohydride (339 mg, 1.6 mmol) were reacted as described for Example 14 to give 216 mg (79%) of product as a colorless hard foam.

MS (ES): 515.23 (MH$^+$) for $C_{26}H_{28}F_2N_4O_5$ $^1$H-NMR (DMSO-d$_6$) δ: 1.18 (m, 1H); 1.92 (m, 1H); 2.05 (ddd, 1H); 2.14 (dd, 1H); 2.34 (ddd, 1H); 2.52 (t, 2H); 2.57 (m, 1H); 2.88 (m, 1H); 3.03 (m, 1H); 3.57 (d, 1H); 3.58 (s, 3H); 3.69 (d, 1H); 4.24-4.33 (m, 6H); 6.61 (d, 1H); 6.87 (s, 1H); 7.21 (ddd, 1H); 7.33 (m, 1H); 7.93-7.96 (m, 2H).

Example 19

Methyl(3R,4R)-1-[2-(5,7-difluoro-2-oxoquinolin-1(2H)-yl)ethyl]-4-{[(2E)-3-(2,5-difluorophenyl)prop-2-en-1-yl]amino}piperidine-3-carboxylate Methyl(3R,4R)-4-amino-1-[2-(5,7-difluoro-2-oxoquinolin-1(2H)-yl)ethyl]piperidine-3-carboxylate (Intermediate 38) (195 mg, 0.53 mmol), (2E)-3-(2,5-difluorophenyl)acrylaldehyde (FR 2872164) (90 mg, 0.53 mmol) and sodium triacetoxy borohydride (339 mg, 1.6 mmol) were reacted as described for Example 6. Chromatography on silica gel with dichloromethane/N,N-dimethylformamide (25:1 to 15:1) gave 119 mg (43%) of product as a colorless oil.

MS (ES): 518.25 (MH$^+$) for $C_{27}H_{27}F_4N_3O_3$ $^1$H-NMR (DMSO-d$_6$) δ: 1.20 (m, 1H); 1.94 (m, 1H); 2.08 (ddd, 1H); 2.16 (dd, 1H); 2.34 (ddd, 1H); 2.53 (t, 2H); 2.61 (ddd, 1H); 2.90 (m, 1H); 3.04 (m, 1H); 3.24 (dd, 1H); 3.39

(dd, 1H); 3.58 (s, 3H); 4.28 (m, 2H); 6.40 (m, 1H); 6.55-6.62 (m, 2H); 7.05-7.25 (m, 3H); 7.32 (d, 1H); 7.42 (m, 1H); 7.95 (d, 1H).

Intermediate 38

Methyl(3R,4R)-4-amino-1-[2-(5,7-difluoro-2-oxo-quinolin-1(2H)-yl)ethyl]piperidine-3-carboxylate Methyl(3R,4R)-4-{[(benzyloxy)carbonyl]amino}-1-[2-(5,7-difluoro-2-oxoquinolin-1(2H)-yl)ethyl]piperidine-3-carboxylate (Intermediate 39) (535 mg, 1.07 mmol) was hydrogenated as described for Intermediate 34 to give 391 mg (quantitative) of the product as a colorless hard foam.

MS (ES): 366 (MH$^+$) for $C_{18}H_{21}F_2N_3O_3$

Intermediate 39

Methyl(3R,4R)-4-{[(benzyloxy)carbonyl]amino}-1-[2-(5,7-difluoro-2-oxoquinolin-1(2H)-yl)ethyl]piperidine-3-carboxylate 5,7-Difluoroquinolin-2(1H)-one (Intermediate 25) (350 mg, 1.93 mmol) was deprotonated with sodium hydride (85 mg, 60% in oil, 2.13 mmol) and alkylated with methyl (3R,4R)-4-{[(benzyloxy)carbonyl]amino}-1-{2-[(methylsulfonyl)oxy]ethyl}piperidine-3-carboxylate (Intermediate 40) (1.93 mmol) as described for Intermediate 20 to give the product as a colorless hard foam, 538 mg (56%).

MS (ES): 500.38 (MH$^+$) for $C_{26}H_{27}F_2N_3O_5$
$^1$H-NMR (60° C.) (DMSO-d$_6$) δ: 1.40 (dddd, 1H); 1.70 (m, 1H); 2.10-1.45 (m, 2H); 2.44 (ddd, 1H); 2.54 (t, 2H); 2.89 (m, 1H); 3.07 (m, 1H); 3.49 (s, 3H); 3.54 (m, 1H); 4.28 (m, 2H); 4.95 (d, 1H); 4.99 (d, 1H); 6.61 (d, 1H); 7.21 (ddd, 1H); 7.29-7.37 (m, 7H); 7.95 (d, 1H).

Intermediate 40

Methyl(3R,4R)-4-{[(benzyloxy)carbonyl]amino}-1-{2-[(methylsulfonyl)oxy]ethyl}piperidine-3-carboxylate Methyl(3R,4R)-4-{[(benzyloxy)carbonyl]amino}-1-(2-hydroxyethyl)piperidine-3-carboxylate (Intermediate 41) (650 mg, 1.93 mmol) was reacted with methanesulfonyl chloride (0.18 mL, 2.32 mmol) in the presence of triethylamine (0.38 mL, 2.7 mmol) as described for Intermediate 6. The crude product was used without delay for the next step.

MS (ES): 415.3 (MH$^+$ for $C_{18}H_{26}N_2O_7S$

Intermediate 41

Methyl(3R,4R)-4-{[(benzyloxy)carbonyl]amino}-1-(2-hydroxyethyl)piperidine-3-carboxylate Methyl(3S,4R)-4-{[(benzyloxy)carbonyl]amino}piperidine-3-carboxylate (WO 2005/066176) (2.0 g, 6.84 mmol), N,N-diisopropylethylamine (1.8 mL, 10.26 mmol) and 2-bromoethanol (0.63 mL, 8.9 mmol) were reacted as described for Intermediate 37 to give 1.38 g (60%) of the product as a colorless oil.

MS (ES): 337.36 (MH$^+$) for $C_{17}H_{24}N_2O_5$
$^1$H-NMR (DMSO-d$_6$) δ: 1.43 (dddd, 1H); 1.70 (m, 1H); 1.97-2.14 (m, 2H); 2.37 (t, 2H); 2.49 (m, 1H); 2.80 (m, 1H); 2.94 (m, 1H); 3.44 (dt, 2H); 3.50 (s, 3H); 3.54 (m, 1H); 4.39 (t, 1H); 4.95 (d, 1H); 5.00 (d, 1H); 7.27-7.38 (m, 6H).

Example 20

Cis(±)6-[({1-[2-(5,7-difluoro-2-oxoquinolin-1(2H)-yl)ethyl]-3-hydroxypiperidin-4-yl}amino)methyl]-2H-pyrido[3,2-b][1,4]oxazin-3(4H)-one Cis(±)1-{2-[4-amino-3-hydroxypiperidin-1-yl]ethyl}-5,7-difluoroquinolin-2(1H)-one (175 mg, 0.54 mmol), 3-oxo-3,4-dihydro-2H-pyrido[3,2-b][1,4]oxazine-6-carbaldehyde (WO 2004/058144) (96 mg, 0.54 mmol) and sodium triacetoxy borohydride (344 mg, 1.6 mmol) were reacted as described for Example 1 to give 186 mg (71%) of the free base of the product as a colorless oil.

MS (ES): 486.24 (MH$^+$) for $C_{24}H_{25}F_2N_5O_5$
$^1$H-NMR (MeOD) δ: 1.67-1.78 (m, 2H); 2.22 (m, 1H); 2.33 (d, 1H); 2.55-2.69 (m, 3H); 2.90 (m, 1H); 3.06 (m, 1H); 3.75 (d, 1H); 3.79 (d, 1H); 3.91 (m, 1H); 4.30-4.46 (m, 2H); 4.59 (s, 2H); 6.61 (d, 1H); 6.93 (ddd, 1H); 6.95 (d, 1H); 7.21 (d, 1H); 7.27 (m, 1H); 7.96 (d, 1H).

Intermediate 42

Cis(±)1-{2-[4-amino-3-hydroxypiperidin-1-yl]ethyl}-5,7-difluoroquinolin-2(1H)-one Cis(±)1-{2-[4-azido-3-hydroxypiperidin-1-yl]ethyl}-5,7-difluoroquinolin-2(1H)-one (Intermediate 43) (190 mg, 0.54 mmol) was hydrogenated as described for Intermediate 34, for 3 hours, to give the product as a colorless oil, 175 mg (quantitative).

MS (ES): 324.02 (MH$^+$) for $C_{16}H_{19}F_2N_3O_2$
$^1$H-NMR (CDCl$_3$) δ: 1.82 (m, 2H); 2.25 (ddd, 1H); 2.39 (d, 1H); 2.62-2.73 (m, 3H); 2.90 (m, 1H); 2.98 (m, 1H); 3.13 (m, 1H); 3.92 (m, 1H); 4.23 (ddd, 1H); 4.44 (ddd, 1H); 6.63 (d, 1H); 6.70 (ddd, 1H); 6.91 (d, 1H); 7.85 (d, 1H).

Intermediate 43

Cis(±)1-{2-[4-azido-3-hydroxypiperidin-1-yl]ethyl}-5,7-difluoroquinolin-2(1H)-one 5,7-Difluoroquinolin-2(1H)-one (Intermediate 25) (389 mg, 2.15 mmol) was deprotonated with sodium hydride (95 mg, 60% in oil, 2.36 mmol) and alkylated with cis(±) 2-(4-azido-3-hydroxypiperidin-1-yl)ethyl methanesulfonate (Intermediate 44) (2.15 mmol) as described for Intermediate 20, except after 24 hours, potassium carbonate (100 mg, 0.72 mmol) was added and the resulting mixture was stirred for another 24 hours at room temperature to give the product as a colorless hard foam, 195 mg (26%).

MS (ES): 350.15 (MH$^+$) for $C_{16}H_{17}F_2N_5O_2$
$^1$H-NMR (DMSO-d$_6$) δ: 1.56 (m, 1H); 1.71 (m, 1H); 2.32 (m, 1H); 2.40 (m, 1H); 2.48 (m, 1H); 2.53 (dd, 2H); 2.59 (m, 1H); 3.61-3.71 (m, 2H); 4.29 (dd, 2H); 5.05 (d, 1H); 6.61 (d, 1H); 7.21 (ddd, 1H); 7.32 (d, 1H); 7.95 (d, 1H).

Intermediate 44

Cis(±)2-(4-azido-3-hydroxypiperidin-1-yl)ethyl methanesulfonate

A solution of cis(±)4-azido-1-(2-hydroxyethyl)piperidin-3-ol (Intermediate 45) (0.4 g, 2.15 mmol) in dry dichloromethane (15 mL) and 2,6-lutidine (0.325 mL, 2.8 mmol) was treated at −20° C. dropwise with a solution of methanesulfonyl chloride (0.175 mL, 2.26 mmol) in dichloromethane (5 mL). The temperature was allowed to reach 0° C. and kept at 0° C. for 10 hours. The resulting reaction mixture was diluted with dichloromethane (50 mL) and washed with saturated aqueous sodium hydrogen carbonate solution (10 mL). The aqueous phase was back extracted with dichloromethane (20 mL) and the combined organic phases were dried over sodium sulfate. The solvent was removed under reduced pressure, and the residue was codistilled with dry DMF (10 mL) without heating. This crude preparation of the mesylate was used without further purification directly for the next step.

MS (ES): 265.02 (MH$^+$) for $C_8H_{16}N_4O_4S$

Intermediate 45

Cis(±)4-azido-1-(2-hydroxyethyl)piperidin-3-ol

Cis(±)4-azidopiperidin-3-ol (prepared following the procedure described in WO 2005/066176 for the chiral material) (0.945 g, 6.65 mmol), N,N-diisopropylethylamine (1.7 mL, 10 mmol) and 2-bromoethanol (0.61 mL, 8.64 mmol) were reacted as described for Intermediate 37, except heating for one hour. The solvent was removed under reduced pressure. The residue was taken up in dichloromethane (100 mL), washed with 1M sodium hydroxide solution (30 mL) and the aqueous phase was back extracted five times with dichloromethane (5×100 mL). The combined organic phases were dried over sodium sulfate. Chromatography on silica gel with dichloromethane/methanol 3:1 gave 1.15 g (93%) of the product as a colorless oil.

MS (ES): 187.24 (MH$^+$) for $C_7H_{14}N_4O_2$
$^1$H-NMR (DMSO-d$_6$) δ: 1.61 (m, 1H); 1.72 (m, 1H); 2.28-2.38 (m, 5H); 2.45 (m, 1H); 3.43 (ddd, 2H); 3.57 (m, 1H); 3.73 (m, 1H); 4.33 (dd, 1H); 5.01 (d, 1H).

Example 21

4-(2-{4-[(2,3-Dihydro[1,4]dioxino[2,3-c]pyridin-7-ylmethyl)amino]piperidin-1-yl}ethyl)-6-methoxy-2H-1,4-benzoxazin-3(4H)-one A mixture of 4-[2-(4-aminopiperidin-1-yl)ethyl]-6-methoxy-2H-1,4-benzoxazin-3(4H)-one trifluoroacetate (Intermediate 46) (0.4 mmol), N,N-diisopropylethylamine (1 mL) and 2,3-dihydro[1,4]dioxino[2,3-c]pyridine-7-carbaldehyde (WO 2004/058144) (74 mg, 0.45 mmol) in dichloroethane/methanol (1:1, 10 mL) was reacted and reduced with sodium cyanoborohydride (50 mg, 0.74 mmol) as described for Example 4. Reverse phase chromatography with water/acetonitrile/trifluoroacetic acid gave the product as the trifluoroacetic acid salt. The salt was dissolved in water and chloroform and basified with saturated sodium carbonate. The layers were separated and the aqueous was extracted with chloroform. The organic extracts were dried over magnesium sulfate and evaporated to dryness to give the free base of the title compound as a gum, 54 mg (32%).

MS (ES): 455.33 (MH$^+$) for $C_{24}H_{30}N_4O_5$
$^1$H-NMR (CDCl$_3$-d) δ: 1.46 (m, 2H); 1.88 (m, 2H); 2.14 (m, 2H); 2.54 (m, 1H); 2.58 (t, J=7.3 Hz, 2H); 2.95 (m, 2H); 3.78 (s, 3H); 3.79 (s, 2H); 4.01 (t, J=7.4 Hz, 2H); 4.29 (m, 4H); 4.52 (s, 2H); 6.50 (dd, J=6.2, 2.7 Hz, 1H); 6.67 (d, J=2.7 Hz, 1H); 6.81 (s, 1H); 6.89 (d, J=8.7 Hz, 1H); 8.08 (s, 1H).

Intermediate 46

4-[2-(4-Aminopiperidin-1-yl)ethyl]-6-methoxy-2H-1,4-benzoxazin 3(4H)-one tert-Butyl{1-[2-(6-methoxy-3-oxo-2,3-dihydro-4H-1,4-benzoxazin-4-yl)ethyl]piperidine-4-yl}carbamate (Intermediate 47) (510 mg, 1.26 mmol) was reacted as described for Intermediate 14. The crude trifluoro acetate of the title compound was used without further purification for the next step (quantitative yield).

MS (ES): 306 (MH$^+$) for $C_{15}H_{22}N_4O_3$

Intermediate 47 tert-Butyl{1-[2-(6-methoxy-3-oxo-2,3-dihydro-4H-1,4-benzoxazin-4-yl)ethyl]piperidin-4-yl}carbamate 6-Methoxy-2H-1,4-benzoxazin-3(4H)-one (Intermediate 48) (380 mg, 2.1 mmol) was deprotonated with sodium hydride (100 mg, 60% in oil, 2.5 mmol) and alkylated with 2-{4-[(tert-butoxycarbonyl)amino]piperidin-1-yl}ethyl methanesulfonate (Intermediate 6) (2.3 mmol) as described for Intermediate 2. Chromatography on silica gel with hexanes/ethyl acetate (1:1) afforded 510 mg (60%) of the product.

MS (ES): 406.49 (MH$^+$) for $C_{21}H_{31}N_3O_5$
$^1$H-NMR (CDCl$_3$-d) δ: 1.34 (m, 2H); 1.36 (m, 2H); 1.62 (m, 2H); 1.98 (m, 2H); 2.43 (m, 2H); 2.84 (m, 2H); 3.20 (m, 1H); 3.73 (s, 3H); 3.96 (m, 2H); 4.53 (s, 2H); 6.56 (m, 1H); 6.76 (m, 1H); 6.92 (m, 1H).

Intermediate 48

6-Methoxy-2H-1,4-benzoxazin-3(4H)-one

To a solution of ethyl(4-methoxy-2-nitrophenoxy)acetate (Intermediate 49) (1.8 g, 7.1 mmol) in acetic acid (20 mL) was added iron powder (1.1 g, 19.9 mmol). The reaction was heated at 90° C. for 3 hours. It was cooled to room temperature, diluted with ethyl acetate, filtered through celite, and concentrated to dryness under reduced pressure. Silica gel chromatography with hexanes/ethyl acetate (7:3) afforded product, 1 g (79%).

MS (ES): 180.15 (MH$^+$) for $C_9H_9NO_3$
$^1$H-NMR (CDCl$_3$-d) δ: 3.75 (s, 3H); 4.55 (s, 2H); 6.40 (d, 1H); 6.50 (dd, 1H); 6.89 (d, 1H); 8.85 (bs, 1H).

Intermediate 49

Ethyl(4-methoxy-2-nitrophenoxy)acetate

A mixture of 4-methoxy-2-nitrophenol (2 g, 11.8 mmol), cesium carbonate (7.7 g, 23.6 mmol) and 2-bromo ethyl acetate (1.31 mL, 11.8 mmol) in acetone (50 mL) was heated at 50° C. overnight. The mixture was heated at 55° C. for an additional 1 hour, then filtered and concentrated to dryness under reduced pressure. Silica gel chromatography with hexanes/ethyl acetate (4:1) afforded product, 1.8 g (60%).

MS (ES): 256.26 (MH$^+$) for $C_{11}H_{13}NO_6$
$^1$H-NMR (CDCl$_3$-d) δ: 1.28 (t, 3H); 3.81 (s, 3H); 4.25 (q, 2H); 4.70 (s, 2H); 7.04 (m, 2H); 7.39 (d, 1H).

Example 22

6-[({1-[2-(6-Methoxy-3-oxo-2,3-dihydro-4H-1,4-benzoxazin-4-yl)ethyl]piperidin-4-yl}amino)methyl]-2H-pyrido[3,2-b][1,4]oxazin-3(4H)-one 4-[2-(4-aminopiperidin-1-yl)ethyl]-6-methoxy-2H-1,4-benzoxazin-3(4H)-one trifluoroacetate (Intermediate 46) (0.4 mmol), 3-oxo-3,4-dihydro-2H-pyrido[3,2-b][1,4]oxazine-6-carbaldehyde (WO 2004/058144) (80 mg, 0.44 mmol) and sodium cyanoborohydride were reacted as described under Example 21, but, the reaction was stirred at room temperature overnight after sodium cyanoborohydride addition to give the title compound as a free base, 30 mg (17%).

MS (ES): 468.27 (MH$^+$) for $C_{24}H_{29}N_5O_5$ $^1$H-NMR (CDCl$_3$-d) δ: 1.56 (m, 2H); 1.96 (m, 2H); 2.18 (m, 3H); 2.62 (m, 3H); 3.01 (m, 2H); 3.79 (s, 3H); 3.84 (s, 2H); 4.06 (m, 2H); 4.51 (s, 2H); 4.63 (s, 2H); 6.51 (1H); 6.67 (s, 1H); 6.89 (1H); 6.95 (1H); 7.20 (1H).

Example 23

6-[({1-[2-(6-Methoxy-3-oxo-2,3-dihydro-4H-1,4-benzothiazin-4-yl)ethyl]piperidin-4-yl}amino)methyl]-2H-pyrido[3,2-b][1,4]oxazin-3(4H)-one 4-[2-(4-Aminopiperidin-1-yl)ethyl]-6-methoxy-2H-1,4-benzothiazin-3(4H)-one (Intermediate 50) (0.9 mmol), 3-oxo-3,4-dihydro-2H-pyrido[3,2-b][1,4]oxazine-6-carbaldehyde (WO 2004/058144) (190 mg, 1.1 mmol) and sodium cyanoborohydride (110 mg, 1.77 mmol) were reacted as described under Example 21, with stirring for 2.5 hours at room temperature after sodium cyanoborohydride addition. The title compound was obtained as a solid, 52 mg (12%).

MS (ES): 484.26 (MH$^+$) for $C_{24}H_{29}N_5O_4S$ $^1$H-NMR (CDCl$_3$-d) δ: 1.49 (m, 2H); 1.91 (m, 3H); 2.16 (m, 2H); 2.54 (m, 1H); 2.61 (m, 2H); 2.96 (m, 2H); 3.33 (s, 2H); 3.81 (s, 5H); 4.09 (m, 2H); 4.63 (s, 2H); 6.58 (dd, 1H); 6.87 (d, 1H); 6.93 (d, 1H); 7.20 (d, 1H); 7.24 (d, 1H).

Intermediate 50

4-[2-(4-Aminopiperidin-1-yl)ethyl]-6-methoxy-2H-1,4-benzothiazin-3(4H)-one tert-Butyl{1-[2-(6-methoxy-3-oxo-2,3-dihydro-4H-1,4-benzothiazin-4-yl)ethyl]piperidin-4-yl}carbamate (Intermediate 51) (750 mg, 1.78 mmol) was reacted as described for Intermediate 14. The crude trifluoro acetate of the title compound was used without further purification for the next step (quantitative yield).

MS (ES): 322 (MH$^+$) for $C_{16}H_{23}N_3O_2S$

Intermediate 51 tert-Butyl{1-[2-(6-methoxy-3-oxo-2,3-dihydro-4H-1,4-benzothiazin-4-yl)ethyl]piperidin-4-yl}carbamate 6-Methoxy-2H-1,4-benzothiazin-3(4H)-one (Intermediate 52) (410 mg, 2.1 mmol) was deprotonated with sodium hydride (100 mg, 60% in oil, 2.5 mmol) and alkylated with 2-{4-[(tert-butoxycarbonyl)amino]piperidin-1-yl}ethyl methanesulfonate (Intermediate 6) (2.3 mmol) as described for Intermediate 2. Chromatography on silica gel with hexanes/ethyl acetate (1:3) afforded 750 mg (85%) of the product.

MS (ES): 422.24 (MH$^+$) for $C_{21}H_{31}N_3O_4S$ $^1$H-NMR (CDCl$_3$-d) δ: 1.40 (m, 2H); 1.45 (s, 9H); 1.92 (m, 2H); 2.22 (m, 2H); 2.62 (t, 2H); 2.88 (m, 2H); 3.35 (s, 2H); 3.49 (m, 1H); 3.82 (s, 3H); 4.08 (t, 2H); 4.43 (s, 1H); 6.61 (dd, 1H); 6.86 (d, 1H); 7.28 (s, 1H).

Intermediate 52

6-Methoxy-2H-1,4-benzothiazin-3(4H)-one

Prepared from ethyl[(4-methoxy-2-nitrophenyl)thio]acetate (Intermediate 53, 3 g, 11 mmol) according to procedure described for preparation of Intermediate 48. Silica gel chromatography with hexanes/ethyl acetate (3:2) afforded desired product, 2 g (93%).

MS (ES): 196.12 (MH$^+$) for $C_9H_9NO_2S$ $^1$H-NMR (CDCl$_3$-d) δ: 3.39 (s, 2H); 3.78 (s, 3H); 6.44 (d, 1H); 6.59 (dd, 1H); 7.20 (d, 1H); 8.63 (bs, 1H).

Intermediate 53

Ethyl[(4-methoxy-2-nitrophenyl)thio]acetate

Ethyl mercaptoacetate (2.3 mL, 21.5 mmol) was dissolved in DMF (20 mL) and cooled to 0° C. Sodium hydride (1 g, 60% in oil, 25.8 mmol) was added and the reaction was stirred for 1 hour. Then a solution of 1-bromo-4-methoxy-2-nitrobenzene (5 g, 21.5 mmol) in DMF (20 mL) was added at 0° C. The reaction mixture was allowed to warm to room temperature and stirred overnight. It was diluted with ethyl acetate, washed with water (four times) and with brine and then dried over magnesium sulfate. Silica gel chromatography with hexanes/ethyl acetate (4:1) afforded the product, 3 g (52%).

MS (ES): 272.14 (MH$^+$) for $C_{11}H_{13}NO_5S$ $^1$H-NMR (CDCl$_3$-d) δ: 1.24 (t, 3H); 3.68 (s, 2H); 3.86 (s, 3H); 4.18 (q, 2H); 7.15 (dd, 1H); 7.47 (d, 1H); 7.65 (d, 1H).

Example 24

4-(2-{4-[(2,3-Dihydro[1,4]dioxino[2,3-c]pyridin-7-ylmethyl)amino]piperidin-1-yl}ethyl)-6-methoxy-2H-1,4-benzothiazin-3(4H)-one 4-[2-(4-Aminopiperidin-1-yl)ethyl]-6-methoxy-2H-1,4-benzothiazin-3(4H)-one (Intermediate 50) (0.9 mmol), 2,3-dihydro[1,4]dioxino[2,3-c]pyridine-7-carbaldehyde (WO 2004/058144) (180 mg, 1.1 mmol), and sodium cyanoborohydride (110 mg, 1.76 mmol) were reacted as described under Example 21 to give 55 mg (13%) product as a dry film.

MS (ES): 471.26 (MH$^+$) for $C_{24}H_{30}N_4O_4S$ $^1$H-NMR (CDCl$_3$-d) δ: 1.47 (m, 2H); 1.91 (m, 2H); 2.15 (m, 2H); 2.54 (m, 1H); 2.60 (t, J=6.4 Hz, 2H); 2.94 (m, 2H); 3.33 (s, 2H); 3.47 (s, 2H); 3.80 (s, 5H); 4.08 (t, 2H); 4.29 (m, 4H); 6.58 (dd, 1H); 6.80 (s, 1H); 6.88 (d, 1H); 7.23 (d, 1H); 8.08 (s, 1H).

Example 25

6-[({1-[2-(6-Fluoro-3-oxo-2,3-dihydro-4H-1,4-benzoxazin-4-yl)ethyl]piperidin-4-yl}amino)methyl]-2H-pyrido[3,2-b][1,4]oxazin-3(4H)-one 4-[2-(4-Aminopiperidin-1-yl)ethyl]-6-fluoro-2H-1,4-benzoxazin-3(4H)-one (Intermediate 54), (0.7 mmol), 3-oxo-3,4-dihydro-2H-pyrido[3,2-b][1,4]oxazine-6-carbaldehyde (WO 2004/058144) (150 mg, 0.84 mmol) and sodium cyanoborohydride (90 mg, 1.4 mmol) were reacted as described under Example 21 to give 51 mg (16%) product as a solid.

MS (ES): 456.24 (MH$^+$) for $C_{23}H_{26}FN_5O_4$ $^1$H-NMR (CDCl$_3$-d) δ: 1.52 (m, 2H); 1.94 (m, 2H); 2.15 (m, 2H); 2.57 (m, 1H); 2.59 (t, J=7.1 Hz, 2H); 2.97 (m, 2H);

3.84 (s, 2H); 4.01 (t, J=7.1 Hz, 2H); 4.54 (s, 2H); 4.62 (s, 2H); 6.68 (m, 1H); 6.86 (m, 1H); 6.89 (m, 1H); 6.95 (d, J=8.1 Hz, 1H); 7.20 (d, J=8.1 Hz, 1H).

Intermediate 54

4-[2-(4-Aminopiperidin-1-yl)ethyl]-6-fluoro-2H-1,4-benzoxazin-3(4H)-one tert-Butyl{1-[2-(6-fluoro-3-oxo-2,3-dihydro-4H-1,4-benzoxazin-4-yl)ethyl]piperidin-4-yl}carbamate (Intermediate 55) (640 mg, 1.56 mmol) was reacted as described for *Intermediate* 14. The crude trifluoro acetate of the title compound was used without further purification for the next step (quantitative yield).
MS (ES): 294 (MH$^+$) for $C_{15}H_{20}FN_3O_2$ Intermediate 55 tert-Butyl{1-[2-(6-fluoro-3-oxo-2,3-dihydro-4H-1,4-benzoxazin-4-yl)ethyl]piperidin-4-yl}carbamate Commercially available 6-fluoro-2H-1,4-benzoxazin-3(4H)-one (350 mg, 2.1 mmol) was deprotonated with sodium hydride and alkylated with 2-{4-[(tert-butoxycarbonyl)amino]piperidin-1-yl}ethyl methanesulfonate (Intermediate 6) (2.3 mmol) as described for Intermediate 2. Chromatography on silica gel with hexanes/ethyl acetate (1:1) gave 550 mg (67%) product.
MS (ES): 394.26 (MH$^+$) for $C_{20}H_{28}FN_3O_4$
$^1$H-NMR (CDCl$_3$-d) δ: 1.39 (m, 2H); 1.43 (s, 9H); 1.92 (m, 2H); 2.20 (m, 2H); 2.58 (t, 2H); 2.88 (m, 2H); 3.45 (m, 1H); 3.98 (t, 2H); 4.41 (m, 1H); 4.55 (s, 2H); 6.68 (m, 1H); 6.85 (m, 1H); 6.91 (m, 1H).

Example 26

4-(2-{4-[(2,3-Dihydro[1,4]dioxino[2,3-c]pyridin-7-ylmethyl)amino]piperidin-1-yl}ethyl)-6-fluoro-2H-1,4-benzoxazin-3(4H)-one 4-[2-(4-Aminopiperidin-1-yl)ethyl]-6-fluoro-2H-1,4-benzoxazin-3(4H)-one (Intermediate 54) (0.7 mmol), 2,3-dihydro[1,4]dioxino[2,3-c]pyridine-7-carbaldehyde (WO 2004/058144) (140 mg, 0.84 mmol), and sodium cyanoborohydride (90 mg, 1.4 mmol) were reacted as described under Example 21 to give 100 mg (32%) product.
MS (ES): 443.24 (MH$^+$) for $C_{23}H_{27}FN_4O_4$
$^1$H-NMR (CDCl$_3$-d) δ: 1.46 (m, 2H); 1.90 (m, 2H); 2.13 (m, 2H); 2.53 (m, 1H); 2.57 (t, 2H); 2.93 (m, 2H); 3.80 (s, 2H); 3.99 (t, 2H); 4.29 (m, 4H); 4.54 (s, 2H); 6.67 (td, 1H); 6.81 (s, 1H); 6.86 (dd, 1H); 6.90 (dd, 1H); 8.09 (s, 1H).

Example 27

6-[({1-[2-(6-Chloro-3-oxo-2,3-dihydro-4H-1,4-benzoxazin-4-yl)ethyl]piperidin-4-yl}amino)methyl]-2H-pyrido[3,2-b][1,4]oxazin-3(4H)-one 4-[2-(4-Aminopiperidin-1-yl)ethyl]-6-chloro-2H-1,4-benzoxazin-3(4H)-one (Intermediate 56) (0.8 mmol), 3-oxo-3,4-dihydro-2H-pyrido[3,2-b][1,4]oxazine-6-carbaldehyde (WO 2004/058144) (150 mg, 0.84 mmol) and sodium cyanoborohydride (90 mg, 1.4 mmol) were reacted as described under Example 21 to give 78 mg (21%) product as a solid.
MS (ES): 472.24 (MH$^+$) for $C_{23}H_{26}ClN_5O_4$
$^1$H-NMR (CDCl$_3$-d) δ: 1.50 (m, 2H); 1.93 (m, 3H); 2.15 (m, 2H); 2.56 (m, 1H); 2.59 (t, 2H); 2.96 (m, 2H); 3.82 (s, 2H); 4.01 (t, 2H); 4.56 (s, 2H); 4.63 (s, 2H); 6.92 (m, 3H); 7.12 (d, 1H); 7.20 (d, 1H).

Intermediate 56

4-[2-(4-Aminopiperidin-1-yl)ethyl]-6-chloro-2H-1,4-benzoxazin-3(4H)-one tert-Butyl{1-[2-(6-chloro-3-oxo-2,3-dihydro-4H-1,4-benzoxazin-4-yl)ethyl]piperidin-4-yl}carbamate (Intermediate 57) (640 mg, 1.56 mmol) was reacted as described for Intermediate 14. The crude trifluoro acetate of the title compound was used without further purification for the next step (quantitative yield).
MS (ES): 310 (MH$^+$) for $C_{15}H_{20}ClN_3O_2$ Intermediate 57 tert-Butyl{1-[2-(6-chloro-3-oxo-2,3-dihydro-4H-1,4-benzoxazin-4-yl)ethyl]piperidin-4-yl}carbamate Commercially available 6-chloro-2H-1,4-benzoxazin-3(4H)-one (380 mg, 2.1 mmol) was deprotonated with sodium hydride and alkylated with 2-{4-[(tert-butoxycarbonyl)amino]piperidin-1-yl}ethyl methanesulfonate (Intermediate 6) (2.3 mmol) as described for Intermediate 2. Chromatography on silica gel with hexanes/ethyl acetate (1:1) gave 640 mg (74%) product.
MS (ES): 410.22 (MH$^+$) for $C_{20}H_{28}ClN_3O_4$
$^1$H-NMR (CDCl$_3$-d) δ: 1.43 (m, 2H); 1.43 (s, 9H); 1.92 (m, 2H); 2.21 (m, 2H); 2.58 (m, 2H); 2.88 (m, 2H); 3.45 (m, 1H); 3.99 (m, 2H); 4.41 (m, 1H); 4.56 (s, 2H); 6.91 (m, 2H); 7.13 (s, 1H).

Example 28

6-[({1-[2-(6-Methoxy-3-oxo-2,3-dihydro-4H-1,4-benzoxazin-4-yl)ethyl]piperidin-4-yl}amino)methyl]-2H-pyrido[3,2-b][1,4]thiazin-3(4H)-one 4-[2-(4-aminopiperidin-1-yl)ethyl]-6-methoxy-2H-1,4-benzoxazin-3(4H)-one (Intermediate 46) (0.2 mmol), 3-oxo-3,4-dihydro-2H-pyrido[3,2-b][1,4]thiazine-6-carbaldehyde (WO 2004/058144) (42 mg, 0.22 mmol) and sodium cyanoborohydride (23 mg, 0.36 mmol) were reacted as described under Example 21 to give 28 mg (32%) of product as a dry film.
MS (ES): 484.27 (MH$^+$) for $C_{24}H_{29}N_5O_4S$
$^1$H-NMR (CDCl$_3$-d) δ: 1.50 (m, 2H); 1.92 (m, 2H); 2.17 (m, 3H); 2.55 (m, 1H); 2.61 (m, 2H); 2.98 (m, 2H); 3.46 (s, 2H); 3.78 (s, 3H); 3.84 (s, 2H); 4.04 (m, 2H); 4.51 (s, 2H); 6.50 (dd, 1H); 6.67 (d, 1H); 6.89 (d, 1H); 6.98 (d, 1H); 7.57 (d, 1H).

Example 29

3-Oxo-4-[2-(4-{[(3-oxo-3,4-dihydro-2H-pyrido[3,2-b][1,4]oxazin-6-yl)methyl]amino}piperidin-1-yl)ethyl]-3,4-dihydro-2H-1,4-benzoxazine-6-carbonitrile 4-[2-(4-aminopiperidin-1-yl)ethyl]-3-oxo-3,4-dihydro-2H-1,4-benzoxazine-6-carbonitrile (Intermediate 58) (0.8 mmol), 3-oxo-3,4-dihydro-2H-pyrido[3,2-b][1,4]oxazine-6-carbaldehyde (WO 2004/058144) (140 mg, 0.79 mmol) and sodium cyanoborohydride (83 mg, 1.32 mmol) were reacted as described under Example 21 to give 60 mg (19%) product as a solid.

MS (ES): 463.32 (MH$^+$) for $C_{24}H_{26}N_6O_4$
$^1$H-NMR (CDCl$_3$-d) δ: 1.49 (m, 2H); 1.94 (m, 2H); 2.14 (m, 2H); 2.56 (m, 1H); 2.59 (t, J=6.7 Hz, 2H); 2.94 (m, 2H); 3.84 (s, 2H); 4.03 (t, 2H); 4.62 (s, 2H); 4.67 (s, 2H); 6.94 (d, 1H); 7.03 (d, 1H); 7.19 (d, 1H); 7.30 (dd, 1H); 7.46 (d, 1H).

Intermediate 58

4-[2-(4-Aminopiperidin-1-yl)ethyl]-3-oxo-3,4-dihydro-2H-1,4-benzoxazine-6-carbonitrile trifluoroacetate tert-Butyl{1-[2-(6-cyano-3-oxo-2,3-dihydro-4H-1,4-benzoxazin-4-yl)ethyl]piperidin-4-yl}carbamate (Intermediate 59) (610 mg, 1.52 mmol) was reacted as described for Intermediate 14. The crude trifluoro acetate of the title compound was used without further purification for the next step (quantitative. yield).

MS (ES): 301 (MH$^+$) for $C_{16}H_{20}N_4O_2$

Intermediate 59 tert-Butyl{1-[2-(6-cyano-3-oxo-2,3-dihydro-4H-1,4-benzoxazin-4-yl)ethyl]piperidin-4-yl}carbamate 3-oxo-3,4-dihydro-2H-1,4-benzoxazine-6-carbonitrile (Intermediate 60) (350 mg, 2.0 mmol) was deprotonated with sodium hydride and alkylated with 2-{4-[(tert-butoxycarbonyl)amino]piperidin-1-yl}ethyl methanesulfonate (Intermediate 6) (2.2 mmol) as described for Intermediate 2. Chromatography on silica gel with hexanes/ethyl acetate (1:3) afforded 610 mg (76%) of the product.

MS (ES): 401.27 (MH$^+$) for $C_{21}H_{28}N_4O_4$
$^1$H-NMR (CDCl$_3$-d) δ: 1.41 (m, 2H); 1.42 (s, 9H); 1.93 (m, 2H); 2.21 (m, 2H); 2.58 (m, 2H); 2.87 (m, 2H); 3.45 (m, 1H); 4.02 (m, 2H); 4.43 (m, 1H); 4.67 (s, 2H); 7.03 (d, 1H); 7.30 (m, 1H); 7.47 (s, 1H).

Intermediate 60

3-Oxo-3,4-dihydro-2H-1,4-benzoxazine-6-carbonitrile

The title compound was prepared similarly to literature procedure (Caliendo, G; et. al.; *Bioorg. Med. Chem. Lett.*, 2002, 10, 2663), but in one step. Commercially available 3-amino-4-hydroxybenzonitrile (2.5 g, 18.6 mmol) was dissolved in chloroform (300 mL) and saturated sodium bicarbonate (90 mL). The biphasic reaction mixture was cooled to 0° C. and bromoacetyl bromide (2.4 mL, 28 mmol) was added dropwise. The reaction was stirred overnight at room temperature. The layers were separated and the aqueous layer was filtered to yield the desired product as a tan solid, 2.3 g (69%).

MS (ES): 175.11 (MH$^+$) for $C_9H_6N_2O_2$
$^1$H-NMR (DMSO-d$_6$) δ: 4.70 (s, 2H); 7.11 (d, 1H); 7.19 (d, 1H); 7.40 (m, 1H); 10.98 (bs, 1H).

Example 30

6-{[(1-{2-[3-Oxo-6-(trifluoromethoxy)-2,3-dihydro-4H-1,4-benzoxazin-4-yl]ethyl}piperidin-4-yl)amino]methyl}-2H-pyrido[3,2-b][1,4]oxazin-3(4H)-one 4-[2-(4-Aminopiperidin-1-yl)ethyl]-6-(trifluoromethoxy)-2H-1,4-benzoxazin-3(4H)-one (Intermediate 61) (0.55 mmol), 3-oxo-3,4-dihydro-2H-pyrido[3,2-b][1,4]oxazine-6-carbaldehyde (WO 2004/058144) (120 mg, 0.66 mmol) and sodium cyanoborohydride (69 mg, 1.1 mmol) were reacted as described under Example 21 to give 44 mg (15%) product as a solid.

MS (ES): 522.25 (MH$^+$) for $C_{24}H_{26}F_3N_5O_5$
$^1$H-NMR (CDCl$_3$-d) δ: 1.53 (m, 2H); 1.95 (m, 2H); 2.14 (m, 2H); 2.59 (t, 2H); 2.59 (m, 1H); 2.96 (m, 2H); 3.85 (s, 2H); 4.02 (t, 2H); 4.59 (s, 2H); 4.63 (s, 2H); 6.85 (d, 1H); 6.96 (d, 3H); 6.97 (d, 1H); 7.20 (d, 1H).

Intermediate 61

4-[2-(4-Aminopiperidin-1-yl)ethyl]-6-(trifluoromethoxy)-2H-1,4-benzoxazin-3(4H)-one tert-Butyl(1-{2-[3-oxo-6-(trifluoromethoxy)-2,3-dihydro-4H-1,4-benzoxazin-4-yl]ethyl}piperidin-4-yl)carbamate (Intermediate 62) (790 mg, 1.72 mmol) was reacted as described for Intermediate 14. The crude trifluoro acetate of the title compound was used without further purification for the next step (quantitative yield).

MS (ES): 360 (MH$^+$) for $C_{16}H_{20}F_3N_3O_3$

Intermediate 62 tert-Butyl(1-{2-[3-oxo-6-(trifluoromethoxy)-2,3-dihydro-4H-1,4-benzoxazin-4-yl]ethyl}piperidin-4-yl)carbamate 6-(Trifluoromethoxy)-2H-1,4-benzoxazin-3(4H)-one (Intermediate 63) (490 mg, 2.0 mmol) was deprotonated with sodium hydride and alkylated with 2-{4-[tert-butoxycarbonyl)amino]piperidin-1-yl}ethyl methanesulfonate (Intermediate 6) (2.2 mmol) as described for Intermediate 2. Chromatography on silica gel with hexanes/ethyl acetate (2:3) afforded 790 mg (86%) of the product.

MS (ES): 460.26 (MH$^+$) for $C_{21}H_{28}F_3N_3O_5$
$^1$H-NMR (CDCl$_3$-d) δ: 1.38 (m, 2H); 1.43 (s, 9H); 1.92 (m, 2H); 2.20 (m, 2H); 2.57 (m, 2H); 2.87 (m, 2H); 3.45 (m, 1H); 4.00 (m, 2H); 4.41 (m, 1H); 4.58 (s, 2H); 6.85 (m, 1H); 6.95 (s, 1H); 6.99 (m, 1H).

Intermediate 63

6-(Trifluoromethoxy)-2H-1,4-benzoxazin-3(4H)-one

Ethyl[2-nitro-4-(trifluoromethoxy)phenoxy]acetate (Intermediate 64) (1.14 g, 3.7 mmol) and iron powder (510 mg, 9.2 mmol) were reacted according to procedure for Intermediate 48, but heating for only one hour. Silica gel chromatography with hexanes/ethyl acetate (4:1) afforded product, 770 mg (90%).

MS (ES): 234.16 (MH$^+$) for $C_9H_6F_3NO_3$
$^1$H-NMR (CDCl$_3$-d) δ: 4.63 (s, 2H); 6.73 (m, 1H); 6.84 (m, 1H); 6.97 (m, 1H); 8.93 (bs, 1H).

Intermediate 64

Ethyl[2-nitro-4-(trifluoromethoxy)phenoxy]acetate

Prepared from 2-nitro-4-(trifluoromethoxy)phenol (2 g, 8.9 mmol) according to procedure for Intermediate 49. Silica gel chromatography with hexanes/ethyl acetate (4:1) afforded product, 1.14 g (41%).

MS (ES): 310.12 (MH$^+$) for $C_{11}H_{10}F_3NO_6$
$^1$H-NMR (CDCl$_3$-d) δ: 1.28 (t, 3H); 4.26 (q, 2H); 4.78 (s, 2H); 7.03 (d, 1H); 7.40 (m, 1H); 7.78 (d, 1H).

Example 31

6-[({1-[2-(6-Fluoro-3-oxo-2,3-dihydro-4H-1,4-benzoxazin-4-yl)ethyl]piperidin-4-yl}amino)methyl]-2H-pyrido[3,2-b][1,4]thiazin-3(4H)-one 4-[2-(4-Aminopiperidin-1-yl)ethyl]-6-fluoro-2H-1,4-benzoxazin-3(4H)-one (Intermediate 54) (0.7 mmol), 3-oxo-3,4-dihydro-2H-pyrido[3,2-b][1,4]thiazine-6-carbaldehyde (WO 2004/058144) (160 mg, 0.82 mmol) and sodium cyanoborohydride (90 mg, 1.4 mmol) were reacted as described under Example 21, (but the reaction mixture was refluxed overnight before reduction with sodium cyanoborohydride at room temperature for 2 hours) to give 76 mg (23%) of product.

MS (ES): 472.25 (MH$^+$) for $C_{23}H_{26}FN_5O_3S$ $^1$H-NMR (CDCl$_3$-d) δ: 1.48 (m, 2H); 1.92 (m, 2H); 2.15 (m, 2H); 2.55 (m, 1H); 2.59 (t, 2H); 2.96 (m, 2H); 3.46 (s, 2H); 3.84 (s, 2H); 4.00 (t, 2H); 4.55 (s, 2H); 6.68 (td, 1H); 6.86 (dd, 1H); 6.91 (dd, 1H); 6.98 (d, 1H); 7.57 (d, 1H).

Example 32

4-(2-{4-[(2,3-Dihydro[1,4]dioxino[2,3-c]pyridin-7-ylmethyl)amino]piperidin-1-yl}ethyl)-3-oxo-3,4-dihydro-2H-1,4-benzoxazine-6-carbonitrile 4-[2-(4-Aminopiperidin-1-yl)ethyl]-3-oxo-3,4-dihydro-2H-1,4-benzoxazine-6-carbonitrile (Intermediate 58) (2.8 mmol), 2,3-dihydro[1,4]dioxino[2,3-c]pyridine-7-carbaldehyde (WO 2004/058144) (550 mg, 3.36 mmol), and sodium cyanoborohydride (350 mg, 5.6 mmol) were reacted as described under Example 21 to give the crude free base. The product was precipitated from chloroform by addition of 2M HCl in ether. The precipitate was collected by filtration to give title compound as the bis HCl salt, 420 mg.

MS (ES): 450.21 (MH$^+$) for $C_{24}H_{27}N_5O_4$ $^1$H-NMR (CDCl$_3$-d) δ: 1.43 (m, 2H); 1.89 (m, 2H); 2.12 (m, 2H); 2.48 (bs, 1H); 2.53 (m, 1H); 2.56 (t, 2H); 2.90 (m, 2H); 3.79 (s, 2H); 4.02 (t, 2H); 4.29 (m, 4H); 4.66 (s, 2H); 6.81 (s, 1H); 7.02 (d, 1H); 7.29 (dd, 1H); 7.37 (d, 1H); 4.66 (s, 1H).

Example 33

6-[({1-[2-(6-Bromo-3-oxo-2,3-dihydro-4H-1,4-benzoxazin-4-yl)ethyl]piperidin-4-yl}amino)methyl]-2H-pyrido[3,2-b][1,4]oxazin-3(4H)-one 4-[2-(4-Aminopiperidin-1-yl)ethyl]-6-bromo-2H-1,4-benzoxazin-3(4H)-one (Intermediate 65) (0.57 mmol), 3-oxo-3,4-dihydro-2H-pyrido[3,2-b][1,4]oxazine-6-carbaldehyde (WO 2004/058144) (120 mg, 0.67 mmol) and sodium cyanoborohydride (72 mg, 1.14 mmol) were reacted as described under Example 21 to give 65 mg (22%) product as a solid.

MS (ES): 516.22 (MH$^+$) for $C_{23}H_{26}BrN_5O_4$ $^1$H-NMR (CDCl$_3$-d) δ: 1.51 (m, 2H); 1.93 (m, 2H); 2.14 (m, 2H); 2.57 (m, 1H); 2.59 (t, 2H); 2.96 (m, 2H); 3.83 (s, 2H); 4.00 (t, 2H); 4.56 (s, 2H); 4.63 (s, 2H); 6.84 (d, 1H); 6.95 (d, 1H); 7.08 (dd, 1H); 7.20 (d, 1H); 7.27 (d, 1H).

Intermediate 65

4-[2-(4-Aminopiperidin-1-yl)ethyl]-6-bromo-2H-1,4-benzoxazin-3(4H)-one tert-Butyl{1-[2-(6-bromo-3-oxo-2,3-dihydro-4H-1,4-benzoxazin-4-yl)ethyl]piperidin-4-yl}carbamate (Intermediate 66) (261 mg, 0.57 mmol) was reacted as described for Intermediate 14. The crude trifluoro acetate of the title compound was used without further purification for the next step (quantitative. yield).

MS (ES): 354 (MH$^+$) for $C_{15}H_{20}BrN_3O_2$

Intermediate 66 tert-Butyl{1-[2-(6-bromo-3-oxo-2,3-dihydro-4H-1,4-benzoxazin-4-yl)ethyl]piperidin-4-yl}carbamate 6-Bromo-2H-1,4-benzoxazin-3(4H)-one (Intermediate 67) (200 mg, 0.87 mmol) was deprotonated with sodium hydride and alkylated with 2-{4-[(tert-butoxycarbonyl)amino]piperidin-1-yl}ethyl methanesulfonate (Intermediate 6) (0.96 mmol) as described for Intermediate 2. Chromatography on silica gel with hexanes/ethyl acetate (1:3) afforded 261 mg (67%) product.

Intermediate 67

6-Bromo-2H-1,4-benzoxazin-3(4H)-one

2-Amino-4-bromophenol (2.1 g, 11 mmol) and bromo acetyl bromide (1.4 mL, 16.5 mmol) were reacted according to the procedure for Intermediate 60 to afford product as a solid, 2.1 g (85%).

MS (ES): 228 (MH$^+$) for $C_8H_6BrNO_2$ $^1$H-NMR (DMSO-d$_6$) δ: 4.58 (s, 2H); 6.90 (d, 1H); 7.00 (d, 1H); 7.06 (dd, 1H); 10.9 (bs, 1H).

Example 34

6-[({1-[2-(6-Hydroxy-3-oxo-2,3-dihydro-4H-1,4-benzoxazin-4-yl)ethyl]piperidin-4-yl}amino)methyl]-2H-pyrido[3,2-b][1,4]oxazin-3(4H)-one A solution of 6-[({1-[2-(6-methoxy-3-oxo-2,3-dihydro-4H-1,4-benzoxazin-4-yl)ethyl]piperidin-4-yl}amino)methyl]-2H-pyrido[3,2-b][1,4]oxazin-3(4H)-one (Example 22) (100 mg, 0.21 mmol) in dichloromethane was cooled to −78° C. and treated with 1M boron tribromide (0.63 mL, 0.63 mmol) dropwise. The reaction mixture was stirred at room temperature overnight. The reaction mixture was cooled to −78° C. and an additional 1 equivalent of 1M boron tribromide was added. The reaction was stirred for 4 hours at room temperature, and then quenched with saturated sodium bicarbonate. The organic layer was separated and the aqueous phase was extracted three times with dichloromethane. The combined organic extracts were dried over magnesium sulfate and concentrated to dryness under reduced pressure to afford crude product, 11 mg (11%), as a solid.

MS (ES): 454.35 (MH$^+$) for $C_{23}H_{27}N_5O_5$ $^1$H-NMR (DMSO-d$_6$) δ: 1.47 (m, 2H); 1.98 (m, 4H); 2.94 (m, 3H); 3.94 (m, 4H); 4.49 (s, 2H); 4.66 (s, 2H); 6.38 (dd, J=6.0, 2.5 Hz, 1H); 6.60 (d, J=2.2 Hz, 1H); 6.80 (d, J=8.7 Hz, 1H); 7.12 (d, J=8.1 Hz, 1H); 7.40 (d, J=8.3 Hz, 1H); 9.33 (s, 1H); 11.29 (s, 1H).

Example 35

4-{2-[4-({[2-(2,5-Difluorophenyl)cyclopropyl]
methyl}amino)piperidin-1-yl]ethyl}-3-oxo-3,4-dihydro-2H-1,4-benzoxazine-6-carbonitrile 4-[2-(4-Aminopiperidin-1-yl)ethyl]-3-oxo-3,4-dihydro-2H-1,4-benzoxazine-6-carbonitrile (Intermediate 58) (1 mmol), 2-(2,5-difluorophenyl)cyclopropanecarbaldehyde (Intermediate 68) (200 mg, 1.1 mmol) and sodium cyanoborohydride (125 mg, 2 mmol) were reacted as described under Example 21 to give 196 mg (42%) product as a gum.

MS (ES): 506.35 (MH$^+$) for $C_{26}H_{28}F_2N_4O_2$ $^1$H-NMR (CDCl$_3$-d) δ: 0.94 (m, 2H); 1.31 (m, 1H); 1.41 (m, 2H); 1.89 (m, 3H); 2.13 (m, 2H); 2.55 (m, 1H); 2.57 (t, 2H); 2.70 (d, 2H); 2.92 (m, 2H); 4.03 (t, 2H); 4.67 (s, 2H); 6.55 (m, 1H); 6.77 (m, 1H); 6.93 (m, 1H); 7.03 (d, 1H); 7.30 (dd, 1H); 7.38 (d, 1H).

Intermediate 68

2-(2,5-Difluorophenyl)cyclopropanecarbaldehyde

To a solution of oxalyl chloride (1.2 mL, 13.5 mmol) in dichloromethane at −78° C. was added dimethyl sulfoxide (1.9 mL, 27 mmol) dropwise and it was stirred at −78° C. for 30 minutes. A solution of [2-(2,5-difluorophenyl)cyclopropyl]methanol (Intermediate 69) (830 mg, 4.5 mmol) in dichloromethane was added dropwise. The reaction mixture was stirred at −78° C. for 30 minutes. Triethylamine (6.3 mL, 45 mmol) was added and the reaction mixture was stirred at room temperature for 2 hours. The solvent was removed under reduced pressure. Silica gel chromatography with hexanes/ethyl acetate (9:1) afforded the desired product, 546 mg (66%).

GC/MS: 182 (M$^+$) for $C_{10}H_8F_2O$ $^1$H-NMR (CDCl$_3$-d) δ: 1.52 (m, 1H); 1.73 (m, 1H); 2.17 (m, 1H); 2.73 (m, 1H); 6.65 (m, 1H); 6.87 (m, 1H); 6.98 (m, 1H); 9.36 (d, 1H).

Intermediate 69

[2-(2,5-Difluorophenyl)cyclopropyl]methanol

To a solution of (2E)-3-(2,5-difluorophenyl)prop-2-en-1-ol (Intermediate 70) (2.12 g, 12.5 mmol) in dichloromethane at −10° C. was added dropwise diethyl zinc (1M, 75 mL, 75 mmol) over 20 minutes. Diiodomethane (6 mL, 75 mmol) was added and the reaction mixture was stirred at room temperature overnight. Saturated ammonium chloride was added carefully to quench the reaction. The reaction mixture was diluted with diethyl ether and the layers were separated. The organic phase was washed with 10% aqueous hydrochloric acid, saturated sodium bicarbonate and brine, then dried over magnesium sulfate and concentrated to dryness under reduced pressure. Silica gel chromatography with hexanes/ethyl acetate (4:1) afforded the product, 940 mg (41%).

GC/MS: 184 (M$^+$) for $C_{10}H_{10}F_2O$ $^1$H-NMR (DMSO-d$_6$) δ: 0.92 (m, 2H); 1.36 (m, 1H); 1.91 (m, 1H); 3.43 (m, 2H); 4.64 (t, 1H); 6.82 (m, 1H); 6.97 (m, 1H); 7.15 (m, 1H).

Intermediate 70

(2E)-3-(2,5-Difluorophenyl)prop-2-en-1-ol

A mixture of (2E)-3-(2,5-difluorophenyl)acrylic acid (1 g, 5.43 mmol) and N,N-diisopropylethylamine (1.7 mL, 9.8 mmol) in tetrahydrofuran (THF) was treated with isobutyl chloroformate (1.4 mL, 10.8 mmol) at room temperature. The reaction mixture was stirred for 30 minutes, and then filtered. The filtrate was cooled to 0° C. and 2M lithium borohydride (4.1 mL, 8.2 mmol) was added dropwise. The reaction mixture was stirred at 0° C. for 30 minutes then at room temperature for 30 minutes. Ice and 1N hydrochloric acid were added to the reaction mixture to adjust the pH to 7. The aqueous layer was extracted with ethyl acetate twice. The combined organic extracts were dried over sodium sulfate and concentrated to dryness under reduced pressure. Silica gel chromatography with hexanes/ethyl acetate (3:2) afforded desired product, 750 mg (82%).

GC/MS: 170 (M$^+$) for $C_9H_8F_2O$ $^1$H-NMR (DMSO-d$_6$) δ: 4.15 (t, 2H); 5.01 (t, 1H); 6.61 (m, 2H); 7.10 (m, 1H); 7.23 (m, 1H); 7.48 (m, 1H).

Example 36

6-[({1-[2-(6,8-Difluoro-3-oxo-2,3-dihydro-4H-1,4-benzoxazin-4-yl)ethyl]piperidin-4-yl}amino)methyl]-2H-pyrido[3,2-b][1,4]oxazin-3(4H)-one 4-[2-(4-Aminopiperidin-1-yl)ethyl]-6,8-difluoro-2H-1,4-benzoxazin-3(4H)-one (Intermediate 71) (1 mmol), 3-oxo-3,4-dihydro-2H-pyrido[3,2-b][1,4]oxazine-6-carbaldehyde (WO 2004/058144) (220 mg, 1.24 mmol) and sodium cyanoborohydride (130 mg, 2.1 mmol) were reacted as described for Example 21 to give 41 mg (8%) product as a dry film.

MS (ES): 474.26 (MH$^+$) for $C_{23}H_{25}F_2N_5O_4$ $^1$H-NMR (DMSO-d$_6$) δ: 1.19 (m, 2H); 1.74 (m, 2H); 1.96 (m, 3H); 2.34 (m, 1H); 2.42 (m, 2H); 2.82 (m, 2H); 3.65 (s, 2H); 3.97 (m, 2H); 4.59 (s, 2H); 4.70 (s, 2H); 7.00 (d, 1H); 7.09 (m, 2H); 7.28 (d, 1H); 11.16 (s, 1H).

Intermediate 71

4-[2-(4-Aminopiperidin-1-yl)ethyl]-6,8-difluoro-2H-1,4-benzoxazin-3(4H)-one tert-Butyl{1-[2-(6,8-difluoro-3-oxo-2,3-dihydro-4H-1,4-benzoxazin-4-yl)ethyl]piperidin-4-yl}carbamate (Intermediate 72) (423 mg, 1 mmol) was reacted as described for Intermediate 14. The crude trifluoro acetate of the title compound was used without further purification for the next step (quantitative yield).

MS (ES): 312 (MH$^+$) for $C_{15}H_{19}F_2N_3O_2$

Intermediate 72 tert-Butyl{1-[2-(6,8-difluoro-3-oxo-2,3-dihydro-4H-1,4-benzoxazin-4-yl)ethyl]piperidin-4-yl}carbamate 6,8-difluoro-2H-1,4-benzoxazin-3(4H)-one (Intermediate 73) (205 mg, 1.11 mmol) was deprotonated with sodium hydride and alkylated with 2-{4-[(tert-butoxycarbonyl)amino]piperidin-1-yl}ethyl methanesulfonate (Intermediate 6) (1.2 mmol) as described for Intermediate 2. Chromatography on silica gel with hexanes/ethyl acetate (1:3) afforded 423 mg (92%) product.

MS (ES): 412.36 (MH$^+$) for $C_{20}H_{27}F_2N_3O_4$

Intermediate 73

6,8-Difluoro-2H-1,4-benzoxazin-3(4H)-one

Commercially available 2-amino-4,6-difluorophenol (1 g, 6.9 mmol) and bromo acetyl bromide (0.9 mL, 10.3 mmol)

were reacted according to the procedure for Intermediate 60 to afford the product as a solid, 208 mg (16%).

MS (ES): 184.34 (M-H⁻) for $C_8H_5F_2NO_2$

¹H-NMR (DMSO-d₆) δ: 4.64 (s, 2H); 6.55 (m, 1H); 6.94 (m, 1H); 10.99 (bs, 1H).

Example 37

4-[2-(4-{[(2E)-3-(2,5-Difluorophenyl)prop-2-en-1-yl]amino}piperidin-1-yl)ethyl]-3-oxo-3,4-dihydro-2H-1,4-benzoxazine-6-carbonitrile 4-[2-(4-Aminopiperidin-1-yl)ethyl]-3-oxo-3,4-dihydro-2H-1,4-benzoxazine-6-carbonitrile (Intermediate 58) (1.5 mmol), (2E)-3-(2,5-difluorophenyl)acrylaldehyde (202 mg, 1.2 mmol) (FR 2872164) (200 mg, 1.1 mmol) and sodium cyanoborohydride were reacted as described under Example 21. Chromatography on silica gel with dichloromethane/methanol gave 168 mg (25%) product MS (ES): 453 (MH⁺) for $C_{25}H_{26}N_4O_2$ ¹H-NMR (CDCl₃) δ: 1.43 (q, 2H); 1.93 (d, 2H); 2.15 (t, 2H); 2.58 (t, 3H); 2.93 (d, 2H); 3.48 (d, 2H); 4.03 (t, 2H); 4.67 (s, 2H); 6.35 (dt, 1H); 6.65 (d, 1H); 6.88 (m, 1H); 6.96 (m, 1H); 7.03 (d, 1H); 7.12 (m, 1H); 7.30 (dd, 1H); 7.40 (d, 1H).

Example 38

6-[({trans-4-[2-(6-Methoxy-3-oxo-2,3-dihydro-4H-1,4-benzoxazin-4-yl)ethyl]cyclohexyl}amino)methyl]-2H-pyrido[3,2-b][1,4]oxazin-3(4H)-one 4-[2-(Trans-4-aminocyclohexyl)ethyl]-6-methoxy-2H-1,4-benzoxazin-3(4H)-one (Intermediate 74) (310 mg, 1.73 mmol), 3-oxo-3,4-dihydro-2H-pyrido[3,2-b][1,4]oxazine-6-carbaldehyde (WO 2004/058144) (1.73 mmol) and sodium cyanoborohydride were reacted as described under Example 21 to give 110 mg (24%) product.

MS (ES): 467 (MH⁺) for $C_{25}H_{30}N_4O_5$

¹H-NMR (CDCl₃) δ: 1.05 (q, 2H); 1.19 (d, 2H); 1.35 (m, 1H); 1.53 (q, 2H); 1.86 (d, 2H); 2.00 (d, 2H); 2.47 (m, 1H); 3.77 (s, 3H); 3.84-3.91 (m, 4H); 4.50 (s, 2H); 4.61 (s, 2H); 6.47 (m, 2H); 6.90 (t, 2H); 7.18 (d, 2H).

Intermediate 74

4-[2-(trans-4-Aminocyclohexyl)ethyl]-6-methoxy-2H-1,4-benzoxazin-3(4H)-one tert-Butyl{trans-4-[2-(6-methoxy-3-oxo-2,3-dihydro-4H-1,4-benzoxazin-4-yl)ethyl]cyclohexyl}carbamate (Intermediate 75) was reacted as described for Intermediate 14. The crude trifluoro acetate of the title compound was used without further purification for the next step (quantitative yield).

MS (ES): 305 (MH⁺) for $C_{17}H_{24}N_2O_3$

Intermediate 75 tert-Butyl{trans-4-[2-(6-methoxy-3-oxo-2,3-dihydro-4H-1,4-benzoxazin-4-yl)ethyl]cyclohexyl}carbamate 6-Methoxy-2H-1,4-benzoxazin-3(4H)-one (Intermediate 48) (310 mg, 1.73 mmol) was deprotonated with sodium hydride and alkylated with 2-{trans-4-[(tert butoxycarbonyl)amino]cyclohexyl}ethyl methanesulfonate (Intermediate 76) (2 mmol) as described for Intermediate 2. Chromatography on silica gel with dichloromethane/methanol (20:1) afforded the product as a solid (58%).

MS (ES): 405 (MH⁺) for $C_{22}H_{32}N_2O_5$

Intermediate 76

2-{trans-4-[(tert Butoxycarbonyl)amino]cyclohexyl}ethyl methanesulfonate

Commercially available tert-butyl[trans-4-(2-hydroxyethyl)cyclohexyl]carbamate (500 mg, 2.05 mmol) was reacted according to the procedure described for Intermediate 6 to give the product as a white solid (yield 92%).

¹H-NMR (CDCl₃) δ: 1.07 (m, 4H); 1.42 (m, 9H); 1.62 (m, 3H); 1.79 (m, 3H); 1.98 (m, 1H); 2.99 (s, 3H); 3.35 (s, br, 1H); 4.24 (t, 2H); 4.35 (s, 1H).

Example 39

3-Oxo-4-[2-(trans-4-{[(3-oxo-3,4-dihydro-2H-pyrido[3,2-b][1,4]oxazin-6-yl)methyl]amino}cyclohexyl)ethyl]-3,4-dihydro-2H-1,4-benzoxazine-6-carbonitrile 4-[2-(Trans-4-aminocyclohexyl)ethyl]-3-oxo-3,4-dihydro-2H-1,4-benzoxazine-6-carbonitrile (Intermediate 77), 3-oxo-3,4-dihydro-2H-pyrido[3,2-b][1,4]oxazine-6-carbaldehyde (WO 2004/058144) (1.73 mmol) and sodium cyanoborohydride were reacted following the procedure described for Example 21 to give the product in 7% yield, as an off-white solid.

MS (ES): 462 (MH⁺) for $C_{25}H_{27}N_5O_4$

¹H-NMR (CDCl₃) δ: 1.05 (q, 2H); 1.45 (m, 5H); 1.88 (d, 2H); 2.07 (d, 2H); 2.65 (t, 1H); 3.90 (m, 2H); 3.95 (s, 2H); 4.61 (s, 2H); 4.66 (s, 2H); 6.97 (d, 1H); 7.04 (d, 1H); 7.17 (d, 1H); 7.20 (d, 1H); 7.31 (dd, 1H).

Intermediate 77

4-[2-(trans-4-Aminocyclohexyl)ethyl]-3-oxo-3,4-dihydro-2H-1,4-benzoxazine-6-carbonitrile tert-Butyl{trans-4-[2-(6-cyano-3-oxo-2,3-dihydro-4H-1,4-benzoxazin-4-yl)ethyl]cyclohexyl}carbamate (Intermediate 78) was reacted as described for Intermediate 14. The crude trifluoro acetate of the title compound was used without further purification for the next step (quantitative yield).

MS (ES): 300 (MH⁺) for $C_{17}H_{21}N_3O_2$

Intermediate 78 tert-Butyl{trans-4-[2-(6-cyano-3-oxo-2,3-dihydro-4H-1,4-benzoxazin-4-yl)ethyl]cyclohexyl}carbamate 3-Oxo-3,4-dihydro-2H-1,4-benzoxazine-6-carbonitrile (Intermediate 60) (350 mg, 2.0 mmol) was deprotonated with sodium hydride and alkylated with 2-{trans-4-[(tert butoxycarbonyl)amino]cyclohexyl}ethyl methanesulfonate (Intermediate 76) as described for Intermediate 2. Chromatography on silica gel with dichloromethane/methanol (20:1) afforded the product as a solid (50%).

MS (ES) 400 (MH⁺) for $C_{22}H_{29}N_3O_4$

Example 40

6-Bromo-4-[2-(4-{[(3-oxo-3,4-dihydro-2H-pyrido[3,2-b][1,4]oxazin-6-yl)methyl]amino}piperidin-1-yl)ethyl]-2H-pyrido[3,2-b][1,4]oxazin-3(4H)-one 4-[2-(4-Aminopiperidin-1-yl)ethyl]-6-bromo-2H-pyrido[3,2-b][1,4]oxazin-3(4H)-one (Intermediate 79), 3-oxo-3,4- dihydro-2H-pyrido[3,2-b][1,4]oxazine-6-carbaldehyde (WO 2004/058144) and sodium cyanoborohydride were reacted as described under Example 21 to give the product as an off-white solid in 64% yield.

MS (ES): 517, 519 (MH$^+$) for $C_{22}H_{25}BrN_6O_4$ $^1$H-NMR (DMSO-d$_6$) δ: 1.25 (q, 2H); 1.81 (d, 5H); 1.98 (t, 2H); 2.6 (s, 2H); 2.89 (m, 2H); 3.15 (s, 1H); 3.83 (s, 2H); 4.05 (t, 2H); 4.62 (s, 2H); 4.76 (s, 2H); 6.97 (d, 1H); 7.04 (d, 1H); 7.23 (d, 1H); 7.34 (dd, 2H); 11.23 (s, br, 1H)

Intermediate 79

4-[2-(4-Aminopiperidin-1-yl)ethyl]-6-bromo-2H-pyrido[3,2-b][1,4]oxazin-3(4H)-one tert-Butyl{1-[2-(6-bromo-3-oxo-2,3-dihydro-4H-pyrido[3,2-b][1,4]oxazin-4-yl)ethyl]piperidin-4-yl}carbamate (Intermediate 80) was reacted as described for Intermediate 14. The crude trifluoro acetate of the title compound was used without further purification for the next step (quantitative yield).

MS (ES): 355/357 (MH$^+$) for $C_{14}H_{19}BrN_4O_2$

Intermediate 80 tert-Butyl{1-[2-(6-bromo-3-oxo-2,3-dihydro-4H-pyrido[3,2-b][1,4]oxazin-4-yl)ethyl]piperidin-4-yl}carbamate 6-Bromo-2H-pyrido[3,2-b][1,4]oxazin-3(4H)-one (WO 2004/058144) (935 mg, 4.08 mmol) was deprotonated with sodium hydride and alkylated with 2-{4-[(tert-butoxycarbonyl)amino]piperidin-1-yl}ethyl methanesulfonate (Intermediate 6) (5.6 mmol) as described for Intermediate 2, but chromatography was omitted, to give the product as a solid in 92% yield.

MS (ES): 455, 457 (MH$^+$) for $C_{19}H_{27}BrN_4O_4$

Example 41

6-[({1-[2-(6-Nitro-3-oxo-2,3-dihydro-4H-1,4-benzoxazin-4-yl)ethyl]piperidin-4-yl}amino)methyl]-2H-pyrido[3,2-b][1,4]oxazin-3(4H)-one 4-[2-(4-Aminopiperidin-1-yl)ethyl]-6-nitro-2H-1,4-benzoxazin-3(4H)-one (Intermediate 81), 3-oxo-3,4-dihydro-2H-pyrido[3,2-b][1,4]oxazine-6-carbaldehyde (WO 2004/058144) and sodium cyanoborohydride were reacted as described under Example 21 to give the product as an off-white solid in 7% yield.

MS (ES): 483 (MH$^+$) for $C_{23}H_{26}N_6O_6$ $^1$H-NMR (CDCl$_3$) δ: 1.55 (q, 2H); 1.92 (d, 2H); 2.15 (t, 2H); 2.64 (t, 3H); 2.95 (d, 2H); 3.86 (s, 2H); 4.08 (t, 2H); 4.62 (s, 2H); 4.71 (s, 2H); 6.93 (d, 1H); 7.03 (d, 1H); 7.17 (d, 1H); 7.90 (dd, 1H); 8.13 (d, 1H).

Intermediate 81

4-[2-(4-Aminopiperidin-1-yl)ethyl]-6-nitro-2H-1,4-benzoxazin-3(4H)-one tert-Butyl{1-[2-(6-nitro-3-oxo-2,3-dihydro-4H-1,4-benzoxazin-4-yl)ethyl]piperidin-4-yl}carbamate (Intermediate 82) was reacted as described for Intermediate 14. The crude trifluoro acetate of the title compound was used without further purification for the next step (quantitative yield).

MS (ES): 321 (MH$^+$) for $C_{15}H_{20}N_4O_4$

Intermediate 82 tert-Butyl{1-[2-(6-nitro-3-oxo-2,3-dihydro-4H-1,4-benzoxazin-4-yl)ethyl]piperidin-4-yl}carbamate 6-Nitro-2H-1,4-benzoxazin-3(4H)-one (Intermediate 83) (776 mg, 4 mmol) was deprotonated with sodium hydride and alkylated with 2-{4-[(tert-butoxycarbonyl)amino]piperidin-1-yl}ethyl methanesulfonate (Intermediate 6) (5.6 mmol) as described for Intermediate 2. The product precipitated upon quenching of the reaction mixture with water and was isolated by filtration in 98% yield, yellow solid.

MS (ES): 421 (MH$^+$) for $C_{20}H_{28}N_4O_6$.

Intermediate 83

6-Nitro-2H-1,4-benzoxazin-3(4H)-one

The title compound was prepared according to the procedure described for Intermediate 60, in 28% yield, yellow solid.

MS (ES$^-$): 193(M-H$^-$) for $C_8H_6N_2O_4$ $^1$H-NMR (DMSO-d$_6$) δ: 4.80 (s, 2H); 7.18 (d, 1H); 7.75 (s, 1H); 7.85 (d, 1H); 11.10 (s, 1H)

Example 42

3-Oxo-4-[2-(4-{[(3-oxo-3,4-dihydro-2H-pyrido[3,2-b][1,4]oxazin-6-yl)methyl]amino}piperidin-1-yl)ethyl]-3,4-dihydro-2H-pyrido[3,2-b][1,4]oxazine-6-carbonitrile and Example 43

3-Oxo-4-[2-(4-{[(3-oxo-3,4-dihydro-2H-pyrido[3,2-b][1,4]oxazin-6-yl)methyl]amino}piperidin-1-yl)ethyl]-3,4-dihydro-2H-pyrido[3,2-b][1,4]oxazine-6-carboxamide A mixture of 6-bromo-4-[2-(4-{[(3-oxo-3,4-dihydro-2H-pyrido[3,2-b][1,4]oxazin-6-yl)methyl]amino}piperidin-1-yl)ethyl]-2H-pyrido[3,2-b][1,4]oxazin-3(4H)-one (Example 40) (200 mg, 0.387 mmol), zinc cyanide (135 mg, 1.14 mmol) and tetrakis(triphenylphosphine) palladium(0) (50 mg, 0.043 mmol) in anhydrous DMF (3 mL) over molecular sieves 3 A was vortexed and then heated in the microwave at 200° C. for one hour. Reverse phase chromatography and generation of the free base as described for Example 21 gave 27 mg (15%) of Example 42 and 23 mg (12%) of Example 43, both off-white solids.

Example 42

MS (ES): 464 (MH$^+$) for $C_{23}H_{25}N_7O_4$ $^1$H-NMR (DMSO-d$_6$) δ: 1.17 (q, 2H); 1.77 (d, 2H); 20.1 (t, 2H); 2.86 (d, 2H); 3.75 (s, 2H); 4.09 (t, 2H); 4.61 (s, 2H); 4.88 (s, 2H); 7.00 (d, 1H); 7.30 (d, 1H); 7.53 (d, 1H); 7.69 (d, 1H); 11.20 (s, br, 1H).

Example 43

MS (ES): 482 (MH$^+$) for $C_{23}H_{27}N_7O_5$ $^1$H-NMR (DMSO-d$_6$) δ: 1.09 (q, 2H); 1.66 (d, 2H); 1.91 (t, 2H); 2.31 (m, 1H); 2.43 (m, 2H); 2.83 (d, 2H); 3.04 (s, 2H); 3.63 (s, 2H) 4.28 (t, 2H); 4.59 (s, 2H); 4.80 (s, 2H); 6.96 (d, 1H); 7.26 (d, 1H); 7.45 (d, 1H); 7.57 (s, 1H); 7.64 (d, 1H); 7.90 (s, 1H); 11.30 (s, br, 1H).

Example 44

Methyl 3-oxo-4-[2-(4-{[(3-oxo-3,4-dihydro-2H-pyrido[3,2-b][1,4]oxazin-6-yl)methyl] amino}piperidin-1-yl)ethyl]-3,4-dihydro-2H-1,4-benzoxazine-6-carboxylate

Methyl 4-[2-(4-aminopiperidin-1-yl)ethyl]-3-oxo-3,4-dihydro-2H-1,4-benzoxazine-6-carboxylate (Intermediate 84), 3-oxo-3,4-dihydro-2H-pyrido[3,2-b][1,4]oxazine-6-carbaldehyde (WO 2004/058144) and sodium cyanoborohydride were reacted as described under Example 21 to give the product as an off-white solid in 13% yield.

MS (ES): 496 (MH$^+$) for $C_{25}H_{29}N_5O_6$
$^1$H-NMR (CDCl$_3$) δ: 1.53 (m, 3H); 2.16 (m, 3H); 2.49 (m, 2H); 2.62 (m, 3H); 3.00 (d, 2H); 3.87 (s, 2H); 3.90 (s, 3H); 4.09 (t, 2H); 4.62 (s, 2H); 4.64 (s, 2H); 6.95 (d, 1H); 6.98 (d, 1H); 7.19 (d, 1H); 7.19 (d, 1H); 7.69 (d, 1H); 7.78 (d, 1H).

Intermediate 84

Methyl 4-[2-(4-aminopiperidin-1-yl)ethyl]-3-oxo-3,4-dihydro-2H-1,4-benzoxazine-6-carboxylate

Methyl 4-(2-{4-[(tert-butoxycarbonyl)amino]piperidin-1-yl}ethyl)-3-oxo-3,4-dihydro-2H-1,4-benzoxazine-6-carboxylate (Intermediate 85) was reacted as described for Intermediate 14. The crude trifluoro acetate of the title compound was used without further purification for the next step (quantitative yield).

MS (ES): 334 (MH$^+$) for $C_{17}H_{23}N_3O_4$

Intermediate 85

Methyl 4-(2-{4-[tert-butoxycarbonyl)amino]piperidin-1-yl}ethyl)-3-oxo-3,4-dihydro-2H-1,4-benzoxazine-6-carboxylate

Methyl 3-oxo-3,4-dihydro-2H-1,4-benzoxazine-6-carboxylate (Intermediate 86) (330 mg, 1.59 mmol) was deprotonated with sodium hydride and alkylated with 2-{4-[(tert-butoxycarbonyl)amino]piperidin-1-yl}ethyl methanesulfonate (Intermediate 6) (5.6 mmol) as described for Intermediate 2. Chromatography on silica gel with dichloromethane/methanol (20:1) gave the product in 85% yield as a yellow solid.

MS (ES): 434 (MH$^+$) for $C_{22}H_{31}N_3O_6$

Intermediate 86

Methyl 3-oxo-3,4-dihydro-2H-1,4-benzoxazine-6-carboxylate

3-Oxo-3,4-dihydro-2H-1,4-benzoxazine-6-carbonitrile (Intermediate 60) was heated with chlorotrimethylsilane in methanol according to literature procedure (Fen-tair Luo et al. *Tetrahedron Letters*, 39, 1998, page 9455-9456). After removal of volatiles, the product was purified by chromatography on silica gel with methanol/dichloromethane (1:20) and obtained as off white solid, 40% yield.

MS (ES): 208 (MH$^+$) for $C_{10}H_9NO_4$
$^1$H-NMR (DMSO-d$_6$) δ: 3.80 (s, 3H); 4.67 (s, 2H); 7.03 (d, 1H); 7.50 (d, 1H); 7.55 (dd, 1H); 10.99 (s, 1H).

Example 45

6-[({1-[2-(6-Acetyl-3-oxo-2,3-dihydro-4H-1,4-benzoxazin-4-yl)ethyl]piperidin-4-yl}amino)methyl]-2H-pyrido[3,2-b][1,4]oxazin-3(4H)-one

6-Acetyl-4-[2-(4-aminopiperidin-1-yl)ethyl]-2H-1,4-benzoxazin-3(4H)-one (Intermediate 87), 3-oxo-3,4-dihydro-2H-pyrido[3,2-b][1,4]oxazine-6-carbaldehyde (WO 2004/058144) and sodium cyanoborohydride were reacted as described under Example 21 to give the product as an off-white solid in 7% yield.

MS (ES): 480 (MH$^+$) for $C_{25}H_{29}N_5O_5$
$^1$H-NMR (CDCl$_3$) δ: 1.49 (m, 2H); 1.98 (d, 2H); 2.13 (t, 2H); 2.57 (s, 3H); 2.60 (m, 3H); 2.94 (d, 2H); 3.82 (s, 2H); 4.09 (t, 2H); 4.60 (s, 2H); 4.64 (s, 2H); 6.90 (d, 1H); 7.01 (d, 1H); 7.16 (d, 1H); 7.58 (d, 1H); 7.74 (s, 1H).

Intermediate 87

6-Acetyl-4-[2-(4-aminopiperidin-1-yl)ethyl]-2H-1,4-benzoxazin-3(4H)-one tert-Butyl{1-[2-(6-acetyl-3-oxo-2,3-dihydro-4H-1,4-benzoxazin-4-yl)ethyl]piperidin-4-yl}carbamate (Intermediate 88) was reacted as described for Intermediate 14. The crude trifluoro acetate of the title compound was obtained as a colorless solid and used without further purification for the next step (quantitative yield).

MS (ES): 318 (MH$^+$) for $C_{17}H_{23}N_3O_3$

Intermediate 88 tert-Butyl{1-[2-(6-acetyl-3-oxo-2,3-dihydro-4H-1,4-benzoxazin-4-yl)ethyl]piperidin-4-yl}carbamate

6-Acetyl-2H-1,4-benzoxazin-3(4H)-one (Intermediate 89) (382 mg, 2.0 mmol) was deprotonated with sodium hydride and alkylated with 2-{4-[tert-butoxycarbonyl)amino]piperidin-1-yl}ethyl methanesulfonate (Intermediate 6) (2.2 mmol) as described for Intermediate 2. Chromatography on silica gel with hexanes/ethyl acetate (1:1) gave the product in 94% yield as a colorless solid.

MS (ES): 418 (MH$^+$) for $C_{22}H_{31}N_3O_5$

Intermediate 89

6-Acetyl-2H-1,4-benzoxazin-3(4H)-one

Ethyl(4-acetyl-2-nitrophenoxy)acetate (Intermediate 90) was reacted with iron in acetic acid as described for Intermediate 48. The crude product was obtained as an off white solid after work up. Recrystallization with ethyl acetate/methanol afforded the product as a colorless solid in 51% yield.

MS (ES): 192 (MH$^+$) for $C_{10}H_9NO_3$
$^1$H-NMR (DMSO-d$_6$) δ: 2.50 (s, 3H); 4.68 (s, 2H); 7.06 (d, 1H); 7.47 (d, 1H); 7.60 (dd, 1H); 10.88 (s, 1H).

Intermediate 90

Ethyl(4-acetyl-2-nitrophenoxy)acetate

1-(4-hydroxy-3-nitrophenyl)ethanone was reacted with cesium carbonate and 2-bromo ethyl acetate as described for Intermediate 49. Chromatography on silica gel with hexanes/ethyl acetate (1:1) gave the product in 69% yield as a pink solid MS (ES): 268 (MH$^+$) for C$_{12}$H$_{13}$NO$_6$
$^1$H-NMR (CDCl$_3$) δ: 1.30 (t, 3H); 2.60 (s, 3H); 4.30 (q, 2H); 4.86 (s, 2H); 7.00 (d, 1H); 8.20 (d, 1H); 8.50 (s, 1H).

Example 46

6-Acetyl-4-(2-{4-[(2,3-dihydro[1,4]dioxino[2,3-c]pyridin-7-ylmethyl)amino]piperidin-1-yl}ethyl)-2H-1,4-benzoxazin-3(4H)-one 6-Acetyl-4-[2-(4-aminopiperidin-1-yl)ethyl]-2H-1,4-benzoxazin-3(4H)-one (Intermediate 87), 2,3-dihydro[1,4]dioxino[2,3-c]pyridine-7-carbaldehyde (WO 2004/058144) and sodium cyanoborohydride were reacted as described for Example 21. The was converted to the free base was treated with HCl in dioxane (2M, excess) and the excess HCl and dioxane were removed under reduced pressure to give the bis hydrochloride salt of the product, 25 mg (9%), as an off-white solid.
MS (ES): 467 (MH$^+$) for C$_{23}$H$_{27}$N$_7$O$_5$
$^1$H-NMR (DMSO-d$_6$) δ: 2.10 (m, 2H); 2.32 (d, 1H); 2.65 (s, 3H); 3.07 (m, 2H); 3.27 (s, 3H) 3.57 (s, 1H); 3.77 (d, 2H); 4.19 (s, 2H); 4.35 (dd, 4H); 4.46 (t, 2H); 4.81 (s, 2H); 7.12 (d, 1H); 7.24 (s, 1H); 7.66 (d, 1H); 7.76 (s, 1H); 8.18 (s, 1H); 9.73 (brs, 2H); 11.06 (brs, 1H).

Example 47

4-(2-{4-[(2,3-Dihydro[1,4]dioxino[2,3-c]pyridin-7-ylmethyl)amino]piperidin-1-yl}ethyl)-6-methyl-2H-1,4-benzoxazin-3(4H)-one 4-[2-(4-Aminopiperidin-1-yl)ethyl]-6-methyl-2H-1,4-benzoxazin-3(4H)-one (Intermediate 91), 2,3-dihydro[1,4]dioxino[2,3-c]pyridine-7-carb aldehyde (WO 2004/058144) and sodium cyanoborohydride were reacted as described for Example 21 to give the product as an oil, 4.7 mg (2%).
MS (ES): 439 (MH$^+$) for C$_{24}$H$_{30}$N$_4$O$_4$
$^1$H-NMR (CDCl$_3$) δ: 2.13 (m, 2H); 2.25 (s, 2H); 2.31 (s, 3H); 2.61 (s, 2H); 3.06 (m, 2H) 3.33 (m, 1H); 3.51 (m, 2H); 4.14 (s, 2H); 4.20-4.40 (m, 6H); 4.53 (s, 2H); 6.70-6.95 (m, 4H); 8.09 (s, 1H).

Intermediate 91

4-[2-(4-Aminopiperidin-1-yl)ethyl]-6-methyl-2H-1,4-benzoxazin-3(4H)-one tert-Butyl{1-[2-(6-methyl-3-oxo-2,3-dihydro-4H-1,4-benzoxazin-4-yl)ethyl]piperidin-4-yl}-carbamate (Intermediate 92) was reacted as described for Intermediate 14. The crude trifluoro acetate of the title compound was obtained as a colorless solid and used without further purification for the next step (quantitative yield).
MS (ES): 290 (MH$^+$) for C$_{16}$H$_{23}$N$_3$O$_2$ Intermediate 92 tert-Butyl{1-[2-(6-methyl-3-oxo-2,3-dihydro-4H-1,4-benzoxazin-4-yl)ethyl]piperidin-4-yl}carbamate Commercially available 6-methyl-2H-1,4-benzoxazin-3(4H)-one (326 mg, 2.0 mmol) was deprotonated with sodium hydride and alkylated with 2-{4-[(tert-butoxycarbonyl)amino]piperidin-1-yl}ethyl methanesulfonate (Intermediate 6) (2.2 mmol) as described for Intermediate 2. Chromatography on silica gel with dichloromethane/methanol (20:1) gave the product in 66% yield as a colorless solid.
MS (ES): 390 (MH$^+$) for C$_{21}$H$_{31}$N$_3$O$_4$ Example 48

3-Oxo-4-[2-(6-{[(3-oxo-3,4-dihydro-2H-pyrido[3,2-b][1,4]oxazin-6-yl)methyl]amino}-3-azabicyclo[3.1.0]hex-3-yl)ethyl]-3,4-dihydro-2H-1,4-benzoxazine-6-carbonitrile 4-[2-(6-Amino-3-azabicyclo[3.1.0]hex-3-yl)ethyl]-3-oxo-3,4-dihydro-2H-1,4-benzoxazine-6-carbonitrile (Intermediate 93), 3-oxo-3,4-dihydro-2H-pyrido[3,2-b][1,4]oxazine-6-carbaldehyde (WO 2004/058144) and sodium cyanoborohydride were reacted as described under Example 21 to give the product as an off-white solid in 6% yield.
MS (ES): 461 (MH$^+$) for C$_{24}$H$_{24}$N$_6$O$_4$
$^1$H-NMR (CDCl$_3$) δ: 2.46 (m, 4H); 2.66 (t, 2H); 3.01 (d, 2H); 3.83 (s, 2H); 3.98 (m, 3H) 4.63 (s, 2H); 4.64 (s, 2H); 6.89 (d, 1H); 7.02 (d, 1H); 7.18 (d, 1H); 7.31 (m, 2H).

Intermediate 93

4-[2-(6-Amino-3-azabicyclo[3.1.0]hex-3-yl)ethyl]-3-oxo-3,4-dihydro-2H-1,4-benzoxazine-6-carbonitrile tert-Butyl{3-[2-(6-cyano-3-oxo-2,3-dihydro-4H-1,4-benzoxazin-4-yl)ethyl]-3-azabicyclo[3.1.0]hex-6-yl}carbamate (Intermediate 94) was reacted as described for Intermediate 14. The crude trifluoro acetate of the title compound was obtained as a colorless solid and used without further purification for the next step (quantitative yield).
MS (ES): 299 (MH$^+$) for C$_{16}$H$_{18}$N$_4$O$_2$.

Intermediate 94 tert-Butyl{3-[2-(6-cyano-3-oxo-2,3-dihydro-4H-1,4-benzoxazin-4-yl)ethyl]-3-azabicyclo[3.1.0]hex-6-yl}carbamate 3-Oxo-3,4-dihydro-2H-1,4-benzoxazine-6-carbonitrile (Intermediate 60) (231 mg, 1.5 mmol) was deprotonated with sodium hydride and alkylated with 2-{6-[(tert-butoxycarbonyl)amino]-3-azabicyclo[3.1.0]hex-3-yl}ethyl methanesulfonate (Intermediate 95) (1.55 mmol) as described for Intermediate 2. Chromatography on silica gel with dichloromethane/methanol (20:1) gave 442 mg (94%) product as a yellow gum.
MS (ES): 399 (MH$^+$) for C$_{21}$H$_{26}$N$_4$O$_4$ Intermediate 95

2-{6-[(tert-Butoxycarbonyl)amino]-3-azabicyclo[3.1.0]hex-3-yl}ethyl methanesulfonate To a mixture of tert-butyl[3-(2-hydroxyethyl)-3-azabicyclo[3.1.0]hex-6-yl]carbamate (Intermediate 96) (376 mg, 1.55 mmol) and triethyl amine (0.283 mL, 3 mmol) in anhydrous chloroform (15 mL) was added at 0° C. methanesulfonyl chloride (228 mg, 3 mmol) via syringe. The reaction was allowed to warm to room temperature over 1 hr and worked up as described for Intermediate 6. The crude mesylate was used for the next step without delay.

Intermediate 96 tert-Butyl[3-(2-hydroxyethyl)-3-azabicyclo[3.1.0]hex-6-yl]carbamate

A mixture of tert-butyl 3-azabicyclo[3.1.0]hex-6-ylcarbamate (T. F. Braish et al. *Synlett,* 1996, page 1100 and T. Norris et al. *J. Chem. Soc. Perkin I,* 2000, page 1615-1622), 2-bromoethanol (669 mg, 3.36 mmol) and N,N-ethyldiisopropyl amine (0.087 mL) in acetonitrile (9 mL) was heated in the microwave at 70° C. for 30 minutes. Chromatography on silica gel with chloroform/methanol (20:1) gave 376 mg (46%) of the product.
MS (EI) 242 for $C_{12}H_{22}N_2O_3$ Example 49

4-(2-{4-[(2,3-Dihydro[1,4]dioxino[2,3-c]pyridin-7-ylmethyl)amino]piperidin-1-yl}ethyl)-2H-1,4-benzoxazin-3(4H)-one 4-[2-(4-Aminopiperidin-1-yl)ethyl]-2H-1,4-benzoxazin-3(4H)-one (Intermediate 97), 2,3-dihydro[1,4]dioxino[2,3-c]pyridine-7-carbaldehyde (WO 2004/058144) and sodium cyanoborohydride were reacted as described for Example 21 to give the product as a off-white solid, 81 mg (16%).
MS (ES): 425 (MH$^+$) for $C_{23}H_{28}N_4O_4$.2HCl
$^1$H-NMR (DMSO-d$_6$) δ: 2.2-3.8 (m, 14H); 3.87 (s, 1H); 4.42 (m, 4H); 4.75 (s, 2H); 7.11 (m, 3H); 7.40-7.60 (m, 2H); 8.29 (s, 1H); 10.01 (s, 2H); 10.01 (s, 2H); 11.35 (brs, 1H).

Intermediate 97

4-[2-(4-Aminopiperidin-1-yl)ethyl]-2H-1,4-benzoxazin-3(4H)-one tert-Butyl{1-[2-(3-oxo-2,3-dihydro-4H-1,4-benzoxazin-4-yl)ethyl]piperidin-4-yl}carbamate (Intermediate 98) was reacted as described for Intermediate 14. The crude trifluoro acetate of the title compound was obtained as a colorless solid and used without further purification for the next step (quantitative yield).
MS (ES): 276 (MH$^+$) for $C_{15}H_{21}N_3O_2$ Intermediate 98 tert-Butyl{1-[2-(3-oxo-2,3-dihydro-4H-1,4-benzoxazin-4-yl)ethyl]piperidin-4-yl}carbamate 2H-1,4-Benzoxazin-3(4H)-one (298 mg, 2.0 mmol) was deprotonated with sodium hydride and alkylated with 2-{4-[(tert-butoxycarbonyl)amino]piperidin-1-yl}ethyl methanesulfonate (Intermediate 6) (2.0 mmol) as described for Intermediate 2. Chromatography on silica gel with dichloromethane/methanol (20:1) gave the product in 63% yield as a yellow gum.
MS (ES): 376 (MH$^+$) for $C_{20}H_{29}N_3O_4$ Example 50

6-{[(1-{2-[6-(1-Hydroxyethyl)-3-oxo-2,3-dihydro-4H-1,4-benzoxazin-4-yl]ethyl}piperidin-4-yl)amino]methyl}-2H-pyrido[3,2-b][1,4]oxazin-3(4H)-one 6-[({1-[2-(6-Acetyl-3-oxo-2,3-dihydro-4H-1,4-benzoxazin-4-yl)ethyl]piperidin-4-yl}amino)methyl]-2H-pyrido[3, 2-b][1,4]oxazin-3(4H)-one (Example 45) (309 mg, 0.645 mmol) was reduced with sodium borohydride (47 mg, 2 equivalents) in methanol (12 mL) at 0° C. After quenching the reaction with water, the reaction mixture was concentrated under reduced pressure and extracted with chloroform. The chloroform layer was washed with brine and dried over magnesium sulfate and concentrated to dryness to give the as an off-white solid, 202 mg (95%).
MS (ES): 482 (MH$^+$) for $C_{25}H_{31}N_5O_5$
$^1$H-NMR (CDCl$_3$) δ: 1.47 (d, 3H); 1.50 (q, 2H); 1.89 (d, 2H); 2.18 (m, 2H); 2.62 (m, 1H) 2.65 (t, 2H); 3.00 (d, 2H); 3.82 (s, 2H); 4.09 (t, 2H); 4.55 (s, 2H); 4.61 (s, 2H); 4.86 (q, 1H) 6.91 (m, 3H); 7.18 (d, 1H); 7.26 (s, 1H).

Example 51

Ethyl N-{1-[2-(6-cyano-3-oxo-2,3-dihydro-4H-1,4-benzoxazin-4-yl)ethyl]piperidin-4-yl}-N-[(2E)-3-(2,5-difluorophenyl)prop-2-en-1-yl]glycinate To a mixture of 4-[2-(4-{[(2E)-3-(2,5-difluorophenyl)prop-2-en-1-yl]amino}piperidin-1-yl)ethyl]-3-oxo-3,4-dihydro-2H-1,4-benzoxazine-6-carbonitrile (Example 37) (120 mg, 0.265 mmol) and ethyl diazoacetate (0.09 mL) in dichloromethane (5 ml) was added rhodium(II) acetate (4 mg, 0.009 mmol) at room temperature. After 72 hrs, the product was concentrated and purified by preparative TLC to give 6.7 mg of product (5%).
MS (ES): 539 (MH$^+$) for $C_{29}H_{32}N_4O_4$
$^1$H-NMR (CDCl$_3$) δ: 1.22 (t, 3H); 1.25 (m, 2H); 1.62 (m, 4H); 1.84 (d, 2H); 2.16 (bs, 2H) 2.60 (m, 2H); 2.70 (m, 1H); 3.03 (m, 2H); 3.37 (s, 2H); 3.45 (d, 2H); 4.07 (m, 2H); 4.11 (q, 2H); 4.68 (s, 2H); 6.32 (dt, 1H); 6.67 (d, 1H); 6.86 (m, 1H); 6.97 (dm, 1H); 7.02 (d, 1H); 7.13 (m, 1H); 7.30 (dd, 1H); 7.45 (s, 1H).

Example 52

6-{[(1-{2-[6-(Methylsulfonyl)-3-oxo-2,3-dihydro-4H-1,4-benzoxazin-4-yl]ethyl}piperidin-4-yl)amino]methyl}-2H-pyrido[3,2-b][1,4]oxazin-3(4H)-one 4-[2-(4-Aminopiperidin-1-yl)ethyl]-6-(methylsulfonyl)-2H-1,4-benzoxazin-3(4H)-one (Intermediate 99), 3-oxo-3,4-dihydro-2H-pyrido[3,2-b][1,4]oxazine-6-carbaldehyde (WO 2004/058144) and sodium cyanoborohydride were reacted as described under Example 21 to give the product as an off-white solid in 8% yield.
MS (ES): 516 (MH$^+$) for $C_{24}H_{29}N_5O_6S$
$^1$H-NMR (CDCl$_3$) δ: 1.53 (m, 2H); 1.87 (d, 2H); 2.13 (t, 4H); 2.54 (m, 1H); 2.60 (t, 2H) 2.93 (d, 2H); 3.05 (s, 3H); 3.82 (s, 2H); 4.08 (t, 2H); 4.60 (s, 2H); 4.66 (s, 2H); 6.90 (d, 1H); 7.10 (d, 1H); 7.16 (d, 1H); 7.56 (d, 1H); 7.72 (s, 1H).

Intermediate 99

4-[2-(4-Aminopiperidin-1-yl)ethyl]-6-(methylsulfonyl)-2H-1,4-benzoxazin-3(4H)-one tert-Butyl(1-{2-[6-(methylsulfonyl)-3-oxo-2,3-dihydro-4H-1,4-benzoxazin-4-yl]ethyl}piperidin-4-yl)carbamate (Intermediate 100) was reacted as described for Intermediate 14. The crude trifluoro acetate of the title compound was obtained as a colorless solid and used without further purification for the next step (quantitative yield).
MS (ES): 353 (MH$^+$) for $C_{16}H_{23}N_3O_4S$

Intermediate 100 tert-Butyl(1-{2-[6-(methylsulfonyl)-3-oxo-2,3-dihydro-4H-1,4-benzoxazin-4-yl]ethyl}piperidin-4-yl)carbamate 6-(Methylsulfonyl)-2H-1,4-benzoxazin-3(4H)-one (Intermediate 101) (280 mg, 1.23 mmol) was deprotonated with sodium hydride and alkylated with 2-{4-[(tert-butoxycarbonyl)amino]piperidin-1-yl}ethyl methanesulfonate (Intermediate 6) (1.62 mmol) as described for Intermediate 2. Chromatography on silica gel with dichloromethane/methanol (20:1) gave the product in 66% yield as a yellow gum.
MS (ES): 454 (MH$^+$) for $C_{21}H_{31}N_3O_6S$

Intermediate 101

6-(Methylsulfonyl)-2H-1,4-benzoxazin-3(4H)-one

4-Methylsulfonyl-2-aminophenol (Intermediate 102) (690 mg, 3.68 mmol) was dissolved in chloroform (30 mL) and saturated sodium bicarbonate (20 mL). The biphasic reaction mixture was cooled to 0° C. and bromoacetyl bromide (889 mg, 4.42 mmol) was added dropwise. The reaction was stirred overnight at room temperature. The layers were separated and the aqueous layer was filtered to yield the desired product as a solid, 280 mg (33%).
MS (ES): 228 (MH$^+$) for $C_9H_9NO_4S$
$^1$H-NMR (DMSO-d$_6$) δ: 3.16 (s, 3H); 4.73 (s, 2H); 7.15 (d, 1H); 7.41 (s, 1H); 7.50 (d, 1H); 11.05 (s, 1H).

Intermediate 102

4-Methylsulfonyl-2-aminophenol

The title compound was prepared by reacting 2-methoxy-5-methylsulfonyl aniline (5.0 g, 24.8 mmol) with boron tribromide (26 mmol, 26 mL, 1M in dichloromethane) in chloroform (30 m L) at 0° C. After 20 minutes, the reaction was quenched with sodium bicarbonate and the ph of the aqueous phase was adjusted to pH 7 and extracted with ethyl acetate. Concentration under reduced pressure gave 690 mg of product as an orange solid (15%).
MS (ES): 188 (MH$^+$) for $C_7H_9NO_3S$

Example 53

6-{[(1-{2-[6-(Ethylsulfonyl)-3-oxo-2,3-dihydro-4H-1,4-benzoxazin-4-yl]ethyl}piperidin-4-yl)amino]methyl}-2H-pyrido[3,2-b][1,4]oxazin-3(4H)-one 4-[2-(4-Aminopiperidin-1-yl)ethyl]-6-(methylsulfonyl)-2H-1,4-benzoxazin-3(4H)-one (Intermediate 103), 3-oxo-3,4-dihydro-2H-pyrido[3,2-b][1,4]oxazine-6-carbaldehyde (WO 2004/058144) and sodium cyanoborohydride were reacted as described under Example 21 to give the product as an off-white solid in 19% yield.
MS (ES): 530 (MH$^+$) for $C_{25}H_{31}N_5O_6S$
$^1$H-NMR (DMSO-d$_6$) δ: 1.11 (t, 3H); 1.30 (q, 2H); 1.74 (d, 2H); 2.00 (t, 2H); 2.40 (m, 3H) 2.82 (d, 2H); 3.32 (m, 4H); 3.67 (s, 2H); 4.05 (t, 2H); 4.60 (s, 2H); 4.78 (s, 2H); 7.01 (d, 1H); 7.28 (d, 1H); 7.30 (d, 1H); 7.50 (d, 1H); 7.68 (s, 1H); 11.18 (brs, 1H).

Intermediate 103

4-[2-(4-Aminopiperidin-1-yl)ethyl]-6-(methylsulfonyl)-2H-1,4-benzoxazin-3(4H)-one tert-Butyl(1-{2-[6-(ethylsulfonyl)-3-oxo-2,3-dihydro-4H-1,4-benzoxazin-4-yl]ethyl}piperidin-4-yl)carbamate (Intermediate 104) was reacted as described for Intermediate 14. The crude trifluoro acetate of the title compound was obtained as a colorless solid and used without further purification for the next step (quantitative yield).
MS (ES): 368 (MH$^+$) for $C_{17}H_{25}N_3O_4S$

Intermediate 104 tert-Butyl(1-{2-[6-(ethylsulfonyl)-3-oxo-2,3-dihydro-4H-1,4-benzoxazin-4-yl]ethyl}piperidin-4-yl)carbamate 6-(Ethylsulfonyl)-2H-1,4-benzoxazin-3(4H)-one (Intermediate 105) (482 mg, 2 mmol) was deprotonated with sodium hydride and alkylated with 2-{4-[tert-butoxycarbonyl)amino]piperidin-1-yl}ethyl methanesulfonate (Intermediate 6) (2.2 mmol) as described for Intermediate 2. Chromatography on silica gel with hexanes/ethyl acetate gave the product in 81% yield as a yellow gum.
MS (ES): 468 (MH$^+$) for $C_{22}H_{33}N_3O_6S$

Intermediate 105

6-(Ethylsulfonyl)-2H-1,4-benzoxazin-3(4H)-one

Commercially available 4-ethylsulfonyl-2-aminophenol (4.02 g, 20 mmol) was dissolved in DMF (30 mL) and mixed with cesium carbonate (6.5 g, 20 mmol). The reaction mixture was cooled to 0° C. and bromoacetyl bromide (4.0 g, 20 mmol) in DMF (5 mL) was added dropwise. The reaction was stirred overnight at room temperature. After aqueous work up, the product was purified by silica gel chromatography with methanol/dichloromethane to give the product as an orange solid, 1.7 g (35%).
MS (ES): 242 (MH$^+$) for $C_{10}H_{11}NO_4S$
$^1$H-NMR (DMSO-d$_6$) δ: 1.09 (t, 3H); 3.24 (q, 2H); 4.72 (s, 2H); 7.16 (d, 1H); 7.37 (s, 1H); 7.41 (d, 1H); 11.00 (s, 1H).

Example 54

6-[({1-[2-(7-Methoxy-2-oxo-2H-3,1-benzoxazin-1(4H)-yl)ethyl]piperidin-4-yl}amino)methyl]-2H-pyrido[3,2-b][1,4]oxazin-3(4H)-one 1-[2-(4-Aminopiperidin-1-yl)ethyl]-7-methoxy-1,4-dihydro-2H-3,1-benzoxazin-2-one trifluoro acetate (Intermediate 106) (324 mg, 0.78 mmol) was converted to the free base using N,N-diisopropylethylamine for 30 minutes and reacted with 3-oxo-3,4-dihydro-2H-pyrido[3,2-b][1,4]oxazine-6-carbaldehyde (WO 2004/058144) (153 mg, 0.86 mmol) and sodium cyanoborohydride (98 mg, 1.56 mmol) as described under Example 21. The reaction mixture was filtered through a 0.45 μm membrane and concentrated to dryness under reduced pressure. Chromatography on silica gel with dichloromethane/methanol (9:1) gave the free base of the title compound as a colorless foam. The free base was taken up in 1,4 dioxane (2 mL), followed by addition of 4M HCl in 1,4-dioxane (0.30 mL). The resulting precipitate was collected by filtration and gave 75 mg (48%) of the bis-hydrochloride salt of the product.

MS (ES): 468.17 (MH$^+$) for C$_{24}$H$_{29}$N$_5$O$_5$
$^1$H NMR (DMSO-d$_6$) δ 2.09 (m, 2H); 2.31-2.44 (m, 2H); 3.00-3.15 (m, 2H); 3.66-3.78 (m, 2H); 3.82 (s, 3H); 4.13-4.22 (m, 2H); 4.22-4.35 (m, 2H); 4.69 (s, 2H); 5.25 (s, 2H); 6.70 (d, 1H); 6.85 (s, 1H); 7.20 (dd, 2H); 7.45 (d, 1H); 9.56-9.71 (m, 2H); 11.05-11.19 (m, 1H); 11.37 (s, 1H).

Intermediate 106

1-[2-(4-Aminopiperidin-1-yl)ethyl]-7-methoxy-1,4-dihydro-2H-3,1-benzoxazin-2-one A solution of tert-butyl{1-[2-(7-methoxy-2-oxo-2H-3,1-benzoxazin-1(4H)-yl)ethyl]piperidin-4-yl}carbamate (Intermediate 107) (319 mg, 0.78 mmol) in dichloromethane (8 mL) was treated at room temperature under vigorous stirring with a trifluoroacetic acid (0.75 mL, 10 mmol). After 2 hours, the reaction mixture was concentrated under reduced pressure to give 324 mg (quantitative) of product as a brown oil.
MS (ES): 302.24 (MH$^+$) for C$_{16}$H$_{23}$N$_3$O$_3$ Intermediate 107 tert-Butyl{1-[2-(7-methoxy-2-oxo-2H-3,1-benzoxazin-1(4H)-yl)ethyl]piperidin-4-yl}carbamate A solution of 7-methoxyquinolin-2(1H)-one (Intermediate 108, 310 mg, 1.8 mmol) in dry N,N-dimethylformamide (5 mL) was treated at 0° C. under stirring with lithium bis(trimethylsilyl)amide (1M in tetrahydrofuran, 1.9 mL, 1.9 mmol). The mixture was then stirred for 30 minutes at room temperature and alkylated with 2-{4-[(tert-butoxycarbonyl)amino]piperidin-1-yl}ethyl methanesulfonate (Intermediate 6, 2.03 mmol) as described for Intermediate 2. Chromatography on silica gel with dichloromethane/methanol (95:5) gave 333 mg (47%) of the product as a colorless solid.
MS (ES): 406 (MH$^+$) for C$_{21}$H$_{31}$N$_3$O$_5$
$^1$H-NMR (CDCl$_3$) δ: 1.34-1.46 (m, 11H); 1.86 (d, 2H); 2.12-2.25 (m, 2H); 2.60-2.64 (m, 2H); 2.60-2.64 (m, 2H); 2.81-2.90 (m, 2H); 3.38-3.45 (m, 1H); 3.76 (s, 3H); 3.97-3.91 (m, 2H); 4.32-4.42 (m, 1H); 5.05 (s, 2H); 6.49-6.56 (m, 2H); 6.94 (d, 1H).

Intermediate 108

7-Methoxyquinolin-2(1H)-one

A solution of (2-amino-4-methoxyphenyl)methanol (Intermediate 109, 744 mg, 4.85 mmol) in toluene (25 mL) was treated with triethylamine (1.36 mL, 9.7 mmol) and triphosgene (1.58 g, 5.34 mL). The reaction was stirred at room temperature for 1.5 hours and then was heated to 110° C. for an additional 2 hours. The reaction was cooled to room temperature, diluted with water (25 mL), filtered, extracted aqueous layer with toluene (3×30 mL) and ethyl acetate (2×20 mL). The combined organic layers were washed with brine, dried over sodium sulfate, and concentrated under reduced pressure. Chromatography on silica gel with hexanes/ethyl acetate (3:2) gave 314 mg (36%) of the product as a colorless solid.
$^1$H-NMR (DMSO-d$_6$) δ: 3.78 (s, 3H); 5.26 (s, 2H); 6.38 (d, 1H); 6.59 (d, 1H); 6.98 (d, 1H); 8.36 (brs, 1H).

Intermediate 109

(2-Amino-4-methoxyphenyl)methanol

To a solution of commercially available 4-methoxy-2-nitrobenzoic acid (4.0 g, 20.66 mmol) in tetrahydrofuran (20 mL) at −15° C. under nitrogen was added N-methylmorpholine (2.2 ml, 20 mmol) followed by isobutyl chloroformate (2.6 mL, 20 mmol) in portions. After 5 min, the reaction was filtered and the solid was rinsed with tetrahydrofuran (20 mL). The filtrate was cooled to −15° C. and a solution of sodium borohydride in water (3 M, 10 mL) was added to the filtrate. The reaction was stirred for 5 min. The reaction mixture was partitioned between water and dichloromethane, and extracted aqueous layer with dichloromethane (3×100 mL). The combined organic layers were washed with brine, dried over magnesium sulfate, and concentrated under reduced pressure. The residue was redissolved in tetrahydrofuran (35 mL) and added palladium (10% on carbon, 400 mg) and stirred under hydrogen gas for 18 hours. The reaction mixture was then filtered through celite and concentrated under reduced pressure. The residue was chromatographed on silica gel with hexanes/ethyl acetate (3:2) gave 744 mg (24% yield) of product as a yellow solid.
$^1$H-NMR (DMSO-d$_6$) δ 3.63 (s, 3H); 4.30 (s, 2H); 4.84-4.96 (m, 2H); 6.08 (dd, 1H); 6.20 (d, 1H); 6.90 (d, 1H).

Example 55

7-Methoxy-3-methyl-1-[2-(4-{[(3-oxo-3,4-dihydro-2H-pyrido[3,2-b][1,4]oxazin-6-yl)methyl]amino}piperidin-1-yl)ethyl]quinazoline-2,4(1H,3H)-dione 1-[2-(4-Aminopiperidin-1-yl)ethyl]-7-methoxyquinazoline-2,4(1H,3H)-dione (Intermediate 110, crude, 153 mg, 0.46 mmol) was converted to the free base with N,N-diisopropylethylamine for 30 min and reacted with 3-oxo-3,4-dihydro-2H-pyrido[3,2-b][1,4]oxazine-6-carbaldehyde (WO 2004/058144) (90 mg, 0.51 mmol) as described under Example 21. The reaction mixture was cooled to 0° C., and sodium triacetoxy borohydride (194 mg, 0.92 mmol) was added. The resulting reaction mixture was stirred at room temperature for 18 hours and then worked up as described for Example 54 to give the bis-hydrochloride salt of the product, 12.5 mg (25%), as a colorless solid.
MS (ES): 495 (MH$^+$) for C$_{25}$H$_{30}$N$_6$O$_5$
$^1$H NMR (DMSO-D6) δ 1.85-2.32 (m, 1H); 3.68-3.88 (m, 3H); 3.89-4.08 (m, 3H); 4.10-4.43 (m, 5H); 4.50-4.78 (m, 5H); 6.91-7.44 (m, 5H); 7.99 (bs, 1H); 9.74 (br s, 2H); 11.16-11.38 (m, 2H).

Intermediate 110

1-[2-(4-Amino-2-oxopiperidin-1-yl)ethyl]-7-methoxy-3-methylquinazoline-2,4(1H,3H)-dione tert-Butyl{1-[2-(7-methoxy-3-methyl-2,4-dioxo-3,4-dihydroquinazolin-1(2H)-yl)ethyl]piperidin-4-yl}carbamate (Intermediate 111, 350 mg, 0.83 mmol) was reacted as described for Intermediate 106. The crude trifluoro acetate of the title compound was obtained as a black oil, 395 mg (quantitative), and used without further purification for the next step.
MS (ES): 319 (MH$^+$) for C$_{17}$H$_{24}$N$_4$O$_3$ Intermediate 111 tert-Butyl{1-[2-(7-methoxy-3-methyl-2,4-dioxo-3,4-dihydroquinazolin-1(2H)-yl)ethyl]piperidin-4-yl}carbamate 7-Methoxy-3-methylquinazoline-2,4(1H,3H)-dione (Intermediate 112, 523 mg, 2.5 mmol) was deprotonated with lithium bis(trimethylsilyl)amide (1M in tetrahydrofuran, 1.9 mL, 1.9 mmol) and alkylated with 2-{4-[tert-butoxycarbonyl)amino]piperidin-1-yl}ethyl methanesulfonate (Intermediate 6, 3.4 mmol) as described for Intermediate 2. Chromatography on silica gel with dichloromethane/methanol (95:5) gave 200 mg (18%) of the product as a colorless solid.

MS (ES): 433 (MH$^+$) for $C_{22}H_{32}N_4O_5$.

$^1$H NMR (CDCl$_3$) δ 1.16-1.28 (m, 1H); 1.14-1.43 (m, 11H); 1.89-2.04 (m, 3H); 2.25-2.47 (m, 2H); 2.80 (d, 3H); 2.94-3.14 (m, 2H); 3.77 (s, 3H); 4.22-4.36 (m, 1H); 4.40-4.56 (m, 1H); 4.99-5.09 (m, 1H); 7.02-7.03 (m, 1H); 7.31-7.47 (m, 2H).

Intermediate 112

7-Methoxy-3-methylquinazoline-2,4(1H,3H)-dione

2-Amino-4-methoxybenzoic acid (Intermediate 113, 950 mg, 6.2 mmol) and 1,3-dimethyl urea (5.4 g, 62 mmol) were heated at 150° C. for 16 hours. The reaction was cooled to 100° C. and diluted with water. The mixture was partitioned between ethyl acetate and water, the aqueous phase extracted with ethyl acetate (3×20 mL) and then chloroform/2-propanol (3:1, 2×20 mL). The combined organic layers were washed with brine, dried over sodium sulfate, and concentrated under reduced pressure. Chromatography on silica gel with hexanes/ethyl acetate (1:2) to give a 350 mg (27%) product as an orange oil.

MS (ES): 205 (MH$^+$) for $C_{10}H_{10}N_2O_3$.

$^1$H-NMR (DMSO-d$_6$) δ: 2.60 (d, 3H); 3.68 (s, 3H); 5.95 (d, 1H); 6.45 (dd, 1H); 6.86 (dd, 1H); 8.47 (s, 1H).

Intermediate 113

2-Amino-4-methoxybenzoic acid

4-Methoxy-2-nitrobenzoic acid (3 g, 16.4 mmol) was hydrogenated over palladium on carbon (10%, 300 mg) in methanol (80 mL) at room temperature and normal pressure for 18 hours. The reaction mixture was filtered through celite and concentrated to dryness under reduce pressure to give 2.50 g (100%) of the product as a colorless solid.

$^1$H NMR (DMSO-d$_6$) δ 3.70 (s, 3H); 6.09 (dd, 1H); 6.23 (d, 1H); 7.59 (d, 1H).

Example 56

4-(2-{4-[(2,3-Dihydro[1,4]dioxino[2,3-c]pyridin-7-ylmethyl)amino]-2-oxopiperidin-1-yl}ethyl)-6-methoxy-2H-1,4-benzoxazin-3(4H)-one 4-[2-(4-Amino-2-oxopiperidin-1-yl)ethyl]-6-methoxy-2H-1,4-benzoxazin-3(4H)-one trifluoroacetate (Intermediate 114, crude, 390 mg, 0.83 mmol) was converted to the free base with N,N-diisopropylethylamine and reacted with 2,3-dihydro[1,4]dioxino[2,3-c]pyridine-7-carbaldehyde (WO 2004/058144) (150 mg, 0.91 mmol) and sodium triacetoxy borohydride (360 mg, 1.7 mmol) as described for Example 55 to give the bis hydrochloride salt of the product as a colorless solid, 89 mg (63%).

MS (ES): 469.19 (MH$^+$) for $C_{24}H_{28}N_4O_6$ $^1$H NMR (DMSO-d$_6$) δ 1.84 (dd, 1H); 2.26 (d, 1H); 2.37-2.46 (m, 1H); 2.68-2.77 (m, 1H); 3.29-3.49 (m, 5H); 3.75 (s, 3H); 4.32-4.42 (m, 4H); 4.52 (s, 2H); 6.56 (dd, 1H); 6.91-6.98 (m, 2H); 7.22 (s, 1H); 8.23 (s, 1H); 9.52 (bs, 2H).

Intermediate 114

4-[2-(4-Amino-2-oxopiperidin-1-yl)ethyl]-6-methoxy-2H-1,4-benzoxazin-3(4H)-one tert-Butyl{1-[2-(6-methoxy-3-oxo-2,3-dihydro-4H-1,4-benzoxazin-4-yl)ethyl]-2-oxopiperidin-4-yl}carbamate (Intermediate 115, 350 mg, 0.83 mmol) was reacted as described for Intermediate 106. The crude trifluoro acetate of the title compound was obtained as a black oil, 395 mg (quantitative), and used without further purification for the next step.

MS (ES): 320 (MH$^+$) for $C_{16}H_{21}N_3O_4$.

Intermediate 115 tert-Butyl{1-[2-(6-methoxy-3-oxo-2,3-dihydro-4H-1,4-benzoxazin-4-yl)ethyl]-2-oxopiperidin-4-yl}carbamate A mixture of tert-butyl{1-[2-(6-methoxy-3-oxo-2,3-dihydro-4H-1,4-benzoxazin-4-yl)ethyl]piperidin-4-yl}carbamate (Intermediate 47, 1.39 g, 3.4 mmol) in water/ethyl acetate (40 mL, 4:1) was treated with sodium periodate (2.8 g, 21.4 mmol) and ruthenium (IV) oxide hydrate (50 mg, 0.34 mmol) at room temperature. After 53 hours, the reaction was diluted with ethyl acetate, the aqueous phase was extracted with ethyl acetate (6×25 mL), and the combined organic layers were mixed with 2-propanol (20 mL) and stirred for 2 hours at room temperature. The reaction mixture was then filtered through celite, dried over sodium sulfate, and concentrated in vacuo. Chromatography on silica gel with dichloromethane/methanol (95:5) gave 350 mg (25%) of the product as a colorless solid.

MS (ES): 415 (MH$^+$) for $C_{29}H_{26}N_3O_6$ $^1$H-NMR (DMSO-d$_6$) δ: 1.37 (s, 9H); 1.51-1.56 (m, 1H); 1.81-1.94 (m, 1H); 2.02-2.11 (m, 1H); 2.33-2.41 (dd, 1H); 3.06-3.12 (m, 1H); 3.27-3.31 (m, 2H); 3.40-3.45 (m, 2H); 3.55-3.65 (m, 1H); 3.75 (s, 3H); 3.99 (t, 2H); 4.52 (s, 2H); 6.57 (dd, 1H); 6.90-6.98 (m, 3H).

Example 57

6-[({1-[2-(6-Methoxy-3-oxo-2,3-dihydro-4H-1,4-benzoxazin-4-yl)ethyl]-2-oxopiperidin-4-yl}amino)methyl]-2H-pyrido[3,2-b][1,4]oxazin-3(4H)-one 4-[2-(4-amino-2-oxopiperidin-1-yl)ethyl]-6-methoxy-2H-1,4-benzoxazin-3(4H)-one trifluoroacetate (Intermediate 114, crude, 335 mg, 1.05 mmol) was converted to the free base with N,N-diisopropylethylamine and reacted with 3-oxo-3,4-dihydro-2H-pyrido[3,2-b][1,4]oxazine-6-carbaldehyde (WO 2004/058144) (205 mg, 1.15 mmol) and sodium triacetoxy borohydride (132 mg, 2.10 mmol) as described for Example 55 to give the bis hydrochloride salt of the product as a colorless solid, 36 mg (46%).

MS (ES): 482.15 (MH$^+$) for $C_{24}H_{27}N_5O_6$ $^1$H NMR (DMSO-d$_6$) δ: 1.75-1.95 (m, 1H); 2.20-2.41 (m, 1H); 2.74 (dd, 1H); 3.76 (s, 3H); 3.92-4.07 (m, 2H); 4.12-4.23 (m, 1H); 4.53-4.62 (m, 2H); 4.69 (s, 2H); 6.57 (dd, 2.26, 1H); 6.90-6.99 (m, 2H); 7.20 (d, 1H); 7.43 (d, 1H); 9.39 (bs, 1H); 11.35 (s, 1H).

Example 58

3-Oxo-4-[2-(2-oxo-4-{[(3-oxo-3,4-dihydro-2H-pyrido[3,2-b][1,4]oxazin-6-yl)methyl]amino}piperidin-1-yl)ethyl]-3,4-dihydro-2H-1,4-benzoxazine-6-carbonitrile 4-[2-(4-Amino-2-oxopiperidin-1-yl)ethyl]-3-oxo-3,4-dihydro-2H-1,4-benzoxazine-6-carbonitrile trifluoroacetate (Intermediate 116, crude, 232 mg, 0.54 mmol) was converted to the free base with N,N-diisopropylethylamine and reacted with 3-oxo-3,4-dihydro-2H-pyrido[3,2-b][1,4]oxazine-6-carbaldehyde (WO 2004/058144) (110 mg, 0.60 mmol) and sodium triacetoxy borohydride (240 mg, 1.10 mmol) as described for Example 55 to give the bis hydrochloride salt of the product as a colorless solid, 65 mg (49%).

MS (ES): 477.35 (MH$^+$) for $C_{24}H_{24}N_6O_5$ $^1$H NMR (DMSO-d$_6$) δ 1.79-1.84 (m, 1H); 2.28-2.42 (m, 2H); 2.70-2.77 (m, 1H); 3.51-3.56 (m, 2H); 4.08-4.16 (m, 4H); 4.68 (s, 3H); 4.73 (s, 3H); 7.14-7.22 (m, 2H); 7.43-7.52 (m, 2H); 9.46 (bs, 1H); 11.35 (s, 1H).

Intermediate 116

4-[2-(4-Amino-2-oxopiperidin-1-yl)ethyl]-3-oxo-3,4-dihydro-2H-1,4-benzoxazine-6-carbonitrile tert-Butyl{1-[2-(6-cyano-3-oxo-2,3-dihydro-4H-1,4-benzoxazin-4-yl)ethyl]-2-oxopiperidin-4-yl}carbamate (Intermediate 117, 225 mg, 0.54 mmol) was reacted as described for Intermediate 106. The crude trifluoro acetate of the title compound was obtained as a red oil, 232 mg (quantitative), and used without further purification for the next step.

MS (ES): 315 (MH$^+$) for $C_{17}H_{18}N_4O_2$

Intermediate 117 tert-Butyl{1-[2-(6-cyano-3-oxo-2,3-dihydro-4H-1,4-benzoxazin-4-yl)ethyl]-2-oxopiperidin-4-yl}carbamate tert-Butyl{1-[2-(6-cyano-3-oxo-2,3-dihydro-4H-1,4-benzoxazin-4-yl)ethyl]piperidin-4-yl}carbamate (Intermediate 59, 835 mg, 2.1 mmol) was reacted with sodium periodate (2.8 g, 13.1 mmol) and ruthenium (IV) oxide hydrate (30 mg, 0.21 mmol) as described for Intermediate 115 for 16 hours, except, chloroform was used for aqueous workup. The product was obtained as a colorless solid, 230 mg (27%).

MS (ES): 415 (MH$^+$) for $C_{21}H_{26}N_4O_5$ $^1$H-NMR (DMSO-d$_6$) δ: 1.36 (s, 9H); 1.42-1.57 (m, 2H); 1.87 (d, 1H); 2.00 (dd, 1H); 2.32 (dd, 1H); 3.38-3.48 (m, 2H); 3.51-3.63 (m, 1H); 4.07 (t, 2H); 4.72 (s, 2H); 6.94 (d, 1H); 7.14 (d, 1H); 7.48 (dd, 1H); 7.84 (d, 1H).

Example 59

6-({4-[3-(7-Methoxy-2-oxo-2H-3,1-benzoxazin-1(4H)-yl)propyl]piperazin-1-yl}methyl)-2H-pyrido[3,2-b][1,4]oxazin-3(4H)-one 7-Methoxy-1-(3-piperazin-1-ylpropyl)-1,4-dihydro-2H-3,1-benzoxazin-2-one trifluoroacetate (Intermediate 118, crude, 886 mg, 1.66 mmol) was converted to the free base with N,N-diisopropylethylamine and reacted with 3-oxo-3,4-dihydro-2H-pyrido[3,2-b][1,4]oxazine-6-carbaldehyde (WO 2004/058144) (220 mg, 1.23 mmol) and sodium triacetoxy borohydride (521 mg, 2.46 mmol) as described for Example 55 to give the free base of the product as a pink foam after chromatography on silica gel with dichloromethane/methanol (93:7), 86 mg (21%).

MS (ES): 468.19 (MH$^+$) for $C_{24}H_{29}N_5O_5$ $^1$H NMR (DMSO-d$_6$) δ: 1.60-1.75 (m, 2H); 2.19-2.44 (m, 9H); 3.37-3.43 (m, 2H); 3.72 (s, 2H); 3.83-3.96 (m, 2H); 4.53 (s, 2H); 4.60 (s, 2H); 6.56 (d, 1H); 6.78 (d, 1H); 6.88-7.02 (m, 2H); 7.29 (d, 1H); 11.22 (s, 1H).

Intermediate 118

6-Methoxy-4-(3-piperazin-1-ylpropyl)-2H-1,4-benzoxazin-3(4H)-one tert-Butyl{1-[2-(7-methoxy-2-oxoquinolin-1(2H)-yl)propyl]piperidin-4-yl}carbamate (Intermediate 119, 500 mg, 1.23 mmol) was reacted as described for Intermediate 106. The crude trifluoro acetate of the title compound was obtained as a yellow oil, 866 mg (quantitative), and used without further purification for the next step.

MS (ES): 306 (MH$^+$) for $C_{16}H_{23}N_3O_3$

Intermediate 119 tert-Butyl 4-[2-(6-methoxy-3-oxo-2,3-dihydro-4H-1,4-benzoxazin-4-yl)propyl]piperazine-1-carboxylate 6-Methoxy-2H-1,4-benzoxazin-3(4H)-one (Intermediate 48, 440 mg, 2.5 mmol) was deprotonated with sodium hydride (125 mg, 60% in oil, 3.2 mmol) and alkylated with tert-butyl 4-{3-[(methylsulfonyl)oxy]propyl}piperazine-1-carboxylate (Intermediate 120, 2.5 mmol) as described for Intermediate 2. Chromatography on silica gel with dichloromethane/2-propanol (95:5) gave 1.25 g (quantitative) of the product as a yellow oil.

MS (ES): 406 (MH$^+$) for $C_{20}H_{29}N_3O_5$ $^1$H-NMR (CDCl$_3$) δ: 1.45 (s, 9H); 1.78-1.90 (m, 2H) 2.36-2.40 (m, 6H); 3.43 (m, 4H); 3.77 (s, 3H); 3.95 (t, 2H); 4.52 (s, 2H); 6.49 (dd, 1H); 6.67 (d, 1H); 6.89 (d, 1H).

Intermediate 120 tert-Butyl 4-{3-[(methylsulfonyl)oxy]propyl}piperazine-1-carboxylate tert-Butyl 4-(3-hydroxypropyl)piperazine-1-carboxylate (Intermediate 121, 2.38 g, 9.8 mmol) was reacted with methanesulfonyl chloride (0.91 mL, 11.7 mmol) in the presence of triethylamine (1.9 mL, 13.7 mmol) as described for Intermediate 6. The crude product was used without further purification for the next step.

$^1$H NMR (CDCl$_3$) δ: 1.44 (s, 9H); 1.94-2.04 (m, 2H); 2.43-2.51 (m, 6H); 3.01 (s, 3H); 3.50-3.40 (m, 4H); 4.28-4.33 (m, 2H).

Intermediate 121 tert-Butyl 4-(3-hydroxypropyl)piperazine-1-carboxylate

A mixture of tert-butyl piperazine-1-carboxylate (2.75 g, 14.8 mmol), 1-bromo-3-propanol (1.43 mL, 16.2 mmol) and potassium carbonate (2.25 mL, 27.5 mmol) in acetonitrile (75 mL) was heated at 95° C. for 4 hours. The solvent was removed under reduced pressure, and the residue was taken up in dichloromethane (300 mL) and washed with water, brine, dried over sodium sulfate and concentrated under reduced pressure. Chromatography on silica gel with methanol in dichloromethane (0-10%) gave a tan solid 2.88 g (80% yield).

MS (ES): 245 (MH$^+$) for $C_{12}H_{24}N_2O_3$.

$^1$H-NMR (CDCl$_3$) δ: 1.44 (m, 9H); 1.70-1.82 (m, 2H); 2.40-2.53 (m, 2H); 2.62-2.65 (m, 2H); 3.43-3.50 (m, 4H); 2.77 (m, 2H); 3.73-3.82 (m, 2H).

Example 60

4-{3-[4-(2,3-Dihydro[1,4]dioxino[2,3-c]pyridin-7-ylmethyl)piperazin-1-yl]propyl}-6-methoxy-2H-1,4-benzoxazin-3(4H)-one 7-Methoxy-1-(3-piperazin-1-ylpropyl)-1,4-dihydro-2H-3,1-benzoxazin-2-one trifluoroacetate (Intermediate 118, crude, 963 mg, 1.81 mmol) was converted to the free base with N,N-diisopropylethylamine and reacted with 2,3-dihydro[1,4]dioxino[2,3-c]pyridine-7-carbaldehyde (WO 2004/058144) (203 mg, 123 mmol) and sodium triacetoxy borohydride (240 mg, 1.10 mmol) as described for Example 55 to give the free base of the product as an oil after chromatography on silica gel with dichloromethane/methanol (93:7), 125 mg (22%).

MS (ES): 455.15 (MH$^+$) for $C_{24}H_{30}N_4O_5$ $^1$H NMR (DMSO-D6) δ: 1.67 (s, 2H); 2.26-2.41 (m, 8H); 3.41 (s, 2H); 3.72 (s, 3H); 3.88 (s, 2H); 4.29 (d, 4H); 4.52 (s, 2H); 6.56 (d, 1H); 6.78 (s, 1H); 6.83-6.99 (m, 3H); 7.99 (s, 1H).

Example 61

4-[2-({1-[(2E)-3-(2,5-Difluorophenyl)prop-2-en-1-yl]piperidin-4-yl}amino)ethyl]-6-methoxy-2H-1,4-benzoxazin-3(4H)-one 1-[(2E)-3-(2,5-difluorophenyl)prop-2-en-1-yl]piperidin-4-amine trifluoroacetate (Intermediate 122, 430 mg, 0.85 mmol) was converted to the free base with N,N-diisopropylethylamine and reacted with (6-methoxy-3-oxo-2,3-dihydro-4H-1,4-benzoxazin-4-yl)acetaldehyde (Intermediate 125, 197 mg, 0.90 mmol) and sodium triacetoxy borohydride (132 mg, 2.10 mmol) as described for Example 55 and purified by Reverse Phase Chromatography with 20 to 75% acetonitrile/water containing 0.1% TFA to give the trifluoroacetic acid salt of the product, 31 mg.

MS (ES): 458.27 (MH$^+$) for $C_{25}H_{29}F_2N_3O_3$

1H NMR (DMSO-D6) δ: 1.85-1.72 (m, 1H); 2.30-2.21 (m, 1H); 3.24-2.8 (m, 2H); 4.05-3.72 (m, 5H); 4.13-4.40 (m, 2H); 4.60 (br s, 2H); 6.61-6.98 (m, 2H); 7.21-7.41 (m, 2H); 7.60 (brs, 1H); 9.04 (brs, 1H).

Intermediate 122

1-[(2E)-3-(2,5-Difluorophenyl)prop-2-en-1-yl]piperidin-4-amine tert-Butyl{1-[(2E)-3-(2,5-difluorophenyl)prop-2-en-1-yl]piperidin-4-yl}carbamate (Intermediate 123, 299 mg, 0.85 mmol) was reacted as described for Intermediate 106. The crude trifluoro acetate of the title compound was obtained as an oil, 430 mg (quantitative), and used without further purification for the next step MS (ES): 253 (MH$^+$) for $C_{14}H_{18}F_2N_2$.

Intermediate 123 tert-Butyl{1-[(2E)-3-(2,5-difluorophenyl)prop-2-en-1-yl]piperidin-4-yl}carbamate A mixture of tert-butyl piperidin-4-ylcarbamate (248 mg, 1.2 mmol), potassium carbonate (188 mg, 1.4 mmol) and 2-[(1E)-3-chloroprop-1-en-1-yl]-1,4-difluorobenzene (Intermediate 124, 257 mg, 1.4 mmol) in ethanol (7 mL) was heated to 80° C. for 18 hours. The mixture was concentrated under reduced pressure, the residue taken up in dichloromethane (20 mL) and water (20 mL), the aqueous phase was back extracted with dichloromethane (2×20 mL) and the combined organic phases were dried over sodium sulfate. Chromatography on silica gel with dichloromethane/methanol (95:5) gave 300 mg (69%) of product as a brown foam.

MS (ES): 353 (MH$^+$) for $C_{19}H_{26}F_2N_2O_2$ $^1$H NMR (CDCl$_3$) δ 1.41-1.53 (m, 11H); 1.96 (d, 2H); 2.07-2.21 (m, 2H); 2.92 (d, 2H); 3.18 (d, 2H); 3.48 (d, 1H); 4.45 (s, 1H); 6.27-6.39 (m, 1H); 6.63 (d, 1H); 6.85-7.01 (m, 2H); 7.12 (ddd, 1H); 7.24-7.28 (m, 1H).

Intermediate 124

2-[(1E)-3-Chloroprop-1-en-1-yl]-1,4-difluorobenzene

A mixture of (2E)-3-(2,5-difluorophenyl)prop-2-en-1-ol (Intermediate 70, 700 mg, 4.12 mmol), 1,4-dioxane (5 mL), and hydrochloric acid (12.1 M, 1 mL) was heated in the microwave at 100° C. for 3 hours. It was concentrated to dryness under reduced pressure, the residue taken up in ethyl acetate (10 mL), washed with water (1×10 mL), saturated sodium bicarbonate solution, brine and dried over sodium sulfate. The solvent was removed under reduced pressure to give 688 mg (89% yield) of product as a yellow oil.

$^1$H NMR (CDCl$_3$) δ 4.24 (dd, 2H); 6.38 (dt, 1H); 6.75 (d, 1H); 6.88-7.04 (m, 2H); 7.13 (ddd, 1H).

Intermediate 125

(6-Methoxy-3-oxo-2,3-dihydro-4H-1,4-benzoxazin-4-yl)acetaldehyde

To a solution of oxalyl chloride (0.26 mL, 3.0 mmol) in dichloromethane (10 mL) at −70° C. was added a solution of dimethyl sulfoxide (DMSO, 0.426 mL, 6.0 mmol) in dichloromethane (10 mL). After thirty minutes a solution of 4-(2-hydroxyethyl)-6-methoxy-2H-1,4-benzoxazin-3(4H)-one (Intermediate 126, 550 mg, 2.5 mmol) in dichloromethane (3.5 mL) was added dropwise and it was stirred for 90 minutes. Triethyl amine (1.74 ml, 12.5 mmol) was added it was stirred at −70° C. for another 45 minutes. The reaction was quenched with water and warmed to 0° C. It was diluted with dichloromethane, the aqueous phase was extracted with dichloromethane (3×25 mL) and the combined organic phases were washed with 1N HCl (2×25 mL), water (25 mL), 1M sodium carbonate solution (2×25 mL), water, brine, dried over magnesium sulfate and concentrated at reduced pressure. Chromatography on silica gel with dichloromethane/methanol (96:4) gave the product as a yellow oil, 292 mg (53%).

MS (ES): 221 (MH$^+$) for $C_{11}H_{12}NO_4$ $^1$H NMR (CDCl$_3$) δ 3.71-3.78 (m, 3H); 4.63 (s, 2H); 4.69 (s, 2H); 6.22 (d, 1H); 6.53 (dd, 1H); 6.95 (d, 1H); 9.67 (s, 1H).

Intermediate 126

4-(2-Hydroxyethyl)-6-methoxy-2H-1,4-benzoxazin-3(4H)-one

To a solution of 4-(2-{[tert-butyl(dimethyl)silyl]oxy}ethyl)-6-methoxy-2H-1,4-benzoxazin-3(4H)-one (Intermediate 127, 1.38 g, 4.1 mmol) in tetrahydrofuran (40 mL) was added tetrabutyl ammonium fluoride (1M in tetrahydrofuran (THF), 4.1 mL, 4.1 mmol). The reaction was stirred at room temperature for two hours. The solvent was removed under reduced pressure and the residue was taken up in dichloromethane, washed with water and dried over magnesium sulfate. Chromatography on silica gel using dichloromethane/methanol (95:5) gave the title compound as a yellow oil (570 mg, 62%).

$^1$H NMR (CDCl$_3$) δ ppm: 3.77 (s, 3H); 3.92 (t, 2H); 4.08 (t, 2H); 4.55 (s, 2H); 6.52 (dd, 1H); 6.68 (d, 1H); 6.90 (d, 1H).

Intermediate 127

4-(2-{[tert-Butyl(dimethyl)silyl]oxy}ethyl)-6-methoxy-2H-1,4-benzoxazin-3(4H)-one To a solution of 6-methoxy-2H-1,4-benzoxazin-3(4H)-one (Intermediate 48) (800 mg, 4.5 mmol) in DMF (16 mL) was added sodium hydride (60% in mineral oil, 260 mg, 6.5 mmol). After 20 minutes, (2-bromoethoxy)(tert-butyl)dimethylsilane (1.4 mL, 6.5 mmol) was added and it was heated to 70° C. in the microwave for 40 minutes. The reaction mixture was partitioned between water (100 mL) and ethyl acetate (100 mL). The aqueous phase was extracted with ethyl acetate (4×50 mL). The combined organic phases were washed with water (6×250 mL), dried over magnesium sulfate and concentrated at reduced pressure to afford the product as a yellow oil which was used without further purification. (1.38 g, 91%).

$^1$H NMR (CDCl$_3$) δ: −0.02 (s, 6H); 0.83 (s, 9H); 3.77 (s, 3H); 3.84-3.91 (m, 2H); 4.01 (t, 2H); 4.52 (s, 2H); 6.50 (dd, 1H); 6.82 (d, 1H); 6.87 (d, 1H).

Example 62

4-(3-{4-[(2E)-3-(2,5-Difluorophenyl)prop-2-en-1-yl]piperazin-1-yl}propyl)-6-methoxy-2H-1,4-benzoxazin-3(4H)-one A solution of 6-methoxy-4-(3-piperazin-1-ylpropyl)-2H-1,4-benzoxazin-3(4H)-one trifluoroacetate (Intermediate 118, 985 mg, 1.52 mmol) in dry ethanol (10 mL) was converted to the free base with N,N-diisopropylethylamine for 30 min and then was added 2-[(1E)-4-chloroprop-1-en-1-yl]-1,4-difluorobenzene (Intermediate 124, 315 mg, 1.67 mmol), and potassium carbonate (230 mg, 1.67 mmol). The mixture was heated at 80° C. for 18 hours, cooled to room temperature and then concentrated to dryness under reduced pressure. The residue was partitioned between water (50 mL) and dichloromethane (100 mL). The organic phase was dried over sodium sulfate and concentrated under reduced pressure. Chromatography on silica gel with dichloromethane/methanol (95:5) gave the free base of the title compound as a yellow foam. The free base was taken up in dichloromethane (14 mL), followed by the addition of 2M HCl in ether (0.41 mL). The precipitate was collected by filtration and to give the bis hydrochloride salt of the product as a colorless solid, 171 mg (79%).

MS (ES): 458.30 (MH$^+$) for C$_{25}$H$_{29}$F$_2$N$_3$O$_3$ $^1$H NMR (DMSO-D6) δ 1.90-2.04 (bs, 2H); 3.15-3.30 (m, 6H); 3.75 (s, 3H); 3.95 (m, 3H); 4.57 (s, 2H); 6.45-6.54 (m, 1H); 6.57-6.61 (m, 1H); 6.81 (d, 1H); 6.93 (d, J=9 Hz, 1H); 7.26-7.33 (m, 2H); 7.56 (m, 1H).

Example 63

6-[({1-[2-(6-Methoxy-2-oxo-1,7-naphthyridin-1(2H)-yl)ethyl]piperidin-4-yl}amino)methyl]-2H-pyrido[3,2-b][1,4]oxazin-3(4H)-one A solution of 1-[2-(4-aminopiperidin-1-yl)ethyl]-6-methoxy-1,7-naphthyridin-2(1H)-one (Intermediate 128, crude, 116 mg, 0.38 mmol) and 3-oxo-3,4-dihydro-2H-pyrido[3,2-b][1,4]oxazine-6-carbaldehyde [WO2004/058144](82 mg, 0.46 mmol) in chloroform/methanol (6 mL, 10:1) was heated over 3 Å molecular sieves at 70° C. for 18 hours. The reaction mixture was cooled to 0° C., and sodium triacetoxy borohydride (180 mg, 0.84 mmol) was added. The resulting reaction mixture was allowed to warm to room temperature and stirred for 18 hours. The reaction was diluted with dichloromethane (50 mL) and water (10 mL). The aqueous phase was separated and evaporated to give a solid. The solid was suspended in methanol and filtered. The resultant solid was dissolved in dichloromethane:methanol (1:1) and treated with 2N HCl in ether to obtain the dihydrochloride salt. The colorless precipitate was collected by filtration and gave 28 mg (14%) of the bis-hydrochloride salt of the product.

MS (ES)$^+$: 465 (MH)$^+$ for C$_{24}$H$_{28}$N$_6$O$_4$ $^1$H NMR (DMSO-D$_6$) δ ppm: 2.04-2.19 (m, 2H); 2.19-2.31 (m, 1H); 2.32-2.45 (m, 3H); 3.05-3.21 (m, 4H) 3.69-3.84 (m, 2H); 3.89 (s, 3H); 4.05-4.20 (m, 2H); 4.62-4.75 (m, 4H); 6.83 (d, 1H); 7.20 (s, 1H); 7.30 (d, 1H); 7.42 (d, 1H); 7.92 (d, 1H); 8.78 (s, 1H); 9.94 (s, 1H); 11.39 (s, 2H).

Intermediate 128

1-[2-(4-Aminopiperidin-1-yl)ethyl]-6-methoxy-1,7-naphthyridin-2(1H)-one

A solution of tert-butyl{1-[2-(6-chloro-2-oxo-1,7-naphthyridin-1(2H)-yl)ethyl]piperidin-4-yl}carbamate (Intermediate 129, 335 mg, 0.83 mmol) was treated with a solution of sodium methoxide in methanol (0.5 M, 4 mL). The reaction was sealed in a tube and heated at 150° C. for 4 hours using microwave irradiation. The reaction was diluted with water and ethyl acetate. The layers were separated. The aqueous phase was washed with ethyl acetate twice. The organic extracts were combined dried over magnesium sulfate and evaporated at reduced pressure to give 116 mg (64%) of the crude product as a yellow oil.

MS (ES): 303 (MH$^+$) for C$_{16}$H$_{22}$N$_4$O$_2$

Intermediate 129 tert-Butyl{1-[2-(7-methoxy-2-oxoquinolin-1(2H)-yl)ethyl]piperidin-4-yl}carbamate 6-Chloro-1,7-naphthyridin-2(1H)-one (J. Org. Chem. 1990, 55, 4744-4750) (360 mg, 2.0 mmol) was deprotonated with sodium hydride (100 mg, 60% in oil, 2.4 mmol) and alkylated with 2-{4-[(tert-butoxycarbonyl)amino]piperidin-1-yl}ethyl methanesulfonate (Intermediate 6) 2.75 mmol) as described for Intermediate 2. Chromatography on silica gel with methanol in dichloromethane (0-10%) gave 334 mg (20%) of the product as a colorless solid.

MS (ES): 407 (MH$^+$) for C$_{20}$H$_{27}$ClN$_4$O$_3$ $^1$H-NMR (DMSO-d$_6$) δ: 1.19-1.32 (m, 1H); 1.36 (s, 9H); 1.56-1.70 (m, 2H); 2.01 (s, 2H); 2.51-2.57 (m, 2H); 2.67-2.75 (m, 1H); 2.83-2.93 (m, 2H); 3.10-3.25 (m, 2H); 3.29-3.31 (m, 1H); 4.30-4.40 (m, 2H); 6.71-6.80 (m, 1H); 6.91 (d, 1H); 7.87 (s, 1H); 7.91 (d, 1H); 8.74 (s, 1H).

Example 64

Methyl 1-[(2E)-3-(2,5-difluorophenyl)prop-2-en-1-yl]-4-[3-(6-cyano-3-oxo-2,3-dihydro-4H-1,4-benzoxazin-4-yl)propyl]piperidine-3-carboxylate A solution of methyl 4-[3-(6-cyano-3-oxo-2,3-dihydro-4H-1,4-benzoxazin-4-yl)propyl]piperidine-3-carboxylate trifluoroacetate (Intermediate 130, crude, 171, 0.48 mmol), (2E)-3-(2,5-difluorophenyl)acrylaldehyde [FR 2872164] (81 mg, 0.48 mmol), and triethylamine (0.13 mL. 0.96 mmol) in chloroform/methanol (6 mL, 10:1) was heated over 3 Å molecular sieves at 70° C. for 3 hours. The reaction mixture was cooled to 0° C., and sodium triacetoxy borohydride (200 mg, 0.94 mmol) was added. The resulting reaction mixture was allowed to warm to room temperature and stir for 18 hours. The reaction was diluted with ethyl acetate (25 mL) and water (10 mL). The aqueous phase was separated and washed twice with ethyl acetate. The organic layers were combined, dried over magnesium sulfate and evaporated at reduced pressure. Chromatography on silica gel with diethyl ether gave the title compound as a off-white foam, (79 mg, 32%).

MS (ES) 510 (MH)$^+$ for $C_{28}H_{29}F_2N_3O_4$.

$^1$H NMR (DMSO-d$_6$) δ 1.10-1.21 (m, 1H); 1.23-1.34 (m, 1H); 1.44-1.55 (m, 3H); 1.67-1.79 (m, 2H); 1.95-2.07 (m, 1H); 2.18-2.29 (m, 1H); 2.31-2.43 (m, 1H); 2.64-2.70 (m, 1H); 2.71-2.80 (m, 1H); 2.82-2.89 (m, 1H); 3.06-3.17 (m, 2H); 3.57 (d, 3H); 3.84-3.96 (m, 2H); 4 4.77 (s, 2H); 6.40-6.51 (m, 1H); 6.56-6.63 (m, 1H); 7.12 (ddd, 1H); 7.17 (d, 2H); 7.20-7.28 (m, 1H); 7.47-7.56 (m, 2H); 7.72 (d, 1H).

Intermediate 130

Methyl 4-[3-(6-cyano-3-oxo-2,3-dihydro-4H-1,4-benzoxazin-4-yl)propyl]piperidine-3-carboxylate A solution of 1-tert-butyl 3-methyl 4-[3-(6-cyano-3-oxo-2,3-dihydro-4H-1,4-benzoxazin-4-yl)propyl]piperidine-1,3-dicarboxylate (Intermediate 131, 220 mg, 0.48 mmol) was reacted as described for Intermediate 106. The crude trifluoro acetate of the title compound was used without further purification for the next step (quantitative).

Intermediate 131

1-tert-Butyl 3-methyl 4-[3-(6-cyano-3-oxo-2,3-dihydro-4H-1,4-benzoxazin-4-yl)propyl]piperidine-1,3-dicarboxylate A solution of 3-oxo-3,4-dihydro-2H-1,4-benzoxazine-6-carbonitrile (Intermediate 60) (265 mg, 1.53 mmol) in dry dimethylformamide (DMF) (5 mL) was treated at 0° C. with sodium hydride (105 mg, 60% in oil, 2.63 mmol) and then stirred for 30 minutes at room temperature. A solution of 1-tert-butyl 3-methyl 4-{3-[(methylsulfonyl)oxy] propyl}piperidine-1,3-dicarboxylate in DMF (Intermediate 132, 0.31 mmol/mL, 5 mL, 1.53 mmol) was then added and the resulting mixture was stirred at room temperature for 96 hours. The reaction was diluted with ethyl acetate and water. The aqueous layer was adjusted to pH3 with 1N HCl. The layers were separated. The aqueous phase was extracted once with ethyl acetate. The combined organic phases were washed four times with water, dried over magnesium sulfate and evaporated at reduced pressure. Chromatography on silica gel with (10-35%) acetone in hexanes gave 445 mg (64%) of the product as a white semi-solid (as a mixture of diastereomers).

MS (ES): 458 (MH$^+$) for $C_{24}H_{31}N_3O_6$ $^1$H NMR (CDCl$_3$) δ: 1.43 and 1.44 (two s, 9H); 1.47-1.9 (m, 7H); 2.56-2.83 (m, 2H); 2.94-3.2 (m, 2H); 3.65 and 3.70 (two s, 3H); 3.76-3.99 (m, 2H); 4.02-4.21 (m, 1H); 4.67 and 4.70 (two s, 2H); 7.04 (m, 1H); 7.11 and 7.18 (two brs, 1H); 7.30 (m, 1H).

Intermediate 132

1-tert-Butyl 3-methyl 4-{3-[(methylsulfonyl)oxy] propyl}piperidine-1,3-dicarboxylate A mixture of 1-tert-butyl 3-methyl 4-(3-hydroxypropyl) piperidine-1,3-dicarboxylate (Intermediate 133, 460 mg, 1.53 mmol) in dry dichloromethane (5 mL) and triethyl amine (0.3 mL, 2.14 mmol) was treated at 0° C. with a solution of methanesulfonyl chloride (0.14 mL, 1.83 mmol) in dichloromethane (5 mL). After 2 hours minutes the reaction was complete by TLC (dichloromethane:methanol 10:1). The reaction was diluted with ethyl acetate and water. The layers were separated. The organic layer was washed with 0.1N HCl, water, saturated sodium bicarbonate, dried over magnesium sulfate. The solvent was removed under reduced pressure and the crude preparation of the mesylate was used without delay for the next step.

Intermediate 133

1-tert-Butyl 3-methyl 4-(3-hydroxypropyl)piperidine-1,3-dicarboxylate

A solution of 1-tert-butyl 3-methyl 4-allylpiperidine-1,3-dicarboxylate [WO2002/072572] (715 mg, 2.53 mmol) in tetrahydrofuran (5 mL) at 0° C. was treated with a solution of 9-BBN in tetrahydrofuran (0.5M, 10.2 mL, 5.1 mmol). After one hour the reaction mixture was allowed to warm to room temperature for 3 hours. The reaction mixture was cooled to 0° C. and treated with water (3 mL), NaOH (3N, 6 mL) and hydrogen peroxide (30% solution, 6 mL). The reaction was allowed to warm to room temperature and stir for one hour. The reaction was diluted with ethyl acetate and water. The layers were separated. The aqueous layer was extracted twice with ethyl acetate. The combined organic layers were dried over magnesium sulfate and concentrated at reduced. Chromatography on silica gel with methanol in dichloromethane (0-10%) gave the product as a colorless oil as a mixture of diastereomers (460 mg, 60%).

MS (ES): 302 (MH$^+$) for $C_{15}H_{27}NO_5$ $^1$H NMR (CDCl$_3$) δ: 1.28-1.39 (m, 1H); 1.43 and 1.44 (two s, 9H); 1.46-1.54 (m, 2H); 1.56-1.67 (m, 3H); 1.73-1.85 (m, 2H); 2.58-2.63 (m, 1H); 3.02-3.12 (m, 1H); 3.27 (dd, 1H); 3.60-3.64 (m, 2H); 3.65 and 3.69 (two s, 3H); 3.71-3.81 (m, 1H); 3.87-3.98 (m, 1H).

Example 65

4-[3-(6-Cyano-3-oxo-2,3-dihydro-4H-1,4-benzoxazin-4-yl)propyl]-1-[(2E)-3-(2,5-difluorophenyl) prop-2-en-1-yl]piperidine-3-carboxylic acid A solution of methyl 1-[(2E)-3-(2,5-difluorophenyl)prop-2-en-1-yl]-4-[3-(6-cyano-3-oxo-2,3-dihydro-4H-1,4-benzoxazin-4-yl)propyl]piperidine-3-carboxylate (Example 64) (73 mg, 0.143 mmol) in methanol (12 mL) and water (5 mL) was treated with sodium hydroxide solution (1N, 1 mL). After 64 hours, the pH was adjusted to 6 with 1N HCl. The mixture was extracted with ethyl acetate (3×30 mL). The combined organic extracts were dried over magnesium sulfate and concentrated at reduced pressure. Chromatography on silica gel using methanol in dichloromethane (0-10%) and trituration with diethyl ether gave the title compound as a colorless solid, mixture of diastereomers, 10 mg (14%).

MS (ES): 496 (MH)$^+$ for $C_{27}H_{27}F_2N_3O_4$ $^1$H NMR (CDCl$_3$) δ: 1.40-1.45 (m, 1H); 1.47-1.52 (m, 1H); 1.60-1.65 (m, 1H); 1.65-1.77 (m, 3H); 2.25-2.37 (m, 2H); 2.70-2.77 (m, 1H); 3.08-3.16 (m, 1H); 3.23-3.30 (m, 1H); 3.30-3.40 (m, 2H); 3.64-3.72 (m, 1H); 3.73-3.84 (m, 1H);

3.86-3.95 (m, 1H); 3.95-4.07 (m, 1H); 4.60-4.71 (m, 3H); 6.21-6.31 (m, 1H); 6.67 (d, 1H); 6.87-6.95 (m, 1H); 6.96-7.01 (m, 1H); 7.01-7.07 (m, 1H); 7.09-7.15 (m, 1H); 7.28-7.31 (m, 1H).

Example 66

7-Fluoro-3-methyl-1-[2-(4-{[(3-oxo-3,4-dihydro-2H-pyrido[3,2-b][1,4]oxazin-6-yl)methyl]amino}piperidin-1-yl)ethyl]quinazoline-2,4(1H,3H)-dione 1-[2-(4-Aminopiperidin-1-yl)ethyl]-7-fluoro-3-methylquinazoline-2,4(1H,3H)-dione trifluoroacetate salt (Intermediate 134) (0.476 mmol, 380 mg crude) was converted to the free base with N,N-diisopropylethylamine (0.5 mL, 3.0 mmol) and reacted with 3-oxo-3,4-dihydro-2H-pyrido[3,2-b][1,4]oxazine-6-carbaldehyde (WO 2004/058144) (102 mg, 0.571 mmol) and sodium triacetoxy borohydride (222 mg, 1.05 mmol) as described for Example 55. The reaction was diluted with dichloromethane and water. The layers were separated. The aqueous layer was extracted with dichloromethane twice. The combined organic layers were dried over magnesium sulfate and evaporated at reduced pressure. Chromatography on silica gel using methanol in dichloromethane (0-9%) with 1% concentrated ammonium hydroxide (aqueous) gave the product as a waxy material. This material was taken up in dichloromethane and washed well with water. The organic phase was dried over magnesium sulfate and evaporated to obtain the title compound as a colorless solid (48 mg, 21%).

MS (ES): 483 (MH)$^+$ for $C_{24}H_{27}FN_6O_4$ $^1$H NMR (DMSO-D6) δ: 1.14-1.28 (m, 2H); 1.71-1.82 (m, 2H); 1.94-2.06 (m, 2H); 2.33-2.44 (m, 2H); 2.83-2.92 (m, 2H); 3.26-3.30 (m, 3H); 3.65-3.72 (m, 2H); 4.17 (t, 2H); 4.60 (s, 2H); 7.00 (d, 1H); 7.13 (td, 1H); 7.29 (d, 1H); 7.36 (dd, 1H); 8.09 (dd, 1H); 11.18 (s, 1H).

Intermediate 134

1-[2-(4-Aminopiperidin-1-yl)ethyl]-7-fluoro-3-methylquinazoline-2,4(1H,3H)-dione tert-Butyl{1-[2-(7-fluoro-3-methyl-2,4-dioxo-3,4-dihydroquinazolin-1(2H)-yl)ethyl]piperidin-4-yl}carbamate (Intermediate 135) (200 mg, 0.476 mmol) was reacted as described for Intermediate 106. The crude trifluoro acetate of the title compound was used without further purification for the next step (quantitative).

MS (ES): 321 (MH)$^+$ for $C_{16}H_{21}FN_4O_2$

Intermediate 135 tert-Butyl{1-[2-(7-fluoro-3-methyl-2,4-dioxo-3,4-dihydroquinazolin-1(2H)-yl)ethyl]piperidin-4-yl}carbamate 7-Fluoro-3-methylquinazoline-2,4(1H,3H)-dione [Intermediate 136] (388 mg, 2.0 mmol) was deprotonated with sodium hydride (100 mg, 60% in oil, 2.4 mmol) and alkylated with 2-{4-[(tert-butoxycarbonyl)amino]piperidin-1-yl}ethyl methanesulfonate (Intermediate 6) 2.75 mmol) as described for Intermediate 2. Chromatography on silica gel using ethyl acetate in hexanes (10-30%) gave the title compound as a yellow oil (200 mg, 24%).

MS (ES): 421 (MH)$^+$ for $C_{21}H_{29}FN_4O_4$ $^1$H NMR (CDCl$_3$) δ: 1.2-1.3 (m, 2H); 1.43 (s, 9H); 1.44-1.5 (m, 1H); 1.9-2.0 (m, 2H); 2.15-2.35 (m, 2H); 2.65 (m, 2H); 2.85-3.0 (m, 1H); 3.45 (s, 3H); 3.46-3.52 (m, 1H); 4.15-4.25 (m, 2H); 4.35-4.5 (m, 1H); 6.8-6.9 (m, 1H); 6.91-7.0 (m, 1H); 8.2-8.26 (m, 1H).

Intermediate 136

7-Fluoro-3-methylquinazoline-2,4(1H,3H)-dione

A suspension of sodium hydride (60% in mineral oil, 368 mg, 9.2 mmol) in dimethylformamide (12 mL) was cooled to 0° C. and treated with 2-amino-4-fluoro-N-methylbenzamide [Intermediate 137] (0.67 g, 4.0 mmol). Phenyl chloroformate (0.6 mL, 0.73 g, 4.7 mmol) was added over 40 minutes. After 1 hour a further portion of phenyl chloroformate (0.6 mL, 0.73 g, 4.7 mmol) was added. The reaction was allowed to warm to room temperature and stir for two hours. The reaction was slowly added to 200 mL of ice. The solid was filtered, washed with methanol to obtain the product (395 mg, 51%).

MS (ES): 193 (M-H)$^-$ for $C_9H_7FN_2O_2$ $^1$H NMR (DMSO-d$_6$) δ: 3.23 (s, 3H); 6.89 (dd, 1H); 7.04 (td, 1H); 7.98 (dd, 1H); 11.56 (s, 1H).

Intermediate 137

2-Amino-4-fluoro-N-methylbenzamide

A mixture of 2-amino 4-fluoro benzoic acid (2.5 g, 16.13 mmol) and 1,3 dimethyl urea (5.85 g, 66.5 mmol) was heated at 150° C. for 24 hours. The reaction was diluted with water, filtered and extracted twice with ethyl acetate. The organic extracts were dried over magnesium sulfate and concentrated at reduced pressure. Chromatography on silica gel with ethyl acetate in hexanes (0-50%) gave the title compound as a waxy solid (670 mg, 25%)

MS (ES): 169 (MH)$^+$ for $C_8H_9FN_2O$ $^1$H NMR (DMSO-D6) δ: 2.69 (d, 3H); 6.29 (td, 1H); 6.43 (dd, 1H); 6.74 (s, 2H); 7.49 (dd, 1H); 8.08-8.22 (m, 1H).

Example 67

7-Chloro-1-(2-{4-[(2,3-dihydro[1,4]dioxino[2,3-c]pyridin-7-ylmethyl)amino]piperidin-1-yl}ethyl)-1,8-naphthyridin-2(1H)-one 1-[2-(4-Aminopiperidin-1-yl)ethyl]-7-chloro-1,8-naphthyridin-2(1H)-one trifluoroacetate (Intermediate 138, crude, 405 mg, 0.76 mmol), di-isopropyl ethylamine (0.38 mL, 2.27 mmol), 2,3-dihydro[1,4]dioxino[2,3-c]pyridine-7-carbaldehyde [WO 2004/058144](180 mg, 1.1 mmol) and sodium cyanoborohydride (100 mg, 1.56 mmol) were reacted as described for Example 21. Chromatography on silica gel using methanol in dichloromethane (0-20% with 1% aqueous ammonium hydroxide) followed by reverse phase chromatography with 20-75% acetonitrile/water/10 mM NH$_4$OAc Buffer) gave the title compound (39 mg, 11%).

MS (ES): 456 (MH)$^+$ for $C_{23}H_{26}ClN_5O_3$ $^1$H NMR (CDCl$_3$) δ 1.32-1.43 (m, 2H); 1.87 (d, 2H); 2.10-2.21 (m, 2H); 2.51-2.61 (m, 1H); 2.69 (t, 2H); 3.08 (d, 2H); 3.81 (s, 2H); 4.21-4.32 (m, 4H); 4.58 (t, 2H); 6.68 (d, 1H); 6.78 (s, 1H); 7.11 (d, 1H); 7.58 (d, 1H); 7.75 (d, 1H); 8.05 (s, 1H).

Intermediate 138

1-[2-(4-Aminopiperidin-1-yl)ethyl]-7-chloro-1,8-naphthyridin-2(1H)-one tert-Butyl{1-[2-(7-chloro-2-oxo-1,8-naphthyridin-1(2H)-yl)ethyl]piperidin-4-yl}carbamate (Intermediate 139, 308 mg, 0.76 mmol) was reacted as described for Intermediate 106. The crude trifluoro acetate of the title compound was used without further purification for the next step (quantitative).

Intermediate 139 tert-Butyl{1-[2-(7-chloro-2-oxo-1,8-naphthyridin-1 (2H)-yl)ethyl]piperidin-4-yl}carbamate A solution of 7-chloro-1,8-naphthyridin-2(1H)-one [*J. Org. Chem.* 1990, 55, 4744-4750] in dry DMF (20 mL) (540 mg, 3.0 mmol) at 0° C. was treated with sodium hydride (144 mg, 60% in mineral oil, 3.6 mmol). The reaction mixture was allowed to warm to room temperature and stirred for 1 hour. The reaction was cooled using an ice bath. A solution of 2-{4-[(tert-butoxycarbonyl)amino]piperidin-1yl}ethyl methanesulfonate in DMF (Intermediate 6), 0.33 mmol/mL, 10 mL, 3.3 mmol) was then added over 1 hour. The reaction was allowed to warm to room temperature and stirred overnight. The reaction mixture was diluted with water and extracted with dichloromethane (3×50 mL). The combined organic layers were washed with saturated sodium chloride solution (3×10 mL), dried over sodium sulfate and evaporated. Chromatography on silica gel using methanol in dichloromethane (0-15%) gave the title compound as a brown foam (711 mg, 58%).

MS (ES): 407 (MH)$^+$ for $C_{20}H_{27}ClN_4O_3$ $^1$H NMR (CDCl$_3$) δ 1.42 (s, 11H); 1.84-1.99 (m, 2H); 2.12-2.22 (m, 1H); 2.22-2.37 (m, 2H); 2.66-2.80 (m, 2H); 3.03-3.19 (m, 1H); 3.39-3.55 (m, 1H); 4.34-4.48 (m, 1H); 4.62 (t, 2H); 6.72 (d, 1H); 7.15 (d, 1H); 7.61 (d, 1H); 7.78 (d, 1H).

Example 68

1-(2-{4-[(2,3-Dihydro[1,4]dioxino[2,3-c]pyridin-7-ylmethyl)amino]piperidin-1-yl}ethyl)-7-methoxy-1, 8-naphthyridin-2(1H)-one A solution of 7-chloro-1-(2-{4-[(2,3-dihydro[1,4]dioxino [2,3-c]pyridin-7-ylmethyl)amino]piperidin-1-yl}ethyl)-1,8-naphthyridin-2(1H)-one (Example 67) (95 mg, 0.21 mmol) in methanol (5 mL) was treated with a solution of sodium methoxide (0.5 M, 1 mL, 0.5 mmol). The reaction mixture was sealed in a tube and heated at 150 C for 1 hour using microwave irradiation. The reaction mixture was concentrated at reduced pressure, partitioned between ethyl acetate and water. The aqueous layer was extracted with ethyl acetate (3×10 mL) and chloroform/methanol (4:1) (3×15 mL). The combined organic extracts were dried over sodium sulfate and concentrated at reduced pressure. Chromatography on silica gel using methanol in dichloromethane (0-50%) gave the product as a colorless solid (29 mg, 31%)

MS (ES): 452 (MH)$^+$ for $C_{24}H_{29}N_5O_4$ $^1$H NMR (CDCl$_3$) δ 1.39-1.54 (m, 2H); 1.90 (d, 2H); 2.13-2.28 (m, 2H); 2.47-2.62 (m, 1H); 2.64-2.76 (m, 2H); 3.06 (d, 2H); 3.80 (s, 2H); 3.99 (s, 3H); 4.26 (dd, 4H); 4.55-4.68 (m, 2H); 6.55 (dd, 2H); 6.80 (s, 1H) 7.53 (d, 1H); 7.68 (d, 1H); 8.06 (s, 1H).

Example 69

1-(2-{4-[(2,3-Dihydro[1,4]dioxino[2,3-c]pyridin-7-ylmethyl)amino]piperidin-1-yl}ethyl)-7-fluoroquinoxalin-2(1H)-one A mixture of 1-[2-(4-aminopiperidin-1-yl)ethyl]-7-fluoroquinoxalin-2(1H)-one (Intermediate 140, 85 mg, 0.29 mmol), 2,3-dihydro[1,4]dioxino[2,3-c]pyridine-7-carbaldehyde (WO 2004/058144) (49 mg, 0.29 mmol) and molecular sieves 3 Å in dry methanol/chloroform (1:1, 10 mL) was heated to 70° C. for 3 hours. The reaction was allowed to cool to room temperature and sodium triacetoxy borohydride (190 mg, 0.88 mmol) was added. After 30 minutes, the reaction was filtered through celite, the filtrate was concentrated to dryness, taken up in 15% methanol/chloroform, and washed with saturated sodium bicarbonate solution. The aqueous phase was reextracted twice with 15% methanol/chloroform. The combined organic phases were dried over magnesium sulfate, filtered, and concentrated to dryness. Chromatography on silica gel with 5% methanol in dichloromethane containing 0.25% ammonium hydroxide gave 70 mg (54%) of the title compound as an off-white solid.

MS (ES): 440 (MH$^+$) for $C_{23}H_{26}FN_5O_3$ $^1$H NMR (DMSO-D6) δ 1.11-1.24 (m, 2H); 1.73 (d, 2H); 2.00 (t, 2H); 2.18 (s, 1H); 2.25-2.38 (m, 1H); 2.51-2.56 (m, 2H); 2.87 (d, 2H); 3.64 (s, 2H); 4.24-4.35 (m, 6H); 6.92 (s, 1H); 7.24 (td, 1H); 7.52 (dd, 1H); 7.87 (dd, 1H); 7.99 (s, 1H); 8.18 (s, 1H).

Intermediate 140

1-[2-(4-Aminopiperidin-1-yl)ethyl]-7-fluoroquinoxalin-2(1H)-one

A solution of tert-butyl{1-[2-(7-fluoro-2-oxoquinoxalin-1 (2H)-yl)ethyl]piperidin-4-yl}carbamate (Intermediate 141, 240 mg, 0.62 mmol) in dichloromethane (20 mL) was treated with trifluoroacetic acid (15 mL). After 45 minutes, the reaction was concentrated to dryness, the residue taken up in methanol/chloroform (15:85, 30 mL) and washed with saturated sodium bicarbonate solution. The aqueous layer was re-extracted with methanol/chloroform (15:85, 3×30 mL. The combined organic phases were dried over magnesium sulfate and concentrated to dryness to give 170 mg (quantitative) of the crude product as an oil.

MS (ES): 291 (MH$^+$) for $C_{15}H_{19}FN_4O$

Intermediate 141 tert-Butyl{1-[2-(7-fluoro-2-oxoquinoxalin-1(2H)-yl) ethyl]piperidin-4-yl}carbamate and Intermediate 142 tert-Butyl{1-[2-(6-fluoro-2-oxoquinoxalin-1(2H)-yl) ethyl]piperidin-4-yl}carbamate A suspension of a 1:1 mixture of 7-fluoroquinoxalin-2 (1H)-one (Intermediate 143) and 6-fluoroquinoxalin-2(1H)-one (Intermediate 144) (1.5 g total, 9.1 mmol) was treated with sodium hydride (60% in oil, 0.44 g, 11.0 mmol) at 0° C. The reaction was allowed to stir at room temperature for 2 hours. The reaction mixture was cooled to 0° C. and 2-{4-[(tert-butoxycarbonyl)amino]piperidin-1-yl}ethyl methanesulfonate (Intermediate 6, 1.33 mmol/mL, 11.0 mmol), dissolved in dry DMF (5 mL) was added and it was stirred at room temperature overnight. The reaction mixture was diluted with water and with diethyl ether (5×50 mL). The combined organic phases were dried over sodium sulfate and concentrated to dryness under reduced pressure. Chromatography with hexanes/acetone (5:1 to 3:1). The higher R$_f$ material was isolated as a mixture of Intermediate 141 with an O-alkylated isomer, which was rechromatographed on silica gel with hexanes/ethyl acetate (1:3) to give pure Intermediate 141 as a colorless solid, 0.24 g, 14%. Isolation of the lower $R_f$ material from the first column gave 0.38 g (21%) of pure Intermediate 142 as a colorless solid.

Intermediate 141

MS (ES): 391 (MH$^+$) for $C_{20}H_{27}FN_4O_3$
$^1$H NMR (DMSO-D6) δ 1.25-1.38 (m, 11H); 1.56-1.68 (m, 2H); 2.01 (t, 2H); 2.50-2.56 (m, 2H); 2.82-2.93 (m, 2H); 3.16 (s, 1H); 4.27 (t, 2H); 6.72 (d, 1H); 7.23 (t, 1H); 7.50 (d, 1H); 7.83-7.91 (m, 1H); 8.17 (s, 1H).

Intermediate 142

MS (ES): 391 (MH$^+$) for $C_{20}H_{27}FN_4O_3$
$^1$H NMR (DMSO-D6) δ 1.24-1.38 (m, 11H); 1.65 (d, 2H); 2.03 (t, 2H); 2.51-2.58 (m, 2H); 2.88 (d, 2H); 3.11-3.26 (m, 1H); 4.31 (t, 2H); 6.75 (d, 1H); 7.57 (td, 1H); 7.63-7.71 (m, 2H); 8.29 (s, 1H).

Intermediate 143

7-Fluoroquinoxalin-2(1H)-one and

Intermediate 144

6-Fluoroquinoxalin-2(1H)-one

A mixture of 4-fluorobenzene-1,2-diamine (5.0 g, 39.7 mmol) and ethyl oxoacetate (50 wt % in toluene, 17 mL, 79.4 mmol) in ethanol (100 mL) was stirred for two hours at room temperature. The precipitate was collected by filtration, washed with ethanol, and dried under vacuum giving 4.5 g of a solid. $^1$H NMR revealed a 1:1 mixture of Intermediates 143 and 144. This mixture was used for the next step.
MS (ES): 165 (MH$^+$) for $C_8H_5FN_2O$

Example 70

6-[({1-[2-(7-Fluoro-2-oxoquinoxalin-1(2H)-yl)ethyl] piperidin-4-yl}amino)methyl]-2H-pyrido[3,2-b][1,4] oxazin-3(4H)-one 1-[2-(4-Aminopiperidin-1-yl)ethyl]-7-fluoroquinoxalin-2 (1H)-one (Intermediate 140, 85 mg crude, 0.29 mmol), 3-oxo-3,4-dihydro-2H-pyrido[3,2-b][1,4]oxazine-6-carbaldehyde (WO 2004/058144) (52 mg, 0.29 mmol) and sodium triacetoxy borohydride (190 mg, 0.88 mmol) were reacted as described according to Example 69 to give 90 mg (69%) of the free base of the product.
MS (ES): 453 (MH$^+$) for $C_{23}H_{25}FN_6O_3$
$^1$H NMR (DMSO-D6) δ 1.12-1.26 (m, 2H); 1.69-1.81 (m, 2H); 2.01 (t, 2H); 2.27-2.42 (m, 1H); 2.51-2.60 (m, 2H); 2.88 (d, 2H); 3.67 (s, 2H); 4.28 (t, 2H); 4.60 (s, 2H); 7.00 (d, 1H); 7.20-7.31 (m, 2H); 7.52 (dd, 1H); 7.88 (dd, 1H); 8.19 (s, 1H); 11.16 (s, 1H).

Example 71

1-(2-{4-[(2,3-Dihydro[1,4]dioxino[2,3-c]pyridin-7-ylmethyl)amino]piperidin-1-yl}ethyl)-6-fluoroquinoxalin-2(1H)-one 1-[2-(4-Aminopiperidin-1-yl)ethyl]-6-fluoroquinoxalin-2 (1H)-one (Intermediate 145, 87 mg, 0.30 mmol), 2,3-dihydro [1,4]dioxino[2,3-c]pyridine-7-carbaldehyde (WO 2004/ 058144) (50 mg, 0.30 mmol), and sodium triacetoxy borohydride (200 mg, 0.90 mmol) were reacted as described for Example 69 to give the free base of the title compound as an oil. The free base was taken up in isopropanol (10 mL) and treated with 2.0M HCl in ether (3 eq). Solvent was removed under reduced pressure. The resulting solid was triturated with dichloromethane/hexanes (2 mL/10 mL). The precipitate was collected by filtration to give 45 mg (29%) of the bis-hydrochloride salt of the product.
MS (ES): 440 (MH$^+$) for $C_{23}H_{26}FN_5O_3$
$^1$H NMR (D$_2$O) δ 1.83-2.06 (m, 2H); 2.42 (d, 2H); 3.17 (t, 2H); 3.48-3.68 (m, 3H); 3.79-4.01 (m, 2H); 4.30-4.41 (m, 4H); 4.43-4.51 (m, 2H); 4.65-4.70 (m, 2H); 7.27-7.30 (m, 1H); 7.44-7.55 (m, 2H); 7.59 (dd, 1H); 8.20-8.25 (m, 2H).

Intermediate 145

1-[2-(4-Aminopiperidin-1-yl)ethyl]-6-fluoroquinoxalin-2(1H)-one tert-Butyl{1-[2-(6-fluoro-2-oxoquinoxalin-1(2H)-yl) ethyl]piperidin-4-yl}carbamate (Intermediate 142, 380 mg, 0.97 mmol) was reacted with trifluoroacetic acid in dichloromethane as described for Intermediate 140 to give 260 mg (93%) of the crude product as an oil.
MS (ES): 291 (MH$^+$) for $C_{15}H_{19}FN_4O$

Example 72

1-(2-{4-[(2,3-Dihydro[1,4]dioxino[2,3-c]pyridin-7-ylmethyl)amino]piperidin-1-yl}ethyl)-7-methoxyquinoxalin-2(1H)-one 1-[2-(4-Aminopiperidin-1-yl)ethyl]-7-methoxyquinoxalin-2(1H)-one (Intermediate 146, 60 mg crude, 0.20 mmol), 2,3-dihydro[1,4]dioxino[2,3-c]pyridine-7-carbaldehyde (WO 2004/058144) (33 mg, 0.20 mmol), and sodium triacetoxy borohydride (130 mg, 0.60 mmol) were reacted as described for Example 69 to give the free base of the title compound as an oil. The free base was taken up in isopropanol and treated with 4.0M HCl in dioxane (3 eq). Solvent was removed under reduced pressure to give 28 mg (27% yield) of the bis-hydrochloride salt of the product.
MS (ES): 452 (MH$^+$) for $C_{24}H_{29}N_5O_4$
$^1$H NMR (D$_2$O) δ 1.86-2.02 (m, 2H); 2.36-2.49 (m, 2H); 3.09-3.23 (m, 2H); 3.52 (t, 2H); 3.56-3.68 (m, 1H); 3.82-3.95 (m, 5H); 4.32-4.40 (m, 4H); 4.43-4.50 (m, 2H); 4.61 (t, 2H); 6.82 (d, 1H); 7.03 (dd, 1H); 7.29 (s, 1H); 7.71 (d, 1H); 7.97 (s, 1H); 8.22 (s, 1H).

Intermediate 146

1-[2-(4-Aminopiperidin-1-yl)ethyl]-7-methoxyquinoxalin-2(1H)-one tert-Butyl{1-[2-(7-methoxy-2-oxoquinoxalin-1(2H)-yl) ethyl]piperidin-4-yl}carbamate (Intermediate 147, 190 mg, 0.47 mmol) was reacted with trifluoroacetic acid in dichloromethane as described for Intermediate 140 to give 110 mg of the crude product as an oil.
MS (ES): 303 (MH$^+$) for $C_{16}H_{22}N_4O_2$

Intermediate 147 tert-Butyl{1-[2-(7-methoxy-2-oxoquinoxalin-1(2H)-yl)ethyl]piperidin-4-yl}carbamate 7-methoxyquinoxalin-2(1H)-one (Intermediate 148, 300 mg, 1.70 mmol) was deprotonated with sodium hydride (100 mg, 60% in oil, 2.56 mmol) and alkylated with 2-{4-[(tert-butoxycarbonyl)amino]piperidin-1-yl}ethyl methanesulfonate (Intermediate 6) (3.4 mmol) as described for Intermediate 2. Chromatography on silica gel with 25% acetone in hexanes gave 200 mg (29%) of the product as a colorless solid.

MS (ES): 403 (MH$^+$) for $C_{21}H_{30}N_4O_4$ $^1$H NMR (DMSO-D6) δ 1.26-1.40 (m, 11H); 1.57-1.72 (m, 2H); 1.97-2.11 (m, 2H); 2.51-2.61 (m, 2H); 2.85-2.98 (m, 2H); 3.19 (s, 1H); 3.92 (s, 3H); 4.32 (t, 2H); 6.76 (d, 1H); 6.95-7.04 (m, 2H); 7.70-7.78 (m, 1H); 8.04 (s, 1H).

Intermediate 148

7-Methoxyquinoxalin-2(1H)-one

A suspension of 2-chloro-7-methoxyquinoxaline (Intermediate 149, 720 mg, 3.70 mmol) in 5M HCl (25 mL) was heated to 110° C. for 1 hour. The reaction was cooled to room temperature and let stand for 24 hours. The resulting precipitate was collected by filtration. A second crop of material was collected after concentration the mother liquor. The two crops were combined and crystallized from methanol to give 550 mg (85%) of the product as an off-white solid.

MS (ES): 177 (MH$^+$) for $C_9H_8N_2O_2$ $^1$H NMR (DMSO-D6) δ 3.83 (s, 3H); 6.76 (d, 1H); 6.91 (dd, 1H); 7.69 (d, 1H); 7.94-8.00 (m, 1H); 12.32 (s, 1H).

Intermediate 149

2-Chloro-7-methoxyquinoxaline

A solution of 4-methoxybenzene-1,2-diamine (16.8 g, 0.12 mmol) in ethanol (250 mL) was treated with a solution of ethyl oxoacetate (50 wt % in toluene, 50 mL, 0.23 mmol) dropwise with cooling in an ice bath. The reaction was allowed to warm to room temperature and after 2 hours, a precipitate was collected by filtration giving 15 g of a brown solid as a 2:1 mixture of 6-methoxyquinoxalin-2(1H)-one to 7-methoxyquinoxalin-2(1H)-one. These isomers were inseparable by TLC. The mixture was suspended in phosphorus oxychloride (150 mL) and heated to reflux for 1 hour. The reaction was cooled to room temperature and was quenched on ice. The pH of the mixture was adjusted to pH 8 with solid sodium carbonate, it was extracted with ethyl acetate, washed with brine, dried over sodium sulfate, filtered, and concentrated to dryness to give 10.4 g of a crude mixture of 2-chloro-6-methoxyquinoxaline and the desired 2-chloro-7-methoxyquinoxaline. Chromatography on silica gel with 5% ethyl acetate in hexanes afforded 0.77 g of the product as a colorless solid.

MS (ES): 195 (MH$^+$) for $C_9H_7ClN_2O$ $^1$H NMR (CDCl$_3$) δ 3.96 (s, 3H); 7.29 (d, 1H); 7.41 (dd, 1H); 7.97 (d, 1H); 8.63 (s, 1H).

Example 73

6-[({1-[2-(7-Methoxy-2-oxoquinoxalin-1(2H)-yl) ethyl]piperidin-4-yl}amino)methyl]-2H-pyrido[3,2-b][1,4]oxazin-3(4H)-one 1-[2-(4-Aminopiperidin-1-yl)ethyl]-7-methoxyquinoxalin-2(1H)-one (Intermediate 146, 60 mg crude, 0.20 mmol), 3-oxo-3,4-dihydro-2H-pyrido[3,2-b][1,4]oxazine-6-carbaldehyde (WO 2004/058144) (36 mg, 0.20 mmol), and sodium triacetoxy borohydride (130 mg, 0.60 mmol) were reacted as described according to Example 69 to give the free base of the product, which was crystallized from dichloromethane/ethyl acetate to give 45 mg (50%) as a colorless solid.

MS (ES): 465 (MH$^+$) for $C_{24}H_{28}N_6O_4$ $^1$H NMR (DMSO-D6) δ 1.06-1.39 (m, 2H); 1.66-1.87 (m, 2H); 2.04 (t, 2H); 2.33-2.49 (m, 1H); 2.56 (t, 2H); 2.92 (d, 2H); 3.70 (s, 2H); 3.92 (s, 3H); 4.32 (t, 2H); 4.61 (s, 2H); 6.86-7.09 (m, 3H); 7.30 (d, 1H); 7.75 (d, 1H); 8.04 (s, 1H); 11.18 (s, 1H).

Example 74

6-[({1-[2-(7-Methoxy-2-oxoquinoxalin-1(2H)-yl) ethyl]piperidin-4-yl}amino)methyl]-2H-pyrido[3,2-b][1,4]thiazin-3(4H)-one 1-[2-(4-Aminopiperidin-1-yl)ethyl]-7-methoxyquinoxalin-2(1H)-one (Intermediate 146, 250 mg crude, 0.83 mmol), 3-oxo-3,4-dihydro-2H-pyrido[3,2-b][1,4]thiazine-6-carbaldehyde (WO 2004/058144) (160 mg, 0.83 mmol), and sodium triacetoxy borohydride (530 mg, 2.50 mmol) were reacted as described according to Example 69. Chromatography on silica gel with 10% methanol in dichloromethane containing 0.25% ammonium hydroxide afforded the free base of the product. This was triturated with dichloromethane and the precipitate was collected by filtration giving 230 mg (58%) of the title compound as a colorless solid.

MS (ES): 481 (MH$^+$) for $C_{24}H_{28}N_6O_3S$ $^1$H NMR (DMSO-D6) δ 1.27 (s, 2H); 1.69-1.90 (m, 2H); 2.04 (t, 2H); 2.39-2.48 (m, 1H); 2.56 (t, 2H); 2.93 (d, 2H); 3.53 (s, 2H); 3.75 (s, 2H); 3.92 (s, 3H); 4.33 (t, 2H); 6.91-7.05 (m, 2H); 7.10 (d, 1H); 7.67-7.83 (m, 2H); 8.04 (s, 1H); 10.88 (s, 1H).

Example 75

1-(2-{4-[(2,3-Dihydro[1,4]dioxino[2,3-c]pyridin-7-ylmethyl)amino]piperidin-1-yl}ethyl)-6,7-difluoroquinoxalin-2(1H)-one 1-[2-(4-Aminopiperidin-1-yl)ethyl]-6,7-difluoroquinoxalin-2(1H)-one (Intermediate 150, 190 mg, 0.62 mmol), 2,3-dihydro[1,4]dioxino[2,3-c]pyridine-7-carbaldehyde (WO 2004/058144) (100 mg, 0.62 mmol), and sodium triacetoxy borohydride (390 mg, 1.90 mmol) were reacted as described according to Example 69. Chromatography on silica gel with 10% methanol in dichloromethane containing 0.25% ammonium hydroxide gave the free base of the product as an oil. The free base was taken up in dichloromethane (2 mL) and diluted with diethyl ether (10 mL). A solution of HCl in diethyl ether (2M, 2.2 eq) was added. The resulting precipitate was collected by filtration to give 180 mg (55%) of the bis-hydrochloride salt of the product.

MS (ES): 458 (MH$^+$) for $C_{23}H_{25}F_2N_5O_3$ $^1$H NMR (D$_2$O) δ 1.82-2.06 (m, 2H); 2.40 (d, 2H); 3.16 (t, 2H); 3.48-3.68 (m, 3H); 3.89 (d, 2H); 4.27-4.38 (m, 4H); 4.39-4.49 (m, 2H); 4.63 (t, 2H); 7.15-7.28 (m, 1H); 7.44-7.61 (m, 1H); 7.69-7.85 (m, 1H); 8.10-8.28 (m, 2H).

Intermediate 150

1-[2-(4-Aminopiperidin-1-yl)ethyl]-6,7-difluoroquinoxalin-2(1H)-one tert-Butyl{1-[2-(6,7-difluoro-2-oxoquinoxalin-1(2H)-yl) ethyl]piperidin-4-yl}carbamate (Intermediate 151, 500 mg, 1.23 mmol) was reacted with trifluoroacetic acid in dichloromethane as described for Intermediate 140 to give 380 mg (quantitative) of the crude product as an oil.

MS (ES): 309 (MH$^+$) for $C_{15}H_{18}F_2N_4O$

Intermediate 151 tert-Butyl{1-[2-(6,7-difluoro-2-oxoquinoxalin-1(2H)-yl)ethyl]piperidin-4-yl}carbamate 6,7-Difluoroquinoxalin-2(1H)-one (Intermediate 152, 1.0 g, 5.50 mmol) was deprotonated with sodium hydride (60% in oil, 0.26 g, 6.60 mmol) and alkylated with 2-{4-[(tert-butoxycarbonyl)amino]piperidin-1-yl}ethyl methanesulfonate (Intermediate 6) (6.6 mmol) as described for Intermediate 2. Chromatography on silica gel with 5% toluene/ethyl acetate gave 500 mg (23%) of the product as a colorless solid.

MS (ES): 409 (MH$^+$) for $C_{20}H_{26}F_2N_4O_3$ $^1$H NMR (DMSO-D6) δ 1.10-1.45 (m, 11H); 1.54-1.75 (m, 2H); 1.90-2.13 (m, 2H); 2.52-2.59 (m, 2H); 2.86 (d, 2H); 3.16 (s, 1H); 4.28 (t, 2H); 6.75 (d, 1H); 7.81 (dd, 1H); 7.96 (dd, 1H); 8.25 (s, 1H).

Intermediate 152

6,7-Difluoroquinoxalin-2(1H)-one

To a stirred solution of 4,5-difluorobenzene-1,2-diamine (4.7 g, 32.6 mmol) in ethanol (75 mL) was added ethyl oxoacetate (50 wt % in toluene, 13.3 mL, 65.3 mmol). The reaction was stirred at room temperature overnight. The resulting precipitate was collected by filtration, washed with ethanol, and dried under reduced pressure to give 4.3 g (73%) of the product as a colorless solid.

MS (ES): 183 (MH$^+$) for $C_8H_4F_2N_2O$ $^1$H NMR (DMSO-D6) δ 7.23 (dd, 1H); 7.93 (dd, 1H); 8.19 (s, 1H); 12.54 (s, 1H).

Example 76

6-[({1-[2-(6,7-Difluoro-2-oxoquinoxalin-1(2H)-yl)ethyl]piperidin-4-yl}amino)methyl]-2H-pyrido[3,2-b][1,4]oxazin-3(4H)-one 1-[2-(4-Aminopiperidin-1-yl)ethyl]-6,7-difluoro quinoxalin-2(1H)-one (Intermediate 150, 190 mg, 0.62 mmol), 3-oxo-3,4-dihydro-2H-pyrido[3,2-b][1,4]oxazine-6-carbaldehyde (WO 2004/058144) (110 mg, 0.62 mmol), and sodium triacetoxy borohydride (390 mg, 1.90 mmol) were reacted as described according to Example 69 to give 180 mg (62%) of the free base of the product as a colorless solid.

MS (ES): 471 (MH$^+$) for $C_{23}H_{24}F_2N_6O_3$ $^1$H NMR (DMSO-D6) δ 1.12-1.26 (m, 2H); 1.69-1.83 (m, 2H); 2.01 (t, 2H); 2.42 (s, 1H); 2.53 (t, 2H); 2.88 (d, 2H); 3.69 (s, 2H); 4.29 (t, 2H); 4.60 (s, 2H); 7.01 (d, 1H); 7.30 (d, 1H); 7.82 (dd, 1H); 7.97 (dd, 1H); 8.25 (s, 1H); 11.18 (s, 1H).

Example 77

1-(2-[4-[(2,3-Dihydro[1,4]dioxino[2,3-c]pyridin-7-ylmethyl)amino]piperidin-1-yl]ethyl)-7,8-difluoro-quinoxalin-2(1H)-one 1-[2-(4-Aminopiperidin-1-yl)ethyl]-7,8-difluoroquinoxalin-2(1H)-one (Intermediate 153, 130 mg, 0.42 mmol), 2,3-dihydro[1,4]dioxino[2,3-c]pyridine-7-carbaldehyde (WO 2004/058144) (70 mg, 0.42 mmol), and sodium triacetoxy borohydride (270 mg, 1.30 mmol) were reacted as described according to Example 71 to give 35 mg (16%) of the bis-hydrochloride salt of the product as a colorless solid.

MS (ES): 458 (MH$^+$) for $C_{23}H_{25}F_2N_5O_3$ $^1$H NMR (D$_2$O) δ 1.89-2.02 (m, 2H); 2.43 (d, 2H); 3.18 (t, 2H); 3.52-3.64 (m, 3H); 3.88 (d, 2H); 4.29-4.34 (m, 4H); 4.38-4.43 (m, 2H); 4.71-4.77 (m, 2H); 7.17 (s, 1H); 7.27-7.38 (m, 1H); 7.62-7.69 (m, 1H); 8.15 (s, 2H).

Intermediate 153

1-[2-(4-Aminopiperidin-1-yl)ethyl]-7,8-difluoroquinoxalin-2(1H)-one tert-Butyl{1-[2-(7,8-difluoro-2-oxoquinoxalin-1(2H)-yl)ethyl]piperidin-4-yl}carbamate (Intermediate 154, 320 mg, 0.78 mmol) was reacted with trifluoroacetic acid in dichloromethane as described for Intermediate 140 to give 240 mg (quantitative) of the crude product as an oil.

MS (ES): 309 (MH$^+$) for $C_{15}H_{18}F_2N_4O$

Intermediate 154 tert-Butyl{1-[2-(7,8-difluoro-2-oxoquinoxalin-1(2H)-yl)ethyl]piperidin-4-yl}carbamate 7,8-Difluoroquinoxalin-2(1H)-one (Intermediate 155—a mixture of regioisomers containing 30% 5,6-difluoroquinoxalin-2(1H)-one, 1.0 g, 5.50 mmol) was deprotonated with sodium hydride (60% in oil, 0.26 g, 6.60 mmol) and alkylated with 2-{4-[(tert-butoxycarbonyl)amino]piperidin-1-yl}ethyl methanesulfonate (Intermediate 6) (6.6 mmol) as described for Intermediate 2. Chromatography on silica gel with 70-100% ethyl acetate in hexanes gave 320 mg of the product as a colorless solid.

MS (ES): 409 (MH$^+$) for $C_{20}H_{26}F_2N_4O_3$ $^1$H NMR (DMSO-D6) δ 1.30 (d, 2H); 1.37 (s, 9H); 1.64 (d, 2H); 2.07 (t, 2H); 2.59 (t, 2H); 2.81 (d, 2H); 3.20 (s, 1H); 4.36 (t, 2H); 6.76 (d, 1H); 7.48 (td, 1H); 7.72 (ddd, 1H); 8.23 (s, 1H).

Intermediate 155

7,8-Difluoroquinoxalin-2(1H)-one 3,4-Difluorobenzene-1,2-diamine (4.6 g, 31.6 mmol) and ethyl oxoacetate (50 wt % in toluene, 13.0 mL, 63.2 mmol) were reacted as described for Intermediate 152 to give 3.7 g of product as an off white solid, mixture with 30% of the regioisomer 5,6-difluoroquinoxalin-2(1H)-one. The mixture was carried on to the next step.

MS (ES): 183 (MH$^+$) for $C_8H_4F_2N_2O$

Example 78

6-[({1-[2-(7,8-Difluoro-2-oxoquinoxalin-1(2H)-yl)ethyl]piperidin-4-yl}amino)methyl]-2H-pyrido[3,2-b][1,4]oxazin-3(4H)-one 1-[2-(4-Aminopiperidin-1-yl)ethyl]-7,8-difluoroquinoxalin-2(1H)-one (Intermediate 153, 130 mg, 0.42 mmol), 3-oxo-3,4-dihydro-2H-pyrido[3,2-b][1,4]oxazine-6-carbaldehyde (WO 2004/058144) (70 mg, 0.42 mmol), and sodium triacetoxy borohydride (270 mg, 1.30 mmol) were reacted as described for Example 69 to give 82 mg (41%) of the free base of the product.

MS (ES): 471 (MH$^+$) for $C_{23}H_{24}F_2N_6O_3$

1H NMR (DMSO-D6) δ 1.07-1.22 (m, 2H); 1.69 (d, 2H); 1.98 (t, 2H); 2.35 (s, 1H); 2.52 (t, 2H); 2.76 (d, 2H); 3.63 (s,

2H); 4.30 (t, 2H); 4.54 (s, 2H); 6.95 (d, 1H); 7.24 (d, 1H); 7.35-7.47 (m, 1H); 7.61-7.71 (m, 1H); 8.17 (s, 1H); 11.12 (s, 1H).

Example 79

6-[({1-[2-(6,7-Dimethoxy-2-oxoquinoxalin-1(2H)-yl)ethyl]piperidin-4-yl}amino)methyl]-2H-pyrido[3,2-b][1,4]oxazin-3(4H)-one 1-[2-(4-Aminopiperidin-1-yl)ethyl]-6,7-dimethoxyquinoxalin-2(1H)-one (Intermediate 156, 75 mg, 0.23 mmol), 3-oxo-3,4-dihydro-2H-pyrido[3,2-b][1,4]oxazine-6-carbaldehyde (WO 2004/058144) (40 mg, 0.23 mmol), and sodium triacetoxy borohydride (150 mg, 0.69 mmol) were reacted as described according to Example 69 to give 78 mg (68%) of the free base of the product as a colorless solid.

MS (ES): 495 (MH$^+$) for $C_{25}H_{30}N_6O_5$ $^1$H NMR (DMSO-D6) δ 1.06-1.38 (m, 2H); 1.65-1.85 (m, 2H); 1.95-2.13 (m, 2H); 2.29-2.42 (m, 1H); 2.51-2.64 (m, 2H); 2.92 (d, 2H); 3.67 (s, 2H); 3.85 (s, 3H); 3.88-4.04 (m, 3H); 4.24-4.45 (m, 2H); 4.52-4.66 (m, 2H); 6.94-7.09 (m, 2H); 7.21-7.37 (m, 2H); 7.98-8.11 (m, 1H); 11.06-11.23 (m, 1H).

Intermediate 156

1-[2-(4-Aminopiperidin-1-yl)ethyl]-6,7-dimethoxyquinoxalin-2(1H)-one tert-Butyl{1-[2-(6,7-dimethoxy-2-oxoquinoxalin-1(2H)-yl)ethyl]piperidin-4-yl}carbamate (Intermediate 157, 100 mg, 0.23 mmol) was reacted with trifluoroacetic acid in dichloromethane as described for Intermediate 140 to give 75 mg (quantitative) of the crude product as an oil.

MS (ES): 333 (MH$^+$) for $C_{17}H_{24}N_4O_3$

Intermediate 157 tert-Butyl{1-[2-(6,7-dimethoxy-2-oxoquinoxalin-1(2H)-yl)ethyl]piperidin-4-yl}carbamate 6,7-Dimethoxyquinoxalin-2(1H)-one (Intermediate 158, 540 mg, 2.60 mmol) was deprotonated with sodium hydride (60% in oil, 2.90 mmol) and alkylated with 2-{4-[(tert-butoxycarbonyl)amino]piperidin-1-yl}ethyl methanesulfonate (Intermediate 6) (3.9 mmol) as described for Intermediate 2. Chromatography on silica gel with 20-50% acetone in hexanes gave 310 mg (28%) of the product as an off-white solid.

MS (ES): 433 (MH$^+$) for $C_{22}H_{32}N_4O_5$ $^1$H NMR (DMSO-D6) δ 1.25-1.39 (m, 11H); 1.63 (d, 2H); 1.98-2.12 (m, 2H); 2.57 (t, 2H); 2.92 (d, 2H); 3.19 (s, 1H); 3.84 (s, 3H); 3.95 (s, 3H); 4.35 (t, 2H); 6.75 (d, 1H); 7.04 (s, 1H); 7.31 (s, 1H); 8.05 (s, 1H).

Intermediate 158

6,7-Dimethoxyquinoxalin-2(1H)-one

A mixture of 1,2-dimethoxy-4,5-dinitrobenzene (5.7 g, 25.0 mmol) in ethanol/acetic acid (140 mL, 1:1) was hydrogenated over palladium on carbon (10%, 1 g) at normal pressure and room temperature for 3 hours, then filtered through a pad of celite. The filtrate containing the crude diamine was treated with ethyl oxoacetate (50 wt % in toluene, 10 mL, 50 mmol) and the reaction was stirred at room temperature overnight. The resulting precipitate was collected by filtration. This material was suspended in a mixture of methanol/dichloromethane and solvent was removed under reduced pressure to remove traces of acetic acid to give 2.0 g (38%) of product as a solid.

MS (ES): 207 (MH$^+$) for $C_{10}H_{10}N_2O_3$ $^1$H NMR (DMSO-D6) δ 3.81-3.83 (m, 3H); 3.83-3.85 (m, 3H); 6.78-6.81 (m, 1H); 7.25-7.27 (m, 1H); 7.97-8.01 (m, 1H); 12.26-12.34 (m, 1H).

Example 80

6-[({1-[2-(7-Methoxy-3-methyl-2-oxoquinoxalin-1(2H)-yl)ethyl]piperidin-4-yl}amino)methyl]-2H-pyrido[3,2-b][1,4]oxazin-3(4H)-one 1-[2-(4-Aminopiperidin-1-yl)ethyl]-7-methoxy-3-methylquinoxalin-2(1H)-one (Intermediate 159, 75 mg, 0.24 mmol), 3-oxo-3,4-dihydro-2H-pyrido[3,2-b][1,4]oxazine-6-carbaldehyde (WO 2004/058144) (42 mg, 0.24 mmol), and sodium triacetoxy borohydride (150 mg, 0.72 mmol) were reacted as described according to Example 69 to give 80 mg (73% yield) of the free base of the product.

MS (ES): 479 (MH$^+$) for $C_{25}H_{30}N_6O_4$ $^1$H NMR (DMSO-D6) δ 1.23 (q, 2H); 1.77 (d, 2H); 2.04 (t, 2H); 2.31-2.45 (m, 4H); 2.51-2.61 (m, 2H); 2.91 (d, 2H); 3.68 (s, 2H); 3.89 (s, 3H); 4.31 (t, 2H); 4.60 (s, 2H); 6.85-7.10 (m, 3H); 7.29 (d, 1H); 7.59-7.73 (m, 1H); 11.17 (s, 1H).

Intermediate 159

1-[2-(4-Aminopiperidin-1-yl)ethyl]-7-methoxy-3-methylquinoxalin-2(1H)-one tert-Butyl{1-[2-(7-methoxy-3-methyl-2-oxoquinoxalin-1(2H)-yl)ethyl]piperidin-4-yl}carbamate (Intermediate 160, 100 mg, 0.24 mmol) was reacted with trifluoroacetic acid in dichloromethane as described for Intermediate 140 to give 75 mg (99% yield) of the crude product as an oil.

MS (ES): 317 (MH$^+$) for $C_{17}H_{24}N_4O_2$

Intermediate 160 tert-Butyl{1-[2-(7-methoxy-3-methyl-2-oxoquinoxalin-1(2H)-yl)ethyl]piperidin-4-yl}carbamate 7-Methoxy-3-methylquinoxalin-2(1H)-one (Intermediate 161, 500 mg, 2.60 mmol) was deprotonated with sodium hydride (60% in oil, 2.90 mmol) and alkylated with 2-{4-[(tert-butoxycarbonyl)amino]piperidin-1-yl}ethyl methanesulfonate (Intermediate 6) (3.9 mmol) as described for Intermediate 2. Chromatography on silica gel with 70% ethyl acetate in hexanes, followed by a second chromatography on silica gel with 20% acetone in hexanes gave 110 mg (10%) of the product as a colorless solid.

MS (ES): 417 (MH$^+$) for $C_{22}H_{32}N_4O_4$ $^1$H NMR (DMSO-D6) δ 1.21-1.46 (m, 11H); 1.65 (d, 2H); 2.05 (t, 2H); 2.38 (s, 3H); 2.51-2.59 (m, 2H); 2.92 (d, 2H); 3.18 (s, 1H); 3.90 (s, 3H); 4.31 (t, 2H); 6.77 (d, 1H); 6.91-7.00 (m, 2H); 7.58-7.73 (m, 1H).

Intermediate 161

7-Methoxy-3-methylquinoxalin-2(1H)-one

A suspension of 3-chloro-6-methoxy-2-methylquinoxaline (Intermediate 162, 1.5 g, 7.21 mmol) in 5M HCl (30 mL) was heated to 110° C. for 1 hour. The reaction mixture was neutralized with saturated sodium carbonate solution, diluted with water and extracted with ethyl acetate (3 times). The combined organic phases were dried over magnesium sulfate and concentrated to a small volume under reduced pressure. The precipitate was collected by filtration to give 1.0 g (71%) of product as an off-white solid.

MS (ES): 191 (MH$^+$) for $C_{10}H_{10}N_2O_2$ $^1$H NMR (DMSO-D6) δ 2.34 (s, 3H); 3.80 (s, 3H); 6.73 (d, 1H); 6.83-6.89 (m, 1H); 7.59 (d, 1H); 12.19 (s, 1H).

Intermediate 162

3-Chloro-6-methoxy-2-methylquinoxaline

A suspension of 4-methoxybenzene-1,2-diamine (5.0 g, 36.2 mmol) in water (100 mL) was heated under sonication for 5 minutes. 2-Oxopropanoic acid (2.5 mL, 36.2 mmol) was added and it was stirred for 2 hours. The precipitate was collected by filtration and dried under vacuum and heating, over phosphorus pentoxide, to give 3.0 g of a mixture of the product together with 6-methoxy-3-methylquinoxalin-2 (1H)-one. This mixture was suspended in phosphorus oxychloride (30 mL) and heated to 115° C. for 30 min. The mixture was quenched on ice and neutralized with solid sodium carbonate. The aqueous mixture was extracted with ethyl acetate (4 times). The combined organic phases were dried over magnesium sulfate, filtered, and concentrated to dryness under reduced pressure. Chromatography on silica gel with 5% ethyl acetate in hexanes and isolation of the higher migrating regioisomer gave 0.9 g of product as an off-white solid.

MS (ES): 209 (MH$^+$) for $C_{10}H_9ClN_2O$ $^1$H NMR (DMSO-D6) δ 2.71 (s, 3H); 3.93 (s, 3H); 7.39 (d, 1H); 7.49 (dd, 1H); 7.95 (d, 1H).

Example 81

1-(2-{4-[(2,3-Dihydro[1,4]dioxino[2,3-c]pyridin-7-ylmethyl)amino]piperidin-1-yl}ethyl)quinolin-2 (1H)-one 1-[2-(4-Aminopiperidin-1-yl)ethyl]quinolin-2(1H)-one (Intermediate 163, 170 mg crude, 0.63 mmol), 2,3-dihydro [1,4]dioxino[2,3-c]pyridine-7-carbaldehyde (WO 2004/058144) (100 mg, 0.63 mmol), and sodium triacetoxy borohydride (400 mg, 1.90 mmol) were reacted as described according to Example 69 to give the free base of the product as an oil. The free base was taken up in dichloromethane (2 mL) and ethanol (8 mL) and treated with a solution of 4M HCl/dioxane (2 eq). The resulting precipitate was collected by filtration to give 188 mg (60%) of the bis-hydrochloride salt of the product as a colorless solid.

MS (ES): 421 (MH$^+$) for $C_{24}H_{28}N_4O_3$ $^1$H NMR (D$_2$O) δ 1.86-2.06 (m, 2H); 2.36-2.54 (m, 2H); 3.06-3.27 (m, 2H); 3.46-3.70 (m, 3H); 3.89 (d, 2H); 4.29-4.42 (m, 4H); 4.42-4.53 (m, 2H); 4.65-4.70 (m, 2H); 6.66 (d, 1H); 7.29 (s, 1H); 7.34 (t, 1H); 7.47 (d, 1H); 7.59-7.78 (m, 2H); 7.95 (d, 1H); 8.22 (s, 1H).

Intermediate 163

1-[2-(4-Aminopiperidin-1-yl)ethyl]quinolin-2(1H)-one

To a solution of tert-butyl{1-[2-(2-oxoquinolin-1(2H)-yl) ethyl]piperidin-4-yl}carbamate (Intermediate 164, 220 mg, 0.59 mmol) in dioxane (5 mL) was added a solution of HCl in dioxane (4M, 9 mL), followed by water (1 mL) and it was stirred at room temperature over night. An addition 5 mL of HCl/dioxane was added to the reaction. After 1 hr, the reaction was concentrated to dryness. The crude product was partitioned between 10% methanol/dichloromethane (50 mL) and 1M sodium hydroxide (50 mL). The aqueous phase was back extracted with 10% methanol/dichloromethane (50 mL) and the combined organic phases were washed with brine, dried over sodium sulfate and concentrated under reduced pressure to give 170 mg (quantitative) of the crude product as an oil.

MS (ES): 272 (MH$^+$) for $C_{16}H_{21}N_3O$

Intermediate 164 tert-Butyl{1-[2-(2-oxoquinolin-1(2H)-yl)ethyl]piperidin-4-yl}carbamate

Quinolin-2(1H)-one (250 mg, 1.7 mmol) was deprotonated with sodium hydride (60% in oil, 70 mg, 1.7 mmol) and alkylated with 2-{4-[(tert-butoxycarbonyl)amino]piperidin-1-yl}ethyl methanesulfonate (Intermediate 6) (1.7 mmol) as described for Intermediate 141. Chromatography on silica gel with 0-5% methanol in dichloromethane gave 220 mg (35%) of product as a colorless solid.

MS (ES): 372 (MH$^+$) for $C_{21}H_{29}N_3O_3$

Example 82

1-(2-{4-[(2,3-Dihydro[1,4]dioxino[2,3-c]pyridin-7-ylmethyl)amino]piperidin-1-yl}ethyl)quinolin-4 (1H)-one 1-[2-(4-Aminopiperidin-1-yl)ethyl]quinolin-4(1H)-one (Intermediate 165, 180 mg crude, 0.66 mmol), 2,3-dihydro [1,4]dioxino[2,3-c]pyridine-7-carbaldehyde (WO 2004/058144) (110 mg, 0.66 mmol), and sodium triacetoxy borohydride (420 mg, 2.0 mmol) were reacted as described according to Example 81 to give the bis-hydrochloride salt of the product 53 mg (16%) as a colorless solid.

MS (ES): 421 (MH$^+$) for $C_{24}H_{28}N_4O_3$ $^1$H NMR (D$_2$O) δ 1.90-2.13 (m, 2H); 2.44 (d, 2H); 3.22 (t, 2H); 3.58-3.70 (m, 3H); 3.77 (d, 2H); 4.33-4.40 (m, 2H); 4.42 (s, 2H); 4.46-4.53 (m, 2H); 4.75-4.86 (m, 2H); 6.47 (d, 1H); 7.36 (s, 1H); 7.51 (t, 1H); 7.68 (d, 1H); 7.77-7.89 (m, 1H); 8.11-8.21 (m, 2H); 8.25 (s, 1H).

Intermediate 165

1-[2-(4-Aminopiperidin-1-yl)ethyl]quinolin-4(1H)-one tert-Butyl{1-[2-(4-oxoquinolin-1(4H)-yl)ethyl]piperidin-4-yl}carbamate (Intermediate 166, 480 mg crude, 1.29 mmol) was reacted with 4M HCl/dioxane in dioxane as described for Intermediate 163 to give 180 mg (51%) of the crude product as an oil.

MS (ES): 272 (MH$^+$) for $C_{16}H_{21}N_3O$

Intermediate 166 tert-Butyl{1-[2-(4-oxoquinolin-1(4H)-yl)ethyl]piperidin-4-yl}carbamate

Quinolin-4(1H)-one (250 mg, 1.7 mmol) was deprotonated with sodium hydride (60% in oil, 70 mg, 1.7 mmol) and alkylated with 2-{4-[(tert-butoxycarbonyl)amino]piperidin- 1-yl}ethyl methanesulfonate (Intermediate 6) (1.7 mmol) as described for Intermediate 141. The precipitate formed in the reaction mixture was collected by filtration to give 480 mg (76%) of product as a colorless solid.

MS (ES): 372 (MH$^+$) for $C_{21}H_{29}N_3O_3$

Example 83

Cis(±)6-[({1-[2-(5,7-difluoro-2-oxoquinolin-1(2H)-yl)ethyl]-3-methoxypiperidin-4-yl}amino)methyl]-2H-pyrido[3,2-b][1,4]oxazin-3(4H)-one Cis(±)1-[2-(4-amino-3-methoxypiperidin-1-yl)ethyl]-5,7-difluoroquinolin-2(1H)-one (Intermediate 167, 140 mg, 0.42 mmol), 3-oxo-3,4-dihydro-2H-pyrido[3,2-b][1,4]oxazine-6-carbaldehyde (WO 2004/058144) (75 mg, 0.42 mmol) and sodium triacetoxy borohydride (250 mg, 1.20 mmol) were reacted as described according to Example 69. Chromatography on silica gel with 5% methanol in dichloromethane containing 0.50% ammonium hydroxide gave 120 mg (57%) of the free base of the product.

MS (ES): 500 (MH$^+$) for $C_{25}H_{27}F_2N_5O_4$ $^1$H NMR (CDCl$_3$) δ 1.66-1.87 (m, 2H); 2.22-2.44 (m, 2H); 2.55-2.83 (m, 3H); 2.93 (d, 1H); 3.14 (d, 1H); 3.34-3.45 (m, 3H); 3.47-3.56 (m, 1H); 3.80-3.86 (m, 2H); 4.25-4.49 (m, 2H); 4.63 (s, 2H); 6.65 (d, 1H); 6.67-6.77 (m, 1H); 6.99 (t, 2H); 7.21 (d, 1H); 7.88 (d, 1H).

Intermediate 167

Cis(±)1-[2-(4-amino-3-methoxypiperidin-1-yl)ethyl]-5,7-difluoroquinolin-2(1H)-one Cis(±)1-{2-[4-(dibenzylamino)-3-methoxypiperidin-1-yl]ethyl}-5,7-difluoroquinolin-2(1H)-one (Intermediate 168, 240 mg, 0.46 mmol) was hydrogenated in methanol/acetonitrile (10 mL, 9:1) over palladium hydroxide on carbon (20%, 120 mg) at room temperature and normal pressure for 4 hours. The reaction mixture was filtered through celite and the filtrate was concentrated to dryness under reduced pressure to give 140 mg (90%) of crude product. This was used without further purification.

MS (ES): 338 (MH$^+$) for $C_{17}H_{21}F_2N_3O_2$

Intermediate 168

Cis(±)1-{2-[4-(dibenzylamino)-3-methoxypiperidin-1-yl]ethyl}-5,7-difluoroquinolin-2(1H)-one A solution of 5,7-difluoroquinolin-2(1H)-one (Intermediate 25, 300 mg, 1.70 mmol) in dry DMF (10 mL) was treated with sodium hydride (60% in oil, 80 mg, 2.00 mmol) with cooling in an ice bath. The reaction was stirred at room temperature for 90 min. The reaction was again cooled in an ice bath and treated with a solution of cis(±)2-[4-(dibenzylamino)-3-methoxypiperidin-1-yl]ethyl methanesulfonate in dry DMF (10 mL) (Intermediate 169, 1.2 eq, 2.00 mmol). The reaction was stirred at room temperature overnight. It was quenched with a small amount of water and concentrated to dryness. Residual DMF was removed by co-evaporating with toluene and the residue was partitioned between ethyl acetate (50 mL) and water (20 mL). The biphasic mixture was filtered, the phases separated and the aqueous phase was back extracted two times with ethyl acetate (2×50 mL). The combined organic phases were dried over magnesium sulfate, filtered, and concentrated to dryness. Chromatography on silica gel with a gradient of 10-20% acetone in hexanes gave 240 mg (27%) of product as a colorless solid.

MS (ES): 518 (MH$^+$) for $C_{31}H_{33}F_2N_3O_2$ $^1$H NMR (DMSO-D6) δ 1.49-1.60 (m, 1H); 1.70-1.84 (m, 1H); 1.92-2.06 (m, 2H); 2.37-2.47 (m, 2H); 2.99-3.12 (m, 1H); 3.16-3.22 (m, 1H); 3.25 (s, 3H); 3.30-3.40 (m, 1H); 3.56 (s, 1H); 3.59-3.86 (m, 4H); 4.28 (t, 2H); 6.62 (d, 1H); 7.15-7.24 (m, 3H); 7.24-7.41 (m, 9H); 7.96 (d, 1H).

Intermediate 169

Cis(±)2-[4-(dibenzylamino)-3-methoxypiperidin-1-yl]ethyl methanesulfonate

Cis(±)2-[4-(dibenzylamino)-3-methoxypiperidin-1-yl]ethanol (Intermediate 170, 740 mg, 2.1 mmol) was reacted with methanesulfonyl chloride (0.20 mL, 2.5 mmol) in the presence of triethylamine (0.41 mL, 2.9 mmol) as described for Intermediate 6. The crude product was presumed to be unstable and was used without further purification directly for the next step.

Intermediate 170

Cis(±)2-[4-(dibenzylamino)-3-methoxypiperidin-1-yl]ethanol

A mixture of cis(±)N,N-dibenzyl-3-methoxypiperidin-4-amine (1.7 g, 5.5 mmol) (WO 2005/068461), bromoethanol (0.5 mL, 7.1 mmol), and N,N-diisopropylethylamine (1.4 mL, 8.3 mmol) were reacted as described for Intermediate 37, but heating for one hour at 70° C. Chromatography on silica gel with 5% methanol in dichloromethane containing 0.25% ammonium hydroxide gave 1.3 g (68%) of product as a colorless solid.

MS (ES): 355 (MH$^+$) for $C_{22}H_{30}N_2O_2$ $^1$H NMR (DMSO-D6) δ 1.44-1.58 (m, 1H); 1.64 (d, 1H); 1.79-2.08 (m, 2H); 2.32 (t, 2H); 2.36-2.45 (m, 1H); 2.88 (d, 1H); 3.13 (d, 1H); 3.30 (s, 3H); 3.40-3.49 (m, 2H); 3.56 (s, 1H); 3.59-3.87 (m, 4H); 4.34 (s, 1H); 7.11-7.24 (m, 2H); 7.24-7.40 (m, 8H)

Example 84

7-Fluoro-2-oxo-1-[2-(4-{[(3-oxo-3,4-dihydro-2H-pyrido[3,2-b][1,4]oxazin-6-yl)methyl]amino}piperidin-1-yl)ethyl]-1,2-dihydroquinoline-5-carbonitrile and Example 85

5-Fluoro-2-oxo-1-[2-(4-{[(3-oxo-3,4-dihydro-2H-pyrido[3,2-b][1,4]oxazin-6-yl)methyl]amino}piperidin-1-yl)ethyl]-1,2-dihydroquinoline-7-carbonitrile A mixture of the regioisomers 1-[2-(4-aminopiperidin-1-yl)ethyl]-7-fluoro-2-oxo-1,2-dihydroquinoline-5-carbonitrile (major isomer) and 1-[2-(4-aminopiperidin-1-yl)ethyl]-5-fluoro-2-oxo-1,2-dihydroquinoline-7-carbonitrile (minor isomer) (Intermediates 171 and 172, 120 mg, 0.38 mmol), 3-oxo-3,4-dihydro-2H-pyrido[3,2-b][1,4]oxazine-6-carbaldehyde (WO 2004/058144) (68 mg, 0.38 mmol) and sodium triacetoxy borohydride (230 mg, 1.1 mmol) were reacted as described according to Example 69. Chromatography on silica gel with 10% methanol in dichloromethane containing 0.5% ammonium hydroxide followed by reverse phase HPLC on a 50×250 mm ODS AQ column eluting with an isocratic gradient of 15% acetonitrile in water containing 0.1% TFA to give the bis TFA salts of Example 84 (68 mg) and Example 85 (21 mg), both as colorless solids.

Example 84

MS (ES): 477 (MH$^+$) for $C_{25}H_{25}FN_6O_3$
$^1$H NMR (DMSO-D6) δ 1.09-1.27 (m, 2H); 1.67-1.83 (m, 2H); 2.00 (t, 2H); 2.31-2.44 (m, 1H); 2.51-2.55 (m, 2H); 2.87 (d, 2H); 3.67 (s, 2H); 4.33 (t, 2H); 4.53-4.64 (m, 2H); 6.81 (d, 1H); 7.00 (d, 1H); 7.28 (d, 1H); 7.78-7.92 (m, 2H); 7.98 (d, 1H); 11.16 (s, 1H).

Example 85

MS (ES): 477 (MH$^+$) for $C_{25}H_{25}FN_6O_3$
$^1$H NMR (DMSO-D6) δ 1.12-1.30 (m, 2H); 1.69-1.83 (m, 2H); 1.95-2.10 (m, 2H); 2.33-2.46 (m, 1H); 2.51-2.57 (m, 2H); 2.89 (d, 2H); 3.68 (s, 2H); 4.31-4.43 (m, 2H); 4.57-4.64 (m, 2H); 6.84 (d, 1H); 7.01 (d, 1H); 7.29 (d, 1H); 7.70 (d, 1H); 7.99 (s, 1H); 8.06 (d, 1H); 11.17 (s, 1H).

Intermediate 171

1-[2-(4-Aminopiperidin-1-yl)ethyl]-7-fluoro-2-oxo-1,2-dihydroquinoline-5-carbonitrile (major isomer)

and

Intermediate 172

1-[2-(4-Aminopiperidin-1-yl)ethyl]-5-fluoro-2-oxo-1,2-dihydroquinoline-7-carbonitrile A mixture of tert-butyl{1-[2-(5-cyano-7-fluoro-2-oxoquinolin-1(2H)-yl)ethyl]piperidin-4-yl}carbamate and tert-butyl{1-[2-(7-cyano-5-fluoro-2-oxoquinolin-1(2H)-yl)ethyl]piperidin-4-yl}carbamate (Intermediates 173 and 174, 170 mg, 0.41 mmol) was reacted with trifluoroacetic acid in dichloromethane as described for Intermediate 140 to give 120 mg (92% yield) of the mixture of regioisomers as an oil. This mixture was carried on without further purification to the next step.
MS (ES): 315 (MH$^+$) for $C_{17}H_{19}FN_4O$ Intermediate 173 tert-Butyl{1-[2-(5-cyano-7-fluoro-2-oxoquinolin-1(2H)-yl)ethyl]piperidin-4-yl}carbamate and Intermediate 174 tert-Butyl{1-[2-(7-cyano-5-fluoro-2-oxoquinolin-1(2H)-yl)ethyl]piperidin-4-yl}carbamate A mixture of tert-butyl{1-[2-(5-bromo-7-fluoro-2-oxoquinolin-1(2H)-yl)ethyl]piperidin-4-yl}carbamate and tert-butyl{1-[2-(7-bromo-5-fluoro-2-oxoquinolin-1(2H)-yl)ethyl]piperidin-4-yl}carbamate (Intermediates 175 and 176, 460 mg, 0.98 mmol) was reacted with potassium cyanide (96 mg, 1.5 mmol), tributyl tin chloride (14 μL/mL in heptane, 0.90 μL, 0.003 mmol), 4,5-Bis(diphenylphosphino)-9,9-dimethylxanthene (XANTPHOS) (3.0 mg, 0.005 mmol) and tris(dibenzylideneacetone)dipalladium (0) (5.0 mg, 0.005 mmol) as described for Intermediate 15. Chromatography on silica gel with acetone/hexanes (1:4) gave 170 mg of the mixture of regioisomers. This mixture was carried on directly to the next step.
MS (ES): 415 (MH$^+$) for $C_{22}H_{27}FN_4O_3$ Intermediate 175 tert-Butyl{1-[2-(5-bromo-7-fluoro-2-oxoquinolin-1(2H)-yl)ethyl]piperidin-4-yl}carbamate and Intermediate 176 tert-Butyl{1-[2-(7-bromo-5-fluoro-2-oxoquinolin-1(2H)-yl)ethyl]piperidin-4-yl}carbamate A mixture of 5-bromo-7-fluoroquinolin-2(1H)-one and 7-bromo-5-fluoroquinolin-2(1H)-one (Intermediate 177 and 178, 3.0 g, 9.4 mmol) was reacted with sodium hydride (60% in oil, 0.20 g, 5.0 mmol) and 2-{4-[tert-butoxycarbonyl)amino]piperidin-1-yl}ethyl methanesulfonate (Intermediate 6, 9.4 mmol) as described for Intermediate 141. Chromatography on silica gel with a gradient of 50-75% ethyl acetate in hexanes gave 0.63 g (33%) of the regioisomeric product mixture, which was carried on without further purification to the next step.
MS (ES): 468, 470 (MH$^+$) for $C_{21}H_{27}BrFN_3O_3$ Intermediate 177

5-Bromo-7-fluoroquinolin-2(1H)-one and

Intermediate 178

7-Bromo-5-fluoroquinolin-2(1H)-one

The compounds were prepared from (2E)-N-(3-bromo-5-fluorophenyl)-3-phenylacrylamide (Intermediate 179, 3.0 g, 9.4 mmol) and aluminium trichloride (6.2 g, 46.9 mmol) as described for Intermediate 17, but the reaction mixture was heated to 90° C. for 30 min, to give 1.5 g of 3:1 mixture of 5-Bromo-7-fluoroquinolin-2(1H)-one and 7-bromo-5-fluoroquinolin-2(1H)-one. This mixture was carried on to the next step without further purification.
MS (ES): 242, 244 (MH$^+$) for $C_9H_5BrFNO$ Intermediate 179

(2E)-N-(3-Bromo-5-fluorophenyl)-3-phenylacrylamide

The compound was prepared from 3-bromo-5-fluoroaniline (Intermediate 180, 5.3 g, 27.9 mmol) and cinnamoylchloride (5.6 g, 33.5 mmol) in the presence of 2,6-lutidine (5.0 mL, 41.9 mmol) as described for Intermediate 18 to give the product as a colorless solid, 7.6 g (85% yield).
MS (ES): 320, 322 (MH$^+$) for $C_{15}H_{11}BrFNO$
$^1$H NMR (DMSO-D6) δ 6.77 (d, 1H); 7.18-7.30 (m, 1H); 7.40-7.52 (m, 3H); 7.55-7.70 (m, 4H); 7.75 (s, 1H); 10.56 (s, 1H).

Intermediate 180

3-Bromo-5-fluoroaniline

To a solution of N-(3-bromo-5-fluorophenyl)acetamide (Intermediate 181, 8.7 g, 37.4 mmol) in ethanol (30 mL) was added concentrated hydrochloric acid (80 mL). The reaction was heated to 100° C. for 1 hr. It was cooled to room temperature and neutralized with 5N sodium hydroxide. The crude product was extracted with ethyl acetate (2×100 mL), the combined organic layers were washed with brine, dried over magnesium sulfate, filtered, and concentrated to dryness. Chromatography on silica gel with a gradient of 5-10% ethyl acetate in hexanes gave 5.3 g (75%) of the product as a yellow oil.

MS (ES): 190, 192 (MH$^+$) for $C_6H_5BrFN$
$^1$H NMR (DMSO-D6) δ 5.46-6.00 (m, 2H); 6.24-6.37 (m, 1H); 6.44-6.53 (m, 1H); 6.54-6.61 (m, 1H).

Intermediate 181

N-(3-Bromo-5-fluorophenyl)acetamide

A mixture of acetamide (2.8 g, 47.2 mmol), palladium acetate (0.50 g, 0.80 mmol), XANTPHOS (0.68 g, 1.2 mmol) and cesium carbonate (18 g, 55.2 mmol) was degassed and purged with nitrogen twice. Dry dioxane (50 mL) was added followed by 1,3-dibromo-5-fluorobenzene (10 g, 39.4 mmol). The reaction was heated to 105° C. overnight and then allowed to cool to room temperature. Dichloromethane was added and the mixture was stirred vigorously for 1 hr. The mixture was filtered. The filtrate was concentrated to dryness. Chromatography on silica gel with 25% ethyl acetate in hexanes gave 4.0 g (44%) of the product as a colorless solid.

MS (ES): 232, 234 (MH$^+$) for $C_8H_7BrFNO$
$^1$H NMR (DMSO-D6) δ 2.01-2.13 (m, 3H); 7.13-7.24 (m, 1H); 7.42-7.54 (m, 1H); 7.57-7.67 (m, 1H); 10.22-10.35 (m, 1H).

Example 86

7-Fluoro-1-[2-(4-{[(2-oxo-1,2-dihydroquinolin-3-yl)methyl]amino}piperidin-1-yl)ethyl]quinoxalin-2(1H)-one A mixture of 1-[2-(4-aminopiperidin-1-yl)ethyl]-7-fluoroquinoxalin-2(1H)-one (Intermediate 140, 130 mg, 0.448 mmol), 2-oxo-1,2-dihydroquinoline-3-carbaldehyde (65 mg, 0.448 mmol) and 3 Å molecular sieves (100 mg) in methanol (6.0 mL) was heated at reflux for 2.5 hours under nitrogen atmosphere. It was cooled to 0° C. and sodium triacetoxy borohydride (189.5 mg, 0.996 mmol) was added and the mixture was allowed to warm to room temperature and stirred overnight. The mixture was filtered and purified through silica gel plug (eluting with 15% methanol in methylene chloride) to give title compound (71 mg).

MS (ES): 448.52 (MH$^+$) for $C_{25}H_{26}FN_5O_2$
$^1$H NMR (DMSO-D6) δ 1.13-1.32 (m, 2H); 1.79 (d, 2H); 2.02 (t, 2H); 2.35-2.45 (m, 1H); 2.52-2.59 (m, 2H); 2.90 (d, 2H); 3.61 (s, 2H); 4.27 (t, 2H); 7.15 (t, 1H); 7.24-7.33 (m, 2H); 7.43 (t, 1H); 7.51 (d, 1H); 7.63 (d, 1H); 7.79-7.92 (m, 2H); 8.17 (s, 1H).

Examples 87-96

The following compounds were synthesized following the procedure described for Example 86, except the compounds were purified by reverse phase HPLC with methanol/water, containing 0.1% TFA to give the TFA salts of the final products.

| Ex | Compound | $^1$H NMR (DMSO-D6) δ ppm | ES | Aldehyde |
|---|---|---|---|---|
| 87 | 1-[2-(4-{[(2,2-Dimethyl-3,4-dihydro-2H-chromen-6-yl)methyl]amino}piperidin-1-yl)ethyl]-5,7-difluoro quinolin-2(1H)-one | 1.27 (s, 6H); 1.64-1.89 (m, 4H); 2.21-2.39 (m, 2H); 2.73 (t, 2H); 2.95-3.18 (m, 2H); 3.80 (s, 2H); 4.08 (s, 2H); 4.53 (s, 2H); 6.67 (d, 1H); 6.76 (d, 1H); 7.19 (d, 1H); 7.24 (s, 1H); 7.31 (t, 1H); 7.43 (d, 1H); 8.03 (d, 1H); 9.02 (s, 2H); 9.75 (s, 1H) | 482 (MH)$^+$ | 2,2-dimethyl chromane-6-carbaldehyde |
| 88 | 1-[2-(4-{[(1,3-Dimethyl-2-oxo-2,3-dihydro-1H-benzimidazol-5-yl)methyl]amino}piperidin-1-yl)ethyl]-5,7-difluoroquinolin-2(1H)-one | 1.80 (s, 2H); 2.34 (s, 2H); 3.01-3.18 (m, 2H); 3.45 (s, 6H); 3.80 (s, 2H); 4.24 (s, 2H); 4.53 (s, 2H); 6.67 (d, 1H); 7.22 (s, 2H); 7.25-7.36 (m, 2H); 7.43 (d, 1H); 8.03 (d, 1H); 9.18 (s, 2H) | 482 (MH)$^+$ | 1,3-dimethyl-2-oxo-2,3-dihydro-1H-benzimidazole-5-carbaldehyde |
| 89 | 5,7-Difluoro-1-(2-{4-[(5,6,7,8-tetrahydro-naphthalen-2-ylmethyl)amino]piperidin-1-yl}ethyl)quinolin-2(1H)-one | 1.72 (s, 4H); 1.77-1.92 (m, 2H); 2.32 (s, 2H); 2.71 (s, 4H); 3.09 (s, 2H); 3.58 (s, 2H); 3.79 (s, 2H); 4.12 (s, 2H); 4.54 (s, 2H); 6.66 (d, 1H); 7.07-7.14 (m, 1H); 7.20 (s, 2H); 7.30 (t, 1H); 7.43 (d, 1H); 8.02 (d, 1H); 9.23 (s, 2H) | 452 (MH)$^+$ | 5,6,7,8-tetrahydro-naphthalene-2-carbaldehyde |
| 90 | 5,7-Difluoro-1-[2-(4-{[(6-fluoro-4H-1,3-benzodioxin-8-yl)methyl]amino}piperidin-1-yl)ethyl]quinolin-2(1H)-one | 1.84 (d, 2H); 2.33 (s, 2H); 3.09 (s, 2H); 3.29-3.44 (m, 2H); 3.80 (s, 2H); 4.16 (s, 2H); 4.54 (s, 2H); 4.91 (s, 2H); 5.32 (s, 2H); 6.66 (d, 1H); 7.01-7.14 (m, 1H); 7.19-7.34 (m, 2H); 7.43 (d, 1H); 8.01 (d, 1H); 9.35 (s, 2H) | 474 (MH)$^+$ | 6-fluoro-4H-1,3-benzodioxine-8-carbaldehyde |
| 91 | 5,7-Difluoro-1-(2-{4-[(1H-indol-6-ylmethyl)amino]piperidin-1-yl}ethyl)quinolin-2(1H)-one | 1.85 (d, 2H); 2.35 (s, 2H); 3.09 (s, 2H); 3.31 (s, 2H); 3.80 (s, 2H); 4.30 (s, 2H); 4.54 (s, 2H); 6.45 (s, 1H); 6.66 (d, 1H); 7.13 (d, 1H); 7.29 (t, 1H); 7.42 (s, 2H); 7.50-7.68 (m, 2H); 8.01 (d, 1H); 9.22 (s, 2H); 11.39 (s, 1H) | 437 (MH)$^+$ | 1H-indole-6-carbaldehyde |

| Ex | Compound | $^1$H NMR (DMSO-D6) δ ppm | ES | Aldehyde |
|---|---|---|---|---|
| 92 | 1-(2-{4-[(2,3-Dihydro-1H-inden-5-ylmethyl)amino]piperidin-1-yl}ethyl)-5,7-difluoroquinolin-2(1H)-one | 1.73-1.89 (m, 2H); 1.94-2.09 (m, 2H); 2.22-2.41 (m, 2H); 2.86 (t, 4H); 3.28 (s, 2H); 3.43-3.54 (m, 2H); 3.78 (s, 2H); 4.16 (s, 2H); 4.53 (s, 2H); 6.67 (d, 1H); 7.20-7.31 (m, 3H); 7.37 (s, 1H); 7.42 (d, 1H); 8.02 (d, 1H); 9.15 (s, 2H) | 438 (MH)$^+$ | indane-5-carbaldehyde |
| 93 | 5,7-Difluoro-1-[2-(4-{[(1-methyl-1H-1,2,3-benzotriazol-5-yl)methyl]amino}piperidin-1-yl)ethyl]quinolin-2(1H)-one | 1.72-1.95 (m, 2H); 2.35 (s, 2H); 2.99-3.18 (m, 2H); 3.31 (s, 2H); 3.79 (s, 2H); 4.32 (s, 3H); 4.41 (s, 2H); 4.54 (s, 2H); 6.66 (d, 1H); 7.29 (t, 1H); 7.42 (d, 1H); 7.69 (d, 1H); 7.94 (d, 1H); 8.02 (d, 1H); 8.23 (s, 1H); 9.43 (s, 2H) | 453 (MH)$^+$ | 1-methyl-1H-1,2,3-benzotriazole-5-carbaldehyde |
| 94 | 5,7-Difluoro-1-(2-{4-[(1H-indol-5-ylmethyl)amino]piperidin-1-yl}ethyl)quinolin-2(1H)-one | 1.80 (s, 2H); 2.36 (s, 2H); 3.11 (s, 2H); 3.40 (s, 2H); 3.80 (s, 2H); 4.26 (s, 2H); 4.52 (s, 2H); 6.47 (s, 1H); 6.67 (d, 1H); 7.21 (d, 1H); 7.31 (t, 1H); 7.37-7.52 (m, 3H); 7.70 (s, 1H); 8.03 (d, 1H); 9.04 (s, 1H); 11.28 (s, 1H) | 437 (MH)$^+$ | 1H-indole-5-carbaldehyde |
| 95 | 5,7-Difluoro-1-[2-(4-{[(4-methyl-3,4-dihydro-2H-1,4-benzoxazin-7-yl)methyl]amino}piperidin-1-yl)ethyl]quinolin-2(1H)-one | 1H NMR (DMSO-D6) δ ppm 1.73 (s, 2H); 2.30 (s, 2H); 2.83 (s, 3H); 2.97-3.15 (m, 2H); 3.24 (s, 2H); 3.30-3.38 (m, 2H); 3.79 (s, 2H); 4.03 (s, 2H); 4.22 (s, 2H); 4.53 (s, 2H); 6.63-6.75 (m, 2H); 6.85 (s, 1H); 6.90 (d, 1H); 7.31 (t, 1H); 7.43 (d, 1H); 8.04 (d, 1H); 8.90 (s, 1H) | 469 (MH)$^+$ | 4-methyl-3,4-dihydro-2H-1,4-benzoxazine-7-carbaldehyde |
| 96 | 1-(2-{4-[(2,1,3-Benzoxadiazol-5-ylmethyl)amino]piperidin-1-yl}ethyl)-7-fluoroquinoxalin-2(1H)-one | 1.13-1.29 (m, 2H); 1.78 (d, 2H); 1.95-2.07 (m, 2H); 2.31-2.43 (m, 1H); 2.51-2.58 (m, 2H); 2.89 (d, 2H); 3.82 (s, 2H); 4.27 (t, 2H); 7.23 (td, 1H); 7.51 (dd, 1H); 7.58 (d, 1H); 7.80-7.89 (m, 2H); 7.96 (d, 1H); 8.18 (s, 1H) | 423 (MH)$^+$ | 2,1,3-benzoxadiazole-5-carbaldehyde |

Example 97

N-{1-[2-(7-Fluoro-2-oxoquinoxalin-1(2H)-yl)ethyl]piperidin-4-yl}-2,3-dihydro-1,4-benzodioxine-6-sulfonamide To a solution of 1-[2-(4-aminopiperidin-1-yl)ethyl]-7-fluoroquinoxalin-2(1H)-one (Intermediate 140, 130 mg, 0.448 mmol) in methylene chloride (10 mL) was added diisopropylethylamine (0.156 mL, 0.996 mmol) and 2,3-dihydro-1,4-benzodioxine-6-sulfonyl chloride (116 mg, 0.493 mmol) and the reaction was stirred for 2.5 hours at room temperature. It was washed with saturated sodium bicarbonate solution and brine, dried over sodium sulfate, and concentrated. The residue was dissolved in HCl in dioxane (4M, 8.0 mL), concentrated, suspended in ethyl acetate and filtered to give the HCl salt of title compound (15.9 mg).

MS (ES): 489 (MH$^+$) for $C_{23}H_{25}FN_4O_5S$ $^1$H NMR (DMSO-D6) δ 1.62-1.83 (m, 3H); 2.92-3.11 (m, 2H); 3.16-3.28 (m, 3H); 3.41-3.50 (m, 3H); 3.59 (d, 2H); 4.47-4.59 (m, 2H); 7.05 (d, 1H); 7.23-7.34 (m, 2H); 7.78 (dd, 1H); 7.83-7.96 (m, 2H); 8.15-8.23 (m, 1H); 10.61 (s, 1H).

Example 98

N-{1-[2-(7-Fluoro-2-oxoquinoxalin-1(2H)-yl)ethyl]piperidin-4-yl}-3-oxo-3,4-dihydro-2H-1,4-benzoxazine-6-sulfonamide 1-[2-(4-Aminopiperidin-1-yl)ethyl]-7-fluoroquinoxalin-2(1H)-one (Intermediate 140, 130 mg, 0.448 mmol) was reacted as described for Example 97 with 3-oxo-3,4-dihydro-2H-1,4-benzoxazine-6-sulfonyl chloride (122 mg, 0.493 mmol) to give the HCl salt of title compound (89 mg).

MS (ES): 502 (MH$^+$) for $C_{23}H_{24}FN_5O_5S$ $^1$H NMR (DMSO-D6) δ 1.55-1.93 (m, 3H); 2.94-3.09 (m, 2H); 3.17-3.30 (m, 2H); 3.50 (d, 1H); 3.61 (d, 2H); 4.53 (d, 2H); 4.69 (s, 2H); 7.12 (d, 1H); 7.28 (t, 1H); 7.32-7.42 (m, 2H); 7.73 (d, 1H); 7.83-7.95 (m, 1H); 8.02 (d, 1H); 8.20 (s, 1H); 10.14 (s, 1H); 11.04 (s, 1H).

Example 99

5-Fluoro-N-{1-[2-(7-fluoro-2-oxoquinoxalin-1(2H)-yl)ethyl]piperidin-4-yl}-1H-indole-2-carboxamide A mixture of 1-[2-(4-aminopiperidin-1-yl)ethyl]-7-fluoroquinoxalin-2(1H)-one (Intermediate 140, 130 mg, 0.448 mmol), 5-fluoro-1H-indole-2-carboxylic acid (96.3 mg, 0.538 mmol), N-(3-Dimethylaminopropyl)-N'-ethylcarbodiimide (EDC) (124 mg, 0.645 mmol) and 1-Hydroxybenzotriazole hydrate (HOBT) (87 mg, 0.645 mmol) in dichloromethane/DMF (4:1, 10 mL) was stirred for 2.5 hours at room temperature. The solvent was removed under reduced pressure and the residue was suspended in methanol, stirred for 45 minutes and then filtered to give title compound (161 mg).

MS (ES): 452 (MH$^+$) for $C_{24}H_{23}F_2N_5O_2$ $^1$H NMR (DMSO-D6) δ 1.78-2.15 (m, 4H); 3.10-3.29 (m, 2H); 3.57 (s, 1H); 3.75 (d, 2H); 4.07 (s, 1H); 4.61 (s, 2H); 6.95-7.10 (m, 1H); 7.19 (s, 1H); 7.23-7.34 (m, 1H); 7.39 (d, 2H); 7.75-7.88 (m, 1H); 7.88-7.98 (m, 1H); 8.23 (s, 1H); 8.67 (d, 1H); 10.44 (s, 1H); 11.74 (s, 1H).

Example 100

N-{1-[2-(5,7-Difluoro-2-oxoquinolin-1(2H)-yl) ethyl]piperidin-4-yl}-6-morpholin-4-ylnicotinamide 1-[2-(4-Aminopiperidin-1-yl)ethyl]-5,7-difluoroquinolin-2(1H)-one (Intermediate 23, 100 mg, 0.326 mmol) was reacted as described for Example 99 with 6-morpholin-4-ylnicotinic acid (81 mg, 0.391 mmol), EDC (94 mg, 0.489 mmol) and HOBT (66 mg, 0.489 mmol) to give title compound (43.6 mg).
MS (ES): 498 (MH$^+$) for $C_{26}H_{29}F_2N_5O_3$
$^1$H NMR (DMSO-D6) δ 1.81-2.12 (m, 5H); 3.09-3.24 (m, 2H); 3.46-3.60 (m, 4H); 3.62-3.78 (m, 6H); 3.97-4.18 (m, 1H); 4.63 (s, 2H); 6.67 (d, 1H); 6.85 (d, 1H); 7.30 (t, 1H); 7.74 (d, 1H); 7.93-8.07 (m, 2H); 8.37 (d, 1H); 8.63 (s, 1H); 10.66 (s, 1H).

Example 101

N-{1-[2-(5,7-Difluoro-2-oxoquinolin-1(2H)-yl) ethyl]piperidin-4-yl}-2,3-dihydro-1,4-benzodioxine-2-carboxamide 1-[2-(4-Aminopiperidin-1-yl)ethyl]-5,7-difluoroquinolin-2(1H)-one (Intermediate 23, 100 mg, 0.326 mmol) was reacted as described for Example 99 with 2,3-dihydro-1,4-benzodioxine-2-carboxylic acid (71 mg, 0.391 mmol), EDC (94 mg, 0.489 mmol) and HOBT (66 mg, 0.489 mmol) to give title compound (73.9 mg).
MS (ES): 470 (MH$^+$) for $C_{25}H_{25}F_2N_3O_4$
$^1$H NMR (DMSO-D6) δ 1.71-2.05 (m, 4H); 3.06-3.21 (m, 2H); 3.22-3.29 (m, 2H); 3.67 (s, 1H); 3.80-4.03 (m, 1H); 4.17 (dd, 1H); 4.31-4.45 (m, 1H); 4.51-4.67 (m, 2H); 4.70-4.79 (m, 1H); 6.58-6.73 (m, 1H); 6.85 (d, 2H); 6.92-7.02 (m, 1H); 7.30 (t, 1H); 7.65 (d, 1H); 8.03 (d, 1H); 8.41 (d, 1H); 10.19 (s, 1H).

Example 102

N-{1-[2-(5,7-Difluoro-2-oxoquinolin-1(2H)-yl) ethyl]piperidin-4-yl}-1-methyl-1H-1,2,3-benzotriazole-5-carboxamide 1-[2-(4-Aminopiperidin-1-yl)ethyl]-5,7-difluoroquinolin-2(1H)-one (Intermediate 23, 100 mg, 0.326 mmol) was reacted as described for Example 99 with 1-methyl-1H-1,2,3-benzotriazole-5-carboxylic acid (70 mg, 0.391 mmol), EDC (94 mg, 0.489 mmol) and HOBT (66 mg, 0.489 mol) to give title compound (67.6 mg).
MS (ES): 467 (MH$^+$) for $C_{24}H_{24}F_2N_6O_2$
$^1$H NMR (DMSO-D6) δ 1.86-2.03 (m, 2H); 2.07 (s, 2H); 3.12-3.25 (m, 2H); 3.42-3.61 (m, 1H); 3.73 (d, 2H); 4.09 (s, 1H); 4.33 (s, 3H); 4.64 (t, 2H); 6.68 (d, 1H); 7.30 (t, 1H); 7.73 (d, 1H); 7.92 (d, 1H); 8.05 (t, 2H); 8.61 (s, 1H); 8.76 (d, 1H); 10.60 (s, 1H).

Example 103

N-{1-[2-(5,7-Difluoro-2-oxoquinolin-1(2H)-yl) ethyl]piperidin-4-yl}-3-(2-methyl-1,3-thiazol-4-yl) benzamide 1-[2-(4-Aminopiperidin-1-yl)ethyl]-5,7-difluoro quinolin-2(1H)-one (Intermediate 23, 100 mg, 0.326 mmol) was reacted as described for Example 99 with 3-(2-methyl-1,3-thiazol-4-yl)benzoic acid (86 mg, 0.391 mmol), EDC (94 mg, 0.489 mmol) and HOBT (66 mg, 0.489 mmol). Solvent removed and the obtained solids were stirred in HCl/dioxane (8.0 mL, 4M) and then filtered to give the HCl salt of title compound (39 mg).
MS (ES): 509 (MH$^+$) for $C_{27}H_{26}F_2N_4O_2S$
$^1$H NMR (DMSO-D6) δ 1.91-2.17 (m, 4H); 2.73 (s, 3H); 3.10-3.39 (m, 3H); 3.50 (s, 1H); 3.71 (d, 2H); 4.64 (s, 2H); 6.68 (d, 1H); 7.30 (t, 1H); 7.51 (t, 1H); 7.72-7.89 (m, 2H); 7.98-8.13 (m, 3H); 8.42 (s, 1H); 8.73 (d, 1H); 10.85 (s, 1H).

Example 104

N-{1-[2-(5,7-Difluoro-2-oxoquinolin-1(2H)-yl) ethyl]piperidin-4-yl}-4-(5-methyl-1,2,4-oxadiazol-3-yl)benzamide 1-[2-(4-Aminopiperidin-1-yl)ethyl]-5,7-difluoroquinolin-2(1H)-one (Intermediate 23, 100 mg, 0.326 mmol) was reacted as described for Example 99 with 4-(5-methyl-1,2,4-oxadiazol-3-yl)benzoic acid (80 mg, 0.391 mmol), EDC (94 mg, 0.489 mmol) and HOBT (66 mg, 0.489 mmol). Solvent removed and the obtained solids were suspended in ethyl acetate and then filtered to give title compound (71.9 mg).
MS (ES): 494 (MH$^+$) for $C_{26}H_{25}F_2N_5O_3$
$^1$H NMR (DMSO-D6) δ 1.77-1.97 (m, 2H); 1.98-2.15 (m, 2H); 2.68 (s, 3H); 3.10-3.27 (m, 2H); 3.75 (d, 2H); 4.05 (s, 1H); 4.60 (t, 2H); 6.69 (d, 1H); 7.32 (t, 1H); 7.46-7.68 (m, 1H); 7.96-8.15 (m, 5H); 8.72 (d, 1H); 9.86 (s, 1H).

Example 105

3-Oxo-4-[2-((2R,5S)-5-{[(3-oxo-3,4-dihydro-2H-pyrido[3,2-b][1,4]oxazin-6-yl)methyl] amino}piperidin-2-yl)ethyl]-3,4-dihydro-2H-1,4-benzoxazine-6-carbonitrile To a solution of tert-butyl(2R,5S)-2-[2-(6-cyano-3-oxo-2,3-dihydro-4H-1,4-benzoxazin-4-yl)ethyl]-5-{[(3-oxo-3,4-dihydro-2H-pyrido[3,2-b][1,4]oxazin-6-yl)methyl] amino}piperidine-1-carboxylate (Intermediate 182, 0.138 g) in dioxane (2 mL) was added 4M HCl/dioxane (1 mL). After 1 hour at room temperature, the reaction was concentrated and evaporated twice from methanol. The solid was suspended in methanol and filtered to yield 73 mg of the name compound as a bis HCl salt.
MS (ESI) 463 (MH$^+$) for $C_{24}H_{26}N_6O_4$
$^1$H NMR (DMSO-D6) δ 1.58-1.63 (m, 1H); 1.65-1.74 (m, 1H); 1.75-1.86 (m, 1H); 1.92-2.03 (m, 1H); 2.13-2.23 (m, 1H); 2.29-2.38 (m, 1H); 3.02-3.14 (m, 1H); 3.14-3.24 (m, 3H); 3.59-3.70 (m, 1H); 3.70-3.78 (m, 1H); 4.01-4.13 (m, 2H); 4.18-4.28 (m, 2H); 4.70 (s, 2H); 4.82 (s, 2H); 7.19 (d, 1H); 7.26 (d, 1H); 7.46 (d, 1H); 7.54 (dd, 1H); 7.77 (d, 1H); 9.51 (s, 1H); 9.70 (s, 1H); 9.82 (s, 1H); 11.36 (s, 1H).

Intermediate 182 tert-Butyl(2R,5S)-2-[2-(6-cyano-3-oxo-2,3-dihydro-4H-1,4-benzoxazin-4-yl)ethyl]-5-{[(3-oxo-3,4-dihydro-2H-pyrido[3,2-b][1,4]oxazin-6-yl)methyl] amino}piperidine-1-carboxylate A mixture of tert-butyl(2R,5S)-5-amino-2-[2-(6-cyano-3-oxo-2,3-dihydro-4H-1,4-benzoxazin-4-yl)ethyl]piperidine-1-carboxylate (Intermediate 183, 0.14 g), 3-oxo-3,4-dihydro-2H-pyrido[3,2-b][1,4]oxazine-6-carbaldehyde (WO 2004/

058144) (75 mg) and 3 Å molecular sieves powder (70 mg) in methanol (8 mL) was heated at 80° C. for 1 hour. The solution was cooled to 0° C. and NaCNBH$_3$ (33 mg) was added. After stirring at room temperature overnight, the reaction was filtered and concentrated. The residue was purified chromatography on silica gel with a gradient of 0-5% methanol in methylene chloride to give 0.14 g.

MS (ESI) 563 (MH$^+$) for $C_{29}H_{34}N_6O_6$ $^1$H NMR (CDCl$_3$) δ 1.37-1.43 (m, 1H); 1.44-1.51 (s, 9H); 1.70-1.81 (m, 2H); 2.11 (m, 1H); 2.89-3.00 (m, 1H); 3.01-3.12 (m, 1H); 3.94-4.05 (m, 1H); 4.20-4.32 (m, 1H); 4.33-4.44 (m, 1H); 4.64 (s, 2H); 4.67 (s, 2H); 6.99 (d, 1H); 7.04 (d, 1H); 7.17-7.24 (m, 2H); 7.32 (dd, 1H).

Intermediate 183 tert-Butyl(2R,5S)-5-amino-2-[2-(6-cyano-3-oxo-2,3-dihydro-4H-1,4-benzoxazin-4-yl)ethyl]piperidine-1-carboxylate tert-Butyl(2R,5S)-5-azido-2-[2-(6-cyano-3-oxo-2,3-dihydro-4H-1,4-benzoxazin-4-yl)ethyl]piperidine-1-carboxylate (Intermediate 184, 0.31 g) was hydrogenated in methanol (10 mL) over 10% Pd/C (90 mg) at normal pressure and room temperature overnight. The reaction was degassed, filtered and purified by chromatography on silica gel with a gradient of 0-10% methanol in methylene chloride to give 0.29 g.

MS (ESI) 401 (MH$^+$) for $C_{21}H_{28}N_4O_4$

Intermediate 184 tert-Butyl(2R,5S)-5-azido-2-[2-(6-cyano-3-oxo-2,3-dihydro-4H-1,4-benzoxazin-4-yl)ethyl]piperidine-1-carboxylate To a solution of tert-butyl(2R,5R)-2-[2-(6-cyano-3-oxo-2,3-dihydro-4H-1,4-benzoxazin-4-yl)ethyl]-5-hydroxypiperidine-1-carboxylate (Intermediate 185, crude, 0.8 g) in THF (20 mL) were successively added triphenylphosphine (1.30 g), diisopropylazodicarboxylate (1 mL) and diphenyl phosphoryl azide (0.90 g). After 4 hours, the reaction was diluted with ethyl acetate, washed with saturated solution of sodium hydrogen carbonate (NaHCO$_3$) and brine, dried over sodium sulfate and concentrated. Chromatography on silica gel with a gradient of 0-5% methanol in methylene chloride gave 0.31 g of product.

MS (ESI) 427 (MH$^+$) for $C_{21}H_{26}N_6O_4$

Intermediate 185 tert-Butyl(2R,5R)-2-[2-(6-cyano-3-oxo-2,3-dihydro-4H-1,4-benzoxazin-4-yl)ethyl]-5-hydroxypiperidine-1-carboxylate To a solution of tert-butyl(2R,5R)-5-{[tert-butyl(dimethyl) silyl]oxy}-2-[2-(6-cyano-3-oxo-2,3-dihydro-4H-1,4-benzoxazin-4-yl)ethyl]piperidine-1-carboxylate (Intermediate 186, 1.01 g) in THF (10 mL) was added tetrabutylammonium fluoride (TBAF) (4 mL). After 5 hours, the reaction was diluted with ethyl acetate, washed with NaHCO$_3$ and brine, dried over sodium sulfate and concentrated. The crude reaction mixture was used without further purification in the next step.

MS (ESI) 402 (MH$^+$) for $C_{21}H_{27}N_3O_5$

Intermediate 186 tert-Butyl(2R,5R)-5-{[tert-butyl(dimethyl)silyl] oxy}-2-[2-(6-cyano-3-oxo-2,3-dihydro-4H-1,4-benzoxazin-4-yl)ethyl]piperidine-1-carboxylate To a solution of tert-butyl(2R,5R)-5-{[tert-butyl(dimethyl) silyl]oxy}-2-(2-hydroxyethyl)piperidine-1-carboxylate (Intermediate 187, 1.27 g) in methylene chloride (15 mL) at 0° C. were added diisopropylethylamine (1.2 mL) and methanesulfonyl chloride (0.50 mL). At the same time in a separate flask, to a solution of 3-oxo-3,4-dihydro-2H-1,4-benzoxazine-6-carbonitrile (Intermediate 60) (0.66 g) in DMF (8 mL) at 0° C. was added 60% suspension in oil of NaH (0.25 g). After 30 minutes, the mesylate solution was diluted with methylene chloride, washed with NaHCO$_3$ and brine, dried over sodium sulfate and concentrated. This residue was dissolved in DMF (5 mL) and added to the sodium salt of Intermediate 60. The reaction was stirred over the weekend, diluted with ethyl acetate, washed with NaHCO$_3$ and brine, dried over sodium sulfate and concentrated to give the product.

MS (ESI) 516 (MH$^+$) for $C_{27}H_{41}N_3O_5Si$

Intermediate 187 tert-Butyl(2R,5R)-5-{[tert-butyl(dimethyl)silyl] oxy}-2-(2-hydroxyethyl)piperidine-1-carboxylate To a solution of tert-butyl(2R,5R)-5-{[tert-butyl(dimethyl) silyl]oxy}-2-vinylpiperidine-1-carboxylate (Intermediate 188, 1.39 g) in THF (20 mL) at 0° C. was added 9-BBN (0.5 M, 15 mL). After 45 minutes, the reaction was diluted with water (3 mL), 3 N NaOH (12 mL) and 30% H$_2$O$_2$ (12 mL). After 15 minutes, the reaction was allowed to warm to room temperature. After 30 minutes, the reaction was diluted with ethyl acetate, washed with 1 N HCl, NaHCO$_3$ and brine, dried (Na$_2$SO$_4$), filtered and concentrated. Chromatography on silica gel with a gradient of 0-5% methanol in methylene chloride gave 1.27 g of product.

MS (ESI) 360 (MH$^+$) for $C_{18}H_{37}NO_4Si$

Intermediate 188 tert-Butyl(2R,5R)-5-{[tert-butyl(dimethyl)silyl] oxy}-2-vinylpiperidine-1-carboxylate To a suspension of zinc dust (12.2 g) in THF (200 mL) and diiodomethane (5 mL) at 0° C. was added trimethylaluminium (2M in hexanes, 6 mL). After the addition the reaction was carefully warmed to room temperature (exothermic reaction!). The reaction was then cooled with an ice bath and a solution of tert-butyl(2R,5R)-5-{[tert-butyl(dimethyl)silyl] oxy}-2-formylpiperidine-1-carboxylate (Intermediate 189, 6.84 g) in THF (40 mL) was added. After 6 hours it was warmed to room temperature, the reaction was diluted with ethyl acetate and slowly quenched with a saturated aqueous solution of NaHCO$_3$. The organic phase was collected and washed with NaHCO$_3$ and brine, dried (Na$_2$SO$_4$), filtered and concentrated. Chromatography on silica gel with a gradient of 0-100% methylene chloride in hexanes gave 3.96 g of product.

MS (ESI) 341 (MH$^+$) for $C_{18}H_{35}NO_3Si$ $^1$H NMR (CDCl$_3$) δ 0.06 (s, 6H); 0.87 (s, 9H); 1.42-1.44 (m, 1H); 1.44 (s, 9H); 1.63-1.81 (m, 2H); 2.44-2.73 (m, 1H);

3.43-3.63 (m, 1H); 3.77-4.16 (m, 1H); 4.50-4.92 (m, 1H); 4.97-5.13 (m, 1H); 5.13-5.26 (m, 1H); 5.58-5.84 (m, 1H).

Intermediate 189 tert-Butyl(2R,5R)-5-{[tert-butyl(dimethyl)silyl]oxy}-2-formylpiperidine-1-carboxylate To a solution of oxalyl chloride (2.4 mL) in methylene chloride (75 mL) at −78° C. was slowly added dimethylsulfoxide (3 mL) in methylene chloride (25 mL). After 10 minutes, a solution of tert-butyl(2R,5R)-5-{[tert-butyl(dimethyl)silyl]oxy}-2-(hydroxymethyl)piperidine-1-carboxylate (Intermediate 190, 7.60 g) in methylene chloride (40 mL) was slowly added. After 30 minutes at −78° C., diisopropylethylamine (10 mL) was added and the reaction warmed to room temperature. The reaction was diluted with ethyl acetate, washed with 0.5 M HCl, NaHCO$_3$ and brine solutions, dried (Na$_2$SO$_4$), filtered and concentrated. Chromatography on silica gel with a gradient of 0-30% ethyl acetate in hexanes gave 6.84 g of product.

MS (ESI) 344 (MH$^+$) for C$_{17}$H$_{33}$NO$_4$Si

Intermediate 190 tert-Butyl(2R,5R)-5-{[tert-butyl(dimethyl)silyl]oxy}-2-(hydroxymethyl)piperidine-1-carboxylate To a solution of 1-tert-butyl 2-ethyl (2R,5R)-5-{[tert-butyl(dimethyl)silyl]oxy}piperidine-1,2-dicarboxylate (Intermediate 191, 9.99 g) in THF (100 mL) was added lithium aluminium hydride (1M in THF, 30 mL). After 2 hours, the reaction was quenched with ethyl acetate, washed with 1 N HCl, NaHCO$_3$ and brine solutions, dried (Na$_2$SO$_4$), filtered and concentrated yielding 7.9 g of product.

MS (ESI) 346 (MH$^+$) for C$_{17}$H$_{35}$NO$_4$Si

Intermediate 191

1-tert-Butyl 2-ethyl(2R,5R)-5-{[tert-butyl(dimethyl)silyl]oxy}piperidine-1,2-dicarboxylate To a solution of 1-tert-butyl 2-ethyl(2R)-5-oxopiperidine-1,2-dicarboxylate (8.8 g) (Bioorganic & Medicinal Chemistry Letters (2002), 12(10), 1387-1390) in methanol (200 mL) at 0° C. was added sodium borohydride (1.80 g). After 2 hours, the reaction was concentrated to dryness. The residue was dissolved in ethyl acetate and washed with 1 N HCl, NaHCO$_3$ and brine solutions, dried (Na$_2$SO$_4$), filtered and concentrated. The crude alcohol was dissolved in DMF (200 mL) and tread with imidazole (7.5 g) and t-BDMSCl (11.5 g). After stirring overnight at room temperature, the reaction was diluted with ethyl acetate and washed with 1 N HCl, NaHCO$_3$ and brine solutions, dried (Na$_2$SO$_4$), filtered and concentrated. Chromatography on silica gel with a gradient of 0-25% ethyl acetate in hexanes gave 9.99 g of product.

MS (ESI) 388 (MH$^+$) for C$_{19}$H$_{37}$NO$_5$Si

1H NMR (CDCl$_3$) δ (rotamers) 0.06 (m, 6H); 0.86 & 0.87 (s, 9H); 1.22-1.30 (m, 3H); 1.42 & 1.46 (s, 9H); 1.61-1.73 (m, 1H); 1.77-1.91 (m, 1H); 2.18-2.31 (m, 1H); 2.58 & 2.69 (dd, 1H); 3.42-3.62 (m, 1H); 3.97 & 4.13 (dd, 1H); 4.14-4.25 (m, 2H); 4.60 & 4.81 (d, 1H).

Example 106

3-Oxo-4-[2-((2S,5R)-5-{[(3-oxo-3,4-dihydro-2H-pyrido[3,2-b][1,4]oxazin-6-yl)methyl]amino}piperidin-2-yl)ethyl]-3,4-dihydro-2H-1,4-benzoxazine-6-carbonitrile The title compound was prepared following the procedure described for Example 105, except, starting from 1-tert-butyl 2-methyl(2S)-5-oxopiperidine-1,2-dicarboxylate (Bioorganic & Medicinal Chemistry Letters (2002), 12(10), 1387-1390).

MS (ESI) 463 (MH$^+$) for C$_{24}$H$_{26}$N$_6$O$_4$ $^1$H NMR (DMSO-D6) δ 1.58-1.63 (m, 1H); 1.65-1.74 (m, 1H); 1.75-1.86 (m, 1H); 1.92-2.03 (m, 1H); 2.13-2.23 (m, 1H); 2.29-2.38 (m, 1H); 3.02-3.14 (m, 1H); 3.14-3.24 (m, 3H); 3.59-3.70 (m, 1H); 3.70-3.78 (m, 1H); 4.01-4.13 (m, 2H); 4.18-4.28 (m, 2H); 4.70 (s, 2H); 4.82 (s, 2H); 7.19 (d, 1H); 7.26 (d, 1H); 7.46 (d, 1H); 7.54 (dd, 1H); 7.77 (d, 1H); 9.51 (s, 1H); 9.70 (s, 1H); 9.82 (s, 1H); 11.36 (s, 1H).

Example 107

6-[({1-[2-(5,7-Difluoro-2-oxoquinoxalin-1(2H)-yl)ethyl]piperidin-4-yl}amino)methyl]-2H-pyrido[3,2-b][1,4]oxazin-3(4H)-one To a solution of 1-[2-(4-aminopiperidin-1-yl)ethyl]-5,7-difluoroquinoxalin-2(1H)-one (Intermediate 192, 0.158 g) in methanol (10 mL) were added 3 Å molecular sieve power (0.15 g) and 3-oxo-3,4-dihydro-2H-pyrido[3,2-b][1,4]oxazine-6-carbaldehyde (WO 2004/058144) (92 mg). After 2 hours at reflux, the reaction was cooled to 0° C. and NaBH(OAc)$_3$ (0.19 g) was added. The reaction was allowed to warm to room temperature and was stirred overnight. It was diluted with ethyl acetate, filtered, washed with saturated solutions of Na$_2$CO$_3$ and brine, dried over sodium sulfate and concentrated. Chromatography on silica gel with 0-20% methanol in dichloromethane. Fractions containing product were collected, concentrated, dissolved in a minimum of CH$_2$Cl$_2$, precipitated with diethyl ether, and filtered to yield 104 mg of product.

MS (ESI) 471 (MH$^+$) for C$_{23}$H$_{24}$F$_2$N$_6$O$_3$ $^1$H NMR (CDCl$_3$) δ 1.15-1.35 (m, 2H); 1.73-1.88 (m, 2H); 1.93-2.09 (m, 2H); 2.51-2.58 (m, 2H); 2.83-2.95 (m, 2H); 3.16 (d, 1H); 3.71-3.84 (m, 1H); 4.21-4.34 (m, 2H); 4.61 (s, 2H); 7.02 (d, 1H); 7.26-7.48 (m, 1H); 8.19 (s, 1H).

Intermediate 192

1-[2-(4-Aminopiperidin-1-yl)ethyl]-5,7-difluoroquinoxalin-2(1H)-one

To a solution of tert-butyl{1-[2-(5,7-difluoro-2-oxoquinoxalin-1(2H)-yl)ethyl]piperidin-4-yl}carbamate (Intermediate 193, 0.21 g) in dioxane (3 mL) and water (1 mL) was added 4 M HCl in dioxane (1 mL). After 30 minutes, additional 4 M HCl/dioxane (3 mL) was added. After 1 hour, the reaction was diluted with chloroform and poured into a saturated solution of Na$_2$CO$_3$. The organic solution was collected, dried (Na$_2$SO$_4$), filtered and concentrated yielding 0.158 g of crude titled compound.

MS (ESI) 309 (MH$^+$) for C$_{15}$H$_{18}$F$_2$N$_4$O

Intermediates 193 tert-Butyl{1-[2-(5,7-difluoro-2-oxoquinoxalin-1 (2H)-yl)ethyl]piperidin-4-yl}carbamate and

Intermediate 194 tert-Butyl{1-[2-(6,8-difluoro-2-oxoquinoxalin-1 (2H)-yl)ethyl]piperidin-4-yl}carbamate A mixture of 5,7-difluoroquinoxalin-2(1H)-one and 6,8-difluoroquinoxalin-2(1H)-one (Intermediate 195) (1.05 g, 5.77 mmol) was deprotonated with sodium hydride (0.31 g, 60% in oil, 7.75 mmol) and alkylated with 2-{4-[tert-butoxycarbonyl)amino]piperidin-1-yl}ethyl methanesulfonate (Intermediate 6) (5.8 mmol) as described for Intermediate 2. The residue obtained after aqueous workup was titurated in diethyl ether and filtered yielding 0.73 g of tert-butyl{1-[2-(5,7-difluoro-2-oxoquinoxalin-1(2H)-yl)ethyl]piperidin-4-yl}carbamate (Intermediate 193). The filtrate was concentrated and the residue was purified by chromatography on silica gel with 0-20% acetone in dichloromethane to yield 111 mg of tert-butyl{1-[2-(6,8-difluoro-2-oxoquinoxalin-1(2H)-yl)ethyl]piperidin-4-yl}carbamate (Intermediate 194).

Intermediate 193

MS (ESI) 409 (MH$^+$) for $C_{20}H_{26}F_2N_4O_3$
$^1$H NMR (CDCl$_3$) δ 1.33-1.42 (m, 2H); 1.44 (s, 9H); 1.89-1.97 (m, 2H); 2.24 (td, 2H); 2.65 (t, 2H); 2.84-2.89 (m, 2H); 3.41-3.52 (m, 1H); 4.27 (t, 2H); 4.41 (s, 1H); 6.87 (td, 1H); 6.93 (dt, 1H); 8.23 (s, 1H).

Intermediate 194

MS (ESI) 409 (MH$^+$) for $C_{20}H_{26}F_2N_4O_3$
$^1$H NMR (CDCl$_3$) δ 1.31-1.42 (m, 2H); 1.44 (s, 9H); 1.86-1.96 (m, 2H); 2.23 (td, 2H); 2.67 (t, 2H); 2.84-2.91 (m, 2H); 3.39-3.51 (m, 1H); 4.34-4.45 (m, 1H); 4.46-4.53 (m, 2H); 7.13 (ddd, 1H); 7.36-7.44 (m, 1H); 8.30 (s, 1H).

Intermediate 195

5,7-Difluoroquinoxalin-2(1H)-one and
6,8-difluoroquinoxalin-2(1H)-one

To a solution of 1,2-diamino-3,5-difluorobenzene (5.11 g) in methanol (100 mL) was added ethylglyoxalate (16 mL). After 6 hours at room temperature, the precipitate was collected by filtration and washed with methanol yielding 2.1 g products, 1:1 mixture of 5,7-difluoroquinoxalin-2(1H)-one and 6,8-difluoroquinoxalin-2(1H)-one.
MS (ESI) 182 (MH$^+$) for $C_8H_4F_2N_2O$

Example 108

6-[({1-[2-(6,8-Difluoro-2-oxoquinoxalin-1(2H)-yl) ethyl]piperidin-4-yl}amino)methyl]-2H-pyrido[3,2-b][1,4]oxazin-3(4H)-one 1-[2-(4-Aminopiperidin-1-yl)ethyl]-6,8-difluoro quinoxalin-2(1H)-one (Intermediate 196, 52 mg) was reacted with 3-oxo-3,4-dihydro-2H-pyrido[3,2-b][1,4]oxazine-6-carbaldehyde (WO 2004/058144) and sodium acetoxyborohydride as described for Example 107 yielding 29 mg of the title compound.
MS (ESI) 471 (MH$^+$) for $C_{23}H_{24}F_2N_6O_3$
$^1$H NMR (DMSO-D6) δ 1.16-1.28 (m, 2H); 1.71-1.82 (m, 2H); 2.04 (t, 2H); 2.35-2.47 (m, 2H); 2.54-2.61 (m, 2H); 2.81-2.90 (m, 2H); 3.70 (s, 2H); 4.32-4.42 (m, 2H); 4.61 (s, 2H); 7.02 (d, 1H); 7.30 (d, 1H); 7.61 (d, 1H); 7.72 (ddd, 1H); 8.33 (s, 1H); 11.17 (s, 1H).

Intermediate 196

1-[2-(4-Aminopiperidin-1-yl)ethyl]-6,8-difluoroquinoxalin-2(1H)-one tert-Butyl{1-[2-(6,8-difluoro-2-oxoquinoxalin-1(2H)-yl) ethyl]piperidin-4-yl}carbamate (Intermediate 194) was deprotected with HCl in dioxane as described for Intermediate 192.
MS (ESI) 309 (MH$^+$) for $C_{15}H_{18}F_2N_4O$

Example 109

2-Oxo-1-[2-(4-{[(3-oxo-3,4-dihydro-2H-pyrido[3,2-b][1,4]oxazin-6-yl)methyl]amino}piperidin-1-yl) ethyl]-1,2-dihydroquinoxaline-6-carbonitrile 1-[2-(4-Aminopiperidin-1-yl)ethyl]-2-oxo-1,2-dihydroquinoxaline-6-carbonitrile (Intermediate 197, 0.125 g) was reacted with 3-oxo-3,4-dihydro-2H-pyrido[3,2-b][1,4]oxazine-6-carbaldehyde (WO 2004/058144) (0.17 g) and NaBH(OAc)$_3$ (0.27 g) as described for Example 107. The residue was purified by reverse phase HPLC with acetonitrile in water containing 0.1% TFA. Fractions containing product were concentrated to remove acetonitrile, neutralized with Na$_2$CO$_3$ solid, extracted with ethyl acetate, dried (Na$_2$SO$_4$), filtered and concentrated. The residue was suspended in diethyl ether and filtered to yield 127 mg of a colorless solid.
MS (ESI) 460 (MH$^+$) for $C_{24}H_{25}N_7O_3$
$^1$H NMR (DMSO-D6) δ 1.14-1.25 (m, 2H); 1.70-1.80 (m, 2H); 1.96-2.07 (m, 2H); 2.33-2.43 (m, 1H); 2.51-2.57 (m, 2H); 2.87 (d, 2H); 3.67 (s, 2H); 4.33 (t, 2H); 4.61 (s, 2H); 7.01 (d, 1H); 7.30 (d, 1H); 7.79 (d, 1H); 8.05 (dd, 1H); 8.36 (d, 2H); 11.16 (s, 1H).

Intermediate 197

1-[2-(4-Aminopiperidin-1-yl)ethyl]-2-oxo-1,2-dihydroquinoxaline-6-carbonitrile

To a solution of tert-butyl{1-[2-(6-cyano-2-oxoquinoxalin-1(2H)-yl)ethyl]piperidin-4-yl}carbamate (Intermediate 198, 0.38 g) in methylene chloride (4 mL) was added at 0° C. TFA (2 mL). After 1 hour, the reaction was diluted with chloroform, washed with saturated solution of Na$_2$CO$_3$, dried (Na$_2$SO$_4$), filtered and concentrated yielding 0.25 g of crude product.
MS (ESI) 298 (MH$^+$) for $C_{16}H_{19}N_5O$

Intermediate 198 tert-Butyl{1-[2-(6-cyano-2-oxoquinoxalin-1(2H)-yl) ethyl]piperidin-4-yl}carbamate and

Intermediate 199 tert-Butyl{1-[2-(7-cyano-2-oxoquinoxalin-1(2H)-yl) ethyl]piperidin-4-yl}carbamate A mixture of 2-oxo-1,2-dihydroquinoxaline-6-carbonitrile and 3-oxo-3,4-dihydroquinoxaline-6-carbonitrile (Intermediate 200, 0.83 g, 4.8 mmol) was deprotonated with sodium hydride (0.30 g, 60% in oil) and alkylated with 2-{4-[(tert-butoxycarbonyl)amino]piperidin-1-yl}ethyl methanesulfonate (Intermediate 6) (4.8 mmol) as described for Intermediate 2. Chromatography on silica gel with 0-25% acetone in dichloromethane gave 38 mg of tert-butyl{1-[2-(7-cyano-2-oxoquinoxalin-1(2H)-yl)ethyl]piperidin-4-yl}carbamate (Intermediate 199) and 0.39 g of tert-butyl{1-[2-(6-cyano-2-oxoquinoxalin-1(2H)-yl)ethyl]piperidin-4-yl}carbamate (Intermediate 198).

MS (ESI) 398 (MH$^+$) for $C_{21}H_{27}N_5O_3$

Intermediate 198

$^1$H NMR (CDCl$_3$) δ 1.31-1.41 (m, 2H); 1.44 (s, 9H); 1.88-1.98 (m, 2H); 2.19-2.29 (m, 2H); 2.67 (t, 2H); 2.83-2.93 (m, 2H); 3.41-3.52 (m, 1H); 4.35 (t, 2H); 4.43 (m, 1H); 7.48 (d, 1H); 7.80 (dd, 1H); 8.20 (d, 1H); 8.35 (s, 1H).

Intermediate 199

$^1$H NMR (CDCl$_3$) δ 1.32-1.42 (m, 2H); 1.44 (s, 9H); 1.89-1.97 (m, 2H); 2.19-2.30 (m, 2H); 2.68 (t, 2H); 2.83-2.93 (m, 2H); 3.42-3.53 (m, 1H); 4.33 (t, 2H); 4.42 (s, 1H); 7.59 (dd, 1H); 7.79 (s, 1H); 7.97 (d, 1H); 8.37 (s, 1H).

Intermediate 200

2-Oxo-1,2-dihydroquinoxaline-6-carbonitrile and 3-oxo-3,4-dihydroquinoxaline-6-carbonitrile To a solution of 3,4-diaminobenzonitrile (0.99 g) in methanol (20 mL) was added ethylglyoxalate (3.5 mL). After stirring overnight at room temperature, the precipitate was collected and washed with methanol. The filtrate was concentrated to give a second crop of product yielding 0.83 g from both batches, 1:1 mixture of 2-oxo-1,2-dihydroquinoxaline-6-carbonitrile and 3-oxo-3,4-dihydroquinoxaline-6-carbonitrile as a brown solid.

MS (ESI) 172 (MH$^+$) for $C_9H_5N_3O$

Example 110

3-Oxo-4-[2-(4-{[(3-oxo-3,4-dihydro-2H-pyrido[3,2-b][1,4]oxazin-6-yl)methyl]amino}piperidin-1-yl)ethyl]-3,4-dihydroquinoxaline-6-carbonitrile 1-[2-(4-Aminopiperidin-1-yl)ethyl]-2-oxo-1,2-dihydroquinoxaline-7-carbonitrile (Intermediate 201, 0.11 g) was reacted with 3-oxo-3,4-dihydro-2H-pyrido[3,2-b][1,4]oxazine-6-carbaldehyde (WO 2004/058144) and sodium acetoxyborohydride as described for Example 107 yielding 17 mg of a colorless solid.

MS (ESI) 460 (MH$^+$) for $C_{24}H_{25}N_7O_3$
$^1$H NMR (DMSO-D6) δ 1.22-1.33 (m, 2H); 1.80-1.91 (m, 2H); 1.98-2.08 (m, 2H); 2.55-2.67 (m, 3H); 2.90-3.01 (m, 2H); 3.79-3.90 (m, 1H); 4.35 (t, 2H); 4.64 (s, 2H); 7.05 (d, 1H); 7.34 (d, 1H); 7.79 (d, 1H); 7.99 (d, 1H); 8.21 (s, 1H); 8.38 (s, 1H); 11.23 (s, 1H).

Intermediate 201

1-[2-(4-Aminopiperidin-1-yl)ethyl]-2-oxo-1,2-dihydroquinoxaline-7-carbonitrile tert-Butyl{1-[2-(7-cyano-2-oxoquinoxalin-1(2H)-yl)ethyl]piperidin-4-yl}carbamate (Intermediate 199) was deprotected with TFA as described for Intermediate 197 to give the crude free base of the product.

MS (ESI) 298 (MH$^+$) for $C_{16}H_{19}N_5O$

Example 111

6-[({1-[2-(6-Methoxy-3-oxopyrido[2,3-b]pyrazin-4(3H)-yl)ethyl]piperidin-4-yl}amino)methyl]-2H-pyrido[3,2-b][1,4]oxazin-3(4H)-one 4-[2-(4-Aminopiperidin-1-yl)ethyl]-6-methoxypyrido[2,3-b]pyrazin-3(4H)-one (Intermediate 202, 0.125 g) was reacted with 3-oxo-3,4-dihydro-2H-pyrido[3,2-b][1,4]oxazine-6-carbaldehyde (WO 2004/058144) (50 mg) and sodium acetoxyborohydride (110 mg) as described for Example 107. Chromatography on silica gel with 0-20% methanol in dichloromethane and trituration of the product from ether gave 37.6 mg of the title compound as acetic acid salt.

MS (ESI) 466 (MH$^+$) for $C_{23}H_{27}N_7O_4$
$^1$H NMR (DMSO-D6) δ 1.18 (q, 2H); 1.74 (d, 2H); 2.03 (t, 2H); 2.32-2.41 (m, 1H); 2.61 (t, 2H); 2.90 (d, 2H); 3.66 (s, 2H); 3.98 (s, 3H); 4.41 (t, 2H); 4.59 (s, 2H); 6.83 (d, 1H); 6.99 (d, 1H); 7.27 (d, 1H); 8.10 (s, 1H); 8.12 (d, 1H); 11.15 (s, 1H).

Intermediate 202

4-[2-(4-Aminopiperidin-1-yl)ethyl]-6-methoxypyrido[2,3-b]pyrazin-3(4H)-one tert-Butyl{1-[2-(6-methoxy-3-oxopyrido[2,3-b]pyrazin-4(3H)-yl)ethyl]piperidin-4-yl}carbamate (Intermediate 203, 0.213 g) was deprotected with TFA as described for Intermediate 197 to give the crude free base of the product, 0.15 g.

MS (ESI) 304 (MH$^+$) for $C_{15}H_{21}N_5O_2$

Intermediate 203 tert-Butyl{1-[2-(6-methoxy-3-oxopyrido[2,3-b]pyrazin-4(3H)-yl)ethyl]piperidin-4-yl}carbamate 6-Methoxypyrido[2,3-b]pyrazin-3(4H)-one (Intermediate 204, 0.085 g, 0.48 mmol) was deprotonated with sodium hydride (0.030 g, 60% in oil, 0.7.5 mmol) and alkylated with 2-{4-[(tert-butoxycarbonyl)amino]piperidin-1-yl}ethyl methanesulfonate (Intermediate 6) (1.05 mmol) as described for Intermediate 2. Chromatography on silica gel with 0-25% acetone in dichloromethane gave 0.13 g of the title compound.

MS (ESI) 404 (MH$^+$) for $C_{20}H_{29}N_5O_4$
$^1$H NMR (CDCl$_3$) δ 1.31-1.40 (m, 2H); 1.40-1.46 (m, 9H); 1.87-1.95 (m, 2H); 2.15-2.27 (m, 2H); 2.69-2.75 (m, 2H); 2.93-3.02 (m, 2H); 3.40-3.51 (m, 1H); 4.02 (s, 3H); 4.35-4.46 (m, 1H); 4.51-4.60 (m, 2H); 6.73 (d, 1H); 8.02 (d, 1H); 8.15 (s, 1H).

Intermediate 204

6-Methoxypyrido[2,3-b]pyrazin-3(4H)-one

To a solution of 3,4-diamino-6-methoxypyridine (1.11 g) in methanol (20 mL) was added ethylglyoxalate (3.5 mL). After stirring overnight at room temperature, it was filtered and washed with methanol (the precipitate contained the undesired regioisomer, 6-methoxypyrido[2,3-b]pyrazin-2(1H)-one). The filtrate was concentrated and suspended in diethyl ether to give 0.18 g product.

MS (ESI) 178 (MH$^+$) for $C_8H_7N_3O_2$
$^1$H NMR (DMSO-D6) δ 6.77 (d, 1H); 8.01 (s, 1H); 8.07 (d, 1H); 12.83 (s, 1H).

Example 112

4-(2-{4-[(2,3-Dihydro[1,4]dioxino[2,3-c]pyridin-7-ylmethyl)amino]piperidin-1-yl}ethyl)-6-methoxypyrido[2,3-b]pyrazin-3(4H)-one 4-[2-(4-Aminopiperidin-1-yl)ethyl]-6-methoxypyrido[2,3-b]pyrazin-3(4H)-one (Intermediate 202, 75 mg) was reacted with 2,3-dihydro[1,4]dioxino[2,3-c]pyridine-7-carbaldehyde (WO 2004/058144) (48 mg) and sodium acetoxyborohydride (0.11) as described for Example 107. Chromatography on silica gel with 0-2% methanol in dichloromethane to give 72 mg of the product.

MS (ESI) 453 (MH$^+$) for $C_{23}H_{28}N_6O_4$ $^1$H NMR (DMSO-D6) δ 1.18 (q, 2H); 1.74 (d, 2H); 2.02 (t, 2H); 2.30-2.40 (m, 1H); 2.60 (t, 2H); 2.89 (d, 2H); 3.65 (s, 2H); 3.98 (s, 3H); 4.26 (dd, 2H); 4.29-4.34 (m, 2H); 4.40 (t, 2H); 6.83 (d, 1H); 6.92 (s, 1H); 7.98 (s, 1H); 8.10 (s, 1H); 8.12 (d, 1H).

Example 113

6-[({1-[2-(6-Chloro-1-oxido-3-oxo-1,2,4-benzotriazin-4(3H)-yl)ethyl]piperidin-4-yl}amino)methyl]-2H-pyrido[3,2-b][1,4]oxazin-3(4H)-one 4-[2-(4-Aminopiperidin-1-yl)ethyl]-6-chloro-1,2,4-benzotriazin-3(4H)-one 1-oxide (Intermediate 205, 0.517 g) was reacted with 3-oxo-3,4-dihydro-2H-pyrido[3,2-b][1,4]oxazine-6-carbaldehyde (WO 2004/058144) (117 mg) and sodium acetoxyborohydride (340 mg) as described for Example 107. Chromatography on silica gel with 0-20% methanol in dichloromethane gave 60 mg of the title compound as acetic acid salt.

MS (ESI) 486 (MH$^+$) for $C_{22}H_{24}ClN_7O_4$ $^1$H NMR (DMSO-D6) δ 1.13-1.24 (m, 2H); 1.69-1.79 (m, 2H); 2.02 (t, 2H); 2.31-2.42 (m, 1H); 2.57 (t, 2H); 2.88 (d, 2H); 3.27-3.39 (m, 2H); 3.67 (s, 2H); 4.26 (t, 2H); 4.60 (s, 2H); 7.00 (d, 1H); 7.28 (d, 1H); 7.43 (dd, 1H); 7.91 (d, 1H); 8.20 (d, 1H); 11.15 (s, 1H).

Intermediate 205

4-[2-(4-Aminopiperidin-1-yl)ethyl]-6-chloro-1,2,4-benzotriazin-3(4H)-one 1-oxide tert-Butyl{1-[2-(6-chloro-1-oxido-3-oxo-1,2,4-benzotriazin-4(3H)-yl)ethyl]piperidin-4-yl}carbamate (Intermediate 206, 0.65 g) was deprotected with TFA as described for Intermediate 197 to give the crude free base of the product, 0.517 g.

MS (ESI) 324 (MH$^+$) for $C_{14}H_{18}ClN_5O_2$

Intermediate 206 tert-Butyl{1-[2-(6-chloro-1-oxido-3-oxo-1,2,4-benzotriazin-4(3H)-yl)ethyl]piperidin-4-yl}carbamate 6-Chloro-1,2,4-benzotriazin-3(4H)-one 1-oxide (FR 2621583, 1.50 g) was deprotonated with sodium hydride (0.42 g, 60% in oil) and alkylated with 2-{4-[(tert-butoxycarbonyl)amino]piperidin-1-yl}ethyl methanesulfonate (Intermediate 6) (1 equivalent) as described for Intermediate 2. The residue obtained after aqueous work up was suspended in diethyl ether and filtered to yield 1.30 g of product.

MS (ESI) 424 (MH$^+$) for $C_{19}H_{26}ClN_5O_4$ $^1$H NMR (CDCl$_3$) δ 1.30-1.41 (m, 2H); 1.44 (s, 9H); 1.88-1.96 (m, 2H); 2.21-2.30 (m, 2H); 2.74 (t, 2H); 2.83-2.92 (m, 2H); 3.41-3.52 (m, 1H); 4.27 (t, 2H); 4.34-4.45 (m, 1H); 7.30 (dd, 1H); 7.53 (d, 1H); 8.27 (d, 1H).

Example 114

6-Chloro-4-(2-{4-[(2,3-dihydro[1,4]dioxino[2,3-c]pyridin-7-ylmethyl)amino]piperidin-1-yl}ethyl)-1,2,4-benzotriazin-3(4H)-one 1-oxide 4-[2-(4-Aminopiperidin-1-yl)ethyl]-6-chloro-1,2,4-benzotriazin-3(4H)-one 1-oxide (Intermediate 205, (0.25 g) was reacted with 2,3-dihydro[1,4]dioxino[2,3-c]pyridine-7-carbaldehyde (WO 2004/058144) (0.14 g) and sodium acetoxyborohydride (0.34 g) as described for Example 107. Chromatography on silica gel with 0-20% methanol in dichloromethane gave 60 mg of the title compound as acetic acid salt (0.37 g).

MS (ESI) 473 (MH$^+$) for $C_{22}H_{25}ClN_6O_4$

1H NMR (DMSO-D6) δ 1.14-1.25 (m, 2H); 1.68-1.78 (m, 2H); 2.02 (t, 2H); 2.31-2.42 (m, 1H); 2.57 (t, 2H); 2.88 (d, 2H); 3.67 (s, 2H); 4.22-4.30 (m, 4H); 4.33 (dd, 2H); 6.93 (s, 1H); 7.44 (dd, 1H); 7.91 (d, 1H); 8.00 (s, 1H); 8.21 (d, 1H).

Example 115

6-[({1-[2-(6-Chloro-3-oxo-1,2,4-benzotriazin-4(3H)-yl)ethyl]piperidin-4-yl}amino)methyl]-2H-pyrido[3,2-b][1,4]oxazin-3(4H)-one 4-[2-(4-Aminopiperidin-1-yl)ethyl]-6-chloro-1,2,4-benzotriazin-3(4H)-one (Intermediate 207, 67 mg) was reacted with 3-oxo-3,4-dihydro-2H-pyrido[3,2-b][1,4]oxazine-6-carbaldehyde (WO 2004/058144) (360 mg) and sodium acetoxyborohydride (76 mg) as described for Example 107. Chromatography on silica gel with 0-20% methanol in dichloromethane and trituration from ether gave 33 mg of the title compound.

MS (ESI) 470 (MH$^+$) for $C_{22}H_{24}ClN_7O_3$ $^1$H NMR (DMSO-D6) δ 1.30-1.42 (m, 2H); 1.88-1.97 (m, 2H); 1.98-2.08 (m, 2H); 2.58-2.67 (m, 2H); 2.90-3.02 (m, 2H); 3.28-3.34 (m, 2H); 3.95-4.07 (m, 2H); 4.26 (t, 2H); 4.66 (s, 2H); 7.08 (d, 1H); 7.39 (d, 1H); 7.56 (dd, 1H); 7.87 (d, 1H); 8.43 (d, 1H); 11.27 (s, 1H).

Intermediate 207

4-[2-(4-Aminopiperidin-1-yl)ethyl]-6-chloro-1,2,4-benzotriazin-3(4H)-one tert-Butyl{1-[2-(6-chloro-3-oxo-1,2,4-benzotriazin-4(3H)-yl)ethyl]piperidin-4-yl}carbamate (Intermediate 208, 74 mg) was deprotected with TFA as described for Intermediate 197 to give the crude free base of the product, 67 mg.

MS (ESI) 307 (MH$^+$) for $C_{14}H_{18}ClN_5O$

Intermediate 208 tert-Butyl{1-[2-(6-chloro-3-oxo-1,2,4-benzotriazin-4(3H)-yl)ethyl]piperidin-4-yl}carbamate To a solution of tert-butyl{1-[2-(6-chloro-1-oxido-3-oxo-1,2,4-benzotriazin-4(3H)-yl)ethyl]piperidin-4-yl}carbamate (Intermediate 206) (0.43 g) in acetic acid (8 mL) and water (2 mL) was added zinc dust (0.50 g). After 30 minutes, the solution was filtered and the filtrate concentrated. The residue was then treated with potassium ferricyanide (1.0 g) in water (20 mL). After 2 hours, the reaction was diluted with ethyl acetate. The aqueous layer was collected, the pH adjusted with solid Na$_2$CO$_3$ and extracted with ethyl acetate. The combined organic washes were dried (Na$_2$SO$_4$), filtered and concentrated. The residue was purified by chromatography on silica gel with 0-25% acetone in dichloromethane to yield 66 mg of the product.

MS (ESI) 407 (MH$^+$) for C$_{19}$H$_{26}$ClN$_5$O$_3$ $^1$H NMR (CDCl$_1$) δ 1.32-1.40 (m, 2H); 1.44 (s, 9H); 1.91 (d, 2H); 2.20-2.30 (m, 2H); 2.75 (t, 2H); 2.87 (d, 2H); 3.40-3.52 (m, 1H); 4.24 (t, 2H); 4.40 (s, 1H); 7.42 (dd, 1H); 7.46 (s, 1H); 8.38 (d, 1H).

Example 116

4-(2-{(2S,5R)-5-[(2,3-Dihydro[1,4]dioxino[2,3-c]pyridin-7-ylmethyl)amino]piperidin-2-yl}ethyl)-3-oxo-3,4-dihydro-2H-1,4-benzoxazine-6-carbonitrile The product was obtained following the procedure described for Example 105, except, the enantiomer of Intermediate 183, tert-butyl(2S,5R)-5-amino-2-[2-(6-cyano-3-oxo-2,3-dihydro-4H-1,4-benzoxazin-4-yl)ethyl]piperidine-1-carboxylate (prepared by the exact route as Intermediate 183, but starting from 1-tert-butyl 2-ethyl(2S,5S)-5-{[tert-butyl(dimethyl)silyl]oxy}piperidine-1,2-dicarboxylate, the enantiomer of Intermediate 191) was reacted with 2,3-dihydro[1,4]dioxino[2,3-c]pyridine-7-carbaldehyde to yield the named compound.

MS (ESI) 449 (MH$^+$) for C$_{24}$H$_{27}$N$_5$O$_4$ $^1$H NMR (DMSO-D6) δ ppm 1.42-1.81 (m, 3H); 1.85-2.03 (m, 1H); 2.16 (d, 1H); 2.28 (d, 1H); 2.98-3.11 (m, 1H); 3.38-3.58 (m, 1H); 3.68 (d, 2H); 4.28 (s, 2H); 4.38 (dd, 4H); 4.80 (s, 2H); 7.18 (d, 1H); 7.31 (s, 1H); 7.52 (d, 1H); 7.75 (s, 1H); 8.26 (s, 1H); 9.46-9.79 (m, 2H); 9.98 (s, 1H).

Example 117

6-[({1-[2-(7-Bromo-2-oxo-2,3-dihydro-1H-pyrido[2,3-b][1,4]oxazin-1-yl)ethyl]piperidin-4-yl}amino)methyl]-2H-pyrido[3,2-b][1,4]oxazin-3(4H)-one 1-[2-(4-Aminopiperidin-1-yl)ethyl]-7-bromo-1H-pyrido[2,3-b][1,4]oxazin-2(3H)-one (Intermediate 209) (2.0 mmol), (3-oxo-3,4-dihydro-2H-pyrido[3,2-b][1,4]oxazine-6-carbaldehyde (WO 2004/058144) (356 mg, 2.0 mmol) and sodium cyanoborohydride (496 mg, 4 equiv) were reacted as described under Example 21 to give the product as an off-white solid 420 mg (41% yield).

MS (ESP): 517. 52 (MH$^+$) for C$_{22}$H$_{25}$BrN$_6$O$_4$ $^1$H-NMR (DMSO-d$_6$) δ: 1.13 (t, 2H); 1.34 (q, 5H); 1.85 (d, 2H); 1.98 (t, 2H); 2.45 (m, 2H); 2.71 (m, 1H); 2.91 (d, 2H); 3.00 (m, 2H); 3.89 (m, 2H); 3.99 (m, 2H); 4.63 (s, 2H); 4.85 (s, 2H); 7.05 (d, 1H); 7.35 (d, 1H); 7.94 (dd, 1H); 11.25 (bs, 1H).

Intermediate 209

1-[2-(4-Aminopiperidin-1-yl)ethyl]-7-bromo-1H-pyrido[2,3-b][1,4]oxazin-2(3H)-one tert-Butyl{1-[2-(7-bromo-2-oxo-2,3-dihydro-1H-pyrido[2,3-b][1,4]oxazin-1-yl)ethyl]piperidin-4-yl}carbamate (Intermediate 210) (0.85 g) was reacted as described for Intermediate 14. The crude trifluoro acetate of the title compound was used without further purification for the next step (quantitative yield).

MS (ESP): 355/357 (MH$^+$) for C$_{14}$H$_{19}$BrN$_4$O$_2$

Intermediate 210 tert-Butyl{1-[2-(7-bromo-2-oxo-2,3-dihydro-1H-pyrido[2,3-b][1,4]oxazin-1-yl)ethyl]piperidin-4-yl}carbamate 6-Bromo-2H-pyrido[3,2-b][1,4]oxazin-3(4H)-one (Intermediate 211) (460 mg, 2.0 mmol) was deprotonated with sodium hydride and alkylated with 2-{4-[tert-butoxycarbonyl)amino]piperidin-1-yl}ethyl methanesulfonate (Intermediate 6) (2.1 mmol) as described for Intermediate 2. Chromatography on silica gel with methanol/dichloromethane gave the product as an oil (0.85 g, 93% yield).

MS (ESP): 455, 457 (MH$^+$) for C$_{19}$H$_{27}$BrN$_4$O$_4$

Intermediate 211

7-Bromo-1H-pyrido[2,3-b][1,4]oxazin-2(3H)-one

Ethyl[(5-bromo-3-nitropyridin-2-yl)oxy]acetate (intermediate 212) (4.3 g, 14.1 mmol) was dissolved in anhydrous THF (10 mL) and concentrated HCl (10 mL) was added at 0° C. Tin chloride (5.0 g, 26.4 mmol) was added in small portions. The reaction was stirred for 1 hr and heated at 65° C. overnight. The reaction mixture was concentrated under reduced pressure, extracted with chloroform, dried over magnesium sulfate and concentrated. Chromatography on silica gel with methanol/chloroform gave the product as a light pink solid (1.2 g, 37% yield).

MS (ESP): 229/231 (MH$^+$) for C$_7$H$_5$BrN$_2$O$_2$ $^1$H-NMR (DMSO-d$_6$) δ: 4.80 (s, 2H); 7.32 (s, 1H); 7.87 (s, 1H); 10.94 (bs, 1H).

Intermediate 212

Ethyl[(5-bromo-3-nitropyridin-2-yl)oxy]acetate

A mixture of 5-bromo-2-chloropyridin-3-ol (4.73 g, 19.9 mmol) and ethyl glycolate (2.9 g, 27.8 mmol) in anhydrous dioxane (20 mL) was treated with sodium hydride (1.12 g, 60% in mineral oil, 28 mmol) in portions (exothermic reaction!). The reaction was then quenched with water and extracted with chloroform and dried over magnesium sulfate. Chromatography on silica gel with ethyl acetate/hexanes gave the product as a light yellow solid (4.8 g, 79% yield).

MS (ESP): 305, 307 (MH$^+$) for C$_9$H$_9$BrN$_2$O$_5$ $^1$H-NMR (DMSO-d$_6$) δ ppm: 1.17 (t, 3H); 4.12 (q, 2H); 5.10 (s, 2H); 8.64 (s, 1H); 8.76 (s, 1H).

Example 118

2-Oxo-1-[2-(4-{[(3-oxo-3,4-dihydro-2H-pyrido[3,2-b][1,4]oxazin-6-yl)methyl]amino}piperidin-1-yl)ethyl]-2,3-dihydro-1H-pyrido[2,3-b][1,4]oxazine-7-carbonitrile and Example 119

2-Oxo-1-[2-(4-{[(3-oxo-3,4-dihydro-2H-pyrido[3,2-b][1,4]oxazin-6-yl)methyl]amino}piperidin-1-yl)ethyl]-2,3-dihydro-1H-pyrido[2,3-b][1,4]oxazine-7-carboxamide A mixture of 6-[({1-[2-(7-bromo-2-oxo-2,3-dihydro-1H-pyrido[2,3-b][1,4]oxazin-1-yl)ethyl]piperidin-4-yl}amino)

methyl]-2H-pyrido[3,2-b][1,4]oxazin-3(4H)-one (Example 117) (110 mg, 0.21 mmol), zinc cyanide (80 mg, 0.683 mmol) and tetrakis(triphenylphosphine) palladium(0) (25 mg, 0.0215 mmol) in anhydrous DMF (2.5 mL) over molecular sieves 3 Å was vortexed and then heated in the microwave at 200° C. for one hour. Reverse phase chromatography and generation of the free base as described for Example 21 gave 20 mg (20%) of Example 118 and 20 mg (20%) of Example 119, both as off-white solids.

Example 118

MS (ESP): 464 (MH$^+$) for $C_{23}H_{25}N_7O_4$
$^1$H-NMR (DMSO-d$_6$) δ: 1.74 (m, 2H); 2.18 (m, 2H); 3.02 (m, 2H); 3.80 (m, 2H); 3.90 (m, 2H); 4.23 (m, 4H); 4.70 (s, 2H); 5.01 (s, 2H); 7.11 (d, 1H); 7.44 (d, 1H); 8.08 (s, 1H); 8.40 (s, 1H); 9.28 (s, 1H); 9.75 (bs, 1H); 11.35 (bs, 1H).

Example 119

MS (ESP): 482 (MH$^+$) for $C_{23}H_{27}N_7O_5$
$^1$H-NMR (DMSO-d$_6$) δ: 1.74 (m, 2H); 2.36 (m, 2H); 3.10 (m, 2H); 3.80 (m, 2H); 4.23 (m, 2H); 4.32 (m, 4H); 4.56 (s, 2H); 4.70 (s, 2H); 4.94 (s, 4H); 7.11 (d, 1H); 7.44 (d, 1H); 7.62 (s, 1H); 7.91 (s, 1H); 8.08 (s, 1H); 8.38 (s, 1H); 9.30 (bs, 2H); 9.60 (bs, 1H); 11.35 (bs, 1H).

Example 120

1-(2-{4-[(2,3-Dihydro[1,4]dioxino[2,3-c]pyridin-7-ylmethyl)amino]-2-methylpiperidin-1-yl}ethyl)-5,7-difluoroquinolin-2(1H)-one A solution of 1-[2-(4-amino-2-methylpiperidin-1-yl)ethyl]-5,7-difluoroquinolin-2(1H)-one (Intermediate 213, crude, 220 mg, 0.69 mmol) and 2,3-dihydro[1,4]dioxino[2,3-c]pyridine-7-carbaldehyde (WO 2004/058144) (114 mg, 0.69 mmol) in dry dichloroethane/methanol (4 mL, 4:1) was heated over 3 Å molecular sieves at 80° C. for 3 hours. The reaction mixture was cooled to 0° C., and sodium triacetoxy borohydride (299 mg, 1.38 mmol) was added. The resulting reaction mixture was stirred at room temperature for 16 hours and then was filtered through a 0.45 μm membrane and concentrated to dryness under reduced pressure. The residue was taken up in dichloromethane (20 mL) and saturated aqueous sodium hydrogen carbonate solution (5 mL). The pH of the aqueous phase was adjusted to pH~10 with 1M aqueous sodium hydroxide solution. The aqueous phase was back extracted twice with dichloromethane (4×20 mL) and the combined organic phases were dried over sodium sulfate and concentrated under reduced pressure. Chromatography on silica gel with dichloromethane/methanol (17:3) gave 195 mg (69%) of the title compound as a white foam.
MS (ESP): 471.22 (MH$^+$) for $C_{25}H_{28}F_2N_4O_3$
$^1$H NMR (300 MHz, DMSO-d$_6$) δ: 0.82-0.91 (m, 4H); 1.16-1.26 (m, 1H); 1.74-1.90 (m, 2H); 2.16-2.25 (m, 2H); 2.34-2.42 (m, 2H); 2.85-2.95 (m, 1H); 3.08 (d, 1H, J=11.5 Hz); 3.76 (s, 2H); 4.27-4.34 (m, 6H); 6.63 (d, 1H, J=9.8 Hz); 6.96 (s, 1H); 7.18-7.32 (m, 2H); 7.94 (d, 1H, J=9.8 Hz); 8.03 (s, 1H).

The intermediates for Example 120 were prepared as follows:

Intermediate 213

1-[2-(4-Amino-2-methylpiperidin-1-yl)ethyl]-5,7-difluoroquinolin-2(1H)-one

A solution of 1-{2-[4-(dibenzylamino)-2-methylpiperidin-1-yl]ethyl}-5,7-difluoroquinolin-2(1H)-one (Intermediate 214 358 mg, 0.71 mmol) in methanol (6 mL) was treated with palladium hydroxide on carbon (100 mg). The reaction was stirred at room temperature under hydrogen gas for 18 hours, filtered through celite, rinsed with methanol (100 mL), and concentrated under reduced pressure to afford 225 mg (96%) of a yellow oil.
MS (ESP): (MH$^+$) for $C_{17}H_{21}F_2N_3O$.
$^1$H-NMR (DMSO-d$_6$) δ: 0.74-0.87 (m, 4H); 1.04-1.17 (dq, 1H, J=12.1, 11.9, 3.7 Hz); 1.54-1.67 (m, 2H); 2.16-2.26 (m, 2H); 2.30-2.39 (m, 1H); 2.84-2.95 (m, 1H); 3.02-3.08 (m, 1H); 4.26 (t, 2H, J=6.7 Hz); 6.63 (d, 1H, J=9.8 Hz); 7.17-7.31 (m, 2H); 7.94 (d, 1H, J=9.8 Hz).

Intermediate 214

1-{2-[4-(Dibenzylamino)-2-methylpiperidin-1-yl]ethyl}-5,7-difluoroquinolin-2(1H)-one A solution of 5,7-difluoroquinolin-2(1H)-one (40 mg, 1.9 mmol) in dry dimethylformamide (DMF) (5 mL) was treated at 0° C. with a cooling bath under stirring with sodium hydride (80 mg, 60% in oil, 2.0 mmol). The cooling bath was removed and the mixture was stirred for 30 minutes at room temperature. A solution of 2-[4-(benzylamino)-2-methylpiperidin-1-yl]ethyl methanesulfonate in DMF (Intermediate 215, 0.58 mmol/mL, 3.5 mL, ~2.03 mmol) was then added and the resulting mixture was stirred over night at room temperature. The DMF was removed under reduced pressure, and the residue was taken up in ethyl acetate (100 mL) and saturated aqueous sodium hydrogencarbonate solution (30 mL). The aqueous phase was back extracted once with ethyl acetate (50 mL). The combined organic phases were dried over sodium sulfate and concentrated under reduced pressure. Chromatography on silica gel with hexanes/acetone (2:1) gave 365 mg (39% yield) of the product as a yellow solid.
MS (ESP): 502 (MH$^+$) for $C_{31}H_{33}F_2N_3O$
$^1$H-NMR (DMSO-d$_6$) δ: 0.89 (d, 3H, J=5.5 Hz); 1.10-1.23 (m, 1H); 1.46-1.54 (m, 1H); 1.70 (t, 2H, J=14.3 Hz); 2.10-2.16 (m, 2H); 2.35-2.44 (m, 2H); 2.82-2.89 (m, 1H); 3.12 (d, 1H, J=10.4 Hz); 3.54 (s, 4H); 4.21-4.26 (m, 2H); 6.61 (d, 1H, 9.8 Hz); 7.16-7.34 (m, 12H); 7.95 (d, 1H).

Intermediate 215

2-[4-(Dibenzylamino)-2-methylpiperidin-1-yl]ethyl methanesulfonate

A mixture 2-[4-(dibenzylamino)-2-methylpiperidin-1-yl] ethanol (Intermediate 216, 660 mg, 1.9 mmol) in dry dichloromethane (6 mL) and triethyl amine (0.375 mL, 2.7 mmol) was treated at 0° C. with methanesulfonyl chloride (0.175 mL, 8.4 mmol). After 45 minutes the reaction was complete by TLC (chloroform/methanol 6:1, rf 0.54). Potassium phosphate buffer (pH 7, 1M, 25 mL) was added, dichloromethane was removed under reduced pressure and it was extracted with ice cold ethyl acetate (2×100 mL) and dried over sodium sulfate. The solvent was removed under reduced pressure and the crude preparation of the mesylate was used without delay for the next step.
MS (ESP): 417.18 (MH$^+$) for $C_{23}H_{32}N_2O_3S$.

Intermediate 216

2-[4-(Dibenzylamino)-2-methylpiperidin-1-yl]ethanol

To a solution of N,N-dibenzyl-2-methylpiperidin-4-amine (Intermediate 217, 880 mg, 3.0 mmol) in acetonitrile (6 mL)

was added triethylamine (0.85 ml, 6.0 mmol) and 2-bromoethanol (0.32 mL, 4.5 mmol). The reaction is stirred at 70° C. at 300 watts in the microwave for 20 minutes. Acetonitrile was removed under reduced pressure, the residue was taken up in dichloromethane (100 mL) and saturated aqueous sodium hydrogen carbonate solution (30 mL) and the aqueous phase was back extracted three times with dichloromethane (3×70 mL). The combined organic phases were dried over sodium sulfate and concentrated to dryness under reduced pressure. Chromatography of the residue on silica gel with dichloromethane/methanol (10:1) gave 660 mg (65% yield) of the product as an orange solid.

MS (ESP): 339.22 (MH$^+$) for $C_{22}H_{30}N_2O$.

$^1$H-NMR (DMSO-d$_6$) δ: 1.01 (d, 3H, J=5.8 Hz), 1.22-1.34 (m, 1H); 1.48-1.56 (m, 1H); 1.69 (d, 2H, J=11.1 Hz); 1.95-2.11 (m, 2H); 2.14-2.30 (m, 1H); 2.38-2.43 (m, 1H); 2.64-2.80 (m, 1H); 2.84-3.00 (m, 1H); 3.37-3.41 (m, 1H); 3.55 (s, 4H); 4.24-4.35 (m, 1H); 7.15-7.22 (m, 2H); 7.24-7.34 (m, 8H).

Intermediate 217

N,N-Dibenzyl-2-methylpiperidin-4-amine

A mixture of ethyl 4-(dibenzylamino)-2-methylpiperidine-1-carboxylate (Intermediate 218, 1.28 g, 3.78 mmol) in dry isopropyl alcohol (30 mL) was added potassium hydroxide (0.65 mL, 8.4 mmol). The reaction was stirred at 105° C. for 6 hours. 2-Propanol was removed under reduced pressure, the residue was taken up in dichloromethane (100 mL), filtered through a 0.5 μm membrane, and concentrated under reduced pressure. Chromatography of the residue on silica gel with dichloromethane/methanol/ammonium hydroxide (85:15:0.1) gave 882 mg (79% yield) of the product as a red oil.

MS (ESP): 295.18 (MH$^+$) for $C_{20}H_{26}N_2$.

$^1$H-NMR (DMSO-d$_6$) δ: 0.98 (d, 3H, J=5.8 Hz); 1.07-1.14 (m, 1H); 1.37 (dq, 1H, J=12.0, 4.2 Hz); 1.68 (t, 2H, J=13 Hz); 2.26-2.36 (m, 2H); 2.40-2.46 (m, 1H); 2.91-2.97 (m, 1H); 3.56 (s, 4H); 7.16-7.20 (m, 2H); 7.25-7.34 (m, 8H).

Intermediate 218

Ethyl 4-(dibenzylamino)-2-methylpiperidine-1-carboxylate

A mixture of ethyl 4-(benzylamino)-2-methylpiperidine-1-carboxylate (Intermediate 219, 1.57 g, 5.7 mmol), cesium carbonate (3.72 g, 11.4 mmol) and benzyl bromide (1.36 mL, 11.4 mmol) in dry DMF (20 mL) was heated at 80° C. for 16 hours. The DMF was removed under reduced pressure, the residue was taken up in ethyl acetate (150 mL) and water (75 mL) and the aqueous phase was back extracted once with ethyl acetate (3×150 mL). The combined organic phases were washed with brine (100 mL) and were dried over sodium sulfate. Chromatography on silica gel with hexanes/ethyl acetate (3:2) gave 1.43 g (68% yield) of the product as a yellow oil.

MS (ESP): 367 (MH$^+$) for $C_{23}H_{30}N_2O_2$.

$^1$H-NMR (DMSO-d$_6$) δ: 1.07-1.16 (m, 6H); 1.47-1.61 (m, 2H); 1.72-1.93 (m, 2H); 2.56-2.70 (m, 1H); 3.11-3.19 (m, 1H); 3.48-3.63 (m, 6H); 3.89-4.00 (m, 2H); 7.17-7.21 (m, 2H); 7.29-7.38 (m, 8H).

Intermediate 219

Ethyl 4-(benzylamino)-2-methylpiperidine-1-carboxylate

A solution of ethyl 2-methyl-4-oxopiperidine-1-carboxylate (2.20 grams, 11.9 mmol) and benzyl benzylamine in dichloroethane/methanol (4:1, 50 mL) was heated over 3 Å molecular sieves at 90° C. for 16 hours. The reaction mixture was cooled to 0° C., and sodium triacetoxy borohydride (5.03 g, 23.8 mmol) was added. The resulting reaction mixture was stirred at room temperature for 30 minutes and then was filtered through a 0.45 μm membrane and concentrated to dryness under reduced pressure. The residue was taken up in aqueous 1N HCl solution and washed with ether (2×50 mL). The pH of the aqueous phase was adjusted to a pH of approximately 7 with 1M aqueous sodium bicarbonate solution. The aqueous phase was back extracted twice with ether (4×50 mL) and the combined organic phases were dried over sodium sulfate and concentrated under reduced pressure. Chromatography on silica gel with dichloromethane/methanol (94:6) gave 1.57 g (47% yield) of a yellow oil.

MS (ESP): 277 (MH$^+$) for $C_{16}H_{24}N_2O_2$.

$^1$H-NMR (DMSO-d$_6$) δ: 1.15 (t, 3H, J=7.1 Hz); 1.30 (d, 3H, J=6.8 Hz); 1.52-1.59 (m, 3H); 1.61-1.71 (m, 1H); 2.80-2.82 (m, 1H); 3.22-3.27 (m, 1H); 3.57-3.73 (m, 3H); 3.95-4.06 (m, 3H); 7.18-7.34 (m, 5H).

Example 121

1-(2-{4-[(2,3-Dihydro[1,4]dioxino[2,3-c]pyridin-7-ylmethyl)amino]piperidin-1-yl}ethyl)-2-oxo-1,2-dihydroquinoline-7-carbonitrile A mixture of 7-chloro-1-(2-{4-[(2,3-dihydro[1,4]dioxino[2,3-c]pyridin-7-ylmethyl)amino]piperidin-1-yl}ethyl)quinolin-2(1H)-one (2.11 g, crude, ~3.47 mmol) and zinc cyanide (244 mg, 2.1 mmol) in dry DMF (8 mL) was degassed and flushed with nitrogen three times. Zinc (174 mg, 0.059 mmol, 51.6 mM solution in heptane) was added, followed by 4,5-bis(diphenylphosphino)-9,9-dimethylxanthene (63 mg, 0.11 mmol) and tris(dibenzylideneacetone)dipalladium (0) (100 mg, 0.11 mmol) and it was degassed and flushed with nitrogen like above. The mixture was stirred for 30 minutes at room temperature and then degassed and flushed with nitrogen again. It was heated at 120° C. for 3 hours. The solvent was removed under reduced pressure and the residue taken up in chloroform/isopropyl alcohol (3:1, 50 mL) and filtered through celite and concentrated under reduced pressure. Chromatography by reverse phase (Column: Atlantis Hilic; Gradient: 90% ACE/0.1% TFA; 5% Water/0.1% TFA; and 5% Isopropanol/0.1% TFA; Flow Rate: 1 mL/min.) afforded 418 mg (20%) of a brown oil as a TFA salt.

MS (ESP): 447.14 (MH$^+$) for $C_{24}H_{26}N_6O_3$ $^1$H NMR (300 MHz, DMSO-d$_6$) δ: 1.75-1.87 (m, 2H); 2.29-2.38 (d, 2H, J=12.6 Hz); 3.00-3.20 (m, 2H); 3.37-3.49 (m, 2H); 3.90 (d, 2H, J=12.6 Hz); 4.24 (br s, 2H); 4.35 (d, 2H, J=4.6 Hz); 4.39 (d, 2H, J=4.6 Hz); 4.62-4.72 (m, 2H); 6.95 (d, 1H, J=9.6); 7.12 (s, 1H); 8.02 (d, 1H, J=7.7 Hz); 8.11 (d, 1H, J=9.6 Hz); 8.21 (s, 1H); 8.47 (d, 1H, J=7.7); 9.18-9.45 (m, 2H).

Example 122

Cis±1-[(2E)-3-(2,5-difluorophenyl)prop-2-en-1-yl]-4-[3-(6-methoxy-3-oxo-2,3-dihydro-4H-1,4-benzoxazin-4-yl)propyl]piperidine-3-carboxylic acid A solution of methyl Cis(±)-1-[(2E)-3-(2,5-difluorophenyl)prop-2-en-1-yl]-4-[3-(6-methoxy-3-oxo-2,3-dihydro-4H-1,4-benzoxazin-4-yl)propyl]piperidine-3-carboxylate (Example 123) (105 mg, 0.204 mmol) in methanol (1 mL) was treated with a solution of sodium hydroxide (1N, 1 mL) the reaction was warmed to 30° C. for 18 hours. The temperature was increased to 60° C. for 6 hours. The solvents were evaporated, the reaction was diluted with ethyl acetate and water. The pH was adjusted to 7 with 1N HCl. The layers were separated. The aqueous phase was extracted with ethyl acetate (2×20 mL). The organic layers were combined dried over magnesium sulfate and concentrated at reduced pressure. The residue was taken up and dichloromethane and precipitated with ether in a dry ice/acetone bath. The solvent was decanted. The solid was dried under high vacuum to obtain 21 mg (20%) of an off-white solid.

MS (ESP): 501 (MH$^+$) for $C_{27}H_{30}F_2N_2O_5$ $^1$H-NMR (400 MHz, DMSO-d$_6$) δ 1.14-1.26 (m, 1H) 1.41-1.53 (m, 1H) 1.57-1.68 (m, 2H) 1.74-1.84 (m, 1H) 1.98-2.10 (m, 1H) 2.89-2.97 (m, 1H) 2.98-3.04 (m, 1H) 3.04-3.12 (m, 1H) 3.12-3.20 (m, 1H) 3.22-3.34 (m, 1H) 3.34-3.45 (m, 2H) 3.71 (s, 3H) 3.81-3.86 (m, 1H) 3.88-3.96 (m, 3H) 4.46 (s, 2H) 6.47-6.58 (m, 2H) 6.63 (s, 1H) 6.85 (d, 2H) 7.06-7.18 (m, 2H) 7.39-7.48 (m, 1H) 8.11 (s, 1H)

Example 123

Methyl cis(±)1-[(2E)-3-(2,5-difluorophenyl)prop-2-en-1-yl]-4-[3-(6-methoxy-3-oxo-2,3-dihydro-4H-1,4-benzoxazin-4-yl)propyl]piperidine-3-carboxylate A solution of methyl 4-[3-(6-methoxy-3-oxo-2,3-dihydro-4H-1,4-benzoxazin-4-yl)propyl]piperidine-3-carboxylate (Intermediate 220) (150 mg, 0.414 mmol) in ethanol (2 mL) was treated with K$_2$CO$_3$ (63 mg, 0.455 mmol) followed by a solution of 2-[(1E)-3-chloroprop-1-en-1-yl]-1,4-difluorobenzene (Intermediate 124) (86 mg, 0.455 mmol) in ethanol (1 mL). The reaction was warmed to 40° C. for 18 hours. The reaction was partitioned between ethyl acetate and water. The aqueous layer was extracted with dichloromethane (2×20 mL). The organic extracts were combined, dried over MgSO$_4$ and concentrated at reduced pressure to obtain a yellow oil. Chromatography on silica gel eluting with (0-2.5%) methanol in dichloromethane gave the title compound as a yellow oil (120 mg, 56%).

MS (ESP): 515 (MH$^+$) for $C_{28}H_{32}F_2N_2O_5$ $^1$H-NMR (400 Mz, DMSO-d$_6$) δ 1.19-1.30 (m, 2H) 1.39-1.49 (m, 2H) 1.49-1.61 (m, 2H) 1.66-1.78 (m, 2H) 2.16-2.28 (m, 1H) 2.36 (s, 1H) 2.64-2.75 (m, 1H) 3.03-3.15 (m, 2H) 3.54 (s, 3H) 3.73 (s, 3H) 3.81-3.92 (m, 2H) 4.52 (s, 2H) 6.39-6.51 (m, 1H) 6.56 (dd, J=8.6, 2 Hz, 2H) 6.71 (d, J=2 Hz, 1H) 6.92 (d, J=8.6 Hz, 1H) 7.07-7.18 (m, 1H) 7.18-7.30 (m, 1H) 7.46-7.57 (m, 1H).

The intermediates for Example 2 were prepared as follows:

Intermediate 220

Methyl 4-[3-(6-methoxy-3-oxo-2,3-dihydro-4H-1,4-benzoxazin-4-yl)propyl]piperidine-3-carboxylate To an ice-cooled solution of 6-methoxy-2H-1,4-benzoxazin-3(4H)-one (Intermediate 48) (407 mg, 2.29 mmol) in DMF was added sodium hydride (110 mg, 2.75 mmol). After stirring for 2 hours a solution of 1-tert-butyl 3-methyl 4-{3-[(methylsulfonyl)oxy]propyl}piperidine-1,3-dicarboxylate (868 mg, ~2.29 mmol) (Intermediate 132) in DMF (5 mL) was added. The reaction was allowed to stir at room temperature for five days. The reaction was diluted with ethyl acetate and water. The pH was adjusted to approximately 3 with 1N HCl. The layers were separated. The aqueous layer was extracted with ethyl acetate (3×30 mL). The combined organic layers were washed with water (4×50 mL), dried over magnesium sulfate and concentrated at reduced pressure to obtain a semi-solid. Chromatography on silica gel eluting with (0-2.5%) methanol in dichloromethane gave the product as a mixture of diastereomers. Reverse phase separation using a 50-60% gradient of acetonitrile in water with 0.1% trifluoroacetic acid gave the cis diastereomer as the faster eluting peak. Upon evaporation of the organic components and extraction of the aqueous with 20% methanol in dichloromethane 150 mg of the cis diastereomer was obtained.

$^1$H NMR (CDCl$_3$) δ 1.19-1.30 (m, 1H); 1.32-1.40 (m, 2H); 1.64-1.75 (m, 2H); 1.77-1.89 (m, 2H); 1.94-2.04 (m, 1H); 2.93-3.01 (m, 1H); 3.06-3.11 (m, 1H); 3.13-3.20 (m, 1H); 3.47-3.53 (m, 1H); 3.54-3.60 (m, 1H); 3.74 (s, 3H); 3.79 (s, 3H); 3.82-3.90 (m, 1H); 3.90-4.00 (m, 1H); 4.49-4.57 (m, 2H); 6.49-6.56 (m, 2H); 6.89-6.97 (m, 1H).

The trans compound was obtained as a mixture of amine and Boc protected material (138 mg) through neutralization of the aqueous layer with sodium bicarbonate before extraction with 20% methanol in dichloromethane. The mixture was dissolved in ethanol (3 mL) and heated in the microwave at 150° C. for four hours.

MS (ESP): 363 (MH$^+$) for $C_{19}H_{26}N_2O_5$

Example 124

1-(2-{4-[(2,3-Dihydro[1,4]dioxino[2,3-c]pyridin-7-ylmethyl)amino]piperidin-1-yl}ethyl)-7-methoxy-3,4-dihydroquinoxalin-2(1H)-one To a solution of 1-(2-{4-[(2,3-dihydro[1,4]dioxino[2,3-c]pyridin-7-ylmethyl)amino]piperidin-1-yl}ethyl)-7-methoxyquinoxalin-2(1H)-one (Example 72, 0.125 g) in ethanol (4 mL) was added sodium borohydride (40 mg). After 3 hour at room temperature, additional sodium borohydride (47 mg) was added. After 30 minutes the reaction was quenched with acetone and concentrated. Chromatography on silica gel with a gradient of dichloromethane to 20% methanol in dichloromethane gave 108 mg of the product as a colorless solid.

MS (ESI) 454 (MH$^+$) for $C_{24}H_{31}N_5O_4$ $^1$H-NMR (DMSO-d$_6$) δ (ppm): 1.36 (m, 2H); 1.78-1.88 (m, 2H); 1.98 (t, 2H); 2.41 (t, 2H); 2.52-2.60 (m, 1H); 2.89 (d, 2H); 3.63 (d, 2H); 3.67 (s, 3H); 3.77-3.87 (m, 2H); 3.88-3.95 (m, 2H); 4.25-4.30 (m, 2H); 4.31-4.36 (m, 2H); 5.65 (s, 1H); 6.46 (dd, 1H); 6.62 (d, 1H); 6.66 (d, 1H); 6.95-7.01 (m, 1H); 8.05 (s, 1H).

Example 125

5,7-Difluoro-1-[2-(4-{[(1-oxo-1,3-dihydro-2-benzofuran-5-yl)methyl]amino}piperidin-1-yl)ethyl]quinolin-2(1H)-one The compound was prepared following the procedure described for Examples 87-96.

MS (ES): 454 (MH$^+$) for $C_{25}H_{25}N_3O_3$ $^1$H-NMR (DMSO-d$_6$) δ (ppm): 1.83 (s, 2H); 2.32 (s, 2H); 3.07 (s, 1H); 3.31 (s, 2H); 3.45 (s, 2H); 3.80 (s, 2H); 4.39 (s, 2H); 4.53 (s, 2H); 5.45 (s, 2H); 6.66 (d, 1H); 7.29 (t, 1H); 7.42 (d, 1H); 7.73 (d, 1H); 7.80 (s, 1H, 7.94 (d, 1H); 8.01 (d, 1H); 9.49 (s, 1H).

Example 126

6-[({1-[2-(7-Methoxy-2-oxoquinoxalin-1(2H)-yl)propyl]piperidin-4-yl}amino)methyl]-2H-pyrido[3,2-b][1,4]oxazin-3(4H)-one 1-[2-(4-aminopiperidin-1-yl)-1-methylethyl]-7-methoxyquinoxalin-2(1H)-one (Intermediate 221) (160 mg crude, 0.51 mmol), 3-oxo-3,4-dihydro-2H-pyrido[3,2-b][1,4]oxazine-6-carbaldehyde (WO 2004/058144) (91 mg, 0.51 mmol), and sodium triacetoxy borohydride (320 mg, 1.5 mmol) were reacted as described according to Example 69. Chromatography on silica gel eluting with 5% methanol/dichloromethane containing 0.25% ammonium hydroxide gave 105 mg (63%) of the title compound as an off-white solid.

MS (ESP): 479 (MH$^+$) for $C_{25}H_{30}N_6O_4$ $^1$H NMR (DMSO-D6) δ (ppm): 0.96 (d, 3H); 0.99-1.14 (m, 2H); 1.71 (t, 2H); 1.95 (s, 1H); 2.10 (t, 1H); 2.22-2.41 (m, 2H); 2.89-3.01 (m, 1H); 3.03-3.14 (m, 1H); 3.64 (s, 2H); 3.90 (s, 3H); 4.11 (q, 1H); 4.27-4.40 (m, 1H); 4.55-4.66 (m, 2H); 6.93-7.04 (m, 3H); 7.23-7.33 (m, 1H); 7.69-7.80 (m, 1H); 8.04 (s, 1H); 11.16 (s, 1H).

Intermediate 221

1-[2-(4-Aminopiperidin-1-yl)-1-methylethyl]-7-methoxyquinoxalin-2(1H)-one

A solution of tert-butyl{1-[2-(7-methoxy-2-oxoquinoxalin-1(2H)-yl)propyl]piperidin-4-yl}carbamate (Intermediate 222, 200 mg, 0.48 mmol) in dichloromethane (30 mL) was treated with trifluoroacetic acid (3 mL). After 2 hours, the reaction was concentrated to dryness. The residue was partitioned between 15% methanol/chloroform. The aqueous phase was re-extracted 3× with 15% methanol/chloroform. The combined organic phases were dried over magnesium sulfate, filtered, and concentrated to dryness giving 160 mg (100%) of the crude product as an oil.

MS (ESP): 317 (MH$^+$) for $C_{17}H_{24}N_4O_2$

Intermediate 222 tert-Butyl{1-[2-(7-methoxy-2-oxoquinoxalin-1(2H)-yl)propyl]piperidin-4-yl}carbamate A solution of 7-methoxyquinoxalin-2(1H)-one (Intermediate 148, 590 mg, 3.35 mmol) in dry DMF (10 mL) was cooled in an ice bath under nitrogen and treated with sodium hydride (60%, 160 mg, 4.02 mmol). The reaction was stirred at room temperature for ~90 minutes. The reaction was again cooled in an ice bath and treated with a solution of 2-{4-[(tert-butoxycarbonyl)amino]piperidin-1-yl}-1-methylethyl methanesulfonate in dry DMF (Intermediate 223, ~0.43 mmol/ml, 4.3 mmol). The reaction was stirred at room temperature overnight. The reaction mixture was concentrated to dryness. Residual DMF was co-evaporated 1× with toluene. The resulting residue was partitioned between ethyl acetate and water. The aqueous phase was re-extracted 3× with ethyl acetate. The organic phases were combined, dried over magnesium sulfate, filtered, and concentrated to dryness. Chromatography on silica gel with 25% acetone/hexanes gave 410 mg (29%) of product which contained ~10% starting material (7-methoxyquinoxalin-2(1H)-one). This material was used directly in the next step.

MS (ESP): 417 (MH$^+$) for $C_{22}H_{32}N_4O_4$ $^1$H NMR (DMSO-D6) δ (ppm): 0.96 (d, 3H); 1.10-1.26 (m, 2H); 1.31-1.42 (m, 9H); 1.53-1.72 (m, 2H); 2.14 (t, 1H); 2.37 (t, 1H); 2.94 (d, 1H); 3.04-3.15 (m, 2H); 3.87-3.96 (m, 3H); 4.06-4.20 (m, 2H); 4.32 (dd, 1H); 6.71 (d, 1H); 6.95-7.05 (m, 2H); 7.71-7.78 (m, 1H); 8.04 (s, 1H).

Intermediate 223

2-{4-[tert-Butoxycarbonyl)amino]piperidin-1-yl}-1-methylethyl methanesulfonate tert-Butyl[1-(2-hydroxypropyl)piperidin-4-yl]carbamate (Intermediate 224, 1.1 g, 4.3 mmol), triethylamine (0.90 mL, 6.5 mmol) and methanesulfonyl chloride (0.37 mL, 4.7 mmol). Were reacted as described for Intermediate 6. The crude mesylate was directly used for the next step.

Intermediate 224 tert-Butyl[1-(2-hydroxypropyl)piperidin-4-yl]carbamate tert-Butyl piperidin-4-ylcarbamate (2.0 g, 10.0 mmol), 1-bromopropan-2-ol (2.8 g, 20.0 mmol, commercial product which also contained 30% of the regioisomer 2-bromopropan-1-ol), triethylamine (4.2 mL, 30.0 mmol), and acetonitrile (15 mL) were combined in a microwave vial and heated to 70° C. for 4 hours. The reaction mixture was concentrated to dryness. The crude product was partitioned between ethyl acetate/water. The aqueous phase was re-extracted 2× with ethyl acetate. The combined organic phases were dried over magnesium sulfate, filtered, and concentrated to dryness. The product was purified by flash chromatography on silica gel eluting with a gradient of 20-30% methanol in dichloromethane to give 1.7 g of the desired product as an oil.

$^1$H NMR (DMSO-D6) δ ppm 1.01 (d, 3H); 1.26-1.48 (m, 11H); 1.64 (d, 2H); 1.85-2.04 (m, 2H); 2.03-2.27 (m, 2H); 2.78 (d, 2H); 3.09-3.29 (m, 1H); 3.62-3.81 (m, 1H); 4.23 (d, 1H); 6.75 (d, 1H).

Example 127

5,7-Difluoro-1-(2-{4-[(5,6,7,8-tetrahydro-1,8-naphthyridin-2-ylmethyl)amino]piperidin-1-yl}ethyl)quinolin-2(1H)-one 1-[2-(4-Aminopiperidin-1-yl)ethyl]-5,7-difluoroquinolin-2(1H)-one (Intermediate 23) (126 mg, 0.410 mmol), 5,6,7,8-tetrahydro-1,8-naphthyridine-2-carbaldehyde (JOC 2004, 69, 1959-1966) (66 mg, 0.410 mmol) and sodium triacetoxy borohydride (52 mg, 0.82 mmol) were reacted as described for Example 6, to give 84.82 mg of the mono acetate salt of the product as a pale yellow foam.

MS (ES): 454.54 (MH$^+$) for $C_{25}H_{29}F_2N_5O$ $^1$H NMR (DMSO-D6) δ (ppm): 1.12-1.27 (m, 2H); 1.67-1.79 (m, 4H); 2.01 (t, 2H); 2.29-2.42 (m, 1H); 2.60 (t, 2H); 2.88 (d, 2H); 3.22 (t, 2H); 3.51 (s, 2H); 4.29 (t, 2H); 6.28 (s, 1H); 6.40 (d, 1H); 6.61 (d, 1H); 7.05 (d, 1H); 7.16-7.26 (m, 1H); 7.31 (d, 1H); 7.96 (d, 1H).

All cited publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula V(A):

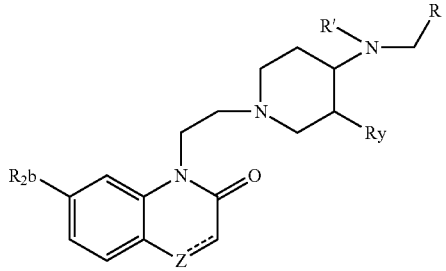

or a pharmaceutically acceptable salt thereof, wherein
R$_2$b is H, halo, cyano, nitro, (C$_1$-C$_6$)alkanoyl, carboxy, (C$_1$-C$_6$)alkoxycarbonyl, (C$_1$-C$_6$)alkyl, hydroxy, halo(C$_1$-C$_6$)alkyl, halo(C$_1$-C$_6$)alkoxy, (C$_1$-C$_6$)alkoxy, NHCO—(C$_1$-C$_6$)alkyl, SO$_2$(C$_1$-C$_6$)alkyl, SO$_2$NH(C$_1$-C$_6$)alkyl, or SO$_2$N((C$_1$-C$_6$)alkyl)$_2$;

Z is CH or N when "- - - -" is a bond, or, when "- - - -" is absent, Z is O or NH;

Ry is fluoro, hydroxy, methoxy, carbomethoxy, or carboxy;

R' is H or (C$_1$-C$_6$)alkyl; and

R is

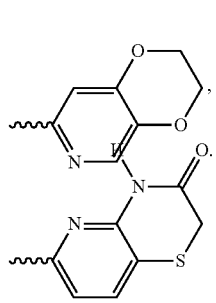 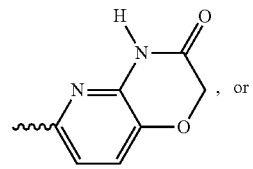

2. A pharmaceutical composition comprising a compound according to claim 1, or a pharmaceutically acceptable salt thereof, admixed with a pharmaceutically acceptable adjuvant, carrier, or excipient.

3. A compound of formula V(A) as claimed in claim 1, which is cis(±)1-(2-{4-[(2,3-dihydro[1,4]dioxino[2,3-c]pyridin-7-ylmethyl)amino]-3-fluoropiperidin-1-yl}ethyl)-2-oxo-1,2-dihydroquinoline-7-carbonitrile, or a pharmaceutically acceptable salt thereof.

4. A pharmaceutical composition comprising a compound according to claim 3, or a pharmaceutically acceptable salt thereof, admixed with a pharmaceutically acceptable adjuvant, carrier or excipient.

* * * * *